United States Patent
Davidson et al.

(10) Patent No.: US 11,473,084 B2
(45) Date of Patent: Oct. 18, 2022

(54) COMPOSITIONS AND METHODS FOR TREATING HUNTINGTON'S DISEASE AND RELATED DISORDERS

(71) Applicant: The Children's Hospital of Philadelphia, Philadelphia, PA (US)

(72) Inventors: Beverly L. Davidson, North Liberty, IA (US); Alejandro Mas Monteys, Philadelphia, PA (US); Shauna Ebanks, Claymont, DE (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 449 days.

(21) Appl. No.: 15/766,549

(22) PCT Filed: Oct. 11, 2016

(86) PCT No.: PCT/US2016/056417
§ 371 (c)(1),
(2) Date: Apr. 6, 2018

(87) PCT Pub. No.: WO2017/062983
PCT Pub. Date: Apr. 13, 2017

(65) Prior Publication Data
US 2019/0055552 A1 Feb. 21, 2019

Related U.S. Application Data

(60) Provisional application No. 62/352,788, filed on Jun. 21, 2016, provisional application No. 62/239,714, filed on Oct. 9, 2015.

(51) Int. Cl.
*C12N 15/113* (2010.01)
*C12N 15/861* (2006.01)
*C12N 15/88* (2006.01)
*C12N 15/66* (2006.01)
*C12N 15/10* (2006.01)
*A61K 48/00* (2006.01)
*A61P 25/00* (2006.01)
*C12N 9/22* (2006.01)

(52) U.S. Cl.
CPC .......... *C12N 15/113* (2013.01); *A61K 48/005* (2013.01); *A61P 25/00* (2018.01); *C12N 9/22* (2013.01); *C12N 15/102* (2013.01); *C12N 15/66* (2013.01); *C12N 15/861* (2013.01); *C12N 15/88* (2013.01); C12N 2310/20 (2017.05); C12N 2330/51 (2013.01); C12N 2800/80 (2013.01)

(58) Field of Classification Search
CPC ..... A61P 25/00; C12N 15/102; C12N 15/113; C12N 15/66; C12N 15/861; C12N 15/88; C12N 2310/20; C12N 2330/51; C12N 2800/80; C12N 9/22; A61K 48/005
USPC .............. 424/93.2; 435/320.1, 455
See application file for complete search history.

(56) References Cited

U.S. PATENT DOCUMENTS

2007/0299027 A1* 12/2007 Hung .................. C12N 15/113
514/44 A
2015/0275208 A1* 10/2015 Oestergaard .......... C07H 21/02
514/44 A

FOREIGN PATENT DOCUMENTS

| WO | 2014/186585 A2 | 11/2014 | |
| WO | WO-2014186585 A2 * | 11/2014 | .......... C12N 15/902 |
| WO | 2015/089351 A1 | 6/2015 | |
| WO | 2015/089354 A1 | 6/2015 | |
| WO | 2015/089419 A2 | 6/2015 | |
| WO | WO-2015089351 A * | 6/2015 | ......... C12N 15/1082 |
| WO | 2016/020399 A1 | 2/2016 | |
| WO | 2017/062605 A1 | 4/2017 | |

OTHER PUBLICATIONS

Gipson et al. RNA Biology, vol. 10, Iss. 11, pp. 1647-1652, Nov. 2013. (See IDS) (Year: 2013).*
Gipson, T.A., et al., "Aberrantly spliced HTT, a new player in Huntington's disease pathogenesis" RNA Biol. (2013) 10(11):11647-52.
Harper, S.Q., et al., "RNA interference improves motor and neuropathological abnormalities in a Huntington's disease mouse model" Proc. Natl. Acad. Sci. (2005) 102(16):15820-5.
Boudreau, R.L., et al., "Nonallele-specific silencing of mutant and wild-type huntingtin demonstrates therapeutic efficacy in Huntington's disease mice" Mol. Ther. (2009) 17(6):11053-63.
Drouet, V., et al., "Sustained Effects of Nonallele-Specific Huntingtin Silencing" Ann. Neurol. (2009) 65:276-285.
Monteys, A.M., et al., "CRISPR/Cas9 Editing of the Mutant Huntingtin Allele In Vitro and In Vivo" Mol. Ther. (2017) 25(1): 12-23.
Lin, L., et al., "Transcriptome sequencing reveals aberrant alternative splicing in Huntington's disease" Hum. Mol. Genet. (2016) 25(16):3454-3466.
Monteys, A.M., et al., "Artificial miRNAs Targeting Mutant Huntingtin Show Preferential Silencing In Vitro and In Vivo" Mol. Ther. Nucleic Acids (2015) 4:e234.
McBride, J.L., et al., "Preclinical safety of RNAi-mediated HTT suppression in the rhesus macaque as a potential therapy for Huntington's disease" Mol. Ther. (2011) 19(12):2152-62.
Johnson, C D., et al., "Huntington's disease: progress toward effective disease-modifying treatments and a cure" Hum. Mol. Genet. (2010) 19(R1):R98-R102.

(Continued)

*Primary Examiner* — Janet L Epps-Smith

(74) *Attorney, Agent, or Firm* — Robert C. Netter, Jr.; Dann, Dorfman, Herrell & Skillman

(57) ABSTRACT

Compositions and methods are provided for the inhibition, treatment and/or prevention of Huntington's disease and related disorders.

20 Claims, 44 Drawing Sheets

Figure 1B:
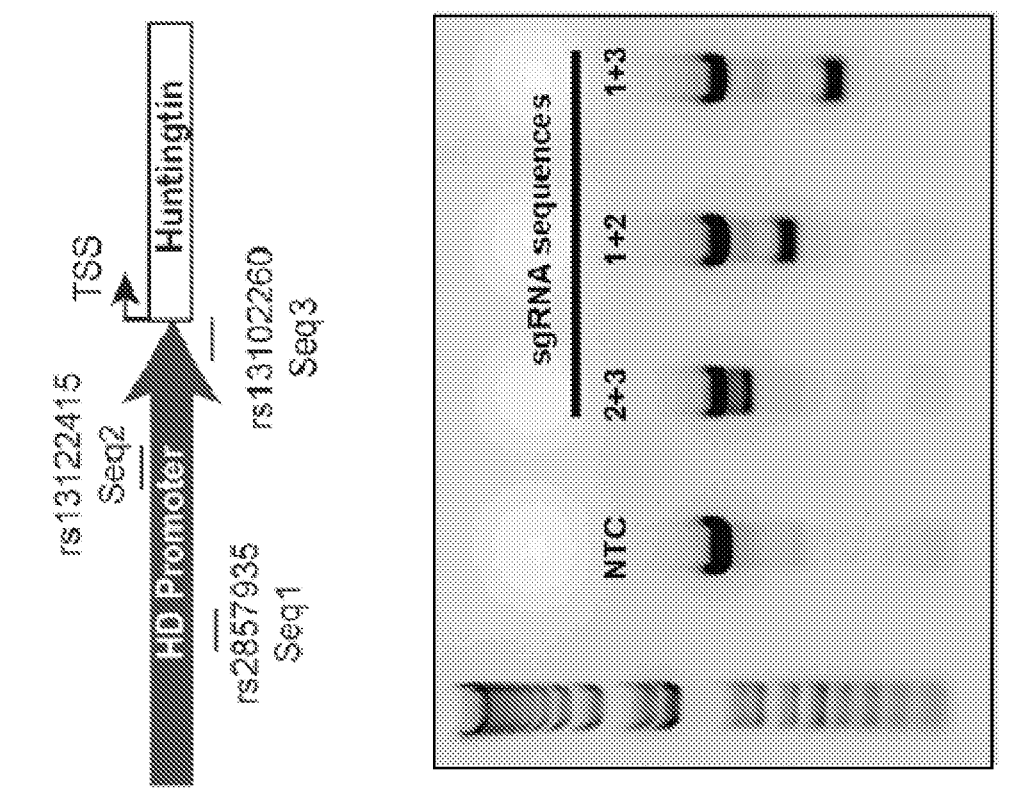

Specification includes a Sequence Listing.

(56) References Cited

OTHER PUBLICATIONS

Courtney, D.G., et al., "CRISPR/Cas9 DNA cleavage at SNP-derived PAM enables both in vitro and in vivo KRT12 mutation-specific targeting" Gene Ther. (2016) 23(1):108-12.
Garriga-Canut, M., et al., "Synthetic zinc finger repressors reduce mutant huntingtin expression in the brain of R6/2 mice" Proc. Natl. Acad. Sci. (2012) 109(45):E3136-45.
Shin, J.W., et al., "Permanent inactivation of Huntington's disease mutation by personalized allele-specific CRISPR/Cas9" Hum. Mol. Genet. (2016) 25(20):14566-4576.
Genbank Accession No. NG_009378, "*Homo sapiens* huntingtin (HTT), RefSeqGene (LRG_763) on chromosome 4", accessed at https://www.ncbi.nlm.nih.gov/nuccore/NG_009378 on Dec. 2, 2021.

* cited by examiner

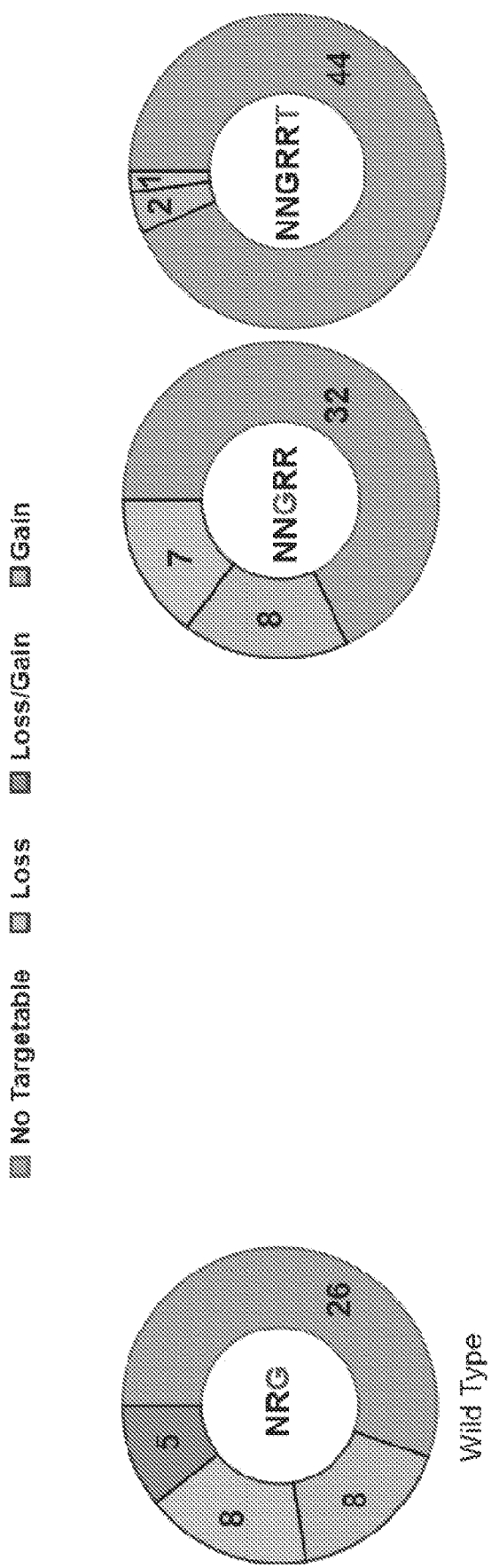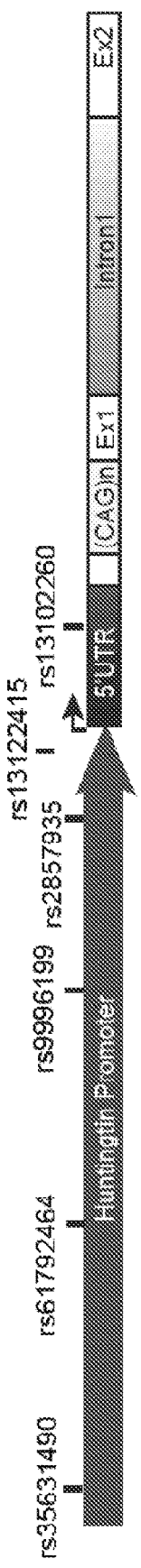
Figure 2B
Figure 2C

| # Variant ID | Location | Sequence Variation |
|---|---|---|
| rs35631490 | Promoter | GTCTGCGTCAGGGTTTCCTTCTTTT[C/G]CAGCCCCACCCCGCGTGCATCCCAC |
| rs73086139 | Promoter | TCAAGGCCTCTTCTCTCTTCTCGGC[A/G]GGACAGGCACAGGCAGGTGGCCAGG |
| rs73086140 | Promoter | GCCAGGTGTCATGCTTAGCTCCCCG[C/G]CCAGTGAGATTCTTTCATTTAACAA |
| rs113541600 | Promoter | TAGGAACCTTATTTCTCTCTCGCTC[-/T]TTTTTTTTTTTTGAGACAGAGTCT |
| rs61791259 | Promoter | GATTACAGGCACCTGCCACCATGCC[C/T]GGCTAATTTTTGTATTTTAGTTGA |
| rs61792460 | Promoter | GAGGGTTTCATCTTGTTGGTCAGGC[A/G]GACTTGAACTCCTGACCTCAGGTGA |
| rs73086144 | Promoter | GCCACTGCGCCTTCATCTCTCTTCT[A/G]TGTATGTGTACGCTGTTTTTCTTT |
| rs73086145 | Promoter | GCTGTTTTTCTTTAGAATGGGGGA[C/G]GTTATCAGGCTCTACATGGTGTGTA |
| rs61792461 | Promoter | TCTACATGGTGTGTAGTCGGCTAGC[A/G]TGTTGTAAGCCTTTCCCTGTGTCAC |
| rs61792462 | Promoter | CTGTGTCACAAGTGCTCATCTGGAA[C/G]AGGATTCTAATGACTGCCTGTGGCT |
| rs61090955 | Promoter | TCATTTTATGTGATTCCTTTCTAGA[A/G]GTACTACTCATTACTTCTGCTTGCA |
| rs77384845 | Promoter | TAGCTGAAGGAAGGACAGGGACTGT[C/T]ATACACTAGCTAAGAGGCAAACTGC |
| rs10011412 | Promoter | agctgaaggaaggacagggactgtC[A/G]TACACTAGCTAAGAGGCAAACTGCT |
| rs61792464 | Promoter | TCCCTCATTCAGGTTGATGTCCTAA[C/G]CCCCAGAACCTCAGAATGGGATTGT |
| rs112435590 | Promoter | TCCATGCCAAGAAGGCAACAGAGAG[G/T]GCCAGGGAGACTGAAGTCATACCCT |
| rs111670395 | Promoter | CCCAGGTTCAAGCAATTCTGCCTCA[A/G]CCTCCGGAATAGCTGGGACTACAGG |
| rs762855 | Promoter | TTGAGAAGGACAGCAGAGAAACAGC[C/T]GTTAGTtcccagttcttgggaggct |
| rs9996199 | Promoter | TGTGGCCTGGCTAAAGTAGGCTTTA[C/G]TGGGCTCCTCTCTGCCTGCATCACC |
| rs143861513 | Promoter | TCCGGGGCGCTGCGCTGGGACCGAT[-/G]GGGGGGCGCCAGGCCTGTGGACACC |
| rs28431418 | Promoter | CTCCCCGCAGGGCTGTCCGGGTGAG[C/T]ATGGCTCTGGCCACGGGCCAGTGTG |
| rs2857935 | Promoter | GGGCGCAGGCCCATGCGGAAAGGAT[A/C/G]CCCCGCCGACGCCTGGAGCGGGGCG |
| rs28616835 | Promoter | GCGCCCGCGCTCGGCGCCCCCTCCA[C/T]GGCCCCGCCCCGTCCATGGCCCCGT |
| rs149624523 | Promoter | CCCCGCCCCGGCCTCGCCACGCCCC[C/T]ACCTCACCACGCCCCCCGCATCGCC |
| rs13122415 | Promoter | attacagtctcaccacgccccgtcc[C/G]CTCTCCGTTGAGCCCCGCGCCTTCG |
| rs113331544 | 5'UTR | GGCCTTGCTGTGTGAGGCAGAACCT[-/GCGGGG]GCGGGGGCAGGGCGGGCTGGTTCC |
| rs13132932 | 5'UTR | TGTGTGAGGCAGAACCTGCGGGGGC[A/G]GGGGCGGGCTGGTTCCCTGGCCAGC |
| rs13102260 | 5'UTR | AGCGTCTGGGACGCAAGGCGCCGTG[A/G]GGGCTGCCGGGACGGGTCCAAGATG |
| rs10009935 | Intron 1 | CTCACTTGGGTCTTCCCTTGTCCTC[C/T]CGCGAGGGGAGGCAGAGCCTTGTTG |
| rs58870770 | Intron 1 | TGAATGAGTTGTGGTTGCCAAGTAA[-/A]GTGGTGAACTTACGTGGTGATTAAT |
| rs34045730 | Intron 1 | GAGGTGTACATTTTACCAGTATTCC[A/T]GTCAGGCTTGCCAGAATACGGGGGG |
| rs28656215 | Intron 1 | GGAAGTCTGTGTGTCGAGTGTACAG[C/T]AGGAGTTAGGAAGTACTCTGGTGCA |
| rs28571971 | Intron 1 | ACAGTAGGAGTTAGGAAGTACTCTG[C/G]TGCAGTTCAGGCCTTTCTCTTACCT |
| rs28583447 | Intron 1 | CAGTAGGAGTTAGGAAGTACTCTGG[C/T]GCAGTTCAGGCCTTTCTCTTACCTC |
| rs28468636 | Intron 1 | TCTCTTACCTCTCAGTATTCTATTT[C/G]CGATCGGATGTGTCCCAGATGGCA |
| rs28564368 | Intron 1 | TATTCTATTTCCGATCGGATGTGT[A/C]CCAGATGGCATTTGGTAAGAATATC |
| rs28485764 | Intron 1 | GATGGCATTTGGTAAGAATATCTCT[A/G]TTAAGACTGATTAATTTTTAGTAAT |
| rs77173925 | Intron 1 | GAATAAATTATTCTAAAGGATGGAA[A/G]AACTTTTTGGATATTTGGAGAAATT |
| rs3905238 | Intron 1 | TTGTATCATGTCAATGTATTACTTA[C/T]GCAAAAATAATACATTAAAAAAAAT |
| rs33950430 | Intron 1 | AGGTATTCACTAATTTTGAGTAACA[-/AACA]CTGCTCACAAAGTTTGGATTTTGGC |
| rs28377140 | Intron 1 | AGGCAATTAATACTTGCTTCTGGCA[C/G]TTTCTTATTCTCCTTCAGATTCCTA |
| rs3856973 | Intron 1 | ttaaaaataaaaataaGTTAACACT[C/T]GATTAACCCTGACATTTCCCTATCC |
| rs4498089 | Intron 1 | AGTGTTAACTTATTTTATTTTTAA[A/G]AAAATTGTTAAGGGCTTTCCAGCAA |
| rs112353753 | Intron 1 | GACATGCACTGCCATGCCTGGGTAA[-/T]TTTTTTTTTTCCCCCGAGACGGAG |
| rs57666989 | Intron 1 | CTGCAAGCTCCGCTTCCCGAGTTCA[C/T]GCCATTCTCCTGCCTCAGTCTCCCA |
| rs10006129 | Intron 1 | tcttgatctcctgacctcgtcatcc[C/G]ccgaccttgtgatccgcccacctcg |
| rs28696693 | Intron 1 | GGTAATTTTGTATTTTTAGTAGAG[A/G]TGGGGTTTTGCCATGATGAGCAGGC |
| rs28393280 | Intron 1 | GGATTTTGAATGCGGAACCAACTGC[A/G]CTTGTTGAACTCTGCTAAGTATAAC |

Figure 3D

| 1000 Genome DATA | | | SpCas9_WT (NRG) | | | | | |
|---|---|---|---|---|---|---|---|---|
| | | | Reference Allele | | | Minor allele | | |
| Ref.Allele | Min. Allele | MAF >0.05 | PAM Motif | Strand | PAM Ref>Min | PAM Motif | Strand | PAM Ref>Min |
| C | G | 0.1074 | TGG | Negative | Loss | - | - | - |
| A | G | 0.0659 | - | - | - | - | - | - |
| C | G | 0.0962 | GGG | Negative | Loss | CGG | Positive | Gain |
| T | delT | 0.2091 | - | - | - | - | - | - |
| C | T | 0.0661 | - | - | - | - | - | - |
| G | A | 0.0966 | - | - | - | - | - | - |
| G | A | 0.0899 | - | - | - | - | - | - |
| C | G | 0.0899 | - | - | - | GAG | Positive | Gain |
| A | G | 0.0901 | - | - | - | - | - | - |
| C | G | 0.0579 | - | - | - | AAG | Positive | Gain |
| A | G | 0.0865 | - | - | - | GAG | Positive | Gain |
| C | T | 0.0984 | - | - | - | - | - | - |
| A | G | 0.1158 | - | - | - | - | - | - |
| G | C | 0.1372 | GGG | Negative | Loss | AAG | Positive | Gain |
| G | T | 0.0881 | AGG | Positive | Loss | - | - | - |
| G | A | 0.0663 | CAG | Positive | Loss | - | - | - |
| G | A (Rev strand) | 0.4828 | - | - | - | - | - | - |
| C | G | 0.1575 | CAG | Negative | Loss | TAG | Positive | Gain |
| - | insG | 0.0599 | - | - | - | - | - | - |
| T | C | 0.1438 | - | - | - | - | - | - |
| G | C/T (Rev Strand) | 0.226 | GGG | Negative | Loss | - | - | - |
| C | T | 0.0839 | - | - | - | - | - | - |
| T | C | 0.0927 | - | - | - | - | - | - |
| C | G | 0.1082 | AGG | Negative | Loss | - | - | - |
| - | insGCGGGG | 0.0851 | - | - | - | - | - | - |
| A | G | 0.0727 | - | - | - | - | - | - |
| G | A | 0.1581 | TGG | Positive | Loss | - | - | - |
| T | C | 0.0877 | - | - | - | CGG | Negative | Gain |
| A | delA | 0.0845 | - | - | - | - | - | - |
| A | T | 0.0589 | - | - | - | - | - | - |
| T | C | 0.1544 | - | - | - | - | - | - |
| G | C | 0.0839 | TGG | Positive | Loss | CAG | Negative | Gain |
| T | C | 0.0839 | - | - | - | - | - | - |
| C | G | 0.0839 | CGG | Negative | Loss | - | - | - |
| C | A | 0.0839 | GGG | Negative | Loss | - | - | - |
| G | A | 0.0845 | - | - | - | - | - | - |
| A | G | 0.0843 | - | - | - | AAG | Positive | Gain |
| A | G (Rev Strand) | 0.4443 | - | - | - | - | - | - |
| AACA | delAACA | 0.0835 | - | - | - | - | - | - |
| G | C | 0.1064 | CAG | Positive | Loss | AAG | Negative | Gain |
| G | A (Rev strand) | 0.4081 | - | - | - | - | - | - |
| A | G | 0.2917 | - | - | - | AAG | Positive | Gain |
| T | delT | 0.1154 | - | - | - | - | - | - |
| C | T | 0.1424 | - | - | - | - | - | - |
| G | C | 0.0845 | - | - | - | GGG | Negative | Gain |
| A | G | 0.0839 | - | - | - | AGG | Positive | Gain |
| A | G | 0.0717 | - | - | - | - | - | - |

Figure 3E

SpCas9_VQR/EQR (NGAN_NGNG/NGAG)

| | Reference Allele | | | Minor allele | |
|---|---|---|---|---|---|
| PAM Motif | Strand | PAM Ref>Min | PAM Motif | Strand | PAM Ref>Min |
| GGAA | Negative | Loss | - | - | - |
| - | - | - | GGCG | Positive | Gain |
| GGCG | Negative | Loss | - | - | - |
| - | - | - | - | - | - |
| - | - | - | - | - | - |
| GGCG | Positive | Loss | - | - | - |
| - | - | - | - | - | - |
| - | - | - | - | - | - |
| - | - | - | AGCG | Positive | Gain |
| - | - | - | AGAG | Positive | Gain |
| - | - | - | - | - | - |
| TGAC | Negative | Loss | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| GGAT | Negative | Loss | - | - | - |
| - | - | - | - | - | - |
| - | - | - | - | - | - |
| GGGG | Positive | Loss | - | - | - |
| - | - | - | GGCG | Positive | Gain |
| - | - | - | GGCG | Positive | Gain |
| - | - | - | TGAG | Positive | Gain |
| CGAG | Negative | Loss | - | - | - |
| - | - | - | - | - | - |
| - | - | - | - | - | - |
| - | - | - | - | - | - |
| - | - | - | - | - | - |
| - | - | - | TGCG | Negative | Gain |
| - | - | - | TGCG | Positive | Gain |
| GGAC/TGGG | Neg/Neg | Loss | - | - | - |
| - | - | - | - | - | - |
| - | - | - | AGAA | Positive | Gain |
| - | - | - | TGCG | Negative | Gain |
| - | - | - | - | - | - |
| - | - | - | - | - | - |
| CGAG | Negative | Loss | | | |
| - | - | - | AGAA | Positive | Gain |
| - | - | - | - | - | - |
| GGCG | Negative | Loss | - | - | - |
| - | - | - | CGGG | Negative | Gain |
| AGAT | Positive | Loss | - | - | - |
| - | - | - | TGCG | Positive | Gain |

Figure 3F

SpCas9_VRER (NGCG)

| Reference Allele | | | Minor allele | | |
|---|---|---|---|---|---|
| PAM Motif | Strand | PAM Ref>Min | PAM Motif | Strand | PAM Ref>Min |
| - | - | - | - | - | - |
| - | - | - | GGCG | Positive | Gain |
| GGCG | Negative | Loss | - | - | - |
| - | - | - | - | - | - |
| - | - | - | - | - | - |
| GGCG | Positive | Loss | - | - | - |
| - | - | - | - | - | - |
| - | - | - | - | - | - |
| - | - | - | AGCG | Positive | Gain |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | AGCG | Negative | Gain |
| - | - | - | GGCG | Positive | Gain |
| - | - | - | GGCG | Positive | Gain |
| - | - | - | - | - | - |
| - | - | - | - | - | - |
| - | - | - | - | - | - |
| - | - | - | - | - | - |
| - | - | - | - | - | - |
| - | - | - | GGCG/TGCG | Pos/Neg | Gain |
| - | - | - | TGCG | Positive | Gain |
| - | - | - | - | - | - |
| - | - | - | - | - | - |
| - | - | - | - | - | - |
| - | - | - | TGCG | Negative | Gain |
| - | - | - | - | - | - |
| - | - | - | - | - | - |
| - | - | - | - | - | - |
| - | - | - | - | - | - |
| - | - | - | - | - | - |
| GGCG | Negative | Loss | - | - | - |
| GGCG | Negative | Loss | - | - | - |
| - | - | - | - | - | - |
| - | - | - | TGCG/AGCG | Pos/Neg | Gain |

Figure 3G

SaCas9 (NNGRRT/NNGRR)

| Reference Allele | | | Minor allele | | |
|---|---|---|---|---|---|
| PAM Motif | Strand | PAM Ref>Min | PAM Motif | Strand | PAM Ref>Min |
| TGGAA | Negative | Loss | - | - | - |
| - | - | - | GCGGG | Positive | Gain |
| - | - | - | - | - | - |
| - | - | - | - | - | - |
| CCGGG | Negative | Loss | - | - | - |
| GCGGA | Positive | Loss | - | - | - |
| - | - | - | - | - | - |
| - | - | - | - | - | - |
| - | - | - | - | - | - |
| - | - | - | AAGAG | Positive | Gain |
| - | - | - | - | - | - |
| - | - | - | - | - | - |
| - | - | - | - | - | - |
| GAGAG | Positive | - | GAGAGT | Positive | Gain |
| - | - | - | - | - | - |
| - | - | - | - | - | - |
| - | - | - | - | - | - |
| GTGAGT | Positive | Loss | GTGAG | Positive | - |
| CGGGG | Negative | - | CGGGGT | Negative | Gain |
| - | - | - | - | - | - |
| - | - | - | GTGGG | Negative | Gain |
| AGGGG | Negative | Loss | - | - | - |
| - | - | - | - | - | - |
| - | - | - | GCGGG | Positive | Gain |
| TGGGG | Positive | Loss | - | - | - |
| - | - | - | CGGGA | Negative | Gain |
| - | - | - | - | - | - |
| - | - | - | - | - | - |
| - | - | - | - | - | - |
| - | - | - | - | - | - |
| CGGAA | Negative | Loss | - | - | - |
| - | - | - | - | - | - |
| - | - | - | - | - | - |
| - | - | - | AAGAA | Positive | Gain |
| - | - | - | - | - | - |
| - | - | - | - | - | - |
| TCGAGT | Negative | Loss | - | - | - |
| - | - | - | AAGAA | Positive | Gain |
| - | - | - | - | - | - |
| - | - | - | - | - | - |
| - | - | - | GGGGG | Negative | Gain |
| - | - | - | - | - | - |
| - | - | - | - | - | - |

Figure 3H

LbCpf1 (TTTN/TTCN/CTTN/TCTN/ATTN/TCCN/TTGN/GTTN/CCCN/CCTN...)

| Reference Allele | | | Minor allele | | |
|---|---|---|---|---|---|
| PAM Motif | Strand | PAM Ref>Min | PAM Motif | Strand | PAM Ref>Min |
| TCCA | Positive | Loss | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | TCTT | Negative | Gain |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| TCCC | Positive | Loss | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| TCCG | Positive | Loss | - | - | - |
| TCCC | Positive | Loss | - | - | - |
| - | - | - | - | - | - |
| - | - | - | - | - | - |
| - | - | - | - | - | - |
| TTTG | Negative | Loss | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |

Figure 3I

AsCpf1(TTTN)

| Reference Allele | | | Minor allele | | |
|---|---|---|---|---|---|
| PAM Motif | Strand | PAM Ref>Min | PAM Motif | Strand | PAM Ref>Min |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| TTTA | Negative | Loss | - | - | - |
| - | - | - | - | - | - |
| - | - | - | - | - | - |
| - | - | - | - | - | - |
| - | - | - | - | - | - |
| - | - | - | - | - | - |
| - | - | - | - | - | - |
| TTTT | Negative | Loss | - | - | - |
| - | - | - | - | - | - |
| TTTG | Negative | Loss | - | - | - |
| - | - | - | - | - | - |
| - | - | - | - | - | - |
| TTTA | Negative | Loss | - | - | - |
| - | - | - | - | - | - |
| - | - | - | - | - | - |
| - | - | - | - | - | - |
| - | - | - | - | - | - |
| - | - | - | - | - | - |

Figure 3J

SNP ID: rs9996199 (C/G) PAM: Gain/Loss

Major allele (C): PAM motif on the negative strand (NAG)

```
                                    3' CCGAGGAGAGACGGACG 5' (72)
(70)  5' GTGGCCTGGCTAAAGTAGGCTTTACTGGGCTCCTCTCTGCCTGCATCAC 3'
(151) 3' CACCGGACCGATTTCATCCGAAATGACCCGAGGAGAGACGGACGTAGTG 5'
                                      PAM
```

Minor Allele (G):PAM motif on the Positive strand (NAG)

```
                              PAM
(71)  5' GTGGCCTGGCTAAAGTAGGCTTTACTGGGCTCCTCTCTGCCTGCATCAC 3'
(152) 3' CACCGGACCGATTTCATCCGAAATCACCCGAGGAGAGACGGACGTAGTG 5'
         5' GCCTGGCTAAAGTAGGCTT 3' (73)
```

SNP ID: rs2857935 (C/G/T) PAM: Loss

Major Allele (C): PAM motif on the Positive strand (NGG)

```
                              PAM
(66)  5' GTCGCCCCGCTCCAGGCGTCGGCGGGGATCCTTTCCGCATGGGCCTGC 3'
(153) 3' CAGCGGGGCGAGGTCCGCAGCCGCCCCTAGGAAAGGCGTACCCGGACG 5'
         5' GCTCCAGGCGTCGGCGG 3' (69)
```

Minor Allele (G): Disruption of the PAM motive.

```
(67)  5' GTCGCCCCGCTCCAGGCGTCGGCGGGGCATCCTTTCCGCATGGGCCTGC 3'
(154) 3' CAGCGGGGCGAGGTCCGCAGCCGCCCGTAGGAAAGGCGTACCCGGACG 5'
```

Minor Allele (T): Disruption of the PAM motive.

```
(68)  5' GTCGCCCCGCTCCAGGCGTCGGCGGGAATCCTTTCCGCATGGGCCTGC 3'
(155) 3' CAGCGGGGCGAGGTCCGCAGCCGCCCTTAGGAAAGGCGTACCCGGACG 5'
```

Figure 3K

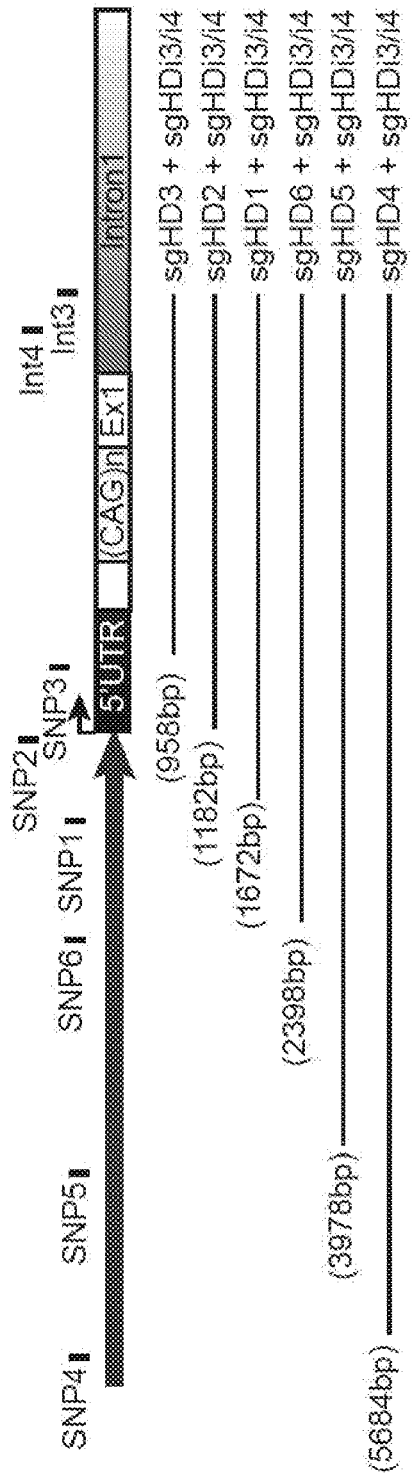
Figure 4A
Figure 4B
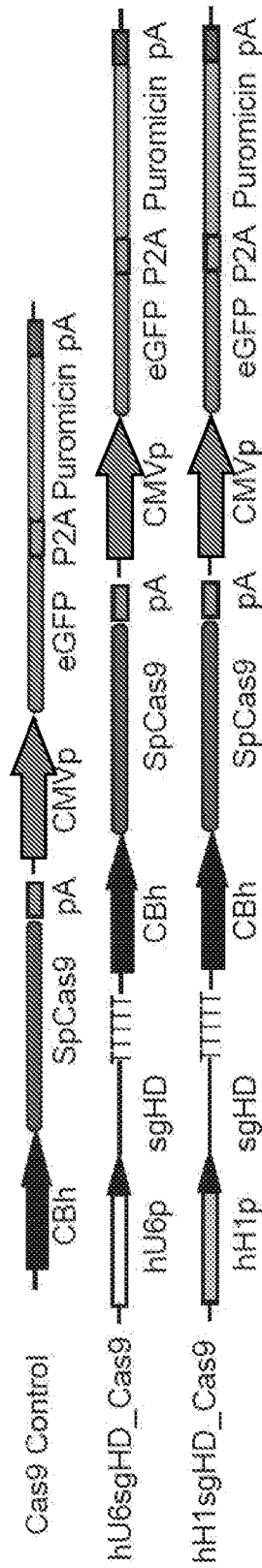
Figure 4C sgHD1B/i3

(121) CGGCTCAGAGTCCACGGCCGCTGTCGCCCGGCTCCAGCGTCGGCGGA------//---ATGCTTTTAGGACGCCGGAGTGGCGGGGAGTGAG (122)
      CGGCTCAGAGTCCACGGCCGCTGTCGCTGTCGCTCGCAGCGTCG-------------------------------CGGCGGGGAGTGGCGGGGCGGGGAGTGAG (123)
      CGGCTCAGAGTCCACGGCCGCCGGCCGCTGTCGCTGCCCAGCGTCG----------------------------CGGCGGGGAGTGGCGGGGCGGGGAGTGAG (124)
      CGGCTCAGAGTCCACGGCCGCCGG------------------------------------------GGGAGTGGCGGGGCGGGGCGGGGAGTGAG (125)
      CGGCTCAGAGTCCACGGCCGCCGGCCGCTGTCGCCCCGCTCCAGGGTCGG-----------------GCGGGGAGTGGCGGGGCGGGGCGGGGAGTGAG (126)

|___HD promoter sequence upstream sgHD1B___| |___HD intron 1 sequence downstream sgHDi3___| sgHD2B/i3

(127) CCCATTACAGTCTCACCACGCCCGTCC%%%%TC%GTT%AGCCCGCGCC---//---ATGCTTTTAGGACGCCGGAGTGGCGGGGAGTGAG (128)
      CCCATTACAGTCTCACCACGCCCCCGTCCCGTCC%C-----------------------------------CGGCGGGGAGTGGCGGGGCGGGGAGTGAGG (129)
      CCCATTACAGTCTCACCACGCCCACGCCCCCGTCCCTCC-------------------------TCGGCGGGGAGTGGCGGGGCGGGGCGGGGAGTGAGG (130)
      CCCATTACAGTCTCACCACGCCCACGCCCCCGTCCCTCC---------------------------TCGGCGGGGAGTGGCGGGGCGGGGAGTGA (131)
      CCCATTACAGTCTCACCACGCCCCCGTCCCCTC--------------------------------GCGGCGGGGAGTGGCGGGGCGGGGCGGGGAGTGAG (132)

|___HD promoter sequence upstream sgHD2B___| |___HD intron 1 sequence downstream sgHDi3___| sgHD3B/i3

(133) CGGCGCCCGGCTCCGCCGGCTCCGCCAGCGTCTN%GGACG%CAAGGCGN%%-//---ATGCTTTTAGGACGCCGG%%%%GAGN%GCGGGGAGTGAG (134)
      CGGCGGCCCGGCTCCGCCGGCTCCGGCCAGCGTCTGGG-----------------------------GGGAGTGGCGGGGGCGGGGCGGGGAGTGAG (135)
      CGCGGCCCCGGCTCCGCCCGGGCCGGCGCAGCGTCTGGACGCTAAGGCG-------------------CGGCGGGGAGTGGCGGGGCGGGGAGTGAG (136)
      CGCGGCCCCGGCTCCGCCGGCTCCGGCCAGCGTCTGGACGCTAAGGCGA------------------TCGGCGGGGAGTGGCGGGGCGGGGAGTGAG (137)
      TCCGGCCCCGGCTCCGCCGGCTCCGGCCAGCGTCTGGACGCTAAGGCGA------------------TCGGCGGGGAGTGGCGGGGCGGGGAGTGAG (138)

|___HD promoter sequence upstream sgHD3B___| |___HD intron 1 sequence downstream sgHDi3___| sgHD4/i3

(139) TGGGGTCTGCGTCAGGGTTTCCTTCTTTTT%%A%GCCCAAACCCCGCGTG%CATC---//---ATGCTTTTAGGACGCCGG%%%%GAGTGGCGGGGAGTGAG (140)
      TGGGGTCTGCGTCAGGGTTCCTTCTCTTTTCCAGCC-----------------------------GGGAGTGGCGGGGCGGGGCGGGGAGTGAG (141)
      TGGGGTCTGCGTCAGGGTTCCTTCTCTTTTCCAGCC-------------------------CGGCGGGGAGTGGCGGGGCGGGGAGTGAG (142)
      TGGGGTCTGCGTCAGGGTTCCTTCTCTTTTCCAGCC-----------------------------TCGGCGGGGAGTGGCGGGGCGGGGAGTGAG (143)
      TGGGGTCTGCGTCAGGGTTCCTTCTCTTTTCTTTTT-----------------------------CGGCGGGGAGTGGCGGGGCGGGGAGTGAG (144)

|___HD promoter sequence upstream sgHD4___| |___HD intron 1 sequence downstream sgHDi3___| sgHD6C/i3

(145) CAGGTGTGGCCTGGCTAAAGTAGGCTTTAC%%%GGCTCCTCTCTGCCTGCATC---//---ATGCTTTTAGGACGCCGG%%%%GAGTGGCGGGGGAGGAGTGAG (146)
      CAGGTGTGGCCTGGCTAAAGTAGGCTTTACTGGG-------------------------------CGGCGGGAGTGGCGGGGCGGGGCGGGGAGGAGTGAG (147)
      CAGGTGTGGCCTGGCTAAAGTAGGCTTTACTGGGC-------------------------------CGGCGGGGAGTGGCGGGGCGGGGCGGGGAGGAGTGAG (148)
      CAGGTGTGGCCTGGCTAAAGTAGGCTTTACTGGGC-------------------------------TCGGCGGGAGTGGCGGGGCGGGGCGGGGAGGAGTGAG (149)
      CAGGTGTGGCCTGGCTAAAGTAGGCTTTACTGGGC-------------------------------CGGCGGGGAGTGGCGGGGCGGGGCGGGGAGGAGTGAG (150)

|___HD promoter sequence upstream sgHD6C___| |___HD intron 1 sequence downstream sgHDi3___|

FIG. 4J

HD PROMOTER TARGETED SNPs

| # Variant ID | Sequence Variation | Ref.Allele | Min. allele |
|---|---|---|---|
| rs35631490 | (74) GTCTGCGTCAGGGTTTCCTTCTTTT[C/G]CAGCCCCACCCCGCGTGCATCCCAC | C | G |

SpCas9_WT (PAM Motif: NRG)
Ref. Allele:
```
                            CGGGGTGGGGCGCACGTAGG (156)
5' GTCTGCGTCAGGGTTTCCTTCTTTTCCAGCCCCACCCCGCGTGCATCCCAC 3' (229)
3' CAGACGCAGTCCCAAAGGAAGAAAAGGTCGGGGTGGGGCGCACGTAGGGTG 5' (230)
                             PAM
```
Minor Allele
```
5' GTCTGCGTCAGGGTTTCCTTCTTTTGCAGCCCCACCCCGCGTGCATCCCAC 3' (231)
3' CAGACGCAGTCCCAAAGGAAGAAAACGTCGGGGTGGGGCGCACGTAGGGTG 5' (232)
```

SpCas9_VQR/EQR (PAM Motif: NGAN-NGNG/NGAG)
Ref. Allele:
```
                            TCGGGGTGGGGCGCACGTAG (157)
5' GTCTGCGTCAGGGTTTCCTTCTTTTCCAGCCCCACCCCGCGTGCATCCCAC 3' (229)
3' CAGACGCAGTCCCAAAGGAAGAAAAGGTCGGGGTGGGGCGCACGTAGGGTG 5' (230)
                             PAM
```
Minor Allele
```
5' GTCTGCGTCAGGGTTTCCTTCTTTTGCAGCCCCACCCCGCGTGCATCCCAC 3' (231)
3' CAGACGCAGTCCCAAAGGAAGAAAACGTCGGGGTGGGGCGCACGTAGGGTG 5' (232)
```

SaCas9(NNGRRT/NNGRR):
Ref. Allele:
```
                            CGGGGTGGGGCGCACGTAGG (156)
5' GTCTGCGTCAGGGTTTCCTTCTTTTCCAGCCCCACCCCGCGTGCATCCCAC 3' (229)
3' CAGACGCAGTCCCAAAGGAAGAAAAGGTCGGGGTGGGGCGCACGTAGGGTG 5' (230)
                             PAM
```
Minor Allele
```
5' GTCTGCGTCAGGGTTTCCTTCTTTTGCAGCCCCACCCCGCGTGCATCCCAC 3' (231)
3' CAGACGCAGTCCCAAAGGAAGAAAACGTCGGGGTGGGGCGCACGTAGGGTG 5' (232)
```

LbCpf1(TTTN/TTCN/CTTN/TCTN/ATTN/TCCN/...):
Ref. Allele:
```
                          PAM
5' GTCTGCGTCAGGGTTTCCTTCTTTTCCAGCCCCACCCCGCGTGCATCCCAC 3' (229)
3' CAGACGCAGTCCCAAAGGAAGAAAAGGTCGGGGTGGGGCGCACGTAGGGTG 5' (230)
                              GCCCCACCCCGCGTGCATCC (158)
```
Minor Allele
```
5' GTCTGCGTCAGGGTTTCCTTCTTTTGCAGCCCCACCCCGCGTGCATCCCAC 3' (231)
3' CAGACGCAGTCCCAAAGGAAGAAAACGTCGGGGTGGGGCGCACGTAGGGTG 5' (232)
```

==============================================================================

| # Variant ID | Sequence Variation | Ref.Allele | Min. allele |
|---|---|---|---|
| rs73086139 | (75) TCAAGGCCTCTTCTCTCTTCTCGGC[A/G]GGACAGGCACAGGCAGGTGGCCAGG | A | G |

SpCas9_VQR/EQR (PAM Motif: NGAN-NGNG/NGAG)
Ref. Allele:
```
5' TCAAGGCCTCTTCTCTCTTCTCGGCAGGACAGGCACAGGCAGGTGGCCAGG 3' (233)
3' AGTTCCGGAGAAGAGAGAAGAGCCGTCCTGTCCGTGTCCGTCCACCGGTCC 5' (234)
```
Minor Allele:
```
                    PAM
5' TCAAGGCCTCTTCTCTCTTCTCGGCGGGACAGGCACAGGCAGGTGGCCAGG 3' (235)
3' AGTTCCGGAGAAGAGAGAAGAGCCGCCCTGTCCGTGTCCGTCCACCGGTCC 5' (236)
       GGCCTCTTCTCTCTTCTCG (159)
```

SpCas9_VRER (PAM Motif: NGCG)
Ref. Allele:
```
5' TCAAGGCCTCTTCTCTCTTCTCGGCAGGACAGGCACAGGCAGGTGGCCAGG 3' (233)
3' AGTTCCGGAGAAGAGAGAAGAGCCGTCCTGTCCGTGTCCGTCCACCGGTCC 5' (234)
```
Minor Allele:
```
                    PAM
5' TCAAGGCCTCTTCTCTCTTCTCGGCGGGACAGGCACAGGCAGGTGGCCAGG 3' (235)
3' AGTTCCGGAGAAGAGAGAAGAGCCGCCCTGTCCGTGTCCGTCCACCGGTCC 5' (236)
       GGCCTCTTCTCTCTTCTCG (159)
```

Figure 5A

SaCas9(NNGRRT/NNGRR):
Ref. Allele:
5' TCAAGGCCTCTTCTCTCTTCTCGGCAGGACAGGCACAGGCAGGTGGCCAGG (233)
3' AGTTCCGGAGAAGAGAGAAGAGCCGTCCTGTCCGTGTCCGTCCACCGGTCC (234)

Minor Allele:
                         PAM
5' TCAAGGCCTCTTCTCTCTTCTCGGCGGGACAGGCACAGGCAGGTGGCCAGG (235)
3' AGTTCCGGAGAAGAGAGAAGAGCCGCCCTGTCCGTGTCCGTCCACCGGTCC (236)
        GGCCTCTTCTCTCTTCTCG (159)

================================================================

Variant ID      Sequence Variation                                    Ref.Allele    Min. allele
rs73086140   (76) GCCAGGTGTCATGCTTAGCTCCCCG[C/G]CCAGTGAGATTCTTTCATTTAACAA    C             G SpCas9_WT (PAM Motif: NRG)
Ref. Allele:
                             TCACTCTAAGAAAGTAAATT (160)
5' GCCAGGTGTCATGCTTAGCTCCCCGCCCAGTGAGATTCTTTCATTTAACAA (237)
3' CGGTCCACAGTACGAATCGAGGGGCGGGTCACTCTAAGAAAGTAAATTGTT (238)
                         PAM
Minor Allele:
                        PAM
5' GCCAGGTGTCATGCTTAGCTCCCCGGCCAGTGAGATTCTTTCATTTAACAA (239)
3' CGGTCCACAGTACGAATCGAGGGGCCGGTCACTCTAAGAAAGTAAATTGTT (240)
       AGGTGTCATGCTTAGCTCCC (161)

SpCas9_VQR/EQR (PAM Motif: NGAN-NGNG/NGAG)
Ref. Allele:
                           GGTCACTCTAAGAAAGTAAATT (162)
5' GCCAGGTGTCATGCTTAGCTCCCCGCCCAGTGAGATTCTTTCATTTAACAA (237)
3' CGGTCCACAGTACGAATCGAGGGGCGGGTCACTCTAAGAAAGTAAATTGTT (238)
                        PAM
Minor Allele:

5' GCCAGGTGTCATGCTTAGCTCCCCGCCAGTGAGATTCTTTCATTTAACAA (239)
   CGGTCCACAGTACGAATCGAGGGGCCGGTCACTCTAAGAAAGTAAATTGTT (240)

SpCas9_VRER (PAM Motif: NGCG)
Ref. Allele:
                           GGTCACTCTAAGAAAGTAAATT (162)
5' GCCAGGTGTCATGCTTAGCTCCCCGCCCAGTGAGATTCTTTCATTTAACAA (237)
3' CGGTCCACAGTACGAATCGAGGGGCGGGTCACTCTAAGAAAGTAAATTGTT (238)
                        PAM
Minor Allele:

5' GCCAGGTGTCATGCTTAGCTCCCCGCCAGTGAGATTCTTTCATTTAACAA (239)
   CGGTCCACAGTACGAATCGAGGGGCCGGTCACTCTAAGAAAGTAAATTGTT (240)

================================================================

Variant ID      Sequence Variation                                    Ref.Allele    Min. allele
rs61791259   (78) GATTACAGGCACCTGCCACCATGCC[C/T]GGCTAATTTTTGTATTTTTAGTTGA    C             T SaCas9 (PAM Motif: NNGRRT)
Ref. Allele:
                            GATTAAAAACATAAAAATCA (163)
5' GATTACAGGCACCTGCCACCATGCCCGGCTAATTTTTGTATTTTTAGTTGA (241)
3' CTAATGTCCGTGGACGGTGGTACGGGCCGATTAAAAACATAAAAATCAACT (242)
                        PAM
Minor Allele:

GATTACAGGCACCTGCCACCATGCCTGGCTAATTTTTGTATTTTTAGTTGA (243)
CTAATGTCCGTGGACGGTGGTACGGACCGATTAAAAACATAAAAATCAACT (244)

================================================================

Variant ID      Sequence Variation                                    Ref.Allele    Min. allele
rs61792460   GAGGGTTTCATCTTGTTGGTCAGGC[A/G]GACTTGAACTCCTGACCTCAGGTGA  (79) G    A SpCas9_VQR/EQR (PAM Motif: NGAN-NGNG/NGAG)
Ref. Allele:
              PAM
GAGGGTTTCATCTTGTTGGTCAGGCGGGACTTGAACTCCTGACCTCAGGTGA (245)
CTCCCAAAGTAGAACAACCAGTCCGCCCTGAACTTGAGGACTGGAGTCCACT (246)
     GGTTTCATCTTGTTGGTCAG (164)

Figure 5B

Minor Allele:
GAGGGTTTCATCTTGTTGGTCAGGCAGACTTGAACTCCTGACCTCAGGTGA (247)
CTCCCAAAGTAGAACAACCAGTCCGTCTGAACTTGAGGACTGGAGTCCACT (248)

SpCas9_VRER (PAM Motif: NGCG)
Ref. Allele:
                      PAM
GAGGGTTTCATCTTGTTGGTCAGGCNGACTTGAACTCCTGACCTCAGGTGA (245)
CTCCCAAAGTAGAACAACCAGTCCGNCTGAACTTGAGGACTGGAGTCCACT (246)
    GGTTTCATCTTGTTGGTCAG (164)

Minor Allele:
GAGGGTTTCATCTTGTTGGTCAGGCAGACTTGAACTCCTGACCTCAGGTGA (247)
CTCCCAAAGTAGAACAACCAGTCCGTCTGAACTTGAGGACTGGAGTCCACT (248)

SaCas9(NNGRRT/NNGRR)
Ref. Allele:
                    PAM
GAGGGTTTCATCTTGTTGGTCAGGCNGACTTGAACTCCTGACCTCAGGTGA (245)
CTCCCAAAGTAGAACAACCAGTCCGNCTGAACTTGAGGACTGGAGTCCACT (246)
   GGGTTTCATCTTGTTGGTCAG (165)

Minor Allele:
GAGGGTTTCATCTTGTTGGTCAGGCAGACTTGAACTCCTGACCTCAGGTGA (247)
CTCCCAAAGTAGAACAACCAGTCCGTCTGAACTTGAGGACTGGAGTCCACT (248)

========================================================================================

| # Variant ID | Sequence Variation | Ref.Allele | Min. allele |
|---|---|---|---|
| rs73086145 | GCTGTTTTTCTTTAGAATGGGGA[C/G]GTTATCAGGCTCTACATGGTGTGTA (81) | C | G |

SpCas9_WT (PAM Motif: NRG)
Ref. Allele:
GCTGTTTTTCTTTAGAATGGGGACGTTATCAGGCTCTACATGGTGTGTA (249)
CGACAAAAAGAAATCTTACCCCCTGCAATAGTCCGAGATGTACCACACAT (250)

Minor Allele
                  PAM
GCTGTTTTTCTTTAGAATGGGGAGGTTATCAGGCTCTACATGGTGTGTA (251)
CGACAAAAAGAAATCTTACCCCCTCCAATAGTCCGAGATGTACCACACAT (252)
    GTTTTTCTTTAGAATGGGG (166)

========================================================================================

| # Variant ID | Sequence Variation | Ref.Allele | Min. allele |
|---|---|---|---|
| rs61792461 | TCTACATGGTGTGTAGTCGGCTAGC[A/G]TGTTGTAAGCCTTTCCCTGTGTCAC (82) | A | G |

SpCas9_VQR/EQR (PAM Motif: NGAN-NGNG/NGAG)
Ref. Allele:
TCTACATGGTGTGTAGTCGGCTAGCATGTTGTAAGCCTTTCCCTGTGTCAC (253)
AGATGTACCACACATCAGCCGATCGTACAACATTCGGAAAGGGACACAGTG (254)

Minor Allele
                           PAM
TCTACATGGTGTGTAGTCGGCTAGCGTGTTGTAAGCCTTTCCCTGTGTCAC (255)
AGATGTACCACACATCAGCCGATCGCACAACATTCGGAAAGGGACACAGTG (256)
    ACATGGTGTGTAGTCGGCTA (167)

SpCas9_VRER (PAM Motif: NGCG)

Ref. Allele:
TCTACATGGTGTGTAGTCGGCTAGCATGTTGTAAGCCTTTCCCTGTGTCAC (253)
AGATGTACCACACATCAGCCGATCGTACAACATTCGGAAAGGGACACAGTG (254)

Minor Allele
                           PAM
TCTACATGGTGTGTAGTCGGCTAGCGTGTTGTAAGCCTTTCCCTGTGTCAC (255)
AGATGTACCACACATCAGCCGATCGCACAACATTCGGAAAGGGACACAGTG (256)
    ACATGGTGTGTAGTCGGCTA (167)

Figure 5C

| # Variant ID | Sequence Variation | Ref.Allele | Min. allele |
|---|---|---|---|
| rs61792462 | CTGTGTCACAAGTGCTCATCTGGAA[C/G]AGGATTCTAATGACTGCCTGTGGCT (81) | C | G |

SpCas9_WT (PAM Motif: NRG)
Ref. Allele:
CTGTGTCACAAGTGCTCATCTGGAACAGGATTCTAATGACTGCCTGTGGCT (257)
GACACAGTGTTCACGAGTAGACCTTGTCCTAAGATTACTGACGGACACCGA (258)

Minor Allele
                    PAM
CTGTGTCACAAGTGCTCATCTGGAAGAGGATTCTAATGACTGCCTGTGGCT (259)
GACACAGTGTTCACGAGTAGACCTTCTCCTAAGATTACTGACGGACACCGA (260)
    GTCACAAGTGCTCATCTGG (168)

SpCas9_VQR/EQR (PAM Motif: NGAN-NGNG/NGAG)
Ref. Allele:
CTGTGTCACAAGTGCTCATCTGGAACAGGATTCTAATGACTGCCTGTGGCT (257)
GACACAGTGTTCACGAGTAGACCTTGTCCTAAGATTACTGACGGACACCGA (258)

Minor Allele
                    PAM
CTGTGTCACAAGTGCTCATCTGGAAGAGGATTCTAATGACTGCCTGTGGCT (259)
GACACAGTGTTCACGAGTAGACCTTCTCCTAAGATTACTGACGGACACCGA (260)
    GTCACAAGTGCTCATCTGGA (169)

SaCas9(NNGRRT/NNGRR)
Ref. Allele:
CTGTGTCACAAGTGCTCATCTGGAACAGGATTCTAATGACTGCCTGTGGCT (257)
GACACAGTGTTCACGAGTAGACCTTGTCCTAAGATTACTGACGGACACCGA (258)

Minor Allele
                    PAM
CTGTGTCACAAGTGCTCATCTGGAAGAGGATTCTAATGACTGCCTGTGGCT (259)
GACACAGTGTTCACGAGTAGACCTTCTCCTAAGATTACTGACGGACACCGA (260)
    GTCACAAGTGCTCATCTGG (168)

LbCpf1(TTTN/TTCN/CTTN/TCTN/ATTN/TCCN/...)
Ref. Allele:
CTGTGTCACAAGTGCTCATCTGGAACAGGATTCTAATGACTGCCTGTGGCT (257)
GACACAGTGTTCACGAGTAGACCTTGTCCTAAGATTACTGACGGACACCGA (258)

Minor Allele
GACACAGTGTTCACGAGTAGACC (170)
CTGTGTCACAAGTGCTCATCTGGAAGAGGATTCTAATGACTGCCTGTGGCT (259)
GACACAGTGTTCACGAGTAGACCTTCTCCTAAGATTACTGACGGACACCGA (260)
                                        PAM

===============================================================================

| # Variant ID | Sequence Variation | Ref.Allele | Min. allele |
|---|---|---|---|
| rs61090955 | TCATTTTATGTGATTCCTTTCTAGA[A/G]GTACTACTCATTACTTCTGCTTGCA (84) | A | G |

SpCas9_WT (PAM Motif: NRG)
Ref. Allele:
TCATTTTATGTGATTCCTTTCTAGAAGTACTACTCATTACTTCTGCTTGCA (261)
AGTAAAATACACTAAGGAAAGATCTTCATGATGAGTAATGAAGACGAACGT (262)

Minor Allele
                    PAM
TCATTTTATGTGATTCCTTTCTAGAGGTACTACTCATTACTTCTGCTTGCA (263)
AGTAAAATACACTAAGGAAAGATCTCCATGATGAGTAATGAAGACGAACGT (264)
    TTTTATGTGATTCCTTTCTA (171)

LbCpf1(TTTN/TTCN/CTTN/TCTN/ATTN/TCCN/...)
Ref. Allele:
 GTAAAATACACTAAGGAAAGA (172)
TCATTTTATGTGATTCCTTTCTAGAAGTACTACTCATTACTTCTGCTTGCA (261)
AGTAAAATACACTAAGGAAAGATCTTCATGATGAGTAATGAAGACGAACGT (262)
                      PAM
Minor Allele
TCATTTTATGTGATTCCTTTCTAGAGGTACTACTCATTACTTCTGCTTGCA (263)
AGTAAAATACACTAAGGAAAGATCTCCATGATGAGTAATGAAGACGAACGT (264)

Figure 5D

```
# Variant ID    Sequence Variation                                                    Ref.Allele    Min. allele
rs77384845    TAGCTGAAGGAAGGACAGGGACTGT[C/T]ATACACTAGCTAAGAGGCAAACTGC (85)            C             T SpCas9_VQR/EQR (PAM Motif: NGAN-NGNG/NGAG)
Ref. Allele:
                              ATGTGATCGATTCTCCG (173)
TAGCTGAAGGAAGGACAGGGACTGTCATACACTAGCTAAGAGGCAAACTGC (265)
ATCGACTTCCTTCCTGTCCCTGACAGTATGTGATCGATTCTCCGTTTGACG (266)
                              PAM
Minor Allele
TAGCTGAAGGAAGGACAGGGACTGTTATACACTAGCTAAGAGGCAAACTGC (267)
ATCGACTTCCTTCCTGTCCCTGACAATATGTGATCGATTCTCCGTTTGACG (268)

==================================================================================================

Variant ID    Sequence Variation                                                    Ref.Allele    Min. allele
rs61792464    TCCCTCATTCAGGTTGATGTCCTAA[C/G]CCCCAGAACCTCAGAATGGGATTGT (87)            G             C SpCas9_WT (PAM Motif: NRG)
Ref. Allele:
                              GGTCTTGGAGTCTTACCCTA (174)
TCCCTCATTCAGGTTGATGTCCTAACCCCCAGAACCTCAGAATGGGATTGT (269)
AGGGAGTAAGTCCAACTACAGGATTGGGGGTCTTGGAGTCTTACCCTAACA (270)
                              PAM
Minor Allele                  PAM
TCCCTCATTCAGGTTGATGTCCTAAGCCCCAGAACCTCAGAATGGGATTGT (271)
AGGGAGTAAGTCCAACTACAGGATTCGGGGTCTTGGAGTCTTACCCTAACA (272)
    TCATTCAGGTTGATGTCCT (175)

LbCpf1(TTTN/TTCN/CTTN/TCTN/ATTN/TCCN/...)
Ref. Allele:
TCCCTCATTCAGGTTGATGTCCTAACCCCCAGAACCTCAGAATGGGATTGT (269)
AGGGAGTAAGTCCAACTACAGGATTGGGGGTCTTGGAGTCTTACCCTAACA (270)

Minor Allele
GGAGTAAGTCCAACTACAGG (176)
TCCCTCATTCAGGTTGATGTCCTAAGCCCCAGAACCTCAGAATGGGATTGT (271)
AGGGAGTAAGTCCAACTACAGGATTCGGGGTCTTGGAGTCTTACCCTAACA (272)
                      PAM ==================================================================================================

Variant ID    Sequence Variation                                                    Ref.Allele    Min. allele
rs112435590   TCCATGCCAAGAAGGCAACAGAGAG[G/T]GCCAGGGAGACTGAAGTCATACCCT (88)            G             T SpCas9_WT (PAM Motif: NRG)
Ref. Allele:
                              PAM
TCCATGCCAAGAAGGCAACAGAGAGGGCCAGGGAGACTGAAGTCATACCCT (273)
AGGTACGGTTCTTCCGTTGTCTCTCCCGGTCCCTCTGACTTCAGTATGGGA (274)
    ATGCCAAGAAGGCAACAGAG (177)

Minor Allele
TCCATGCCAAGAAGGCAACAGAGAGTGCCAGGGAGACTGAAGTCATACCCT (275)
AGGTACGGTTCTTCCGTTGTCTCTCACGGTCCCTCTGACTTCAGTATGGGA (276)

SaCas9(NNGRRT/NNGRR)
Ref. Allele:
                      PAM
TCCATGCCAAGAAGGCAACAGAGAGGGCCAGGGAGACTGAAGTCATACCCT (273)
AGGTACGGTTCTTCCGTTGTCTCTCCCGGTCCCTCTGACTTCAGTATGGGA (274)
TCCATGCCAAGAAGGCAACA (178)
Minor Allele
                      PAM
TCCATGCCAAGAAGGCAACAGAGAGTGCCAGGGAGACTGAAGTCATACCCT (275)
AGGTACGGTTCTTCCGTTGTCTCTCACGGTCCCTCTGACTTCAGTATGGGA (276)
TCCATGCCAAGAAGGCAACA (178)
==================================================================================================

Variant ID    Sequence Variation                                                    Ref.Allele    Min. allele
rs111670395   CCCAGGTTCAAGCAATTCTGCCTCA[A/G]CCTCCGGAATAGCTGGGACTACAGG (89)   G        A SpCas9_WT (PAM Motif: NRG)
Ref. Allele:
                              PAM
CCCAGGTTCAAGCAATTCTGCCTCAGCCTCCGGAATAGCTGGGACTACAGG (277)
GGGTCCAAGTTCGTTAAGACGGAGTCGGAGGCCTTATCGACCCTGATGTCC (278)
    GGTTCAAGCAATTCTGCCT (179)
```

Figure 5E

Minor Allele
CCCAGGTTCAAGCAATTCTGCCTCAACCTCCGGAATAGCTGGGACTACAGG (279)
GGGTCCAAGTTCGTTAAGACGGAGTTGGAGGCCTTATCGACCCTGATGTCC (280)

---

§ Variant ID     Sequence Variation                                              Ref.Allele    Min. allele
rs9996199    TGTGGCCTGGCTAAAGTAGGCTTTA[C/G]TGGGCTCCTCTCTGCCTGCATCACC (91)           C              G

SpCas9_WT (PAM Motif: NRG)
Ref. Allele:
                          CCGAGGAGAGACGGACG (180)
TGTGGCCTGGCTAAAGTAGGCTTTACTGGGCTCCTCTCTGCCTGCATCACC (281)
ACACCGGACCGATTTCATCCGAAATGACCCGAGGAGAGACGGACGTAGTGG (282)
                                PAM
Minor Allele
                              PAM
TGTGGCCTGGCTAAAGTAGGCTTTAGTGGGCTCCTCTCTGCCTGCATCACC (283)
ACACCGGACCGATTTCATCCGAAATCACCCGAGGAGAGACGGACGTAGTGG (284)
    GGCCTGGCTAAAGTAGGCTT (181)

---

§ Variant ID     Sequence Variation                                              Ref.Allele    Min. allele
rs28431418   CTCCCCGCAGGGCTGTCCGGGTGAG[C/T]ATGGCTCTGGCCACGGGCCAGTGTG (93)  T        C

SaCas9(NNGRRT/NNGRR)
Ref. Allele:
                      PAM
CTCCCCGCAGGGCTGTCCGGGTGAGTATGGCTCTGGCCACGGGCCAGTGTG (285)
GAGGGGCGTCCCGACAGGCCCACTCATACCGAGACCGGTGCCCGGTCACAC (286)
 TCCCCGCAGGGCTGTCCGG (182)

Minor Allele      PAM
CTCCCCGCAGGGCTGTCCGGGTGAGCATGGCTCTGGCCACGGGCCAGTGTG (287)
GAGGGGCGTCCCGACAGGCCCACTCGTACCGAGACCGGTGCCCGGTCACAC (288)
TCCCCGCAGGGCTGTCCGG (182)

---

§ Variant ID     Sequence Variation                                              Ref.Allele  Min. allele
rs2857935    GGGCGCAGGCCCATGCGGAAAGGAT[A/C/G]CCCCGCCGACGCCTGGAGCGGGCG (94)     G     C/T (Rev Strand)

SpCas9_WT (PAM Motif: NRG)
Ref. Allele:
                          GGCGGCTGCGGACCTCG (183)
GGGCGCAGGCCCATGCGGAAAGGATCCCCCGCCGACGCCTGGAGCGGGCG (289)
CCCGCGTCCGGGTACGCCTTTCCTAGGGGCGGCTGCGGACCTCGCCCCGC (290)
                    PAM
Minor Allele
GGGCGCAGGCCCATGCGGAAAGGATGCCCCGCCGACGCCTGGAGCGGGCG (291)
CCCGCGTCCGGGTACGCCTTTCCTACGGGGCGGCTGCGGACCTCGCCCCGC (292)

SpCas9_VQR/EQR (PAM Motif: NGAN-NGNG/NGAG)
Ref. Allele:
                         GGGCGGCTGCGGACCTCG (183)
GGGCGCAGGCCCATGCGGAAAGGATCCCCCGCCGACGCCTGGAGCGGGCG (289)
CCCGCGTCCGGGTACGCCTTTCCTAGGGGCGGCTGCGGACCTCGCCCCGC (290)
                     PAM
Minor Allele
GGGCGCAGGCCCATGCGGAAAGGATGCCCCGCCGACGCCTGGAGCGGGCG (291)
CCCGCGTCCGGGTACGCCTTTCCTACGGGGCGGCTGCGGACCTCGCCCCGC (292)

SaCas9(NNGRRT/NNGRR)
Ref. Allele:                   GGCTGCGGACCTCGCCCG (184)
GGGCGCAGGCCCATGCGGAAAGGATCCCCCGCCGACGCCTGGAGCGGGCG (289)
CCCGCGTCCGGGTACGCCTTTCCTAGGGGCGGCTGCGGACCTCGCCCCGC (290)
                      PAM
Minor Allele                   GGCTGCGGACCTCGCCCG (184)
GGGCGCAGGCCCATGCGGAAAGGATACCCCGCCGACGCCTGGAGCGGGCG (293)
CCCGCGTCCGGGTACGCCTTTCCTATGGGGCGGCTGCGGACCTCGCCCCGC (294)
                       PAM

Figure 5F

LbCpf1(TTTN/TTCN/CTTN/TCTN/ATTN/TCCN/...):
Ref. Allele:
```
                               PAM
GGGCGCAGGCCCATGCGGAAAGGATCCCCGCCGACGCCTGGAGCGGGGCG (289)
CCCGCGTCCGGGTACGCCTTTCCTAGGGGGCGGCTGCGGACCTCGCCCCGC (290)
                          CCGCCGACGCCTGGAGCGGG (185)
```
Minor Allele
```
GGGCGCAGGCCCATGCGGAAAGGATACCCCGCCGACGCCTGGAGCGGGGCG (293)
CCCGCGTCCGGGTACGCCTTTCCTATGGGGCGGCTGCGGACCTCGCCCCGC (294)
```

================================================================================

| # Variant ID | Sequence Variation | Ref.Allele | Min. allele |
|---|---|---|---|
| rs149624523 | CCCCGCCCGGCCTCGCCACGCCCC[C/T]ACCTCACCACGCCCCCGCATCGCC (96) | T | C |

SaCas9(NNGRRT/NNGRR)
Ref. Allele:
```
CCCCGCCCGGCCTCGCCACGCCCCTACCTCACCACGCCCCCGCATCGCC (295)
GGGGCGGGCCGGAGCGGTGCGGGATGGAGTGGTGCGGGGGCGTAGCGG (296)
```

Minor Allele
```
                                GAGTGGTGCGGGGGCGTAG (186)
CCCCGCCCGGCCTCGCCACGCCCCCACCTCACCACGCCCCCGCATCGCC (297)
GGGGCGGGCCGGAGCGGTGCGGGGGTGGAGTGGTGCGGGGGCGTAGCGG (298)
                    PAM
```

================================================================================

| # Variant ID | Sequence Variation | Ref.Allele | Min. allele |
|---|---|---|---|
| rs13122415 | attacagtctcaccacgccccgtcc[C/G]CTCTCCGTTGAGCCCCGCGCCTTCG (97) | C | G |

SpCas9_NT (PAM Motif: NRG)
Ref. Allele:
```
                          GAGGCAACTCGGGGCGCGG (187)
ATTACAGTCTCACCACGCCCCGTCCCCTCTCCGTTGAGCCCCGCGCCTTCG (299)
TAATGTCAGAGTGGTGCGGGGCAGGGGAGAGGCAACTCGGGGCGCGGAAGC (300)
                     PAM
```
Minor Allele
```
ATTACAGTCTCACCACGCCCCGTCCGCTCTCCGTTGAGCCCCGCGCCTTCG (301)
TAATGTCAGAGTGGTGCGGGGCAGGCGAGAGGCAACTCGGGGCGCGGAAGC (302)
```

SpCas9_VQR/EQR (PAM Motif: NGAN-NGNG/NGAG)

Ref. Allele:
```
ATTACAGTCTCACCACGCCCCGTCCCCTCTCCGTTGAGCCCCGCGCCTTCG (299)
TAATGTCAGAGTGGTGCGGGGCAGGGGAGAGGCAACTCGGGGCGCGGAAGC (300)
```

Minor Allele
```
                          AGAGGCAACTCGGGGCG (188)
ATTACAGTCTCACCACGCCCCGTCCGCTCTCCGTTGAGCCCCGCGCCTTCG (301)
TAATGTCAGAGTGGTGCGGGGCAGGCGAGAGGCAACTCGGGGCGCGGAAGC (302)
                           PAM
```

SpCas9_VRER (PAM Motif: NGCG)

Ref. Allele:
```
ATTACAGTCTCACCACGCCCCGTCCCCTCTCCGTTGAGCCCCGCGCCTTCG (299)
TAATGTCAGAGTGGTGCGGGGCAGGGGAGAGGCAACTCGGGGCGCGGAAGC (300)
```

Minor Allele
```
                          AGAGGCAACTCGGGGCG (188)
ATTACAGTCTCACCACGCCCCGTCCGCTCTCCGTTGAGCCCCGCGCCTTCG (301)
TAATGTCAGAGTGGTGCGGGGCAGGCGAGAGGCAACTCGGGGCGCGGAAGC (302)
                           PAM
```

SaCas9(NNGRRT/NNGRR)

Ref. Allele:
```
                          GAGGCAACTCGGGGCG (189)
ATTACAGTCTCACCACGCCCCGTCCCCTCTCCGTTGAGCCCCGCGCCTTCG (299)
TAATGTCAGAGTGGTGCGGGGCAGGGGAGAGGCAACTCGGGGCGCGGAAGC (300)
                     PAM
```
Minor Allele
```
ATTACAGTCTCACCACGCCCCGTCCGCTCTCCGTTGAGCCCCGCGCCTTCG (301)
TAATGTCAGAGTGGTGCGGGGCAGGCGAGAGGCAACTCGGGGCGCGGAAGC (302)
```

Figure 5G

Variant ID    Sequence Variation                                                                                    Ref.Allele    Min. allele
rs113331544 GGCCTTGCTGTGTGAGGCAGAACCT[-/GCGGGG]GCGGGGGCAGGGGCGGGCTGGTTCC (98)    -    insGCGGGG

SpCas9_VQR/EQR (PAM Motif: NGAN-NGNG/NGAG)
Ref. Allele:
                                              PAM
GGCCTTGCTGTGTGAGGCAGAACCTGCGGGGCAGGGGCGGGCTGGTTCC (303)
CCGGAACGACACACTCCGTCTTGGACGCCCCGTCCCCGCCCGACCAAGG (304)
     GCTGTGTGAGGCAGAACCT (190)
Minor Allele
                                              PAM
GGCCTTGCTGTGTGAGGCAGAACCTGCGGGGCGGGGGCAGGGGCGGGCTGGTTCC (305)
CCGGAACGACACACTCCGTCTTGGACGCCCCGCCCCCGTCCCCGCCCGACCAAGG (306)
            GTGAGGCAGAACCTGCGGGG (191)

SpCas9_VRER (PAM Motif: NGCG)
Ref. Allele:
                                              PAM
GGCCTTGCTGTGTGAGGCAGAACCTGCGGGGCAGGGGCGGGCTGGTTCC (303)
CCGGAACGACACACTCCGTCTTGGACGCCCCGTCCCCGCCCGACCAAGG (304)
     GCTGTGTGAGGCAGAACCT (190)
Minor Allele
                                              PAM
GGCCTTGCTGTGTGAGGCAGAACCTGCGGGGCGGGGGCAGGGGCGGGCTGGTTCC (305)
CCGGAACGACACACTCCGTCTTGGACGCCCCGCCCCCGTCCCCGCCCGACCAAGG (306)
            GTGAGGCAGAACCTGCGGGG (191)

===============================================================================

Variant ID    Sequence Variation                                                                                    Ref.Allele    Min. allele
rs13132932  TGTCTGAGGCAGAACCTGCGGGGGC[A/G]GGGGCGGGCTGGTTCCCTGGCCAGC (99)    A    G

SpCas9_VQR/EQR (PAM Motif: NGAN-NGNG/NGAG)
Ref. Allele:
TGTGTGAGGCAGAACCTGCGGGGCAGGGGCGGGCTGGTTCCCTGGCCAGC (307)
ACACACTCCGTCTTGGACGCCCCGTCCCCGCCCGACCAAGGGACCGGTCG (308)
Minor Allele
                                    PAM
TGTGTGAGGCAGAACCTGCGGGGCGGGGCGGGCTGGTTCCCTGGCCAGC (309)
ACACACTCCGTCTTGGACGCCCCGCCCCGCCCGACCAAGGGACCGGTCG (310)
       GAGGCAGAACCTGCGGGG (192)

SpCas9_VRER (PAM Motif: NGCG)
Ref. Allele:
TGTGTGAGGCAGAACCTGCGGGGCAGGGGCGGGCTGGTTCCCTGGCCAGC (307)
ACACACTCCGTCTTGGACGCCCCGTCCCCGCCCGACCAAGGGACCGGTCG (308)

Minor Allele
                                    PAM
TGTGTGAGGCAGAACCTGCGGGGCGGGGCGGGCTGGTTCCCTGGCCAGC (309)
ACACACTCCGTCTTGGACGCCCCGCCCCGCCCGACCAAGGGACCGGTCG (310)
       GAGGCAGAACCTGCGGGG (192)

SaCas9 (NNGRRT/NNGRR)
Ref. Allele:
TGTGTGAGGCAGAACCTGCGGGGCAGGGGCGGGCTGGTTCCCTGGCCAGC (307)
ACACACTCCGTCTTGGACGCCCCGTCCCCGCCCGACCAAGGGACCGGTCG (308)

Minor Allele          PAM
TGTGTGAGGCAGAACCTGCGGGGCGGGGCGGGCTGGTTCCCTGGCCAGC (309)
ACACACTCCGTCTTGGACGCCCCGCCCCGCCCGACCAAGGGACCGGTCG (310)
       GAGGCAGAACCTGCGGGG (192)

===============================================================================

Variant ID    Sequence Variation                                                                                    Ref.Allele    Min. allele
rs13102260  AGCGTCTGGGACGCAAGGCGCCGTG[A/G]GGGCTGCCGGGACGGGTCCAAGATG        G    A
                                                                       (100)
SpCas9_WT (PAM Motif: NRG)
Ref. Allele:
                                PAM
AGCGTCTGGGACGCAAGGCGCCGTGGGGGCTGCCGGGACGGGTCCAAGATG (311)
TCGCAGACCCTGCGTTCCGCGGCACCCCCGACGGCCCTGCCCAGGTTCTAC (312)
     GTCTGGGACGCAAGGCGCCG (193)

Figure 5H

Minor Allele
AGCGTCTGGGACGCAAGGCGCCGTGAGGGCTGCCGGGACGGGTCCAAGATG (313)
TCGCAGACCCTGCGTTCCGCGGCACTCCCGACGGCCCTGCCCAGGTTCTAC (314)

SpCas9_VQR/EQR (PAM Motif: NGAN-NGNG/NGAG)
Ref. Allele:
AGCGTCTGGGACGCAAGGCGCCGTGCGGGCTGCCGGGACGGGTCCAAGATG (311)
TCGCAGACCCTGCGTTCCGCGGCACCCCCGACGGCCCTGCCCAGGTTCTAC (312)

Minor Allele
                          PAM
AGCGTCTGGGACGCAAGGCGCCGTGAGGGCTGCCGGGACGGGTCCAAGATG (313)
TCGCAGACCCTGCGTTCCGCGGCACTCCCGACGGCCCTGCCCAGGTTCTAC (314)
    GTCTGGGACGCAAGGCGCCG (193)

SaCas9(NNGRRT/NNGRR)
Ref. Allele:
                  PAM
AGCGTCTGGGACGCAAGGCGCCGTGCGGGCTGCCGGGACGGGTCCAAGATG (311)
TCGCAGACCCTGCGTTCCGCGGCACCCCCGACGGCCCTGCCCAGGTTCTAC (312)
 GCGTCTGGGACGCAAGGCGCCG (194)

Minor Allele
AGCGTCTGGGACGCAAGGCGCCGTGAGGGCTGCCGGGACGGGTCCAAGATG (313)
TCGCAGACCCTGCGTTCCGCGGCACTCCCGACGGCCCTGCCCAGGTTCTAC (314)

===============================================================================

Variant ID    Sequence Variation                                Ref.Allele    Min. allele
rs10009935   CTCACTTGGGTCTTCCCTTGTCCTC[C/T]CGCGAGGGGAGGCAGAGCCTTGTTG    T      C
                                                    (101)

SpCas9_WT (PAM Motif: NRG)

Ref. Allele:
CTCACTTGGGTCTTCCCTTGTCCTCTCGCGAGGGGAGGCAGAGCCTTGTTG (315)
GAGTGAACCCAGAAGGGAACAGGAGAGCGCTCCCCTCCGTCTCGGAACAAC (316)
Minor Allele
                          GCTCCCCTCCGTCTCGG (195)
CTCACTTGGGTCTTCCCTTGTCCTCCCGCGAGGGGAGGCAGAGCCTTGTTG (317)
GAGTGAACCCAGAAGGGAACAGGAGGGCGCTCCCCTCCGTCTCGGAACAAC (318)
                            PAM SpCas9_VQR/EQR (PAM Motif: NGAN-NGNG/NGAG)
Ref. Allele:
                      CGCTGCCCTCCGTCTCGG (196)
CTCACTTGGGTCTTCCCTTGTCCTCTCGCGAGGGGAGGCAGAGCCTTGTTG (315)
GAGTGAACCCAGAAGGGAACAGGAGAGCGCTCCCCTCCGTCTCGGAACAAC (316)
                      PAM
Minor Allele
CTCACTTGGGTCTTCCCTTGTCCTCCCGCGAGGGGAGGCAGAGCCTTGTTG (317)
GAGTGAACCCAGAAGGGAACAGGAGGGCGCTCCCCTCCGTCTCGGAACAAC (318)

SaCas9(NNGRRT/NNGRR)
Ref. Allele:
CTCACTTGGGTCTTCCCTTGTCCTCTCGCGAGGGGAGGCAGAGCCTTGTTG (315)
GAGTGAACCCAGAAGGGAACAGGAGAGCGCTCCCCTCCGTCTCGGAACAAC (316)

Minor Allele
                      GCTCCCCTCCGTCTCGG (196)
CTCACTTGGGTCTTCCCTTGTCCTCCCGCGAGGGGAGGCAGAGCCTTGTTG (317)
GAGTGAACCCAGAAGGGAACAGGAGGGCGCTCCCCTCCGTCTCGGAACAAC (318)
                      PAM

===============================================================================

Variant ID    Sequence Variation                                Ref.Allele    Min. allele
rs58870770   TGAATGAGTTGTGGTTGCCAAGTAA[-/A]GTGGTGAACTTACGTGGTGATTAAT (102)    A      delA LbCpf1(TTTN/TTCN/CTTN/TCTN/ATTN/TCCN/...):
Ref. Allele:
CTTACTCAACACCAACGGTTC (197)
TGAATGAGTTGTGGTTGCCAAGTAAGTGGTGAACTTACGTGGTGATTAAT (319)
ACTTACTCAACACCAACGGTTCATTTCACCACTTGAATGCACCACTAATTA (320)
                        PAM

Figure 5I

Minor Allele
TGAATGAGTTGTGGTTGCCAAGTAAGTGGTGAACTTACGTGGTGATTAAT (321)
ACTTACTCAACACCAACGGTTCATTCACCACTTGAATGCACCACTAATTA (322)

AsCpf1(TTTN)
Ref. Allele:
CTTACTCAACACCAACGGTTC (197)
TGAATGAGTTGTGGTTGCCAAGTAAAGTGGTGAACTTACGTGGTGATTAAT (319)
ACTTACTCAACACCAACGGTTCATTTCACCACTTGAATGCACCACTAATTA (320)
              PAM Minor Allele
TGAATGAGTTGTGGTTGCCAAGTAAGTGGTGAACTTACGTGGTGATTAAT (321)
ACTTACTCAACACCAACGGTTCATTCACCACTTGAATGCACCACTAATTA (322)

======================================================================

| # Variant ID | Sequence Variation | Ref.Allele | Min. allele |
|---|---|---|---|
| rs28571971 | ACAGTAGGAGTTAGGAAGTACTCTG{C/G}TGCAGTTCAGGCCTTTCTCTTACCT (105) | G | C |

SpCas9_WT (PAM Motif: NRG)
Ref. Allele:
          PAM
ACAGTAGGAGTTAGGAAGTACTCTGGTGCAGTTCAGGCCTTTCTCTTACCT (323)
TGTCATCCTCAATCCTTCATGAGACCACGTCAAGTCCGGAAAGAGAATGGA (324)
    GGAGTTAGGAAGTACTC (198)
Minor Allele:
                GTCAAGTCCGGAAAGAGAATGG (199)
ACAGTAGGAGTTAGGAAGTACTCTGCTGCAGTTCAGGCCTTTCTCTTACCT (325)
TGTCATCCTCAATCCTTCATGAGACGACGTCAAGTCCGGAAAGAGAATGGA (326)
               PAM

======================================================================

| # Variant ID | Sequence Variation | Ref.Allele | Min. allele |
|---|---|---|---|
| rs28583447 | CAGTAGGAGTTAGGAAGTACTCTGG{C/T}GCAGTTCAGGCCTTTCTCTTACCTC (106) | T | C |

SpCas9_VQR/EQR (PAM Motif: NGAN-NGNG/NGAG)
Ref. Allele:
CAGTAGGAGTTAGGAAGTACTCTGGTGCAGTTCAGGCCTTTCTCTTACCTC (327)
GTCATCCTCAATCCTTCATGAGACCACGTCAAGTCCGGAAAGAGAATGGAG (328)

Minor Allele:          TCAAGTCCGGAAAGAGAATG (200)
CAGTAGGAGTTAGGAAGTACTCTGGCGCAGTTCAGGCCTTTCTCTTACCTC (329)
GTCATCCTCAATCCTTCATGAGACCGCGTCAAGTCCGGAAAGAGAATGGAG (330)
               PAM

SpCas9_VRER (PAM Motif: NGCG)
Ref. Allele:
CAGTAGGAGTTAGGAAGTACTCTGGTGCAGTTCAGGCCTTTCTCTTACCTC (327)
GTCATCCTCAATCCTTCATGAGACCACGTCAAGTCCGGAAAGAGAATGGAG (328)

Minor Allele:      PAM
CAGTAGGAGTTAGGAAGTACTCTGGCGCAGTTCAGGCCTTTCTCTTACCTC (329)
GTCATCCTCAATCCTTCATGAGACCGCGTCAAGTCCGGAAAGAGAATGGAG (330)
    GGAGTTAGGAAGTACTCTG (201)

Minor Allele:          TCAAGTCCGGAAAGAGAATG (200)
CAGTAGGAGTTAGGAAGTACTCTGGCGCAGTTCAGGCCTTTCTCTTACCTC (329)
GTCATCCTCAATCCTTCATGAGACCGCGTCAAGTCCGGAAAGAGAATGGAG (330)
               PAM

======================================================================

| # Variant ID | Sequence Variation | Ref.Allele | Min. allele |
|---|---|---|---|
| rs28468636 | TCTCTTACCTCTCAGTATTCTATTT[C/G]CGATCTGGATGTGTCCCAGATGGCA (107) | C | G |

SpCas9_WT (PAM Motif: NRG)
Ref. Allele:          TAGACCTACACAGGGTCTA (202)
TCTCTTACCTCTCAGTATTCTATTTCCGATCTGGATGTGTCCCAGATGGCA (331)
AGAGAATGGAGAGTCATAAGATAAAGGCTAGACCTACACAGGGTCTACCGT (332)
               PAM Minor Allele
TCTCTTACCTCTCAGTATTCTATTTGCGATCTGGATGTGTCCCAGATGGCA (333)
AGAGAATGGAGAGTCATAAGATAAACGCTAGACCTACACAGGGTCTACCGT (334)

SpCas9_VQR/EQR (PAM Motif: NGAN-NGNG/NGAG)
Ref. Allele:

Figure 5J

```
TCTCTTACCTCTCAGTATTCTATTTCCGATCTGGATGTGTCCCAGATGGCA (331)
AGAGAATGGAGAGTCATAAGATAAAGGCTAGACCTACACAGGGTCTACCGT (332)

Minor Allele             PAM
TCTCTTACCTCTCAGTATTCTATTTCGGATCTGGATGTGTCCCAGATGGCA (333)
AGAGAATGGAGAGTCATAAGATAAACGCTAGACCTACACAGGGTCTACCGT (334)
       ACCTCTCAGTATTCTATTT (203)

SpCas9_VRER (PAM Motif: NGCG)
Ref. Allele:
TCTCTTACCTCTCAGTATTCTATTTCCGATCTGGATGTGTCCCAGATGGCA (331)
AGAGAATGGAGAGTCATAAGATAAAGGCTAGACCTACACAGGGTCTACCGT (332)

Minor Allele             PAM
TCTCTTACCTCTCAGTATTCTATTTCCGATCTGGATGTGTCCCAGATGGCA (333)
AGAGAATGGAGAGTCATAAGATAAACGCTAGACCTACACAGGGTCTACCGT (334)
       ACCTCTCAGTATTCTATTT (203)

SaCas9(NNGRRT/NNGRR):
Ref. Allele:             TAGACCTACACAGGGTCTA (202)
TCTCTTACCTCTCAGTATTCTATTTCCGATCTGGATGTGTCCCAGATGGCA (331)
AGAGAATGGAGAGTCATAAGATAAAGGCTAGACCTACACAGGGTCTACCGT (332)
                         PAM Minor Allele
TCTCTTACCTCTCAGTATTCTATTTCCGATCTGGATGTGTCCCAGATGGCA (333)
AGAGAATGGAGAGTCATAAGATAAACGCTAGACCTACACAGGGTCTACCGT (334)

LbCpf1(TTTN/TTCN/CTTN/TCTN/ATTN/TCCN/…):

Ref. Allele:             PAM
TCTCTTACCTCTCAGTATTCTATTTCCGATCTGGATGTGTCCCAGATGGCA (331)
AGAGAATGGAGAGTCATAAGATAAAGGCTAGACCTACACAGGGTCTACCGT (332)
                   ATCTGGATGTGTCCCAGATG (204)
Minor Allele
TCTCTTACCTCTCAGTATTCTATTTCGATCTGGATGTGTCCCAGATGGCA (333)
AGAGAATGGAGAGTCATAAGATAAACGCTAGACCTACACAGGGTCTACCGT (334)
```

```
# Variant ID    Sequence Variation                                              Ref.Allele   Min. allele
rs28564368  TATTCTATTTCCGATCTGGATGTGT[A/C]CCAGATGGCATTTGGTAAGAATATC    C        A
                                                                (108)
```

```
SpCas9_WT (PAM Motif: NRG)
Ref. Allele:             TCTACCGTAAACCATTCTTA (205)
TATTCTATTTCCGATCTGGATGTGTCCCAGATGGCATTTGGTAAGAATATC (335)
ATAAGATAAAGGCTAGACCTACACAGGGTCTACCGTAAACCATTCTTATAG (336)
                         PAM
Minor Allele
TATTCTATTTCCGATCTGGATGTGTACCAGATGGCATTTGGTAAGAATATC (337)
ATAAGATAAAGGCTAGACCTACACATGGTCTACCGTAAACCATTCTTATAG (338)

SpCas9_VQR/EQR (PAM Motif: NGAN-NGNG/NGAG)
Ref. Allele:             GTCTACCGTAAACCATTCTT (206)
TATTCTATTTCCGATCTGGATGTGTCCCAGATGGCATTTGGTAAGAATATC (335)
ATAAGATAAAGGCTAGACCTACACAGGGTCTACCGTAAACCATTCTTATAG (336)
                         PAM
Minor Allele
TATTCTATTTCCGATCTGGATGTGTACCAGATGGCATTTGGTAAGAATATC (337)
ATAAGATAAAGGCTAGACCTACACATGGTCTACCGTAAACCATTCTTATAG (338)

Ref. Allele:             TCTACCGTAAACCATTCTTA (205)
TATTCTATTTCCGATCTGGATGTGTCCCAGATGGCATTTGGTAAGAATATC (335)
ATAAGATAAAGGCTAGACCTACACAGGGTCTACCGTAAACCATTCTTATAG (336)
                         PAM
Minor Allele
TATTCTATTTCCGATCTGGATGTGTACCAGATGGCATTTGGTAAGAATATC (337)
ATAAGATAAAGGCTAGACCTACACATGGTCTACCGTAAACCATTCTTATAG (338)

LbCpf1(TTTN/TTCN/CTTN/TCTN/ATTN/TCCN/…):
Ref. Allele:             PAM
TATTCTATTTCCGATCTGGATGTGTCCCAGATGGCATTTGGTAAGAATATC (335)
ATAAGATAAAGGCTAGACCTACACAGGGTCTACCGTAAACCATTCTTATAG (336)
                         AGATGGCATTTGGTAAGAATAT (207)
Minor Allele
TATTCTATTTCCGATCTGGATGTGTACCAGATGGCATTTGGTAAGAATATC (337)
ATAAGATAAAGGCTAGACCTACACATGGTCTACCGTAAACCATTCTTATAG (338)
```

Figure 5K

```
# Variant ID      Sequence Variation                                                    Ref.Allele    Min. allele
rs77173925    GAATAAATTATTCTAAAGGATGGAA[A/G]AACTTTTTGGATATTTGGAGAAATT         A         G
                                                                   (110)
```

SpCas9_WT (PAM Motif: NRG)
Ref. Allele:
GAATAAATTATTCTAAAGGATGGAAAAACTTTTTGGATATTTGGAGAAATT (339)
CTTATTTAATAAGATTTCCTACCTTTTTGAAAAACCTATAAACCTCTTTAA (340)

Minor Allele            PAM
GAATAAATTATTCTAAAGGATGGAA<u>GAA</u>CTTTTTGGATATTTGGAGAAATT (341)
CTTATTTAATAAGATTTCCTACCTTCTTGAAAAACCTATAAACCTCTTTAA (342)
    AAATTATTCTAAAGGATGG (208)

SpCas9_VQR/EQR (PAM Motif: NGAN-NGNG/NGAG)
Ref. Allele:
GAATAAATTATTCTAAAGGATGGAAAAACTTTTTGGATATTTGGAGAAATT (339)
CTTATTTAATAAGATTTCCTACCTTTTTGAAAAACCTATAAACCTCTTTAA (340)

Minor Allele            PAM
GAATAAATTATTCTAAAGGATGGAA<u>GAA</u>CTTTTTGGATATTTGGAGAAATT (341)
CTTATTTAATAAGATTTCCTACCTTCTTGAAAAACCTATAAACCTCTTTAA (342)
      ATTATTCTAAAGGATGGAA (209)

SaCas9(NNGRRT/NNGRR):
Ref. Allele:
GAATAAATTATTCTAAAGGATGGAAAAACTTTTTGGATATTTGGAGAAATT (339)
CTTATTTAATAAGATTTCCTACCTTTTTGAAAAACCTATAAACCTCTTTAA (340)

Minor Allele            PAM
GAATAAATTATTCTAAAGGATGGA<u>AGAA</u>CTTTTTGGATATTTGGAGAAATT (341)
CTTATTTAATAAGATTTCCTACCTTCTTGAAAAACCTATAAACCTCTTTAA (342)
        AATTATTCTAAAGGATGG (210)

AsCpf1(TTTN)
Ref. Allele:
       ATTTAATAAGATTTCCTACC (211)
GAATAAATTATTCTAAAGGATGGAAAAACTTTTTGGATATTTGGAGAAATT (339)
CTTATTTAATAAGATTTCCTACC<u>TTTT</u>GAAAAACCTATAAACCTCTTTAA (340)
                        PAM Minor Allele
GAATAAATTATTCTAAAGGATGGAAGAACTTTTTGGATATTTGGAGAAATT (341)
CTTATTTAATAAGATTTCCTACCTTCTTGAAAAACCTATAAACCTCTTTAA (342)

```
# Variant ID      Sequence Variation                                                    Ref.Allele    Min. allele
rs3905238     TTGTATCATGTCAATGTATTACTTA[C/T]GCAAAAATAATACATTAAAAAAAAT        A         G (Rev Strand)
                                                                   (111)
```

SpCas9_VQR/EQR (PAM Motif: NGAN-NGNG/NGAG)
Ref. Allele:
TTGTATCATGTCAATGTATTACTTATGCAAAAATAATACATTAAAAAAAAT (343)
AACATAGTACAGTTACATAATGAATACGTTTTTATTATGTAATTTTTTTTA (344)

Minor Allele                  TTTTATTATGTAATTTTT (212)
TTGTATCATGTCAATGTATTACTTACGCAAAAATAATACATTAAAAAAAAT (345)
AACATAGTACAGTTACATAATGAATGC<u>GTT</u>TTTATTATGTAATTTTTTTTA (346)
                           PAM

SpCas9_VRER (PAM Motif: NGCG)
Ref. Allele:
TTGTATCATGTCAATGTATTACTTATGCAAAAATAATACATTAAAAAAAAT (343)
AACATAGTACAGTTACATAATGAATACGTTTTTATTATGTAATTTTTTTTA (344)

Minor Allele                  TTTTATTATGTAATTTTT (212)
TTGTATCATGTCAATGTATTACTTACGCAAAAATAATACATTAAAAAAAAT (345)
AACATAGTACAGTTACATAATGAATGC<u>GTT</u>TTTATTATGTAATTTTTTTTA (346)
                           PAM

Figure 5L

```
§ Variant ID    Sequence Variation                                                        Ref.Allele    Min. allele
rs33950430  AGGTATTCACTAATTTTGAGTAACA[-/AACA]CTGCTCACAAAGTTTGGATTTTGGC    AACA    delAACA
                                                    (112)

LbCpf1(TTTN/TTCN/CTTN/TCTN/ATTN/TCCN/…):
Ref. Allele:
    ATAAGTGATTAAAACTCATT (213)
AGGTATTCACTAATTTTGAGTAACAAACACTGCTCACAAAGTTTGGATTTTGGC (347)
TCCATAAGTGATTAAAACTCATTGTTTGTGACGAGTGTTTCAAACCTAAAACCG (348)
                        PAM Minor Allele
AGGTATTCACTAATTTTGAGTAACACTGCTCACAAAGTTTGGATTTTGGC (349)
TCCATAAGTGATTAAAACTCATTGTGACGAGTGTTTCAAACCTAAAACCG (350)

AsCpf1(TTTN)
Ref. Allele:
    ATAAGTGATTAAAACTCATT (213)
AGGTATTCACTAATTTTGAGTAACAAACACTGCTCACAAAGTTTGGATTTTGGC (347)
TCCATAAGTGATTAAAACTCATTGTTTGTGACGAGTGTTTCAAACCTAAAACCG (348)
                        PAM Minor Allele
AGGTATTCACTAATTTTGAGTAACACTGCTCACAAAGTTTGGATTTTGGC (349)
TCCATAAGTGATTAAAACTCATTGTGACGAGTGTTTCAAACCTAAAACCG (350)
```

```
§ Variant ID    Sequence Variation                                                        Ref.Allele    Min. allele
rs28377140  AGGCAATTAATACTTGCTTCTGGCA[C/G]TTTCTTATTCTCCTTCAGATTCCTA    G    C
                                                    (113)

SpCas9_WT (PAM Motif: NRG)
Ref. Allele:              PAM
AGGCAATTAATACTTGCTTCTGGCACTTTCTTATTCTCCTTCAGATTCCTA (351)
TCCGTTAATTATGAACGAAGACCGTCAAAGAATAAGAGGAAGTCTAAGGAT (352)
    ATTAATACTTGCTTCTGG (214)

Minor Allele    (215) AGAATAAGAGGAAGTCTAAGG
AGGCAATTAATACTTGCTTCTGGCATTTCTTATTCTCCTTCAGATTCCTA (353)
TCCGTTAATTATGAACGAAGACCGTGAAAGAATAAGAGGAAGTCTAAGGAT (354)
                    PAM
```

```
§ Variant ID    Sequence Variation                                                        Ref.Allele    Min. allele
rs3856973   ttaaaaataaaaataaGTTAACACT[C/T]GATTAACCCTGACATTTCCCTATCC    G    A (Rev strand)
                                                    (114)

SpCas9_VQR/EQR (PAM Motif: NGAN-NGNG/NGAG)

Ref. Allele:              CTAATTGGGACTGTAAAGGG (216)
TTAAAAATAAAAATAAGTTAACACTCGATTAACCCTGACATTTCCCTATCC (355)
AATTTTTATTTTTATTCAATTGTGAGCTAATTGGGACTGTAAAGGGATAGG (356)
                        PAM
Minor Allele
TTAAAAATAAAAATAAGTTAACACTTGATTAACCCTGACATTTCCCTATCC (357)
AATTTTTATTTTTATTCAATTGTGAACTAATTGGGACTGTAAAGGGATAGG (358)

SaCas9(NNGRRT/NNGRR):
Ref. Allele:              AATTGGGACTGTAAAGGG (217)
TTAAAAATAAAAATAAGTTAACACTCGATTAACCCTGACATTTCCCTATCC (355)
AATTTTTATTTTTATTCAATTGTGAGCTAATTGGGACTGTAAAGGGATAGG (356)
                        PAM
Minor Allele
TTAAAAATAAAAATAAGTTAACACTTGATTAACCCTGACATTTCCCTATCC (357)
AATTTTTATTTTTATTCAATTGTGAACTAATTGGGACTGTAAAGGGATAGG (358)

LbCpf1(TTTN/TTCN/CTTN/TCTN/ATTN/TCCN/…):
Ref. Allele:
TTAAAAATAAAAATAAGTTAACACTCGATTAACCCTGACATTTCCCTATCC (355)
AATTTTTATTTTTATTCAATTGTGAGCTAATTGGGACTGTAAAGGGATAGG (356)

Minor Allele    PAM
TTAAAAATAAAAATAAGTTAACACTTGATTAACCCTGACATTTCCCTATCC (357)
AATTTTTATTTTTATTCAATTGTGAACTAATTGGGACTGTAAAGGGATAGG (358)
            (218) ATTAACCCTGACATTTCCCTA
```

```
§ Variant ID    Sequence Variation                                                        Ref.Allele    Min. allele
rs4498089   AGTGTTAACTTATTTTTATTTTTAA[A/G]AAAATTGTTAAGGGCTTTCCAGCAA    A    G
                                                    (115)

SpCas9_WT (PAM Motif: NRG)
Ref. Allele:
```

Figure 5M

AGTGTTAACTTATTTTTATTTTTAAAAAAATTGTTAAGGGCTTTCCAGCAA (359)
TCACAATTGAATAAAAATAAAAATTTTTTTAACAATTCCCGAAAGGTCGTT (360)

Minor Allele      PAM
AGTGTTAACTTATTTTTATTTTTAAGAAAATTGTTAAGGGCTTTCCAGCAA (361)
TCACAATTGAATAAAAATAAAAATTCTTTTAACAATTCCCGAAAGGTCGTT (362)
    GTTAACTTATTTTTATTTTT (219)

SpCas9_VQR/EQR (PAM Motif: NGAN-NGNG/NGAG)
Ref. Allele:
AGTGTTAACTTATTTTTATTTTTAAAAAAATTGTTAAGGGCTTTCCAGCAA (359)
TCACAATTGAATAAAAATAAAAATTTTTTTAACAATTCCCGAAAGGTCGTT (360)

Minor Allele      PAM
AGTGTTAACTTATTTTTATTTTTAAGAAAATTGTTAAGGGCTTTCCAGCAA (361)
TCACAATTGAATAAAAATAAAAATTCTTTTAACAATTCCCGAAAGGTCGTT (362)
    GTTAACTTATTTTTATTTTTA (220)

SaCas9 (NNGRRT/NNGRR):
Ref. Allele:
AGTGTTAACTTATTTTTATTTTTAAAAAAATTGTTAAGGGCTTTCCAGCAA (359)
TCACAATTGAATAAAAATAAAAATTTTTTTAACAATTCCCGAAAGGTCGTT (360)

Minor Allele      PAM
AGTGTTAACTTATTTTTATTTTTAAGAAAATTGTTAAGGGCTTTCCAGCAA (361)
TCACAATTGAATAAAAATAAAAATTCTTTTAACAATTCCCGAAAGGTCGTT (362)
    GTTAACTTATTTTTATTTTT (219)
AsCpf1 (TTTN)
Ref. Allele:
 CACAATTGAATAAAAATAAAA (221)
AGTGTTAACTTATTTTTATTTTTAAAAAAATTGTTAAGGGCTTTCCAGCAA (359)
TCACAATTGAATAAAAATAAAAATTTTTTTAACAATTCCCGAAAGGTCGTT (360)
           PAM
Minor Allele
AGTGTTAACTTATTTTTATTTTTAAGAAAATTGTTAAGGGCTTTCCAGCAA (361)
TCACAATTGAATAAAAATAAAAATTCTTTTAACAATTCCCGAAAGGTCGTT (362)

===============================================================================

Variant ID    Sequence Variation                                                      Ref.Allele   Min. allele
rs57666989  CTGCAAGCTCCGCTTCCCGAGTTCA[C/T]GCCATTCTCCTGCCTCAGTCTCCCA      C       T
                                                         (117)
SpCas9_VQR/EQR (PAM Motif: NGAN-NGNG/NGAG)
Ref. Allele:              TAAGAGGACGGAGTCAGAGGC (222)
CTGCAAGCTCCGCTTCCCGAGTTCACGCCATTCTCCTGCCTCAGTCTCCCA (363)
GACGTTCGAGGCGAAGGGCTCAAGTGCGGTAAGAGGACGGAGTCAGAGGGT (364)
              PAM
Minor Allele
CTGCAAGCTCCGCTTCCCGAGTTCATGCCATTCTCCTGCCTCAGTCTCCCA (365)
GACGTTCGAGGCGAAGGGCTCAAGTACGGTAAGAGGACGGAGTCAGAGGGT (366)

SpCas9_VRER (PAM Motif: NGCG)
Ref. Allele:              TAAGAGGACGGACTCAGAGC (223)
CTGCAAGCTCCGCTTCCCGAGTTCACGCCATTCTCCTGCCTCAGTCTCCCA (363)
GACGTTCGAGGCGAAGGGCTCAAGTGCGGTAAGAGGACGGAGTCAGAGGGT (364)
              PAM
Minor Allele
CTGCAAGCTCCGCTTCCCGAGTTCATGCCATTCTCCTGCCTCAGTCTCCCA (365)
GACGTTCGAGGCGAAGGGCTCAAGTACGGTAAGAGGACGGAGTCAGAGGGT (366)

===============================================================================

Variant ID    Sequence Variation                                                      Ref.Allele   Min. allele
rs10006129  tcttgatctcctgacctcgtcatcc[C/G]ccgaccttgtgatccgcccacctcg    G       C
                                                         (118)

SpCas9_WT (PAM Motif: NRG)
Ref. Allele:
TCTTGATCTCCTGACCTCGTCATCCGCCGACCTTGTGATCCGCCCACCTCG (367)
AGAACTAGAGGACTGGAGCAGTAGGCGGCTGGAACACTAGGCGGGTGGAGC (368)

Minor Allele              CTGGAACACTAGGCGGGTGG (224)
TCTTGATCTCCTGACCTCGTCATCCCCCGACCTTGTGATCCGCCCACCTCG (369)
AGAACTAGAGGACTGGAGCAGTAGGGGGCTGGAACACTAGGCGGGTGGAGC (370)

Figure 5N

```
SpCas9_VQR/EQR (PAM Motif: NGAN-NGNG/NGAG)
Ref. Allele:
TCTTGATCTCCTGACCTCGTCATCCCCGACCTTGTGATCCGCCCACCTCG (367)
AGAACTAGAGGACTGGAGCAGTAGGCGGCTGGAACACTAGGCGGGTGGAGC (368)

Minor Allele        (224) CTGGAACACTAGGCGGGTGG
TCTTGATCTCCTGACCTCGTCATCCCCGACCTTGTGATCCGCCCACCTCG (369)
AGAACTAGAGGACTGGAGCAGTAGGCGGGCTGGAACACTAGGCGGGTGGAGC (370)
                              PAM SpCas9_VRER (PAM Motif: NGCG)
Ref. Allele:        CTGGAACACTAGGCGGGTGG (224)
TCTTGATCTCCTGACCTCGTCATCCCCGACCTTGTGATCCGCCCACCTCG (367)
AGAACTAGAGGACTGGAGCAGTAGGCGGCTGGAACACTAGGCGGGTGGAGC (368)
                         PAM
Minor Allele
TCTTGATCTCCTGACCTCGTCATCCCCCGACCTTGTGATCCGCCCACCTCG (369)
AGAACTAGAGGACTGGAGCAGTAGGGGGCTGGAACACTAGGCGGGTGGAGC (370)

SaCas9 (NNGRRT/NNGRR):
Ref. Allele:
TCTTGATCTCCTGACCTCGTCATCCCCGACCTTGTGATCCGCCCACCTCG (367)
AGAACTAGAGGACTGGAGCAGTAGGCGGCTGGAACACTAGGCGGGTGGAGC (368)

Minor Allele        (224) CTGGAACACTAGGCGGGTGG
TCTTGATCTCCTGACCTCGTCATCCCCGACCTTGTGATCCGCCCACCTCG (369)
AGAACTAGAGGACTGGAGCAGTAGGGGGCTGGAACACTAGGCGGGTGGAGC (370)
                              PAM
```

| # Variant ID | Sequence Variation | Ref.Allele | Min. allele |
|---|---|---|---|
| rs28696693 | CCTAATTTTTGTATTTTTACTAGAC{A/G}TGGGGTTTTGCCATGATGAGCAGGC (119) | A | G |

```
SpCas9 (PAM Motif: NRG)
Ref. Allele:
GGTAATTTTTGTATTTTTAGTAGAGATGGGGTTTTGCCATGATGAGCAGGC (371)
CCATTAAAAACATAAAAATCATCTCTACCCCAAAACGGTACTACTCGTCCG (372)

Minor Allele       PAM
GGTAATTTTTGTATTTTTAGTAGAGGTGGGGTTTTGCCATGATGAGCAGGC (373)
CCATTAAAAACATAAAAATCATCTCCACCCCAAAACGGTACTACTCGTCCG (374)
    ATTTTTGTATTTTTAGTAG (225)

SpCas9_VQR/EQR (PAM Motif: NGAN-NGNG/NGAG)
Ref. Allele:         PAM
GGTAATTTTTGTATTTTTAGTAGAGATGGGGTTTTGCCATGATGAGCAGGC (371)
CCATTAAAAACATAAAAATCATCTCTACCCCAAAACGGTACTACTCGTCCG (372)
      TTTTTGTATTTTTAGTAG (226)
Minor Allele
GGTAATTTTTGTATTTTTAGTAGAGGTGGGGTTTTGCCATGATGAGCAGGC (373)
CCATTAAAAACATAAAAATCATCTCCACCCCAAAACGGTACTACTCGTCCG (374)
```

| # Variant ID | Sequence Variation | Ref.Allele | Min. allele |
|---|---|---|---|
| rs28393280 | GGATTTTGAATGCGGAACCAACTGC{A/G}CTTGTTGAACTCTGCTAAGTATAAC (120) | A | G |

```
SpCas9_VQR/EQR (PAM Motif: NGAN-NGNG/NGAG)
Ref. Allele:
GGATTTTGAATGCGGAACCAACTGCACTTGTTGAACTCTGCTAAGTATAAC (375)
CCTAAAACTTACGCCTTGGTTGACGTGAACAACTTGAGACGATTCATATTG (376)

Minor Allele:        PAM
GGATTTTGAATGCGGAACCAACTGCGCTTGTTGAACTCTGCTAAGTATAAC (377)
CCTAAAACTTACGCCTTGGTTGACGCGAACAACTTGAGACGATTCATATTG (378)
   ATTTTGAATGCGGAACCAAC (227)

SpCas9_VRER (PAM Motif: NGCG)
Ref. Allele:
GGATTTTGAATGCGGAACCAACTGCACTTGTTGAACTCTGCTAAGTATAAC (375)
CCTAAAACTTACGCCTTGGTTGACGTGAACAACTTGAGACGATTCATATTG (376)

Minor Allele:        PAM
GGATTTTGAATGCGGAACCAACTGCGCTTGTTGAACTCTGCTAAGTATAAC (377)
CCTAAAACTTACGCCTTGGTTGACGCGAACAACTTGAGACGATTCATATTG (378)
   ATTTTGAATGCGGAACCAAC (227)

Minor Allele:                    ACAACTTGAGACGATTCAT (228)
GGATTTTGAATGCGGAACCAACTGCGCTTGTTGAACTCTGCTAAGTATAAC (377)
CCTAAAACTTACGCCTTGGTTGACGCGAACAACTTGAGACGATTCATATTG (378)
                         PAM
```

Figure 50

Sequence sgHD1
Complementary guide:   5'GCTCCAGGCGTCGGCGG 3' (sgHD1) (n=17 nt)(379)
sgRNA expression cassette: hU6 promoter Major Allele (C): Have a PAM motif on the Positive strand (NGG)
GTCGCCCGCTCCAGGCGTCGGCGGGGATCCTTTCCGCATGGGCCTGCGCC (389)
CAGCGGGGCGAGGTCCGCAGCCGCCCCTAGGAAAGGCGTACCCGGACGCGG (390)
          GCTCCAGGCGTCGGCGG (379)

Minor Allele (G): Disruption of the PAM motive.
GTCGCCCGCTCCAGGCGTCGGCGGGGATCCTTTCCGCATGGGCCTGCGCC (391)
CAGCGGGGCGAGGTCCGCAGCCGCCCCTAGGAAAGGCGTACCCGGACGCGG (392)

Sequence sgHD2
Complementary guide:   5'GGCGCGGGGCTCAACGGAG 3' (sgHD2) (n=19 nt)(380)
sgRNA expression cassette: hU6 promoter Major Allele (C): Has a PAM motif on the Negative strand (NGG)
                           GAGGCAACTCGGGGCGCGG (380)
TTACAGTCTCACCACGCCCCGTCCCTCTCCGTTGAGCCCCGCGCCTTC (393)
AATGTCAGAGTGGTGCGGGGCAGGGAGAGGCAACTCGGGGCGCGGAAG (394)

Minor Allele (G): Disruption of the PAM motive
TTACAGTCTCACCACGCCCCGTCCCTCTCCGTTGAGCCCCGCGCCTTC (395)
AATGTCAGAGTGGTGCGGGGCAGGGAGAGGCAACTCGGGGCGCGGAAG (396)

Sequence sgHD3
Complementary guide:   5'GTCTGGGACGCAAGGCGCCG3' (sgHD3) (n=20 nt)(381)
sgRNA expression cassette: hU6 promoter Major Allele (G): Has a PAM motif on the Positive strand (NGG) Use U6 promoter
GCGTCTGGGACGCAAGGCGCCGTGGGGCTGCCGGGACGGGTCCAAGAT (397)
CGCAGACCCTGCGTTCCGCGGCACCCCCGACGGCCCTGCCCAGGTTCTA (398)
   GTCTGGGACGCAAGGCGCCG (381)

Minor Allele (A): Loss PAM motif on the Positive strand (NGG) Use U6 promoter
GCGTCTGGGACGCAAGGCGCCGTGAGGGCTGCCGGGACGGGTCCAAGAT (399)
CGCAGACCCTGCGTTCCGCGGCACTCCCGACGGCCCTGCCCAGGTTCTA (400)

Sequence sgHD4
Complementary guide: 5' GATGCACGCGGGGTGGGGC 3' (n=19 nt)(382)
sgRNA expression cassette: hU6 promoter Major Allele: Has a PAM motif on the negative strand (NGG))
                           3' CGGGGTGGGGCGCACGTAG 5'(382)
5' TCTGCGTCAGGGTTTCCTTCTTTTCAGCCCCACCCCGCGTGCATCCCA 3'(401)
3' AGACGCAGTCCCAAAGGAAGAAAAGTCGGGGTGGGGCGCACGTAGGGT 5'(402)

Minor Allele: SNP produces a Loss of the PAM motif.
5' TCTGCGTCAGGGTTTCCTTCTTTTCAGCCCCACCCCGCGTGCATCCCA 3'(403)
3' AGACGCAGTCCCAAAGGAAGAAAAGTCGGGGTGGGGCGCACGTAGGGT     (404)

Figure 6A

Sequence sgHD5g and sgHD5c
Complementary guide: 5'ATTCAGGTTGATGTCCT 3' (sgHD5g) (n=17 nt)(383)
Complementary guide: 5'ATCCCATTCTGAGGTTCTGG 3 (sgHD5c) (n=20 nt)(384)
sgRNA expression cassette: hH1 promoter Major Allele: Has a PAM motif on the Positive strand (NAG)
5'CCCTCATTCAGGTTGATGTCCTAAGCCCCAGAACCTCAGAATGGGATTG 3' (405)
3' GGGAGTAAGTCCAACTACAGGATTCGGGGTCTTGGAGTCTTACCCTAAC 5'(406)
      ATTCAGGTTGATGTCCT (383)

Minor Allele: generates a PAM motif on the Negative strand (NAG)
                    GGTCTTGGAGTCTTACCCTA (384)
5'CCCTCATTCAGGTTGATGTCCTAACCCCAGAACCTCAGAATGGGATTG 3'(407)
3'GGGAGTAAGTCCAACTACAGGATTGGGGTCTTGGAGTCTTACCCTAAC 5'(408)

Sequence sgHD6c and sgHD6g
Complementary guide: 5'GCAGGCAGAGAGGAGCC 3' (sgHD6c) (n=17 nt)(385)
Complementary guide: 5'GCCTGGCTAAAGTAGGCTT 3 (sgHD6g) (n=19 nt)(386)
sgRNA expression cassette: hU6 promoter Major Allele (C): Have a PAM motif on the negative strand (NAG)
                    CCGAGGAGAGACGGACG (385)
5' GTGGCCTGGCTAAAGTAGGCTTTACTGGGCTCCTCTCTGCCTGCATCAC 3'(409)
3' CACCGGACCGATTTCATCCGAAATGACCCGAGGAGAGACGGACGTAGTG 5'(410)

Minor Allele (G): Generates a PAM motif on the Positive strand (NAG)
5' GTGGCCTGGCTAAAGTAGGCTTTACTGGGCTCCTCTCTGCCTGCATCAC 3'(411)
3' CACCGGACCGATTTCATCCGAAATCACCCGAGGAGAGACGGACGTAGTG 5'(412)
      GCCTGGCTAAAGTAGGCTT (386)

Sequence sgHDi3
Complementary guide: 5'GCTTTTAGGACGCCTCGG 3' (sgHDi3) (n=18 nt)
sgRNA expression cassette: hU6 promoter   (387)

5' AATGCTTTTAGGACGCCTCGCGGGAGTGGCGGGGCAGGGGGGGGCG 3 (413)
3' TTACGAAAATCCTGCGGAGCCGCCCTCACCGCCCCGTCCCCCCCCGC 5'(414)
      GCTTTTAGGACGCCTCGG (387)

Sequence sgHDi4
Complementary guide: 5' GCGGGACACTTCGAGAGG 3' (sgHDi4) (n=18 nt)
sgRNA expression cassette: hU6 promoter   (388)

5' GGCGCGGGACACTTCGAGAGGAGGCGGGGTTTGGAGCTGGAGAGATGT 3'(415)
3' CCGCGCCCTGTGAAGCTCTCCTCCGCCCCAAACCTCGACCTCTCTACA 5'(416)
      GCGGGACACTTCGAGAGG (388)

Figure 6B

| | ND31551 | | ND33392 | |
|---|---|---|---|---|
| HD Allele | Normal | Mutant | Normal | Mutant |
| CAG repeat | 18 | 39 | 17 | 57 |
| rs2857935 | C | G | G | C |
| PAM motif | Present | Absent | Absent | Present |

|         | sgHD1 | sgHD2 | sgHD3 | sgHDi3 |
|---------|-------|-------|-------|--------|
| Comp. (nt) | 17 | 19 | 20 | 18 |
| 0 mm    | 1     | 1     | 1     | 1      |
| 1 mm    | 2     | 0     | 0     | 0      |
| 2 mm    | 32    | 1     | 0     | 2      |
| 3 mm    | 382   | 38    | 6     | 18     |
| Total   | 416   | 40    | 7     | 21     |

Figure 8A

|            | sgHD1 | sgHD2 | sgHD3 | sgHDi3 |
|------------|-------|-------|-------|--------|
| Intergenic | 71    | 11    | 2     | 6      |
| Promoter   | 58    | 4     | 0     | 1      |
| 5'UTR      | 64    | 3     | 0     | 0      |
| Intron     | 143   | 20    | 5     | 13     |
| Exon       | 75    | 1     | 0     | 1      |
| 3'UTR      | 5     | 1     | 0     | 0      |
| Total      | 416   | 40    | 7     | 21     |

Figure 8B

```
5' GTTTAATTGAGTTGTCATATGTTAATAACGGTAT 3'
5' ATACCGTTATTAACATATGACAACTCAATTAAAC 3' (Rev Complement)

TGTCGCCCCGCTCCAGGCGTCGGTC------------------------------------GGCGGGAGTGGCGGGGCAGGGGGGG
TGTCGCCCCGCTCCAGGCGTCGG---ATACCGTTATTAACATATGACAACTCAATTAAAC--CGGCGGGAGTGGCGGGGCAGGGGGGG
TGTCGCCCCGCTCCAGGCGTCG-------GTTATTAACATATGACAACTCAATTAAAC--------CGGCGGGAGTGGCGGGGCAGGGGGGG
TGTCGCCCCGCTCCAGGCGTCGG-GTTTAATTGAGTTGTCATATGTTAATAACGGTATCTCGGCGGGAGTGGCGGGGCAGGGGGGG
TCGCCCCGCTCCAGGCGTCGG---------TATTAACATATGACAACTCAATTAAAC------CGGCGGGAGTGGCGGGGCAGGGGGGG
TGTCGCCCCGCTCCAGGCGTCGG-----------ATTAACATATGACAACTCAATTAAAC------------CGGGAGTGGCGGGGCAGGGGGGG
```

| HTT Promoter | ODN | HTT Intron1 |

Figure 8C

| Gene    | Chromosome | Strand | Mismatches | Mismatch position | Location   | Guide  | Indels     |
|---------|------------|--------|------------|-------------------|------------|--------|------------|
| SLC45A4 | chr8       | -      | 2          | GCTCCAtGCGgCGGCGG | Exon       | sgHD1  | Undetected |
| CHRNA2  | chr8       | +      | 3          | GCTtCAGGCGTaGGgGG | Exon       | sgHD1  | Undetected |
| TRIB1   | chr8       | +      | 3          | GCTCCgGGgGcCGGCGG | Exon       | sgHD1  | Undetected |
| SMARCD1 | chr12      | +      | 3          | GCTCCAaGCGgCGGCGc | Exon       | sgHD1  | Undetected |
| COX11   | chr17      | +      | 3          | GCTcTTAGGcCGCCgCGG | Exon/5'UTR | sgHDi3 | Undetected |
| STT3B   | chr3       | +      | 2          | GCaCCAGGCGgCGGCGG | 5'UTR      | sgHD1  | Undetected |
| NUP210  | chr3       | -      | 3          | GCTTTaGGAtGCCTtGG | Intron     | sgHDi3 | Undetected |
| DNAJC16 | chr1       | +      | 3          | aCTTTTAGGAgGCCTaGG | Intron    | sgHDi3 | Undetected |
| LEPR    | chr1       | +      | 3          | GCaTTTAGGAgGCCTaGG | Intron    | sgHDi3 | Undetected |
| CBFA2T3 | chr16      | +      | 1          | GCTCCAGGCGTgGGCGG | Intron     | sgHD1  | Undetected |
| NAV2    | chr11      | +      | 2          | GCTTTTgGGACGCCTCaG | Intron    | sgHDi3 | Undetected |

Figure 8D

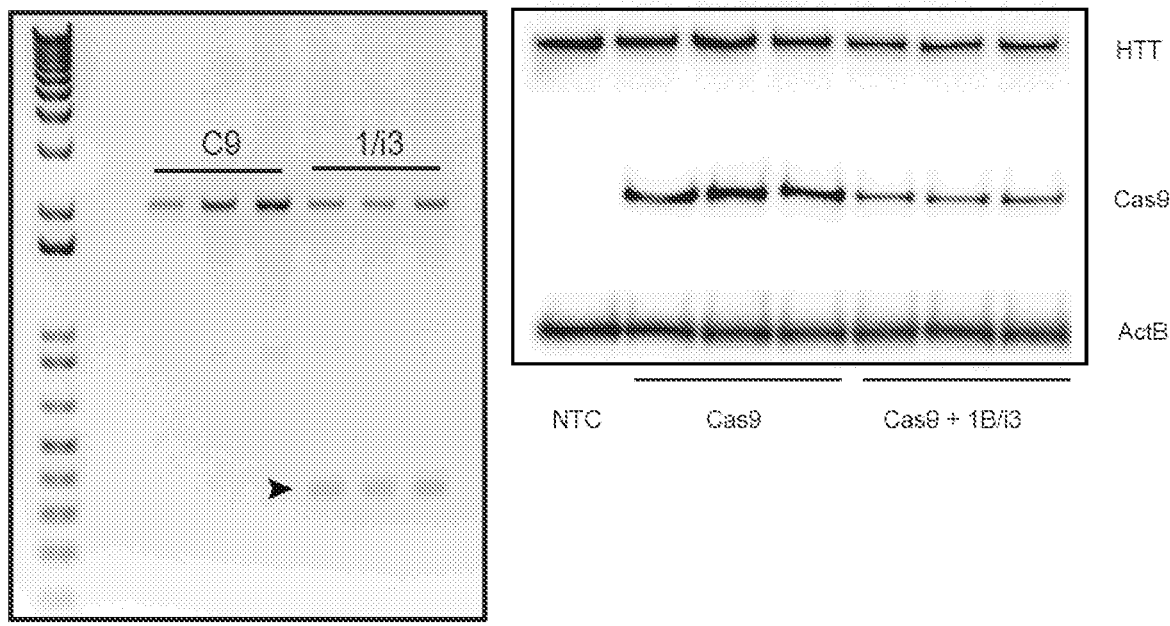
Figure 9D
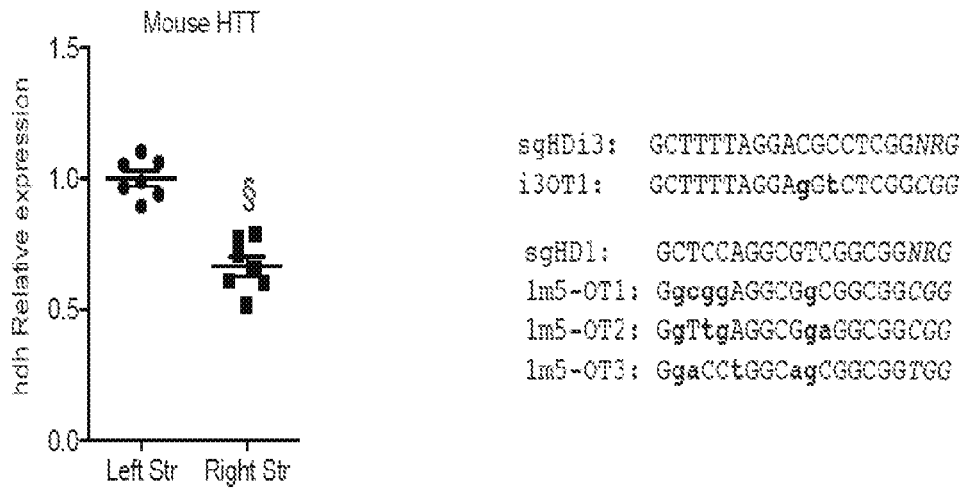
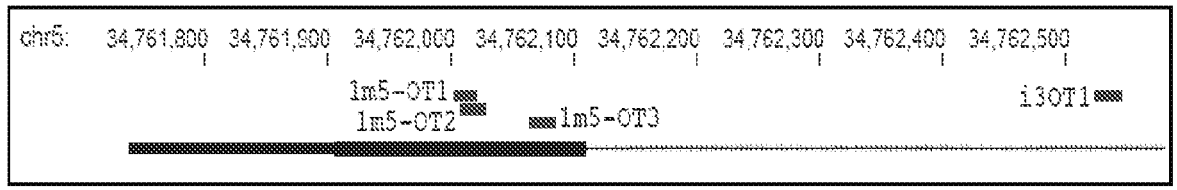
Figure 9E

```
                              SEQUENCE LISTING

<160> NUMBER OF SEQ ID NOS: 442

<210> SEQ ID NO 1
<211> LENGTH: 21
<212> TYPE: DNA
<213> ORGANISM: Artificial Sequence
<220> FEATURE:
<223> OTHER INFORMATION: PosCRPAS1

<400> SEQUENCE: 1
caccgctcca ggcgtcggcg g                                                 21

<210> SEQ ID NO 2
<211> LENGTH: 21
<212> TYPE: DNA
<213> ORGANISM: Artificial Sequence
<220> FEATURE:
<223> OTHER INFORMATION: NegCRPAS1

<400> SEQUENCE: 2
aaacccgccg acgcctggag c                                                 21

<210> SEQ ID NO 3
<211> LENGTH: 23
<212> TYPE: DNA
<213> ORGANISM: Artificial Sequence
<220> FEATURE:
<223> OTHER INFORMATION: PosCRPAS2

<400> SEQUENCE: 3
caccggcgcg gggctcaacg gag                                               23

<210> SEQ ID NO 4
<211> LENGTH: 23
<212> TYPE: DNA
<213> ORGANISM: Artificial Sequence
<220> FEATURE:
<223> OTHER INFORMATION: NegCRPAS2

<400> SEQUENCE: 4
aaacctccgt tgagccccgc gcc                                               23

<210> SEQ ID NO 5
<211> LENGTH: 24
<212> TYPE: DNA
<213> ORGANISM: Artificial Sequence
<220> FEATURE:
<223> OTHER INFORMATION: PosCRPAS3

<400> SEQUENCE: 5
caccgtctgg gacgcaaggc gccg                                              24

<210> SEQ ID NO 6
<211> LENGTH: 24
<212> TYPE: DNA
<213> ORGANISM: Artificial Sequence
<220> FEATURE:
<223> OTHER INFORMATION: NegCRPAS3

<400> SEQUENCE: 6
aaaccggcgc cttgcgtccc agac                                              24
```

```
<210> SEQ ID NO 7
<211> LENGTH: 23
<212> TYPE: DNA
<213> ORGANISM: Artificial Sequence
<220> FEATURE:
<223> OTHER INFORMATION: PosCRPAS4

<400> SEQUENCE: 7
caccgatgca cgcggggtgg ggc                                               23

<210> SEQ ID NO 8
<211> LENGTH: 23
<212> TYPE: DNA
<213> ORGANISM: Artificial Sequence
<220> FEATURE:
<223> OTHER INFORMATION: NegCRPAS4

<400> SEQUENCE: 8
aaacgcccca ccccgcgtgc atc                                               23

<210> SEQ ID NO 9
<211> LENGTH: 21
<212> TYPE: DNA
<213> ORGANISM: Artificial Sequence
<220> FEATURE:
<223> OTHER INFORMATION: PosCRPAS5G

<400> SEQUENCE: 9
tcccattcag gttgatgtcc t                                                 21

<210> SEQ ID NO 10
<211> LENGTH: 21
<212> TYPE: DNA
<213> ORGANISM: Artificial Sequence
<220> FEATURE:
<223> OTHER INFORMATION: NegCRPAS5G

<400> SEQUENCE: 10
aaacaggaca tcaacctgaa t                                                 21

<210> SEQ ID NO 11
<211> LENGTH: 24
<212> TYPE: DNA
<213> ORGANISM: Artificial Sequence
<220> FEATURE:
<223> OTHER INFORMATION: PosCRPAS5C

<400> SEQUENCE: 11
tcccatccca ttctgaggtt ctgg                                              24

<210> SEQ ID NO 12
<211> LENGTH: 24
<212> TYPE: DNA
<213> ORGANISM: Artificial Sequence
<220> FEATURE:
<223> OTHER INFORMATION: NegCRPAS5C

<400> SEQUENCE: 12
aaacccagaa cctcagaatg ggat                                              24

<210> SEQ ID NO 13
<211> LENGTH: 21
<212> TYPE: DNA
<213> ORGANISM: Artificial Sequence
<220> FEATURE:
<223> OTHER INFORMATION: PosCRPAS6C
```

```
<400> SEQUENCE: 13
caccgcaggc agagaggagc c                                              21

<210> SEQ ID NO 14
<211> LENGTH: 21
<212> TYPE: DNA
<213> ORGANISM: Artificial Sequence
<220> FEATURE:
<223> OTHER INFORMATION: NegCRPAS6C

<400> SEQUENCE: 14
aaacggctcc tctctgcctg c                                              21

<210> SEQ ID NO 15
<211> LENGTH: 23
<212> TYPE: DNA
<213> ORGANISM: Artificial Sequence
<220> FEATURE:
<223> OTHER INFORMATION: PosCRPAS6G

<400> SEQUENCE: 15
caccgcctgg ctaaagtagg ctt                                            23

<210> SEQ ID NO 16
<211> LENGTH: 23
<212> TYPE: DNA
<213> ORGANISM: Artificial Sequence
<220> FEATURE:
<223> OTHER INFORMATION: NegCRPAS6G

<400> SEQUENCE: 16
aaacaagcct actttagcca ggc                                            23

<210> SEQ ID NO 17
<211> LENGTH: 22
<212> TYPE: DNA
<213> ORGANISM: Artificial Sequence
<220> FEATURE:
<223> OTHER INFORMATION: PosCRi3

<400> SEQUENCE: 17
caccgctttt aggacgcctc gg                                             22

<210> SEQ ID NO 18
<211> LENGTH: 22
<212> TYPE: DNA
<213> ORGANISM: Artificial Sequence
<220> FEATURE:
<223> OTHER INFORMATION: NegCRi3

<400> SEQUENCE: 18
aaacccgagg cgtcctaaaa gc                                             22

<210> SEQ ID NO 19
<211> LENGTH: 22
<212> TYPE: DNA
<213> ORGANISM: Artificial Sequence
<220> FEATURE:
<223> OTHER INFORMATION: PosCRi4

<400> SEQUENCE: 19
caccgcggga cacttcgaga gg                                             22

<210> SEQ ID NO 20
```

```
<211> LENGTH: 22
<212> TYPE: DNA
<213> ORGANISM: Artificial Sequence
<220> FEATURE:
<223> OTHER INFORMATION: NegCRi4

<400> SEQUENCE: 20
aaaccctctc gaagtgtccc gc                                              22

<210> SEQ ID NO 21
<211> LENGTH: 17
<212> TYPE: DNA
<213> ORGANISM: Artificial Sequence
<220> FEATURE:
<223> OTHER INFORMATION: Fwd1SNP

<400> SEQUENCE: 21
gaccacgcgc attctct                                                    17

<210> SEQ ID NO 22
<211> LENGTH: 22
<212> TYPE: DNA
<213> ORGANISM: Artificial Sequence
<220> FEATURE:
<223> OTHER INFORMATION: Fwd4SNP

<400> SEQUENCE: 22
ggaaacagga cagatgaagg ag                                              22

<210> SEQ ID NO 23
<211> LENGTH: 22
<212> TYPE: DNA
<213> ORGANISM: Artificial Sequence
<220> FEATURE:
<223> OTHER INFORMATION: Fwd5SNP

<400> SEQUENCE: 23
cagctcagac ggaagtgtat tt                                              22

<210> SEQ ID NO 24
<211> LENGTH: 22
<212> TYPE: DNA
<213> ORGANISM: Artificial Sequence
<220> FEATURE:
<223> OTHER INFORMATION: Fwd6SNP

<400> SEQUENCE: 24
ctcccaagaa ctgggaacta ac                                              22

<210> SEQ ID NO 25
<211> LENGTH: 22
<212> TYPE: DNA
<213> ORGANISM: Artificial Sequence
<220> FEATURE:
<223> OTHER INFORMATION: Rev3Cleavage

<400> SEQUENCE: 25
accaccgtga tcatgaacta aa                                              22

<210> SEQ ID NO 26
<211> LENGTH: 18
<212> TYPE: DNA
<213> ORGANISM: Artificial Sequence
<220> FEATURE:
<223> OTHER INFORMATION: Rev1SNP

<400> SEQUENCE: 26
```
cgggactgca tggtaagg                                              18

<210> SEQ ID NO 27
<211> LENGTH: 18
<212> TYPE: DNA
<213> ORGANISM: Artificial Sequence
<220> FEATURE:
<223> OTHER INFORMATION: Sqe1SNP

<400> SEQUENCE: 27
gctgtccggg tgagtatg                                              18

<210> SEQ ID NO 28
<211> LENGTH: 18
<212> TYPE: DNA
<213> ORGANISM: Artificial Sequence
<220> FEATURE:
<223> OTHER INFORMATION: FwdSNP2

<400> SEQUENCE: 28
cccacctctc accttcct                                              18

<210> SEQ ID NO 29
<211> LENGTH: 20
<212> TYPE: DNA
<213> ORGANISM: Artificial Sequence
<220> FEATURE:
<223> OTHER INFORMATION: RevSNP2

<400> SEQUENCE: 29
cagcatgatt gacagcccta                                            20

<210> SEQ ID NO 30
<211> LENGTH: 17
<212> TYPE: DNA
<213> ORGANISM: Artificial Sequence
<220> FEATURE:
<223> OTHER INFORMATION: Seq2SNP

<400> SEQUENCE: 30
ccgcgacact tcacaca                                               17

<210> SEQ ID NO 31
<211> LENGTH: 17
<212> TYPE: DNA
<213> ORGANISM: Artificial Sequence
<220> FEATURE:
<223> OTHER INFORMATION: FwdSNP3

<400> SEQUENCE: 31
ccgcgacact tcacaca                                               17

<210> SEQ ID NO 32
<211> LENGTH: 18
<212> TYPE: DNA
<213> ORGANISM: Artificial Sequence
<220> FEATURE:
<223> OTHER INFORMATION: RevSNP3

<400> SEQUENCE: 32
tgctgctgga aggacttg                                              18

<210> SEQ ID NO 33
<211> LENGTH: 20
<212> TYPE: DNA

```
<213> ORGANISM: Artificial Sequence
<220> FEATURE:
<223> OTHER INFORMATION: Seq3SNP

<400> SEQUENCE: 33
tagggctgtc aatcatgctg                                                   20

<210> SEQ ID NO 34
<211> LENGTH: 20
<212> TYPE: DNA
<213> ORGANISM: Artificial Sequence
<220> FEATURE:
<223> OTHER INFORMATION: Rev4SNP

<400> SEQUENCE: 34
gggaattgag ggcggtttat                                                   20

<210> SEQ ID NO 35
<211> LENGTH: 20
<212> TYPE: DNA
<213> ORGANISM: Artificial Sequence
<220> FEATURE:
<223> OTHER INFORMATION: Seq4SNP

<400> SEQUENCE: 35
tttaccagct cctggctttc                                                   20

<210> SEQ ID NO 36
<211> LENGTH: 21
<212> TYPE: DNA
<213> ORGANISM: Artificial Sequence
<220> FEATURE:
<223> OTHER INFORMATION: Rev5SNP

<400> SEQUENCE: 36
gagcatgtcc gtgtcctaat c                                                 21

<210> SEQ ID NO 37
<211> LENGTH: 20
<212> TYPE: DNA
<213> ORGANISM: Artificial Sequence
<220> FEATURE:
<223> OTHER INFORMATION: Seq5SNP

<400> SEQUENCE: 37
tccctggcta gcacttactt                                                   20

<210> SEQ ID NO 38
<211> LENGTH: 21
<212> TYPE: DNA
<213> ORGANISM: Artificial Sequence
<220> FEATURE:
<223> OTHER INFORMATION: Rev6SNP

<400> SEQUENCE: 38
tgtgattagt gcagcgagaa g                                                 21

<210> SEQ ID NO 39
<211> LENGTH: 22
<212> TYPE: DNA
<213> ORGANISM: Artificial Sequence
<220> FEATURE:
<223> OTHER INFORMATION: Seq6SNP

<400> SEQUENCE: 39
ctgtttctct gctgtccttc tc                                                22
```

<210> SEQ ID NO 40
<211> LENGTH: 18
<212> TYPE: DNA
<213> ORGANISM: Artificial Sequence
<220> FEATURE:
<223> OTHER INFORMATION: Fwd HTT

<400> SEQUENCE: 40
tcggtgcagc ggctcctc                                              18

<210> SEQ ID NO 41
<211> LENGTH: 21
<212> TYPE: DNA
<213> ORGANISM: Artificial Sequence
<220> FEATURE:
<223> OTHER INFORMATION: Rev HTT

<400> SEQUENCE: 41
atggcgaccc tggaaaagct g                                          21

<210> SEQ ID NO 42
<211> LENGTH: 17
<212> TYPE: DNA
<213> ORGANISM: Artificial Sequence
<220> FEATURE:
<223> OTHER INFORMATION: FwdActB

<400> SEQUENCE: 42
ttcgcgggcg acgatgc                                               17

<210> SEQ ID NO 43
<211> LENGTH: 20
<212> TYPE: DNA
<213> ORGANISM: Artificial Sequence
<220> FEATURE:
<223> OTHER INFORMATION: RevActB

<400> SEQUENCE: 43
cgtacatggc tggggtgttg                                            20

<210> SEQ ID NO 44
<211> LENGTH: 20
<212> TYPE: DNA
<213> ORGANISM: Artificial Sequence
<220> FEATURE:
<223> OTHER INFORMATION: CBFA2T3_Fwd

<400> SEQUENCE: 44
tctgtggttc agccgacttc                                            20

<210> SEQ ID NO 45
<211> LENGTH: 20
<212> TYPE: DNA
<213> ORGANISM: Artificial Sequence
<220> FEATURE:
<223> OTHER INFORMATION: CBFA2T3_Rev

<400> SEQUENCE: 45
acacaatacc gtggcagagg                                            20

<210> SEQ ID NO 46
<211> LENGTH: 20
<212> TYPE: DNA
<213> ORGANISM: Artificial Sequence
<220> FEATURE:

```
<223> OTHER INFORMATION: SLC45A_Fwd

<400> SEQUENCE: 46
gacccaagct tgccgtagta                                                  20

<210> SEQ ID NO 47
<211> LENGTH: 20
<212> TYPE: DNA
<213> ORGANISM: Artificial Sequence
<220> FEATURE:
<223> OTHER INFORMATION: SLC45A_Rev

<400> SEQUENCE: 47
acctgttcag catcgacgag                                                  20

<210> SEQ ID NO 48
<211> LENGTH: 20
<212> TYPE: DNA
<213> ORGANISM: Artificial Sequence
<220> FEATURE:
<223> OTHER INFORMATION: STT3B_Fwd

<400> SEQUENCE: 48
cctaacggac ctgtcgcttt                                                  20

<210> SEQ ID NO 49
<211> LENGTH: 20
<212> TYPE: DNA
<213> ORGANISM: Artificial Sequence
<220> FEATURE:
<223> OTHER INFORMATION: STT3B_Rev

<400> SEQUENCE: 49
tgagggacga cttgtgcttg                                                  20

<210> SEQ ID NO 50
<211> LENGTH: 20
<212> TYPE: DNA
<213> ORGANISM: Artificial Sequence
<220> FEATURE:
<223> OTHER INFORMATION: NAV2_Fwd

<400> SEQUENCE: 50
ccacgagtgc acacagtttg                                                  20

<210> SEQ ID NO 51
<211> LENGTH: 20
<212> TYPE: DNA
<213> ORGANISM: Artificial Sequence
<220> FEATURE:
<223> OTHER INFORMATION: NAV2_Rev

<400> SEQUENCE: 51
ctcaaggact gctggctcaa                                                  20

<210> SEQ ID NO 52
<211> LENGTH: 20
<212> TYPE: DNA
<213> ORGANISM: Artificial Sequence
<220> FEATURE:
<223> OTHER INFORMATION: NUP210_Fwd

<400> SEQUENCE: 52
agctgcgtga tcttgaccaa                                                  20
```

```
<210> SEQ ID NO 53
<211> LENGTH: 20
<212> TYPE: DNA
<213> ORGANISM: Artificial Sequence
<220> FEATURE:
<223> OTHER INFORMATION: NUP210_Rev

<400> SEQUENCE: 53
ggtggttcag gctctttcca                                              20

<210> SEQ ID NO 54
<211> LENGTH: 20
<212> TYPE: DNA
<213> ORGANISM: Artificial Sequence
<220> FEATURE:
<223> OTHER INFORMATION: DNAJC16_Fwd

<400> SEQUENCE: 54
tctcatgcac ctcctcccat                                              20

<210> SEQ ID NO 55
<211> LENGTH: 20
<212> TYPE: DNA
<213> ORGANISM: Artificial Sequence
<220> FEATURE:
<223> OTHER INFORMATION: DNAJC16_Rev

<400> SEQUENCE: 55
tgagtgcagc gacatgatca                                              20

<210> SEQ ID NO 56
<211> LENGTH: 20
<212> TYPE: DNA
<213> ORGANISM: Artificial Sequence
<220> FEATURE:
<223> OTHER INFORMATION: LEPR_Fwd

<400> SEQUENCE: 56
tgagatgtgc ctccctcaga                                              20

<210> SEQ ID NO 57
<211> LENGTH: 20
<212> TYPE: DNA
<213> ORGANISM: Artificial Sequence
<220> FEATURE:
<223> OTHER INFORMATION: LEPR_Rev

<400> SEQUENCE: 57
aactagtggc atgcgtttgc                                              20

<210> SEQ ID NO 58
<211> LENGTH: 20
<212> TYPE: DNA
<213> ORGANISM: Artificial Sequence
<220> FEATURE:
<223> OTHER INFORMATION: CHRNA2_Fwd

<400> SEQUENCE: 58
ccttctgcat gtggggtgat                                              20

<210> SEQ ID NO 59
<211> LENGTH: 20
<212> TYPE: DNA
<213> ORGANISM: Artificial Sequence
<220> FEATURE:
<223> OTHER INFORMATION: CHRNA2_Rev
```

-continued

<400> SEQUENCE: 59
tgagatcatc ccgtccacct                                              20

<210> SEQ ID NO 60
<211> LENGTH: 20
<212> TYPE: DNA
<213> ORGANISM: Artificial Sequence
<220> FEATURE:
<223> OTHER INFORMATION: TRIB1_Fwd

<400> SEQUENCE: 60
tcccgggact taaaaagccg                                              20

<210> SEQ ID NO 61
<211> LENGTH: 20
<212> TYPE: DNA
<213> ORGANISM: Artificial Sequence
<220> FEATURE:
<223> OTHER INFORMATION: TRIB1_Rev

<400> SEQUENCE: 61
acctggtcaa atggcgtctt                                              20

<210> SEQ ID NO 62
<211> LENGTH: 20
<212> TYPE: DNA
<213> ORGANISM: Artificial Sequence
<220> FEATURE:
<223> OTHER INFORMATION: SMARCD1_Fwd

<400> SEQUENCE: 62
tatggttttc cctcccggac                                              20

<210> SEQ ID NO 63
<211> LENGTH: 20
<212> TYPE: DNA
<213> ORGANISM: Artificial Sequence
<220> FEATURE:
<223> OTHER INFORMATION: SMARCD1_Rev

<400> SEQUENCE: 63
agcaggtgtg taactgcctc                                              20

<210> SEQ ID NO 64
<211> LENGTH: 20
<212> TYPE: DNA
<213> ORGANISM: Artificial Sequence
<220> FEATURE:
<223> OTHER INFORMATION: COX11_Fwd

<400> SEQUENCE: 64
gttagaggct gcggaccttt                                              20

<210> SEQ ID NO 65
<211> LENGTH: 20
<212> TYPE: DNA
<213> ORGANISM: Artificial Sequence
<220> FEATURE:
<223> OTHER INFORMATION: COX11_Rev

<400> SEQUENCE: 65
gccgtttctt aggccagagt                                              20

<210> SEQ ID NO 66
<211> LENGTH: 49

-continued

<210> SEQ ID NO 66
<211> LENGTH: 49
<212> TYPE: DNA
<213> ORGANISM: Artificial Sequence
<220> FEATURE:
<223> OTHER INFORMATION: SNP1 major allele

<400> SEQUENCE: 66
gtcgccccgc tccaggcgtc ggcggggat cctttccgca tgggcctgc        49

<210> SEQ ID NO 67
<211> LENGTH: 49
<212> TYPE: DNA
<213> ORGANISM: Artificial Sequence
<220> FEATURE:
<223> OTHER INFORMATION: SNP1 minor allele (G)

<400> SEQUENCE: 67
gtcgccccgc tccaggcgtc ggcggggcat cctttccgca tgggcctgc        49

<210> SEQ ID NO 68
<211> LENGTH: 49
<212> TYPE: DNA
<213> ORGANISM: Artificial Sequence
<220> FEATURE:
<223> OTHER INFORMATION: SNP1 minor allele (T)

<400> SEQUENCE: 68
gtcgccccgc tccaggcgtc ggcggggaat cctttccgca tgggcctgc        49

<210> SEQ ID NO 69
<211> LENGTH: 17
<212> TYPE: DNA
<213> ORGANISM: Artificial Sequence
<220> FEATURE:
<223> OTHER INFORMATION: sgHD1

<400> SEQUENCE: 69
gctccaggcg tcggcgg        17

<210> SEQ ID NO 70
<211> LENGTH: 49
<212> TYPE: DNA
<213> ORGANISM: Artificial Sequence
<220> FEATURE:
<223> OTHER INFORMATION: rs9996199 major allele

<400> SEQUENCE: 70
gtggcctggc taaagtaggc tttactgggc tcctctctgc ctgcatcac        49

<210> SEQ ID NO 71
<211> LENGTH: 49
<212> TYPE: DNA
<213> ORGANISM: Artificial Sequence
<220> FEATURE:
<223> OTHER INFORMATION: rs9996199 minor allele

<400> SEQUENCE: 71
gtggcctggc taaagtaggc tttagtgggc tcctctctgc ctgcatcac        49

<210> SEQ ID NO 72
<211> LENGTH: 17
<212> TYPE: DNA
<213> ORGANISM: Artificial Sequence
<220> FEATURE:
<223> OTHER INFORMATION: rs9996199 major allele target sequence

<400> SEQUENCE: 72
gcaggcagag aggagcc                                                                    17

<210> SEQ ID NO 73
<211> LENGTH: 19
<212> TYPE: DNA
<213> ORGANISM: Artificial Sequence
<220> FEATURE:
<223> OTHER INFORMATION: rs9996199 minor allele target sequence

<400> SEQUENCE: 73
gcctggctaa agtaggctt                                                                  19

<210> SEQ ID NO 74
<211> LENGTH: 51
<212> TYPE: DNA
<213> ORGANISM: Artificial Sequence
<220> FEATURE:
<223> OTHER INFORMATION: rs35631490
<220> FEATURE:
<221> NAME/KEY: misc_feature
<222> LOCATION: 26
<223> OTHER INFORMATION: n = c or g

<400> SEQUENCE: 74
gtctgcgtca gggtttcctt cttttncagc cccaccccgc gtgcatccca c                              51

<210> SEQ ID NO 75
<211> LENGTH: 51
<212> TYPE: DNA
<213> ORGANISM: Artificial Sequence
<220> FEATURE:
<223> OTHER INFORMATION: rs73086139
<220> FEATURE:
<221> NAME/KEY: misc_feature
<222> LOCATION: 26
<223> OTHER INFORMATION: n = a or g

<400> SEQUENCE: 75
tcaaggcctc ttctctcttc tcggcnggac aggcacaggc aggtggccag g                              51

<210> SEQ ID NO 76
<211> LENGTH: 51
<212> TYPE: DNA
<213> ORGANISM: Artificial Sequence
<220> FEATURE:
<223> OTHER INFORMATION: rs73086140
<220> FEATURE:
<221> NAME/KEY: misc_feature
<222> LOCATION: 26
<223> OTHER INFORMATION: n = c or g

<400> SEQUENCE: 76
gccaggtgtc atgcttagct ccccgnccag tgagattctt tcatttaaca a                              51

<210> SEQ ID NO 77
<211> LENGTH: 51
<212> TYPE: DNA
<213> ORGANISM: Artificial Sequence
<220> FEATURE:
<223> OTHER INFORMATION: rs113541600
<220> FEATURE:
<221> NAME/KEY: misc_feature
<222> LOCATION: 26
<223> OTHER INFORMATION: n = t or absent

<400> SEQUENCE: 77
taggaacctt atttctctct cgctcntttt tttttttttg agacagagtc t                              51

```
<210> SEQ ID NO 78
<211> LENGTH: 51
<212> TYPE: DNA
<213> ORGANISM: Artificial Sequence
<220> FEATURE:
<223> OTHER INFORMATION: rs61791259
<220> FEATURE:
<221> NAME/KEY: misc_feature
<222> LOCATION: 26
<223> OTHER INFORMATION: n = c or t

<400> SEQUENCE: 78
gattacaggc acctgccacc atgccnggct aattttttgta tttttagttg a        51

<210> SEQ ID NO 79
<211> LENGTH: 51
<212> TYPE: DNA
<213> ORGANISM: Artificial Sequence
<220> FEATURE:
<223> OTHER INFORMATION: rs61792460
<220> FEATURE:
<221> NAME/KEY: misc_feature
<222> LOCATION: 26
<223> OTHER INFORMATION: n = a or g

<400> SEQUENCE: 79
gagggtttca tcttgttggt caggcngact tgaactcctg acctcaggtg a          51

<210> SEQ ID NO 80
<211> LENGTH: 51
<212> TYPE: DNA
<213> ORGANISM: Artificial Sequence
<220> FEATURE:
<223> OTHER INFORMATION: rs73086144
<220> FEATURE:
<221> NAME/KEY: misc_feature
<222> LOCATION: 26
<223> OTHER INFORMATION: n = a or g

<400> SEQUENCE: 80
gccactgcgc cttcatctct cttctntgta tgtgtacgct gttttttctt t          51

<210> SEQ ID NO 81
<211> LENGTH: 51
<212> TYPE: DNA
<213> ORGANISM: Artificial Sequence
<220> FEATURE:
<223> OTHER INFORMATION: rs73086145
<220> FEATURE:
<221> NAME/KEY: misc_feature
<222> LOCATION: 26
<223> OTHER INFORMATION: n = c or g

<400> SEQUENCE: 81 gctgttttt ctttagaatg ggggangtta tcaggctcta catggtgtgt a           51

<210> SEQ ID NO 82
<211> LENGTH: 51
<212> TYPE: DNA
<213> ORGANISM: Artificial Sequence
<220> FEATURE:
<223> OTHER INFORMATION: rs61792461
<220> FEATURE:
<221> NAME/KEY: misc_feature
<222> LOCATION: 26
<223> OTHER INFORMATION: n = a or g

<400> SEQUENCE: 82
tctacatggt gtgtagtcgg ctagcntgtt gtaagccttt ccctgtgtca c          51
```

```
<210> SEQ ID NO 83
<211> LENGTH: 51
<212> TYPE: DNA
<213> ORGANISM: Artificial Sequence
<220> FEATURE:
<223> OTHER INFORMATION: rs61792462
<220> FEATURE:
<221> NAME/KEY: misc_feature
<222> LOCATION: 26
<223> OTHER INFORMATION: n = c or g

<400> SEQUENCE: 83
ctgtgtcaca agtgctcatc tggaanagga ttctaatgac tgcctgtggc t          51

<210> SEQ ID NO 84
<211> LENGTH: 51
<212> TYPE: DNA
<213> ORGANISM: Artificial Sequence
<220> FEATURE:
<223> OTHER INFORMATION: rs61090955
<220> FEATURE:
<221> NAME/KEY: misc_feature
<222> LOCATION: 26
<223> OTHER INFORMATION: n = a or g

<400> SEQUENCE: 84
tcattttatg tgattccttt ctagangtac tactcattac ttctgcttgc a          51

<210> SEQ ID NO 85
<211> LENGTH: 51
<212> TYPE: DNA
<213> ORGANISM: Artificial Sequence
<220> FEATURE:
<223> OTHER INFORMATION: rs77384845
<220> FEATURE:
<221> NAME/KEY: misc_feature
<222> LOCATION: 26
<223> OTHER INFORMATION: n = c or t

<400> SEQUENCE: 85
tagctgaagg aaggacaggg actgtnatac actagctaag aggcaaactg c          51

<210> SEQ ID NO 86
<211> LENGTH: 51
<212> TYPE: DNA
<213> ORGANISM: Artificial Sequence
<220> FEATURE:
<223> OTHER INFORMATION: rs10011412
<220> FEATURE:
<221> NAME/KEY: misc_feature
<222> LOCATION: 26
<223> OTHER INFORMATION: n = a or g

<400> SEQUENCE: 86
agctgaagga aggacaggga ctgtcntaca ctagctaaga ggcaaactgc t          51

<210> SEQ ID NO 87
<211> LENGTH: 51
<212> TYPE: DNA
<213> ORGANISM: Artificial Sequence
<220> FEATURE:
<223> OTHER INFORMATION: rs61792464
<220> FEATURE:
<221> NAME/KEY: misc_feature
<222> LOCATION: 26
<223> OTHER INFORMATION: n = c or g

<400> SEQUENCE: 87
tccctcattc aggttgatgt cctaanccccc agaacctcag aatgggattg t          51
```

<210> SEQ ID NO 88
<211> LENGTH: 51
<212> TYPE: DNA
<213> ORGANISM: Artificial Sequence
<220> FEATURE:
<223> OTHER INFORMATION: rs112435590
<220> FEATURE:
<221> NAME/KEY: misc_difference
<222> LOCATION: 26
<223> OTHER INFORMATION: n = g or t

<400> SEQUENCE: 88
tccatgccaa gaaggcaaca gagagngcca gggagactga agtcataccc t     51

<210> SEQ ID NO 89
<211> LENGTH: 51
<212> TYPE: DNA
<213> ORGANISM: Artificial Sequence
<220> FEATURE:
<223> OTHER INFORMATION: rs111670395
<220> FEATURE:
<221> NAME/KEY: misc_feature
<222> LOCATION: 26
<223> OTHER INFORMATION: n = a or g

<400> SEQUENCE: 89
cccaggttca agcaattctg cctcancctc cggaatagct gggactacag g     51

<210> SEQ ID NO 90
<211> LENGTH: 51
<212> TYPE: DNA
<213> ORGANISM: Artificial Sequence
<220> FEATURE:
<223> OTHER INFORMATION: rs762855
<220> FEATURE:
<221> NAME/KEY: misc_feature
<222> LOCATION: 26
<223> OTHER INFORMATION: n = c or t

<400> SEQUENCE: 90
ttgagaagga cagcagagaa acagcngtta gttcccagtt cttgggaggc t     51

<210> SEQ ID NO 91
<211> LENGTH: 51
<212> TYPE: DNA
<213> ORGANISM: Artificial Sequence
<220> FEATURE:
<223> OTHER INFORMATION: rs9996199
<220> FEATURE:
<221> NAME/KEY: misc_feature
<222> LOCATION: 26
<223> OTHER INFORMATION: n = c or g

<400> SEQUENCE: 91
tgtggcctgg ctaaagtagg ctttantggg ctcctctctg cctgcatcac c     51

<210> SEQ ID NO 92
<211> LENGTH: 51
<212> TYPE: DNA
<213> ORGANISM: Artificial Sequence
<220> FEATURE:
<223> OTHER INFORMATION: rs143861513
<220> FEATURE:
<221> NAME/KEY: misc_feature
<222> LOCATION: 26
<223> OTHER INFORMATION: n = g or absent

<400> SEQUENCE: 92
tccggggcgc tgcgctggga ccgatngggg ggcgccaggc ctgtggacac c         51

<210> SEQ ID NO 93
<211> LENGTH: 51
<212> TYPE: DNA
<213> ORGANISM: Artificial Sequence
<220> FEATURE:
<223> OTHER INFORMATION: rs28431418
<220> FEATURE:
<221> NAME/KEY: misc_feature
<222> LOCATION: 26
<223> OTHER INFORMATION: n = c or t

<400> SEQUENCE: 93
ctccccgcag ggctgtccgg gtgagnatgg ctctggccac gggccagtgt g         51

<210> SEQ ID NO 94
<211> LENGTH: 51
<212> TYPE: DNA
<213> ORGANISM: Artificial Sequence
<220> FEATURE:
<223> OTHER INFORMATION: rs2857935
<220> FEATURE:
<221> NAME/KEY: misc_feature
<222> LOCATION: 26
<223> OTHER INFORMATION: n = a, c, or g

<400> SEQUENCE: 94
gggcgcaggc ccatgcggaa aggatncccc gccgacgcct ggagcggggc g         51

<210> SEQ ID NO 95
<211> LENGTH: 51
<212> TYPE: DNA
<213> ORGANISM: Artificial Sequence
<220> FEATURE:
<223> OTHER INFORMATION: rs28616835
<220> FEATURE:
<221> NAME/KEY: misc_feature
<222> LOCATION: 26
<223> OTHER INFORMATION: n = c or t

<400> SEQUENCE: 95
gcgcccgcgc tcggcgcccc ctccanggcc ccgccccgtc catggcccg t          51

<210> SEQ ID NO 96
<211> LENGTH: 51
<212> TYPE: DNA
<213> ORGANISM: Artificial Sequence
<220> FEATURE:
<223> OTHER INFORMATION: rs149624523
<220> FEATURE:
<221> NAME/KEY: misc_feature
<222> LOCATION: 26
<223> OTHER INFORMATION: n = c or t

<400> SEQUENCE: 96
ccccgccccg gcctcgccac gccccnacct caccacgccc ccgcatcgc c          51

<210> SEQ ID NO 97
<211> LENGTH: 51
<212> TYPE: DNA
<213> ORGANISM: Artificial Sequence
<220> FEATURE:
<223> OTHER INFORMATION: rs13122415
<220> FEATURE:
<221> NAME/KEY: misc_feature
<222> LOCATION: 26
<223> OTHER INFORMATION: n = c or g

<400> SEQUENCE: 97
attacagtct caccacgccc cgtccnctct ccgttgagcc ccgcgccttc g            51

<210> SEQ ID NO 98
<211> LENGTH: 56
<212> TYPE: DNA
<213> ORGANISM: Artificial Sequence
<220> FEATURE:
<223> OTHER INFORMATION: rs113331544
<220> FEATURE:
<221> NAME/KEY: misc_feature
<222> LOCATION: (26)...(31)
<223> OTHER INFORMATION: sequence is gcgggg or absent

<400> SEQUENCE: 98
ggccttgctg tgtgaggcag aacctnnnnn ngcgggggca ggggcgggct ggttcc        56

<210> SEQ ID NO 99
<211> LENGTH: 51
<212> TYPE: DNA
<213> ORGANISM: Artificial Sequence
<220> FEATURE:
<223> OTHER INFORMATION: rs13132932
<220> FEATURE:
<221> NAME/KEY: misc_feature
<222> LOCATION: 26
<223> OTHER INFORMATION: n = a or g

<400> SEQUENCE: 99
tgtgtgaggc agaacctgcg ggggcngggg cgggctggtt ccctggccag c            51

<210> SEQ ID NO 100
<211> LENGTH: 51
<212> TYPE: DNA
<213> ORGANISM: Artificial Sequence
<220> FEATURE:
<223> OTHER INFORMATION: rs13102260
<220> FEATURE:
<221> NAME/KEY: misc_feature
<222> LOCATION: 26
<223> OTHER INFORMATION: n = a or g

<400> SEQUENCE: 100
agcgtctggg acgcaaggcg ccgtgngggc tgccgggacg ggtccaagat g            51

<210> SEQ ID NO 101
<211> LENGTH: 51
<212> TYPE: DNA
<213> ORGANISM: Artificial Sequence
<220> FEATURE:
<223> OTHER INFORMATION: rs10009935
<220> FEATURE:
<221> NAME/KEY: misc_feature
<222> LOCATION: 26
<223> OTHER INFORMATION: n = c or t

<400> SEQUENCE: 101
ctcacttggg tcttcccttg tcctcncgcg aggggaggca gagccttgtt g            51

<210> SEQ ID NO 102
<211> LENGTH: 51
<212> TYPE: DNA
<213> ORGANISM: Artificial Sequence
<220> FEATURE:
<223> OTHER INFORMATION: rs58870770
<220> FEATURE:
<221> NAME/KEY: misc_feature
<222> LOCATION: 26
<223> OTHER INFORMATION: n = a or absent -continued

```
<400> SEQUENCE: 102
tgaatgagtt gtggttgcca agtaangtgg tgaacttacg tggtgattaa t         51

<210> SEQ ID NO 103
<211> LENGTH: 51
<212> TYPE: DNA
<213> ORGANISM: Artificial Sequence
<220> FEATURE:
<223> OTHER INFORMATION: rs34045730
<220> FEATURE:
<221> NAME/KEY: misc_feature
<222> LOCATION: 26
<223> OTHER INFORMATION: n = a or t

<400> SEQUENCE: 103
gaggtgtaca ttttaccagt attccngtca ggcttgccag aatacggggg g         51

<210> SEQ ID NO 104
<211> LENGTH: 51
<212> TYPE: DNA
<213> ORGANISM: Artificial Sequence
<220> FEATURE:
<223> OTHER INFORMATION: rs28656215
<220> FEATURE:
<221> NAME/KEY: misc_feature
<222> LOCATION: 26
<223> OTHER INFORMATION: n = c or t

<400> SEQUENCE: 104
ggaagtctgt gtgtcgagtg tacagnagga gttaggaagt actctggtgc a         51

<210> SEQ ID NO 105
<211> LENGTH: 51
<212> TYPE: DNA
<213> ORGANISM: Artificial Sequence
<220> FEATURE:
<223> OTHER INFORMATION: rs28571971
<220> FEATURE:
<221> NAME/KEY: misc_feature
<222> LOCATION: 26
<223> OTHER INFORMATION: n = c or g

<400> SEQUENCE: 105
acagtaggag ttaggaagta ctctgntgca gttcaggcct ttctcttacc t         51

<210> SEQ ID NO 106
<211> LENGTH: 51
<212> TYPE: DNA
<213> ORGANISM: Artificial Sequence
<220> FEATURE:
<223> OTHER INFORMATION: rs28583447
<220> FEATURE:
<221> NAME/KEY: misc_feature
<222> LOCATION: 26
<223> OTHER INFORMATION: n = c or t

<400> SEQUENCE: 106
cagtaggagt taggaagtac tctggngcag ttcaggcctt tctcttacct c         51

<210> SEQ ID NO 107
<211> LENGTH: 51
<212> TYPE: DNA
<213> ORGANISM: Artificial Sequence
<220> FEATURE:
<223> OTHER INFORMATION: rs28468636
<220> FEATURE:
<221> NAME/KEY: misc_feature
<222> LOCATION: 26
<223> OTHER INFORMATION: n = c or g
```

<400> SEQUENCE: 107
tctcttacct ctcagtattc tatttncgat ctggatgtgt cccagatggc a           51

<210> SEQ ID NO 108
<211> LENGTH: 51
<212> TYPE: DNA
<213> ORGANISM: Artificial Sequence
<220> FEATURE:
<223> OTHER INFORMATION: rs28564368
<220> FEATURE:
<221> NAME/KEY: misc_feature
<222> LOCATION: 26
<223> OTHER INFORMATION: n = a or c

<400> SEQUENCE: 108
tattctattt ccgatctgga tgtgtnccag atggcatttg gtaagaatat c           51

<210> SEQ ID NO 109
<211> LENGTH: 51
<212> TYPE: DNA
<213> ORGANISM: Artificial Sequence
<220> FEATURE:
<223> OTHER INFORMATION: rs28485764
<220> FEATURE:
<221> NAME/KEY: misc_feature
<222> LOCATION: 26
<223> OTHER INFORMATION: n = a or g

<400> SEQUENCE: 109
gatggcattt ggtaagaata tctctnttaa gactgattaa ttttagtaa t            51

<210> SEQ ID NO 110
<211> LENGTH: 51
<212> TYPE: DNA
<213> ORGANISM: Artificial Sequence
<220> FEATURE:
<223> OTHER INFORMATION: rs77173925
<220> FEATURE:
<221> NAME/KEY: misc_feature
<222> LOCATION: 26
<223> OTHER INFORMATION: n = a or g

<400> SEQUENCE: 110
gaataaatta ttctaaagga tggaanaact ttttggatat ttggagaaat t           51

<210> SEQ ID NO 111
<211> LENGTH: 51
<212> TYPE: DNA
<213> ORGANISM: Artificial Sequence
<220> FEATURE:
<223> OTHER INFORMATION: rs3905238
<220> FEATURE:
<221> NAME/KEY: misc_feature
<222> LOCATION: 26
<223> OTHER INFORMATION: n = c or t

<400> SEQUENCE: 111
ttgtatcatg tcaatgtatt acttangcaa aaataataca ttaaaaaaaa t           51

<210> SEQ ID NO 112
<211> LENGTH: 54
<212> TYPE: DNA
<213> ORGANISM: Artificial Sequence
<220> FEATURE:
<223> OTHER INFORMATION: rs33950430
<220> FEATURE:
<221> NAME/KEY: misc_feature
<222> LOCATION: (26)...(29)

```
<223> OTHER INFORMATION: sequence is aaca or absent

<400> SEQUENCE: 112
aggtattcac taattttgag taacannnnc tgctcacaaa gtttggattt tggc          54

<210> SEQ ID NO 113
<211> LENGTH: 51
<212> TYPE: DNA
<213> ORGANISM: Artificial Sequence
<220> FEATURE:
<223> OTHER INFORMATION: rs28377140
<220> FEATURE:
<221> NAME/KEY: misc_feature
<222> LOCATION: 26
<223> OTHER INFORMATION: n = c or g

<400> SEQUENCE: 113
aggcaattaa tacttgcttc tggcantttc ttattctcct tcagattcct a              51

<210> SEQ ID NO 114
<211> LENGTH: 51
<212> TYPE: DNA
<213> ORGANISM: Artificial Sequence
<220> FEATURE:
<223> OTHER INFORMATION: rs3856973
<220> FEATURE:
<221> NAME/KEY: misc_feature
<222> LOCATION: 26
<223> OTHER INFORMATION: n = c or t

<400> SEQUENCE: 114
ttaaaaataa aaataagtta acactngatt aaccctgaca tttccctatc c              51

<210> SEQ ID NO 115
<211> LENGTH: 51
<212> TYPE: DNA
<213> ORGANISM: Artificial Sequence
<220> FEATURE:
<223> OTHER INFORMATION: rs4498089
<220> FEATURE:
<221> NAME/KEY: misc_feature
<222> LOCATION: 26
<223> OTHER INFORMATION: n = a or g

<400> SEQUENCE: 115
agtgttaact tatttttatt tttaanaaaa ttgttaaggg ctttccagca a              51

<210> SEQ ID NO 116
<211> LENGTH: 51
<212> TYPE: DNA
<213> ORGANISM: Artificial Sequence
<220> FEATURE:
<223> OTHER INFORMATION: rs112353753
<220> FEATURE:
<221> NAME/KEY: misc_feature
<222> LOCATION: 26
<223> OTHER INFORMATION: n = t or absent

<400> SEQUENCE: 116
gacatgcact gccatgcctg ggtaantttt ttttttccc ccgagacgga g               51

<210> SEQ ID NO 117
<211> LENGTH: 51
<212> TYPE: DNA
<213> ORGANISM: Artificial Sequence
<220> FEATURE:
<223> OTHER INFORMATION: rs57666989
<220> FEATURE:
<221> NAME/KEY: misc_feature
```

<222> LOCATION: 26
<223> OTHER INFORMATION: n = c or t

<400> SEQUENCE: 117
ctgcaagctc cgcttcccga gttcangcca ttctcctgcc tcagtctccc a      51

<210> SEQ ID NO 118
<211> LENGTH: 51
<212> TYPE: DNA
<213> ORGANISM: Artificial Sequence
<220> FEATURE:
<223> OTHER INFORMATION: rs10006129
<220> FEATURE:
<221> NAME/KEY: misc_feature
<222> LOCATION: 26
<223> OTHER INFORMATION: n = c or g

<400> SEQUENCE: 118
tcttgatctc ctgacctcgt catccnccga ccttgtgatc cgcccacctc g      51

<210> SEQ ID NO 119
<211> LENGTH: 51
<212> TYPE: DNA
<213> ORGANISM: Artificial Sequence
<220> FEATURE:
<223> OTHER INFORMATION: rs28696693
<220> FEATURE:
<221> NAME/KEY: misc_feature
<222> LOCATION: 26
<223> OTHER INFORMATION: n = a or g

<400> SEQUENCE: 119
ggtaattttt gtattttag tagagntggg gttttgccat gatgagcagg c        51

<210> SEQ ID NO 120
<211> LENGTH: 51
<212> TYPE: DNA
<213> ORGANISM: Artificial Sequence
<220> FEATURE:
<223> OTHER INFORMATION: rs28393280
<220> FEATURE:
<221> NAME/KEY: misc_feature
<222> LOCATION: 26
<223> OTHER INFORMATION: n = a or g

<400> SEQUENCE: 120
ggattttgaa tgcggaacca actgcncttg ttgaactctg ctaagtataa c      51

<210> SEQ ID NO 121
<211> LENGTH: 51
<212> TYPE: DNA
<213> ORGANISM: Artificial Sequence
<220> FEATURE:
<223> OTHER INFORMATION: Synthetic sequence

<400> SEQUENCE: 121
cggctcagag tccacggccg gctgtcgccc cgctccaggc gtcggcgggg g      51

<210> SEQ ID NO 122
<211> LENGTH: 55
<212> TYPE: DNA
<213> ORGANISM: Artificial Sequence
<220> FEATURE:
<223> OTHER INFORMATION: Synthetic sequence

<400> SEQUENCE: 122
atgcttttag gacgcctcgg cgggagtggc ggggcggggg ggggcgggga gtgag   55

<210> SEQ ID NO 123
<211> LENGTH: 82
<212> TYPE: DNA
<213> ORGANISM: Artificial Sequence
<220> FEATURE:
<223> OTHER INFORMATION: Synthetic sequence

<400> SEQUENCE: 123
cggctcagag tccacggccg gctgtcgccc cgctccaggc gtcgcggcgg gagtggcggg    60 gcggggggggg gcggggagtg ag                                            82

<210> SEQ ID NO 124
<211> LENGTH: 82
<212> TYPE: DNA
<213> ORGANISM: Artificial Sequence
<220> FEATURE:
<223> OTHER INFORMATION: Synthetic sequence

<400> SEQUENCE: 124
cggctcagag tccacggccg gctgtcgccc cgcccaggc gtcgcggcgg gagtggcggg    60 gcggggggggg gcggggagtg ag                                            82

<210> SEQ ID NO 125
<211> LENGTH: 56
<212> TYPE: DNA
<213> ORGANISM: Artificial Sequence
<220> FEATURE:
<223> OTHER INFORMATION: Synthetic sequence

<400> SEQUENCE: 125
cggctcagag tccacggccg gcgggagtgg cggggcgggg ggggcgggg agtgag          56

<210> SEQ ID NO 126
<211> LENGTH: 82
<212> TYPE: DNA
<213> ORGANISM: Artificial Sequence
<220> FEATURE:
<223> OTHER INFORMATION: Synthetic sequence

<400> SEQUENCE: 126
cggctcagag tccacggccg gctgtcgccc cgctccaggc gtcggggcgg gagtggcggg    60 gcggggggggg gcggggagtg ag                                            82

<210> SEQ ID NO 127
<211> LENGTH: 50
<212> TYPE: DNA
<213> ORGANISM: Artificial Sequence
<220> FEATURE:
<223> OTHER INFORMATION: Synthetic sequence

<400> SEQUENCE: 127
cccattacag tctcaccacg ccccgtcccc tctccgttga gccccgcgcc                50

<210> SEQ ID NO 128
<211> LENGTH: 55
<212> TYPE: DNA
<213> ORGANISM: Artificial Sequence
<220> FEATURE:
<223> OTHER INFORMATION: Synthetic sequence

<400> SEQUENCE: 128
atgcttttag gacgcctcgg cgggagtggc ggggcggggg ggggcgggga gtgag          55

<210> SEQ ID NO 129
<211> LENGTH: 73
<212> TYPE: DNA
<213> ORGANISM: Artificial Sequence
<220> FEATURE:
<223> OTHER INFORMATION: Synthetic sequence

<400> SEQUENCE: 129

```
cccattacag tctcaccacg ccccgtcccc tctcccggcg ggagtgcggg gcggggggg      60 gcggggagtg agg                                                        73
```

<210> SEQ ID NO 130
<211> LENGTH: 74
<212> TYPE: DNA
<213> ORGANISM: Artificial Sequence
<220> FEATURE:
<223> OTHER INFORMATION: Synthetic sequence

<400> SEQUENCE: 130

```
cccattacag tctcaccacg ccccgtcccc tctcctcggc gggagtgcgg ggcgggggg      60 ggcggggagt gagg                                                       74
```

<210> SEQ ID NO 131
<211> LENGTH: 73
<212> TYPE: DNA
<213> ORGANISM: Artificial Sequence
<220> FEATURE:
<223> OTHER INFORMATION: Synthetic sequence

<400> SEQUENCE: 131

```
cccattacag tctcaccacg ccccgtcccc tctcccggcg ggagtggcgg ggcggggggg     60
gggcggggag tga                                                        73
```

<210> SEQ ID NO 132
<211> LENGTH: 73
<212> TYPE: DNA
<213> ORGANISM: Artificial Sequence
<220> FEATURE:
<223> OTHER INFORMATION: Synthetic sequence

<400> SEQUENCE: 132

```
cccattacag tctcaccacg ccccgtcccc tctcgcggcg ggagtggcgg ggcggggggg     60
ggcggggagt gag                                                        73
```

<210> SEQ ID NO 133
<211> LENGTH: 49
<212> TYPE: DNA
<213> ORGANISM: Artificial Sequence
<220> FEATURE:
<223> OTHER INFORMATION: Synthetic sequence

<400> SEQUENCE: 133

```
cgcggccccg cctccgccgg cgcagcgtct gggacgcaag gcgccgtgg                 49
```

<210> SEQ ID NO 134
<211> LENGTH: 55
<212> TYPE: DNA
<213> ORGANISM: Artificial Sequence
<220> FEATURE:
<223> OTHER INFORMATION: Synthetic sequence

<400> SEQUENCE: 134

```
atgcttttag gacgcctcgg cgggagtggc ggggcggggg ggggcgggga gtgag          55
```

<210> SEQ ID NO 135
<211> LENGTH: 71
<212> TYPE: DNA
<213> ORGANISM: Artificial Sequence
<220> FEATURE:
<223> OTHER INFORMATION: Synthetic sequence

<400> SEQUENCE: 135
cgcggccccg cctccgccgg cgcagcgtct gggcggcggg agtggcgggg cggggggggg    60
cggggagtga g                                                         71

<210> SEQ ID NO 136
<211> LENGTH: 82
<212> TYPE: DNA
<213> ORGANISM: Artificial Sequence
<220> FEATURE:
<223> OTHER INFORMATION: Synthetic sequence

<400> SEQUENCE: 136
cgcggccccg cctccgccgg cgcagcgtct gggacgcaag gcgtcggcgg gagtggcggg    60 gcggggggggg gcggggagtg ag                                            82

<210> SEQ ID NO 137
<211> LENGTH: 83
<212> TYPE: DNA
<213> ORGANISM: Artificial Sequence
<220> FEATURE:
<223> OTHER INFORMATION: Synthetic sequence

<400> SEQUENCE: 137
cgcggccccg cctccgccgg cgcagcgtct gggacgcaag gcgatcggcg ggagtggcgg    60
ggcggggggg ggcggggagt gag                                            83

<210> SEQ ID NO 138
<211> LENGTH: 81
<212> TYPE: DNA
<213> ORGANISM: Artificial Sequence
<220> FEATURE:
<223> OTHER INFORMATION: Synthetic sequence

<400> SEQUENCE: 138
tccggccccg cctccgccgg cgcagcgtct gggacgcaag gcgcggcggg agtggcgggg    60
cggggggggg cggggagtga g                                              81

<210> SEQ ID NO 139
<211> LENGTH: 51
<212> TYPE: DNA
<213> ORGANISM: Artificial Sequence
<220> FEATURE:
<223> OTHER INFORMATION: Synthetic sequence

<400> SEQUENCE: 139
tggggtctgc gtcagggttt ccttcttttc cagccccacc ccgcgtgcat c             51

<210> SEQ ID NO 140
<211> LENGTH: 55
<212> TYPE: DNA
<213> ORGANISM: Artificial Sequence
<220> FEATURE:
<223> OTHER INFORMATION: Synthetic sequence

<400> SEQUENCE: 140
atgcttttag gacgcctcgg cgggagtggc ggggcggggg ggggcgggga gtgag         55

<210> SEQ ID NO 141
<211> LENGTH: 69
<212> TYPE: DNA
<213> ORGANISM: Artificial Sequence
<220> FEATURE:
<223> OTHER INFORMATION: Synthetic sequence

<400> SEQUENCE: 141
tggggtctgc gtcagggttt ccttcttttc cagcccggga gtggcggggcg gggggggcg    60 gggagtgag                                                            69

<210> SEQ ID NO 142
<211> LENGTH: 73
<212> TYPE: DNA
<213> ORGANISM: Artificial Sequence
<220> FEATURE:
<223> OTHER INFORMATION: Synthetic sequence

<400> SEQUENCE: 142
tggggtctgc gtcagggttt ccttcttttc agcccggcg ggagtggcgg ggcggggggg     60
ggcggggagt gag                                                       73

<210> SEQ ID NO 143
<211> LENGTH: 73
<212> TYPE: DNA
<213> ORGANISM: Artificial Sequence
<220> FEATURE:
<223> OTHER INFORMATION: Synthetic sequence

<400> SEQUENCE: 143
tggggtctgc gtcagggttt ccttcttttc agcccggcg ggagtggcgg ggcggggggg     60
ggcggggagt gag                                                       73

<210> SEQ ID NO 144
<211> LENGTH: 67
<212> TYPE: DNA
<213> ORGANISM: Artificial Sequence
<220> FEATURE:
<223> OTHER INFORMATION: Synthetic sequence

<400> SEQUENCE: 144
tggggtctgc gtcagggttt ccttcttttc ggcgggagtg gcggggcggg ggggggcggg    60
gagtgag                                                              67

<210> SEQ ID NO 145
<211> LENGTH: 52
<212> TYPE: DNA
<213> ORGANISM: Artificial Sequence
<220> FEATURE:
<223> OTHER INFORMATION: Synthetic sequence

<400> SEQUENCE: 145
caggtgtggc ctggctaaag taggctttac tgggctcctc tctgcctgca tc            52

<210> SEQ ID NO 146
<211> LENGTH: 55
<212> TYPE: DNA
<213> ORGANISM: Artificial Sequence
<220> FEATURE:
<223> OTHER INFORMATION: Synthetic sequence

<400> SEQUENCE: 146

```
atgcttttag gacgcctcgg cgggagtggc ggggcggggg ggggcgggga gtgag      55
```

<210> SEQ ID NO 147
<211> LENGTH: 72
<212> TYPE: DNA
<213> ORGANISM: Artificial Sequence
<220> FEATURE:
<223> OTHER INFORMATION: Synthetic sequence

<400> SEQUENCE: 147

```
caggtgtggc ctggctaaag taggctttac tgggcggcgg gagtggcggg gcggggggg      60
gcggggagtg ag                                                         72
```

<210> SEQ ID NO 148
<211> LENGTH: 74
<212> TYPE: DNA
<213> ORGANISM: Artificial Sequence
<220> FEATURE:
<223> OTHER INFORMATION: Synthetic sequence

<400> SEQUENCE: 148

```
caggtgtggc ctggctaaag taggctttac tgggctcggc gggagtggcg ggcgggggg      60
gggcggggag tgag                                                       74
```

<210> SEQ ID NO 149
<211> LENGTH: 73
<212> TYPE: DNA
<213> ORGANISM: Artificial Sequence
<220> FEATURE:
<223> OTHER INFORMATION: Synthetic sequence

<400> SEQUENCE: 149

```
caggtgtggc ctggctaaag taggctttac tgggccggcg ggagtggcgg ggcggggggg     60
ggcggggagt gag                                                        73
```

<210> SEQ ID NO 150
<211> LENGTH: 73
<212> TYPE: DNA
<213> ORGANISM: Artificial Sequence
<220> FEATURE:
<223> OTHER INFORMATION: Synthetic sequence

<400> SEQUENCE: 150

```
caggtgtggc ctggctaaag taggctttac tgggccggcg ggagtggcgg ggcggggggg     60
ggcggggagt gag                                                        73
```

<210> SEQ ID NO 151
<211> LENGTH: 49
<212> TYPE: DNA
<213> ORGANISM: Artificial Sequence
<220> FEATURE:
<223> OTHER INFORMATION: Synthetic sequence

<400> SEQUENCE: 151

```
gtgatgcagg cagagaggag cccagtaaag cctactttag ccaggccac               49
```

<210> SEQ ID NO 152
<211> LENGTH: 49
<212> TYPE: DNA
<213> ORGANISM: Artificial Sequence
<220> FEATURE:
<223> OTHER INFORMATION: Synthetic sequence

<400> SEQUENCE: 152
gtgatgcagg cagagaggag cccactaaag cctactttag ccaggccac                49

<210> SEQ ID NO 153
<211> LENGTH: 49
<212> TYPE: DNA
<213> ORGANISM: Artificial Sequence
<220> FEATURE:
<223> OTHER INFORMATION: Synthetic sequence

<400> SEQUENCE: 153
gcaggcccat gcggaaagga tcccccgccg acgcctggag cggggcgac                49

<210> SEQ ID NO 154
<211> LENGTH: 49
<212> TYPE: DNA
<213> ORGANISM: Artificial Sequence
<220> FEATURE:
<223> OTHER INFORMATION: Synthetic sequence

<400> SEQUENCE: 154
gcaggcccat gcggaaagga tgccccgccg acgcctggag cggggcgac                49

<210> SEQ ID NO 155
<211> LENGTH: 49
<212> TYPE: DNA
<213> ORGANISM: Artificial Sequence
<220> FEATURE:
<223> OTHER INFORMATION: Synthetic sequence

<400> SEQUENCE: 155
gcaggcccat gcggaaagga ttccccgccg acgcctggag cggggcgac                49

<210> SEQ ID NO 156
<211> LENGTH: 20
<212> TYPE: DNA
<213> ORGANISM: Artificial Sequence
<220> FEATURE:
<223> OTHER INFORMATION: Synthetic sequence

<400> SEQUENCE: 156
ggatgcacgc ggggtggggc                                                20

<210> SEQ ID NO 157
<211> LENGTH: 20
<212> TYPE: DNA
<213> ORGANISM: Artificial Sequence
<220> FEATURE:
<223> OTHER INFORMATION: Synthetic sequence

<400> SEQUENCE: 157
gatgcacgcg gggtggggct                                                20

<210> SEQ ID NO 158
<211> LENGTH: 20
<212> TYPE: DNA
<213> ORGANISM: Artificial Sequence
<220> FEATURE:
<223> OTHER INFORMATION: Synthetic sequence

<400> SEQUENCE: 158
gccccacccc gcgtgcatcc                                                20

<210> SEQ ID NO 159
<211> LENGTH: 19
<212> TYPE: DNA

```
<213> ORGANISM: Artificial Sequence
<220> FEATURE:
<223> OTHER INFORMATION: Synthetic sequence

<400> SEQUENCE: 159
ggcctcttct ctcttctcg                                            19

<210> SEQ ID NO 160
<211> LENGTH: 20
<212> TYPE: DNA
<213> ORGANISM: Artificial Sequence
<220> FEATURE:
<223> OTHER INFORMATION: Synthetic sequence

<400> SEQUENCE: 160
ttaaatgaaa gaatctcact                                           20

<210> SEQ ID NO 161
<211> LENGTH: 20
<212> TYPE: DNA
<213> ORGANISM: Artificial Sequence
<220> FEATURE:
<223> OTHER INFORMATION: Synthetic sequence

<400> SEQUENCE: 161
aggtgtcatg cttagctccc                                           20

<210> SEQ ID NO 162
<211> LENGTH: 22
<212> TYPE: DNA
<213> ORGANISM: Artificial Sequence
<220> FEATURE:
<223> OTHER INFORMATION: Synthetic sequence

<400> SEQUENCE: 162
ttaaatgaaa gaatctcact gg                                        22

<210> SEQ ID NO 163
<211> LENGTH: 20
<212> TYPE: DNA
<213> ORGANISM: Artificial Sequence
<220> FEATURE:
<223> OTHER INFORMATION: Synthetic sequence

<400> SEQUENCE: 163
actaaaaata caaaaattag                                           20

<210> SEQ ID NO 164
<211> LENGTH: 20
<212> TYPE: DNA
<213> ORGANISM: Artificial Sequence
<220> FEATURE:
<223> OTHER INFORMATION: Synthetic sequence

<400> SEQUENCE: 164
ggtttcatct tgttggtcag                                           20

<210> SEQ ID NO 165
<211> LENGTH: 21
<212> TYPE: DNA
<213> ORGANISM: Artificial Sequence
<220> FEATURE:
<223> OTHER INFORMATION: Synthetic sequence

<400> SEQUENCE: 165
gggtttcatc ttgttggtca g                                         21
```

```
<210> SEQ ID NO 166
<211> LENGTH: 20
<212> TYPE: DNA
<213> ORGANISM: Artificial Sequence
<220> FEATURE:
<223> OTHER INFORMATION: Synthetic sequence

<400> SEQUENCE: 166 gtttttctt tagaatgggg                                              20

<210> SEQ ID NO 167
<211> LENGTH: 20
<212> TYPE: DNA
<213> ORGANISM: Artificial Sequence
<220> FEATURE:
<223> OTHER INFORMATION: Synthetic sequence

<400> SEQUENCE: 167
acatggtgtg tagtcggcta                                             20

<210> SEQ ID NO 168
<211> LENGTH: 19
<212> TYPE: DNA
<213> ORGANISM: Artificial Sequence
<220> FEATURE:
<223> OTHER INFORMATION: Synthetic sequence

<400> SEQUENCE: 168
gtcacaagtg ctcatctgg                                              19

<210> SEQ ID NO 169
<211> LENGTH: 20
<212> TYPE: DNA
<213> ORGANISM: Artificial Sequence
<220> FEATURE:
<223> OTHER INFORMATION: Synthetic sequence

<400> SEQUENCE: 169
gtcacaagtg ctcatctgga                                             20

<210> SEQ ID NO 170
<211> LENGTH: 23
<212> TYPE: DNA
<213> ORGANISM: Artificial Sequence
<220> FEATURE:
<223> OTHER INFORMATION: Synthetic sequence

<400> SEQUENCE: 170
ccagatgagc acttgtgaca cag                                         23

<210> SEQ ID NO 171
<211> LENGTH: 20
<212> TYPE: DNA
<213> ORGANISM: Artificial Sequence
<220> FEATURE:
<223> OTHER INFORMATION: Synthetic sequence

<400> SEQUENCE: 171
ttttatgtga ttcctttcta                                             20

<210> SEQ ID NO 172
<211> LENGTH: 21
<212> TYPE: DNA
<213> ORGANISM: Artificial Sequence
<220> FEATURE:
```

<223> OTHER INFORMATION: Synthetic sequence

<400> SEQUENCE: 172
agaaaggaat cacataaaat g                                               21

<210> SEQ ID NO 173
<211> LENGTH: 17
<212> TYPE: DNA
<213> ORGANISM: Artificial Sequence
<220> FEATURE:
<223> OTHER INFORMATION: Synthetic sequence

<400> SEQUENCE: 173
gcctcttagc tagtgta                                                    17

<210> SEQ ID NO 174
<211> LENGTH: 20
<212> TYPE: DNA
<213> ORGANISM: Artificial Sequence
<220> FEATURE:
<223> OTHER INFORMATION: Synthetic sequence

<400> SEQUENCE: 174
atcccattct gaggttctgg                                                 20

<210> SEQ ID NO 175
<211> LENGTH: 19
<212> TYPE: DNA
<213> ORGANISM: Artificial Sequence
<220> FEATURE:
<223> OTHER INFORMATION: Synthetic sequence

<400> SEQUENCE: 175
tcattcaggt tgatgtcct                                                  19

<210> SEQ ID NO 176
<211> LENGTH: 20
<212> TYPE: DNA
<213> ORGANISM: Artificial Sequence
<220> FEATURE:
<223> OTHER INFORMATION: Synthetic sequence

<400> SEQUENCE: 176
ggacatcaac ctgaatgagg                                                 20

<210> SEQ ID NO 177
<211> LENGTH: 20
<212> TYPE: DNA
<213> ORGANISM: Artificial Sequence
<220> FEATURE:
<223> OTHER INFORMATION: Synthetic sequence

<400> SEQUENCE: 177
atgccaagaa ggcaacagag                                                 20

<210> SEQ ID NO 178
<211> LENGTH: 20
<212> TYPE: DNA
<213> ORGANISM: Artificial Sequence
<220> FEATURE:
<223> OTHER INFORMATION: Synthetic sequence

<400> SEQUENCE: 178
tccatgccaa gaaggcaaca                                                 20

```
<210> SEQ ID NO 179
<211> LENGTH: 19
<212> TYPE: DNA
<213> ORGANISM: Artificial Sequence
<220> FEATURE:
<223> OTHER INFORMATION: Synthetic sequence

<400> SEQUENCE: 179
ggttcaagca attctgcct                                                19

<210> SEQ ID NO 180
<211> LENGTH: 17
<212> TYPE: DNA
<213> ORGANISM: Artificial Sequence
<220> FEATURE:
<223> OTHER INFORMATION: Synthetic sequence

<400> SEQUENCE: 180
gcaggcagag aggagcc                                                  17

<210> SEQ ID NO 181
<211> LENGTH: 20
<212> TYPE: DNA
<213> ORGANISM: Artificial Sequence
<220> FEATURE:
<223> OTHER INFORMATION: Synthetic sequence

<400> SEQUENCE: 181
ggcctggcta aagtaggctt                                               20

<210> SEQ ID NO 182
<211> LENGTH: 19
<212> TYPE: DNA
<213> ORGANISM: Artificial Sequence
<220> FEATURE:
<223> OTHER INFORMATION: Synthetic sequence

<400> SEQUENCE: 182
tccccgcagg gctgtccgg                                                19

<210> SEQ ID NO 183
<211> LENGTH: 17
<212> TYPE: DNA
<213> ORGANISM: Artificial Sequence
<220> FEATURE:
<223> OTHER INFORMATION: Synthetic sequence

<400> SEQUENCE: 183
gctccaggcg tcggcgg                                                  17

<210> SEQ ID NO 184
<211> LENGTH: 19
<212> TYPE: DNA
<213> ORGANISM: Artificial Sequence
<220> FEATURE:
<223> OTHER INFORMATION: Synthetic sequence

<400> SEQUENCE: 184
gccccgctcc aggcgtcgg                                                19

<210> SEQ ID NO 185
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 185
ccgccgacgc ctggagcggg                                            20

<210> SEQ ID NO 186
<211> LENGTH: 20
<212> TYPE: DNA
<213> ORGANISM: Artificial Sequence
<220> FEATURE:
<223> OTHER INFORMATION: Synthetic sequence

<400> SEQUENCE: 186
gatgcggggg gcgtggtgag                                            20

<210> SEQ ID NO 187
<211> LENGTH: 19
<212> TYPE: DNA
<213> ORGANISM: Artificial Sequence
<220> FEATURE:
<223> OTHER INFORMATION: Synthetic sequence

<400> SEQUENCE: 187
ggcgcggggc tcaacggag                                             19

<210> SEQ ID NO 188
<211> LENGTH: 17
<212> TYPE: DNA
<213> ORGANISM: Artificial Sequence
<220> FEATURE:
<223> OTHER INFORMATION: Synthetic sequence

<400> SEQUENCE: 188
gcggggctca acggaga                                               17

<210> SEQ ID NO 189
<211> LENGTH: 16
<212> TYPE: DNA
<213> ORGANISM: Artificial Sequence
<220> FEATURE:
<223> OTHER INFORMATION: Synthetic sequence

<400> SEQUENCE: 189
gcggggctca acggag                                                16

<210> SEQ ID NO 190
<211> LENGTH: 19
<212> TYPE: DNA
<213> ORGANISM: Artificial Sequence
<220> FEATURE:
<223> OTHER INFORMATION: Synthetic sequence

<400> SEQUENCE: 190
gctgtgtgag gcagaacct                                             19

<210> SEQ ID NO 191
<211> LENGTH: 20
<212> TYPE: DNA
<213> ORGANISM: Artificial Sequence
<220> FEATURE:
<223> OTHER INFORMATION: Synthetic sequence

<400> SEQUENCE: 191
gtgaggcaga acctgcgggg                                            20

<210> SEQ ID NO 192
<211> LENGTH: 18

```
<212> TYPE: DNA
<213> ORGANISM: Artificial Sequence
<220> FEATURE:
<223> OTHER INFORMATION: Synthetic sequence

<400> SEQUENCE: 192
gaggcagaac ctgcgggg                                                    18

<210> SEQ ID NO 193
<211> LENGTH: 20
<212> TYPE: DNA
<213> ORGANISM: Artificial Sequence
<220> FEATURE:
<223> OTHER INFORMATION: Synthetic sequence

<400> SEQUENCE: 193
gtctgggacg caaggcgccg                                                  20

<210> SEQ ID NO 194
<211> LENGTH: 22
<212> TYPE: DNA
<213> ORGANISM: Artificial Sequence
<220> FEATURE:
<223> OTHER INFORMATION: Synthetic sequence

<400> SEQUENCE: 194
gcgtctggga cgcaaggcgc cg                                               22

<210> SEQ ID NO 195
<211> LENGTH: 17
<212> TYPE: DNA
<213> ORGANISM: Artificial Sequence
<220> FEATURE:
<223> OTHER INFORMATION: Synthetic sequence

<400> SEQUENCE: 195
ggctctgcct cccctcg                                                     17

<210> SEQ ID NO 196
<211> LENGTH: 18
<212> TYPE: DNA
<213> ORGANISM: Artificial Sequence
<220> FEATURE:
<223> OTHER INFORMATION: Synthetic sequence

<400> SEQUENCE: 196
ggctctgcct cccctcgc                                                    18

<210> SEQ ID NO 197
<211> LENGTH: 21
<212> TYPE: DNA
<213> ORGANISM: Artificial Sequence
<220> FEATURE:
<223> OTHER INFORMATION: Synthetic sequence

<400> SEQUENCE: 197
cttggcaacc acaactcatt c                                                21

<210> SEQ ID NO 198
<211> LENGTH: 17
<212> TYPE: DNA
<213> ORGANISM: Artificial Sequence
<220> FEATURE:
<223> OTHER INFORMATION: Synthetic sequence

<400> SEQUENCE: 198
```
ggagttagga agtactc						17

<210> SEQ ID NO 199
<211> LENGTH: 22
<212> TYPE: DNA
<213> ORGANISM: Artificial Sequence
<220> FEATURE:
<223> OTHER INFORMATION: Synthetic sequence

<400> SEQUENCE: 199
ggtaagagaa aggcctgaac tg					22

<210> SEQ ID NO 200
<211> LENGTH: 20
<212> TYPE: DNA
<213> ORGANISM: Artificial Sequence
<220> FEATURE:
<223> OTHER INFORMATION: Synthetic sequence

<400> SEQUENCE: 200
gtaagagaaa ggcctgaact					20

<210> SEQ ID NO 201
<211> LENGTH: 19
<212> TYPE: DNA
<213> ORGANISM: Artificial Sequence
<220> FEATURE:
<223> OTHER INFORMATION: Synthetic sequence

<400> SEQUENCE: 201
ggagttagga agtactctg					19

<210> SEQ ID NO 202
<211> LENGTH: 19
<212> TYPE: DNA
<213> ORGANISM: Artificial Sequence
<220> FEATURE:
<223> OTHER INFORMATION: Synthetic sequence

<400> SEQUENCE: 202
atctgggaca catccagat					19

<210> SEQ ID NO 203
<211> LENGTH: 19
<212> TYPE: DNA
<213> ORGANISM: Artificial Sequence
<220> FEATURE:
<223> OTHER INFORMATION: Synthetic sequence

<400> SEQUENCE: 203
acctctcagt attctattt					19

<210> SEQ ID NO 204
<211> LENGTH: 20
<212> TYPE: DNA
<213> ORGANISM: Artificial Sequence
<220> FEATURE:
<223> OTHER INFORMATION: Synthetic sequence

<400> SEQUENCE: 204
atctgggaca catccagatg					20

<210> SEQ ID NO 205
<211> LENGTH: 20
<212> TYPE: DNA
<213> ORGANISM: Artificial Sequence

```
<220> FEATURE:
<223> OTHER INFORMATION: Synthetic sequence

<400> SEQUENCE: 205
attcttacca aatgccatct                                               20

<210> SEQ ID NO 206
<211> LENGTH: 20
<212> TYPE: DNA
<213> ORGANISM: Artificial Sequence
<220> FEATURE:
<223> OTHER INFORMATION: Synthetic sequence

<400> SEQUENCE: 206
ttcttaccaa atgccatctg                                               20

<210> SEQ ID NO 207
<211> LENGTH: 22
<212> TYPE: DNA
<213> ORGANISM: Artificial Sequence
<220> FEATURE:
<223> OTHER INFORMATION: Synthetic sequence

<400> SEQUENCE: 207
agatggcatt tggtaagaat at                                            22

<210> SEQ ID NO 208
<211> LENGTH: 19
<212> TYPE: DNA
<213> ORGANISM: Artificial Sequence
<220> FEATURE:
<223> OTHER INFORMATION: Synthetic sequence

<400> SEQUENCE: 208
aaattattct aaaggatgg                                                19

<210> SEQ ID NO 209
<211> LENGTH: 19
<212> TYPE: DNA
<213> ORGANISM: Artificial Sequence
<220> FEATURE:
<223> OTHER INFORMATION: Synthetic sequence

<400> SEQUENCE: 209
attattctaa aggatggaa                                                19

<210> SEQ ID NO 210
<211> LENGTH: 18
<212> TYPE: DNA
<213> ORGANISM: Artificial Sequence
<220> FEATURE:
<223> OTHER INFORMATION: Synthetic sequence

<400> SEQUENCE: 210
aattattcta aaggatgg                                                 18

<210> SEQ ID NO 211
<211> LENGTH: 20
<212> TYPE: DNA
<213> ORGANISM: Artificial Sequence
<220> FEATURE:
<223> OTHER INFORMATION: Synthetic sequence

<400> SEQUENCE: 211
ccatccttta gaataattta                                               20
```

<210> SEQ ID NO 212
<211> LENGTH: 19
<212> TYPE: DNA
<213> ORGANISM: Artificial Sequence
<220> FEATURE:
<223> OTHER INFORMATION: Synthetic sequence

<400> SEQUENCE: 212 tttttttaatg tattatttt                                           19

<210> SEQ ID NO 213
<211> LENGTH: 20
<212> TYPE: DNA
<213> ORGANISM: Artificial Sequence
<220> FEATURE:
<223> OTHER INFORMATION: Synthetic sequence

<400> SEQUENCE: 213
ttactcaaaa ttagtgaata                                           20

<210> SEQ ID NO 214
<211> LENGTH: 18
<212> TYPE: DNA
<213> ORGANISM: Artificial Sequence
<220> FEATURE:
<223> OTHER INFORMATION: Synthetic sequence

<400> SEQUENCE: 214
attaatactt gcttctgg                                             18

<210> SEQ ID NO 215
<211> LENGTH: 21
<212> TYPE: DNA
<213> ORGANISM: Artificial Sequence
<220> FEATURE:
<223> OTHER INFORMATION: Synthetic sequence

<400> SEQUENCE: 215
ggaatctgaa ggagaataag a                                         21

<210> SEQ ID NO 216
<211> LENGTH: 20
<212> TYPE: DNA
<213> ORGANISM: Artificial Sequence
<220> FEATURE:
<223> OTHER INFORMATION: Synthetic sequence

<400> SEQUENCE: 216
gggaaatgtc agggttaatc                                           20

<210> SEQ ID NO 217
<211> LENGTH: 18
<212> TYPE: DNA
<213> ORGANISM: Artificial Sequence
<220> FEATURE:
<223> OTHER INFORMATION: Synthetic sequence

<400> SEQUENCE: 217
gggaaatgtc agggttaa                                             18

<210> SEQ ID NO 218
<211> LENGTH: 21
<212> TYPE: DNA
<213> ORGANISM: Artificial Sequence
<220> FEATURE:
<223> OTHER INFORMATION: Synthetic sequence

<400> SEQUENCE: 218
attaaccctg acatttccct a                                             21

<210> SEQ ID NO 219
<211> LENGTH: 20
<212> TYPE: DNA
<213> ORGANISM: Artificial Sequence
<220> FEATURE:
<223> OTHER INFORMATION: Synthetic sequence

<400> SEQUENCE: 219
gttaacttat ttttattttt                                               20

<210> SEQ ID NO 220
<211> LENGTH: 21
<212> TYPE: DNA
<213> ORGANISM: Artificial Sequence
<220> FEATURE:
<223> OTHER INFORMATION: Synthetic sequence

<400> SEQUENCE: 220
gttaacttat ttttattttt a                                             21

<210> SEQ ID NO 221
<211> LENGTH: 21
<212> TYPE: DNA
<213> ORGANISM: Artificial Sequence
<220> FEATURE:
<223> OTHER INFORMATION: Synthetic sequence

<400> SEQUENCE: 221
aaaataaaaa taagttaaca c                                             21

<210> SEQ ID NO 222
<211> LENGTH: 21
<212> TYPE: DNA
<213> ORGANISM: Artificial Sequence
<220> FEATURE:
<223> OTHER INFORMATION: Synthetic sequence

<400> SEQUENCE: 222
gggagactga ggcaggagaa t                                             21

<210> SEQ ID NO 223
<211> LENGTH: 20
<212> TYPE: DNA
<213> ORGANISM: Artificial Sequence
<220> FEATURE:
<223> OTHER INFORMATION: Synthetic sequence

<400> SEQUENCE: 223
ggagactgag gcaggagaat                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic sequence

<400> SEQUENCE: 224
ggtgggcgga tcacaaggtc                                               20

<210> SEQ ID NO 225

```
<211> LENGTH: 19
<212> TYPE: DNA
<213> ORGANISM: Artificial Sequence
<220> FEATURE:
<223> OTHER INFORMATION: Synthetic sequence

<400> SEQUENCE: 225 attttgtat ttttagtag                                                      19

<210> SEQ ID NO 226
<211> LENGTH: 18
<212> TYPE: DNA
<213> ORGANISM: Artificial Sequence
<220> FEATURE:
<223> OTHER INFORMATION: Synthetic sequence

<400> SEQUENCE: 226
tttttgtatt tttagtag                                                      18

<210> SEQ ID NO 227
<211> LENGTH: 20
<212> TYPE: DNA
<213> ORGANISM: Artificial Sequence
<220> FEATURE:
<223> OTHER INFORMATION: Synthetic sequence

<400> SEQUENCE: 227
attttgaatg cggaaccaac                                                    20

<210> SEQ ID NO 228
<211> LENGTH: 19
<212> TYPE: DNA
<213> ORGANISM: Artificial Sequence
<220> FEATURE:
<223> OTHER INFORMATION: Synthetic sequence

<400> SEQUENCE: 228
tacttagcag agttcaaca                                                     19

<210> SEQ ID NO 229
<211> LENGTH: 51
<212> TYPE: DNA
<213> ORGANISM: Artificial Sequence
<220> FEATURE:
<223> OTHER INFORMATION: Synthetic sequence

<400> SEQUENCE: 229
gtctgcgtca gggtttcctt cttttccagc cccaccccgc gtgcatccca c                 51

<210> SEQ ID NO 230
<211> LENGTH: 51
<212> TYPE: DNA
<213> ORGANISM: Artificial Sequence
<220> FEATURE:
<223> OTHER INFORMATION: Synthetic sequence

<400> SEQUENCE: 230
gtgggatgca cgcggggtgg ggctggaaaa gaaggaaacc ctgacgcaga c                 51

<210> SEQ ID NO 231
<211> LENGTH: 51
<212> TYPE: DNA
<213> ORGANISM: Artificial Sequence
<220> FEATURE:
<223> OTHER INFORMATION: Synthetic sequence

<400> SEQUENCE: 231
```

```
gtctgcgtca gggtttcctt cttttgcagc cccaccccgc gtgcatccca c         51
```

<210> SEQ ID NO 232
<211> LENGTH: 51
<212> TYPE: DNA
<213> ORGANISM: Artificial Sequence
<220> FEATURE:
<223> OTHER INFORMATION: Synthetic sequence

<400> SEQUENCE: 232

```
gtgggatgca cgcggggtgg ggctgcaaaa gaaggaaacc ctgacgcaga c         51
```

<210> SEQ ID NO 233
<211> LENGTH: 51
<212> TYPE: DNA
<213> ORGANISM: Artificial Sequence
<220> FEATURE:
<223> OTHER INFORMATION: Synthetic sequence

<400> SEQUENCE: 233

```
tcaaggcctc ttctctcttc tcggcaggac aggcacaggc aggtggccag g         51
```

<210> SEQ ID NO 234
<211> LENGTH: 51
<212> TYPE: DNA
<213> ORGANISM: Artificial Sequence
<220> FEATURE:
<223> OTHER INFORMATION: Synthetic sequence

<400> SEQUENCE: 234

```
cctggccacc tgcctgtgcc tgtcctgccg agaagagaga agaggccttg a         51
```

<210> SEQ ID NO 235
<211> LENGTH: 51
<212> TYPE: DNA
<213> ORGANISM: Artificial Sequence
<220> FEATURE:
<223> OTHER INFORMATION: Synthetic sequence

<400> SEQUENCE: 235

```
tcaaggcctc ttctctcttc tcggcgggac aggcacaggc aggtggccag g         51
```

<210> SEQ ID NO 236
<211> LENGTH: 51
<212> TYPE: DNA
<213> ORGANISM: Artificial Sequence
<220> FEATURE:
<223> OTHER INFORMATION: Synthetic sequence

<400> SEQUENCE: 236

```
cctggccacc tgcctgtgcc tgtcccgccg agaagagaga agaggccttg a         51
```

<210> SEQ ID NO 237
<211> LENGTH: 51
<212> TYPE: DNA
<213> ORGANISM: Artificial Sequence
<220> FEATURE:
<223> OTHER INFORMATION: Synthetic sequence

<400> SEQUENCE: 237

```
gccaggtgtc atgcttagct ccccgcccag tgagattctt tcatttaaca a         51
```

<210> SEQ ID NO 238
<211> LENGTH: 51
<212> TYPE: DNA

```
<213> ORGANISM: Artificial Sequence
<220> FEATURE:
<223> OTHER INFORMATION: Synthetic sequence

<400> SEQUENCE: 238
ttgttaaatg aaagaatctc actgggcggg gagctaagca tgacacctgg c                51

<210> SEQ ID NO 239
<211> LENGTH: 51
<212> TYPE: DNA
<213> ORGANISM: Artificial Sequence
<220> FEATURE:
<223> OTHER INFORMATION: Synthetic sequence

<400> SEQUENCE: 239
gccaggtgtc atgcttagct ccccggccag tgagattctt tcatttaaca a                51

<210> SEQ ID NO 240
<211> LENGTH: 51
<212> TYPE: DNA
<213> ORGANISM: Artificial Sequence
<220> FEATURE:
<223> OTHER INFORMATION: Synthetic sequence

<400> SEQUENCE: 240
ttgttaaatg aaagaatctc actggccggg gagctaagca tgacacctgg c                51

<210> SEQ ID NO 241
<211> LENGTH: 51
<212> TYPE: DNA
<213> ORGANISM: Artificial Sequence
<220> FEATURE:
<223> OTHER INFORMATION: Synthetic sequence

<400> SEQUENCE: 241
gattacaggc acctgccacc atgcccggct aattttttgta tttttagttg a               51

<210> SEQ ID NO 242
<211> LENGTH: 51
<212> TYPE: DNA
<213> ORGANISM: Artificial Sequence
<220> FEATURE:
<223> OTHER INFORMATION: Synthetic sequence

<400> SEQUENCE: 242
tcaactaaaa atacaaaaat tagccgggca tggtggcagg tgcctgtaat c                51

<210> SEQ ID NO 243
<211> LENGTH: 51
<212> TYPE: DNA
<213> ORGANISM: Artificial Sequence
<220> FEATURE:
<223> OTHER INFORMATION: Synthetic sequence

<400> SEQUENCE: 243
gattacaggc acctgccacc atgcctggct aattttttgta tttttagttg a               51

<210> SEQ ID NO 244
<211> LENGTH: 51
<212> TYPE: DNA
<213> ORGANISM: Artificial Sequence
<220> FEATURE:
<223> OTHER INFORMATION: Synthetic sequence

<400> SEQUENCE: 244
tcaactaaaa atacaaaaat tagccaggca tggtggcagg tgcctgtaat c                51
```

<210> SEQ ID NO 245
<211> LENGTH: 51
<212> TYPE: DNA
<213> ORGANISM: Artificial Sequence
<220> FEATURE:
<223> OTHER INFORMATION: Synthetic sequence

<400> SEQUENCE: 245
gagggtttca tcttgttggt caggcggact tgaactcctg acctcaggtg a       51

<210> SEQ ID NO 246
<211> LENGTH: 51
<212> TYPE: DNA
<213> ORGANISM: Artificial Sequence
<220> FEATURE:
<223> OTHER INFORMATION: Synthetic sequence

<400> SEQUENCE: 246
tcacctgagg tcaggagttc aagtccgcct gaccaacaag atgaaaccct c       51

<210> SEQ ID NO 247
<211> LENGTH: 51
<212> TYPE: DNA
<213> ORGANISM: Artificial Sequence
<220> FEATURE:
<223> OTHER INFORMATION: Synthetic sequence

<400> SEQUENCE: 247
gagggtttca tcttgttggt caggcagact tgaactcctg acctcaggtg a       51

<210> SEQ ID NO 248
<211> LENGTH: 51
<212> TYPE: DNA
<213> ORGANISM: Artificial Sequence
<220> FEATURE:
<223> OTHER INFORMATION: Synthetic sequence

<400> SEQUENCE: 248
tcacctgagg tcaggagttc aagtctgcct gaccaacaag atgaaaccct c       51

<210> SEQ ID NO 249
<211> LENGTH: 51
<212> TYPE: DNA
<213> ORGANISM: Artificial Sequence
<220> FEATURE:
<223> OTHER INFORMATION: Synthetic sequence

<400> SEQUENCE: 249
gctgtttttt ctttagaatg ggggacgtta tcaggctcta catggtgtgt a       51

<210> SEQ ID NO 250
<211> LENGTH: 51
<212> TYPE: DNA
<213> ORGANISM: Artificial Sequence
<220> FEATURE:
<223> OTHER INFORMATION: Synthetic sequence

<400> SEQUENCE: 250
tacacaccat gtagagcctg ataacgtccc ccattctaaa gaaaaaacag c       51

<210> SEQ ID NO 251
<211> LENGTH: 51
<212> TYPE: DNA
<213> ORGANISM: Artificial Sequence
<220> FEATURE:

<223> OTHER INFORMATION: Synthetic sequence

<400> SEQUENCE: 251
gctgtttttt ctttagaatg ggggaggtta tcaggctcta catggtgtgt a                    51

<210> SEQ ID NO 252
<211> LENGTH: 51
<212> TYPE: DNA
<213> ORGANISM: Artificial Sequence
<220> FEATURE:
<223> OTHER INFORMATION: Synthetic sequence

<400> SEQUENCE: 252
tacacaccat gtagagcctg ataacctccc ccattctaaa gaaaaaacag c                    51

<210> SEQ ID NO 253
<211> LENGTH: 51
<212> TYPE: DNA
<213> ORGANISM: Artificial Sequence
<220> FEATURE:
<223> OTHER INFORMATION: Synthetic sequence

<400> SEQUENCE: 253
tctacatggt gtgtagtcgg ctagcatgtt gtaagccttt ccctgtgtca c                    51

<210> SEQ ID NO 254
<211> LENGTH: 51
<212> TYPE: DNA
<213> ORGANISM: Artificial Sequence
<220> FEATURE:
<223> OTHER INFORMATION: Synthetic sequence

<400> SEQUENCE: 254
gtgacacagg gaaaggctta caacatgcta gccgactaca caccatgtag a                    51

<210> SEQ ID NO 255
<211> LENGTH: 51
<212> TYPE: DNA
<213> ORGANISM: Artificial Sequence
<220> FEATURE:
<223> OTHER INFORMATION: Synthetic sequence

<400> SEQUENCE: 255
tctacatggt gtgtagtcgg ctagcgtgtt gtaagccttt ccctgtgtca c                    51

<210> SEQ ID NO 256
<211> LENGTH: 51
<212> TYPE: DNA
<213> ORGANISM: Artificial Sequence
<220> FEATURE:
<223> OTHER INFORMATION: Synthetic sequence

<400> SEQUENCE: 256
gtgacacagg gaaaggctta caacacgcta gccgactaca caccatgtag a                    51

<210> SEQ ID NO 257
<211> LENGTH: 51
<212> TYPE: DNA
<213> ORGANISM: Artificial Sequence
<220> FEATURE:
<223> OTHER INFORMATION: Synthetic sequence

<400> SEQUENCE: 257
ctgtgtcaca agtgctcatc tggaacagga ttctaatgac tgcctgtggc t                    51

<210> SEQ ID NO 258
<211> LENGTH: 51
<212> TYPE: DNA
<213> ORGANISM: Artificial Sequence
<220> FEATURE:
<223> OTHER INFORMATION: Synthetic sequence

<400> SEQUENCE: 258
agccacaggc agtcattaga atcctgttcc agatgagcac ttgtgacaca g        51

<210> SEQ ID NO 259
<211> LENGTH: 51
<212> TYPE: DNA
<213> ORGANISM: Artificial Sequence
<220> FEATURE:
<223> OTHER INFORMATION: Synthetic sequence

<400> SEQUENCE: 259
ctgtgtcaca agtgctcatc tggaagagga ttctaatgac tgcctgtggc t        51

<210> SEQ ID NO 260
<211> LENGTH: 51
<212> TYPE: DNA
<213> ORGANISM: Artificial Sequence
<220> FEATURE:
<223> OTHER INFORMATION: Synthetic sequence

<400> SEQUENCE: 260
agccacaggc agtcattaga atcctcttcc agatgagcac ttgtgacaca g        51

<210> SEQ ID NO 261
<211> LENGTH: 51
<212> TYPE: DNA
<213> ORGANISM: Artificial Sequence
<220> FEATURE:
<223> OTHER INFORMATION: Synthetic sequence

<400> SEQUENCE: 261
tcattttatg tgattccttt ctagaagtac tactcattac ttctgcttgc a        51

<210> SEQ ID NO 262
<211> LENGTH: 51
<212> TYPE: DNA
<213> ORGANISM: Artificial Sequence
<220> FEATURE:
<223> OTHER INFORMATION: Synthetic sequence

<400> SEQUENCE: 262
tgcaagcaga agtaatgagt agtacttcta gaaaggaatc acataaaatg a        51

<210> SEQ ID NO 263
<211> LENGTH: 51
<212> TYPE: DNA
<213> ORGANISM: Artificial Sequence
<220> FEATURE:
<223> OTHER INFORMATION: Synthetic sequence

<400> SEQUENCE: 263
tcattttatg tgattccttt ctagaggtac tactcattac ttctgcttgc a        51

<210> SEQ ID NO 264
<211> LENGTH: 51
<212> TYPE: DNA
<213> ORGANISM: Artificial Sequence
<220> FEATURE:
<223> OTHER INFORMATION: Synthetic sequence

<400> SEQUENCE: 264
tgcaagcaga agtaatgagt agtacctcta gaaaggaatc acataaaatg a        51

<210> SEQ ID NO 265
<211> LENGTH: 51
<212> TYPE: DNA
<213> ORGANISM: Artificial Sequence
<220> FEATURE:
<223> OTHER INFORMATION: Synthetic sequence

<400> SEQUENCE: 265
tagctgaagg aaggacaggg actgtcatac actagctaag aggcaaactg c        51

<210> SEQ ID NO 266
<211> LENGTH: 51
<212> TYPE: DNA
<213> ORGANISM: Artificial Sequence
<220> FEATURE:
<223> OTHER INFORMATION: Synthetic sequence

<400> SEQUENCE: 266
gcagtttgcc tcttagctag tgtatgacag tccctgtcct tccttcagct a        51

<210> SEQ ID NO 267
<211> LENGTH: 51
<212> TYPE: DNA
<213> ORGANISM: Artificial Sequence
<220> FEATURE:
<223> OTHER INFORMATION: Synthetic sequence

<400> SEQUENCE: 267
tagctgaagg aaggacaggg actgttatac actagctaag aggcaaactg c        51

<210> SEQ ID NO 268
<211> LENGTH: 51
<212> TYPE: DNA
<213> ORGANISM: Artificial Sequence
<220> FEATURE:
<223> OTHER INFORMATION: Synthetic sequence

<400> SEQUENCE: 268
gcagtttgcc tcttagctag tgtataacag tccctgtcct tccttcagct a        51

<210> SEQ ID NO 269
<211> LENGTH: 51
<212> TYPE: DNA
<213> ORGANISM: Artificial Sequence
<220> FEATURE:
<223> OTHER INFORMATION: Synthetic sequence

<400> SEQUENCE: 269
tccctcattc aggttgatgt cctaaccccc agaacctcag aatgggattg t        51

<210> SEQ ID NO 270
<211> LENGTH: 51
<212> TYPE: DNA
<213> ORGANISM: Artificial Sequence
<220> FEATURE:
<223> OTHER INFORMATION: Synthetic sequence

<400> SEQUENCE: 270
acaatcccat tctgaggttc tggggttag gacatcaacc tgaatgaggg a        51

<210> SEQ ID NO 271
<211> LENGTH: 51

```
<212> TYPE: DNA
<213> ORGANISM: Artificial Sequence
<220> FEATURE:
<223> OTHER INFORMATION: Synthetic sequence

<400> SEQUENCE: 271
tccctcattc aggttgatgt cctaagcccc agaacctcag aatgggattg t         51

<210> SEQ ID NO 272
<211> LENGTH: 51
<212> TYPE: DNA
<213> ORGANISM: Artificial Sequence
<220> FEATURE:
<223> OTHER INFORMATION: Synthetic sequence

<400> SEQUENCE: 272
acaatcccat tctgaggttc tggggcttag gacatcaacc tgaatgaggg a         51

<210> SEQ ID NO 273
<211> LENGTH: 51
<212> TYPE: DNA
<213> ORGANISM: Artificial Sequence
<220> FEATURE:
<223> OTHER INFORMATION: Synthetic sequence

<400> SEQUENCE: 273
tccatgccaa gaaggcaaca gagagggcca gggagactga agtcataccc t         51

<210> SEQ ID NO 274
<211> LENGTH: 51
<212> TYPE: DNA
<213> ORGANISM: Artificial Sequence
<220> FEATURE:
<223> OTHER INFORMATION: Synthetic sequence

<400> SEQUENCE: 274
agggtatgac ttcagtctcc ctggccctct ctgttgcctt cttggcatgg a         51

<210> SEQ ID NO 275
<211> LENGTH: 51
<212> TYPE: DNA
<213> ORGANISM: Artificial Sequence
<220> FEATURE:
<223> OTHER INFORMATION: Synthetic sequence

<400> SEQUENCE: 275
tccatgccaa gaaggcaaca gagagtgcca gggagactga agtcataccc t         51

<210> SEQ ID NO 276
<211> LENGTH: 51
<212> TYPE: DNA
<213> ORGANISM: Artificial Sequence
<220> FEATURE:
<223> OTHER INFORMATION: Synthetic sequence

<400> SEQUENCE: 276
agggtatgac ttcagtctcc ctggcactct ctgttgcctt cttggcatgg a         51

<210> SEQ ID NO 277
<211> LENGTH: 51
<212> TYPE: DNA
<213> ORGANISM: Artificial Sequence
<220> FEATURE:
<223> OTHER INFORMATION: Synthetic sequence

<400> SEQUENCE: 277
```

-continued

```
cccaggttca agcaattctg cctcagcctc cggaatagct gggactacag g         51

<210> SEQ ID NO 278
<211> LENGTH: 51
<212> TYPE: DNA
<213> ORGANISM: Artificial Sequence
<220> FEATURE:
<223> OTHER INFORMATION: Synthetic sequence

<400> SEQUENCE: 278
cctgtagtcc cagctattcc ggaggctgag gcagaattgc ttgaacctgg g         51

<210> SEQ ID NO 279
<211> LENGTH: 51
<212> TYPE: DNA
<213> ORGANISM: Artificial Sequence
<220> FEATURE:
<223> OTHER INFORMATION: Synthetic sequence

<400> SEQUENCE: 279
cccaggttca agcaattctg cctcaacctc cggaatagct gggactacag g         51

<210> SEQ ID NO 280
<211> LENGTH: 51
<212> TYPE: DNA
<213> ORGANISM: Artificial Sequence
<220> FEATURE:
<223> OTHER INFORMATION: Synthetic sequence

<400> SEQUENCE: 280
cctgtagtcc cagctattcc ggaggttgag gcagaattgc ttgaacctgg g         51

<210> SEQ ID NO 281
<211> LENGTH: 51
<212> TYPE: DNA
<213> ORGANISM: Artificial Sequence
<220> FEATURE:
<223> OTHER INFORMATION: Synthetic sequence

<400> SEQUENCE: 281
tgtggcctgg ctaaagtagg ctttactggg ctcctctctg cctgcatcac c         51

<210> SEQ ID NO 282
<211> LENGTH: 51
<212> TYPE: DNA
<213> ORGANISM: Artificial Sequence
<220> FEATURE:
<223> OTHER INFORMATION: Synthetic sequence

<400> SEQUENCE: 282
ggtgatgcag gcagagagga gcccagtaaa gcctacttta gccaggccac a         51

<210> SEQ ID NO 283
<211> LENGTH: 51
<212> TYPE: DNA
<213> ORGANISM: Artificial Sequence
<220> FEATURE:
<223> OTHER INFORMATION: Synthetic sequence

<400> SEQUENCE: 283
tgtggcctgg ctaaagtagg ctttagtggg ctcctctctg cctgcatcac c         51

<210> SEQ ID NO 284
<211> LENGTH: 51
<212> TYPE: DNA
<213> ORGANISM: Artificial Sequence
```

<220> FEATURE:
<223> OTHER INFORMATION: Synthetic sequence

<400> SEQUENCE: 284
ggtgatgcag gcagagagga gcccactaaa gcctacttta gccaggccac a          51

<210> SEQ ID NO 285
<211> LENGTH: 51
<212> TYPE: DNA
<213> ORGANISM: Artificial Sequence
<220> FEATURE:
<223> OTHER INFORMATION: Synthetic sequence

<400> SEQUENCE: 285
ctccccgcag ggctgtccgg gtgagtatgg ctctggccac gggccagtgt g          51

<210> SEQ ID NO 286
<211> LENGTH: 51
<212> TYPE: DNA
<213> ORGANISM: Artificial Sequence
<220> FEATURE:
<223> OTHER INFORMATION: Synthetic sequence

<400> SEQUENCE: 286
cacactggcc cgtggccaga gccatactca cccggacagc cctgcgggga g          51

<210> SEQ ID NO 287
<211> LENGTH: 51
<212> TYPE: DNA
<213> ORGANISM: Artificial Sequence
<220> FEATURE:
<223> OTHER INFORMATION: Synthetic sequence

<400> SEQUENCE: 287
ctccccgcag ggctgtccgg gtgagcatgg ctctggccac gggccagtgt g          51

<210> SEQ ID NO 288
<211> LENGTH: 51
<212> TYPE: DNA
<213> ORGANISM: Artificial Sequence
<220> FEATURE:
<223> OTHER INFORMATION: Synthetic sequence

<400> SEQUENCE: 288
cacactggcc cgtggccaga gccatgctca cccggacagc cctgcgggga g          51

<210> SEQ ID NO 289
<211> LENGTH: 51
<212> TYPE: DNA
<213> ORGANISM: Artificial Sequence
<220> FEATURE:
<223> OTHER INFORMATION: Synthetic sequence

<400> SEQUENCE: 289
gggcgcaggc ccatgcggaa aggatccccc gccgacgcct ggagcggggc g          51

<210> SEQ ID NO 290
<211> LENGTH: 51
<212> TYPE: DNA
<213> ORGANISM: Artificial Sequence
<220> FEATURE:
<223> OTHER INFORMATION: Synthetic sequence

<400> SEQUENCE: 290
cgccccgctc caggcgtcgg cgggggatcc tttccgcatg ggcctgcgcc c          51

```
<210> SEQ ID NO 291
<211> LENGTH: 51
<212> TYPE: DNA
<213> ORGANISM: Artificial Sequence
<220> FEATURE:
<223> OTHER INFORMATION: Synthetic sequence

<400> SEQUENCE: 291
gggcgcaggc ccatgcggaa aggatgcccc gccgacgcct ggagcggggc g        51

<210> SEQ ID NO 292
<211> LENGTH: 51
<212> TYPE: DNA
<213> ORGANISM: Artificial Sequence
<220> FEATURE:
<223> OTHER INFORMATION: Synthetic sequence

<400> SEQUENCE: 292
cgccccgctc caggcgtcgg cggggcatcc tttccgcatg ggcctgcgcc c         51

<210> SEQ ID NO 293
<211> LENGTH: 51
<212> TYPE: DNA
<213> ORGANISM: Artificial Sequence
<220> FEATURE:
<223> OTHER INFORMATION: Synthetic sequence

<400> SEQUENCE: 293
gggcgcaggc ccatgcggaa aggataccCC gccgacgcct ggagcggggc g        51

<210> SEQ ID NO 294
<211> LENGTH: 51
<212> TYPE: DNA
<213> ORGANISM: Artificial Sequence
<220> FEATURE:
<223> OTHER INFORMATION: Synthetic sequence

<400> SEQUENCE: 294
cgccccgctc caggcgtcgg cggggtatcc tttccgcatg ggcctgcgcc c         51

<210> SEQ ID NO 295
<211> LENGTH: 51
<212> TYPE: DNA
<213> ORGANISM: Artificial Sequence
<220> FEATURE:
<223> OTHER INFORMATION: Synthetic sequence

<400> SEQUENCE: 295
ccccgccccg gcctcgccac gcccctacct caccacgccc ccgcatcgc c         51

<210> SEQ ID NO 296
<211> LENGTH: 51
<212> TYPE: DNA
<213> ORGANISM: Artificial Sequence
<220> FEATURE:
<223> OTHER INFORMATION: Synthetic sequence

<400> SEQUENCE: 296
ggcgatgcgg ggggcgtggt gaggtagggg cgtggcgagg ccggggcggg g        51

<210> SEQ ID NO 297
<211> LENGTH: 51
<212> TYPE: DNA
<213> ORGANISM: Artificial Sequence
<220> FEATURE:
<223> OTHER INFORMATION: Synthetic sequence
```

<400> SEQUENCE: 297
ccccgccccg gcctcgccac gcccccacct caccacgccc ccgcatcgc c        51

<210> SEQ ID NO 298
<211> LENGTH: 51
<212> TYPE: DNA
<213> ORGANISM: Artificial Sequence
<220> FEATURE:
<223> OTHER INFORMATION: Synthetic sequence

<400> SEQUENCE: 298
ggcgatgcgg gggcgtggt gaggtggggg cgtggcgagg ccggggcggg g        51

<210> SEQ ID NO 299
<211> LENGTH: 51
<212> TYPE: DNA
<213> ORGANISM: Artificial Sequence
<220> FEATURE:
<223> OTHER INFORMATION: Synthetic sequence

<400> SEQUENCE: 299
attacagtct caccacgccc cgtccctct ccgttgagcc ccgcgccttc g        51

<210> SEQ ID NO 300
<211> LENGTH: 51
<212> TYPE: DNA
<213> ORGANISM: Artificial Sequence
<220> FEATURE:
<223> OTHER INFORMATION: Synthetic sequence

<400> SEQUENCE: 300
cgaaggcgcg gggctcaacg gagaggggac ggggcgtggt gagactgtaa t        51

<210> SEQ ID NO 301
<211> LENGTH: 51
<212> TYPE: DNA
<213> ORGANISM: Artificial Sequence
<220> FEATURE:
<223> OTHER INFORMATION: Synthetic sequence

<400> SEQUENCE: 301
attacagtct caccacgccc cgtccgctct ccgttgagcc ccgcgccttc g        51

<210> SEQ ID NO 302
<211> LENGTH: 51
<212> TYPE: DNA
<213> ORGANISM: Artificial Sequence
<220> FEATURE:
<223> OTHER INFORMATION: Synthetic sequence

<400> SEQUENCE: 302
cgaaggcgcg gggctcaacg gagagcggac ggggcgtggt gagactgtaa t        51

<210> SEQ ID NO 303
<211> LENGTH: 50
<212> TYPE: DNA
<213> ORGANISM: Artificial Sequence
<220> FEATURE:
<223> OTHER INFORMATION: Synthetic sequence

<400> SEQUENCE: 303
ggccttgctg tgtgaggcag aacctgcggg ggcaggggcg ggctggttcc           50

<210> SEQ ID NO 304

```
<211> LENGTH: 50
<212> TYPE: DNA
<213> ORGANISM: Artificial Sequence
<220> FEATURE:
<223> OTHER INFORMATION: Synthetic sequence

<400> SEQUENCE: 304
ggaaccagcc cgcccctgcc cccgcaggtt ctgcctcaca cagcaaggcc          50

<210> SEQ ID NO 305
<211> LENGTH: 56
<212> TYPE: DNA
<213> ORGANISM: Artificial Sequence
<220> FEATURE:
<223> OTHER INFORMATION: Synthetic sequence

<400> SEQUENCE: 305
ggccttgctg tgtgaggcag aacctgcggg ggcgggggca ggggcgggct ggttcc    56

<210> SEQ ID NO 306
<211> LENGTH: 56
<212> TYPE: DNA
<213> ORGANISM: Artificial Sequence
<220> FEATURE:
<223> OTHER INFORMATION: Synthetic sequence

<400> SEQUENCE: 306
ggaaccagcc cgcccctgcc cccgcccccg caggttctgc ctcacacagc aaggcc    56

<210> SEQ ID NO 307
<211> LENGTH: 51
<212> TYPE: DNA
<213> ORGANISM: Artificial Sequence
<220> FEATURE:
<223> OTHER INFORMATION: Synthetic sequence

<400> SEQUENCE: 307
tgtgtgaggc agaacctgcg ggggcagggg cgggctggtt ccctggccag c        51

<210> SEQ ID NO 308
<211> LENGTH: 51
<212> TYPE: DNA
<213> ORGANISM: Artificial Sequence
<220> FEATURE:
<223> OTHER INFORMATION: Synthetic sequence

<400> SEQUENCE: 308
gctggccagg gaaccagccc gcccctgccc ccgcaggttc tgcctcacac a        51

<210> SEQ ID NO 309
<211> LENGTH: 51
<212> TYPE: DNA
<213> ORGANISM: Artificial Sequence
<220> FEATURE:
<223> OTHER INFORMATION: Synthetic sequence

<400> SEQUENCE: 309
tgtgtgaggc agaacctgcg ggggcggggg cgggctggtt ccctggccag c        51

<210> SEQ ID NO 310
<211> LENGTH: 51
<212> TYPE: DNA
<213> ORGANISM: Artificial Sequence
<220> FEATURE:
<223> OTHER INFORMATION: Synthetic sequence

<400> SEQUENCE: 310
```
gctggccagg gaaccagccc gcccccgccc ccgcaggttc tgcctcacac a          51

<210> SEQ ID NO 311
<211> LENGTH: 51
<212> TYPE: DNA
<213> ORGANISM: Artificial Sequence
<220> FEATURE:
<223> OTHER INFORMATION: Synthetic sequence

<400> SEQUENCE: 311
agcgtctggg acgcaaggcg ccgtgggggc tgccgggacg ggtccaagat g          51

<210> SEQ ID NO 312
<211> LENGTH: 51
<212> TYPE: DNA
<213> ORGANISM: Artificial Sequence
<220> FEATURE:
<223> OTHER INFORMATION: Synthetic sequence

<400> SEQUENCE: 312
catcttggac ccgtcccggc agcccccacg gcgccttgcg tcccagacgc t          51

<210> SEQ ID NO 313
<211> LENGTH: 51
<212> TYPE: DNA
<213> ORGANISM: Artificial Sequence
<220> FEATURE:
<223> OTHER INFORMATION: Synthetic sequence

<400> SEQUENCE: 313
agcgtctggg acgcaaggcg ccgtgagggc tgccgggacg ggtccaagat g          51

<210> SEQ ID NO 314
<211> LENGTH: 51
<212> TYPE: DNA
<213> ORGANISM: Artificial Sequence
<220> FEATURE:
<223> OTHER INFORMATION: Synthetic sequence

<400> SEQUENCE: 314
catcttggac ccgtcccggc agccctcacg gcgccttgcg tcccagacgc t          51

<210> SEQ ID NO 315
<211> LENGTH: 51
<212> TYPE: DNA
<213> ORGANISM: Artificial Sequence
<220> FEATURE:
<223> OTHER INFORMATION: Synthetic sequence

<400> SEQUENCE: 315
ctcacttggg tcttcccttg tcctctcgcg aggggaggca gagccttgtt g          51

<210> SEQ ID NO 316
<211> LENGTH: 51
<212> TYPE: DNA
<213> ORGANISM: Artificial Sequence
<220> FEATURE:
<223> OTHER INFORMATION: Synthetic sequence

<400> SEQUENCE: 316
caacaaggct ctgcctcccc tcgcgagagg acaagggaag acccaagtga g          51

<210> SEQ ID NO 317
<211> LENGTH: 51
<212> TYPE: DNA

```
<213> ORGANISM: Artificial Sequence
<220> FEATURE:
<223> OTHER INFORMATION: Synthetic sequence

<400> SEQUENCE: 317
ctcacttggg tcttcccttg tcctcccgcg aggggaggca gagccttgtt g        51

<210> SEQ ID NO 318
<211> LENGTH: 51
<212> TYPE: DNA
<213> ORGANISM: Artificial Sequence
<220> FEATURE:
<223> OTHER INFORMATION: Synthetic sequence

<400> SEQUENCE: 318
caacaaggct ctgcctcccc tcgcgggagg acaagggaag acccaagtga g        51

<210> SEQ ID NO 319
<211> LENGTH: 51
<212> TYPE: DNA
<213> ORGANISM: Artificial Sequence
<220> FEATURE:
<223> OTHER INFORMATION: Synthetic sequence

<400> SEQUENCE: 319
tgaatgagtt gtggttgcca agtaaagtgg tgaacttacg tggtgattaa t        51

<210> SEQ ID NO 320
<211> LENGTH: 51
<212> TYPE: DNA
<213> ORGANISM: Artificial Sequence
<220> FEATURE:
<223> OTHER INFORMATION: Synthetic sequence

<400> SEQUENCE: 320
attaatcacc acgtaagttc accactttac ttggcaacca caactcattc a        51

<210> SEQ ID NO 321
<211> LENGTH: 50
<212> TYPE: DNA
<213> ORGANISM: Artificial Sequence
<220> FEATURE:
<223> OTHER INFORMATION: Synthetic sequence

<400> SEQUENCE: 321
tgaatgagtt gtggttgcca agtaagtggt gaacttacgt ggtgattaat          50

<210> SEQ ID NO 322
<211> LENGTH: 50
<212> TYPE: DNA
<213> ORGANISM: Artificial Sequence
<220> FEATURE:
<223> OTHER INFORMATION: Synthetic sequence

<400> SEQUENCE: 322
attaatcacc acgtaagttc accacttact tggcaaccac aactcattca          50

<210> SEQ ID NO 323
<211> LENGTH: 51
<212> TYPE: DNA
<213> ORGANISM: Artificial Sequence
<220> FEATURE:
<223> OTHER INFORMATION: Synthetic sequence

<400> SEQUENCE: 323
acagtaggag ttaggaagta ctctggtgca gttcaggcct ttctcttacc t        51
```

<210> SEQ ID NO 324
<211> LENGTH: 51
<212> TYPE: DNA
<213> ORGANISM: Artificial Sequence
<220> FEATURE:
<223> OTHER INFORMATION: Synthetic sequence

<400> SEQUENCE: 324
aggtaagaga aaggcctgaa ctgcaccaga gtacttccta actcctactg t    51

<210> SEQ ID NO 325
<211> LENGTH: 51
<212> TYPE: DNA
<213> ORGANISM: Artificial Sequence
<220> FEATURE:
<223> OTHER INFORMATION: Synthetic sequence

<400> SEQUENCE: 325
acagtaggag ttaggaagta ctctgctgca gttcaggcct ttctcttacc t    51

<210> SEQ ID NO 326
<211> LENGTH: 51
<212> TYPE: DNA
<213> ORGANISM: Artificial Sequence
<220> FEATURE:
<223> OTHER INFORMATION: Synthetic sequence

<400> SEQUENCE: 326
aggtaagaga aaggcctgaa ctgcagcaga gtacttccta actcctactg t    51

<210> SEQ ID NO 327
<211> LENGTH: 51
<212> TYPE: DNA
<213> ORGANISM: Artificial Sequence
<220> FEATURE:
<223> OTHER INFORMATION: Synthetic sequence

<400> SEQUENCE: 327
cagtaggagt taggaagtac tctggtgcag ttcaggcctt tctcttacct c    51

<210> SEQ ID NO 328
<211> LENGTH: 51
<212> TYPE: DNA
<213> ORGANISM: Artificial Sequence
<220> FEATURE:
<223> OTHER INFORMATION: Synthetic sequence

<400> SEQUENCE: 328
gaggtaagag aaaggcctga actgcaccag agtacttcct aactcctact g    51

<210> SEQ ID NO 329
<211> LENGTH: 51
<212> TYPE: DNA
<213> ORGANISM: Artificial Sequence
<220> FEATURE:
<223> OTHER INFORMATION: Synthetic sequence

<400> SEQUENCE: 329
cagtaggagt taggaagtac tctggcgcag ttcaggcctt tctcttacct c    51

<210> SEQ ID NO 330
<211> LENGTH: 51
<212> TYPE: DNA
<213> ORGANISM: Artificial Sequence
<220> FEATURE:

<223> OTHER INFORMATION: Synthetic sequence

<400> SEQUENCE: 330
gaggtaagag aaaggcctga actgcgccag agtacttcct aactcctact g        51

<210> SEQ ID NO 331
<211> LENGTH: 51
<212> TYPE: DNA
<213> ORGANISM: Artificial Sequence
<220> FEATURE:
<223> OTHER INFORMATION: Synthetic sequence

<400> SEQUENCE: 331
tctcttacct ctcagtattc tatttccgat ctggatgtgt cccagatggc a        51

<210> SEQ ID NO 332
<211> LENGTH: 51
<212> TYPE: DNA
<213> ORGANISM: Artificial Sequence
<220> FEATURE:
<223> OTHER INFORMATION: Synthetic sequence

<400> SEQUENCE: 332
tgccatctgg gacacatcca gatcggaaat agaatactga gaggtaagag a        51

<210> SEQ ID NO 333
<211> LENGTH: 51
<212> TYPE: DNA
<213> ORGANISM: Artificial Sequence
<220> FEATURE:
<223> OTHER INFORMATION: Synthetic sequence

<400> SEQUENCE: 333
tctcttacct ctcagtattc tatttgcgat ctggatgtgt cccagatggc a        51

<210> SEQ ID NO 334
<211> LENGTH: 51
<212> TYPE: DNA
<213> ORGANISM: Artificial Sequence
<220> FEATURE:
<223> OTHER INFORMATION: Synthetic sequence

<400> SEQUENCE: 334
tgccatctgg gacacatcca gatcgcaaat agaatactga gaggtaagag a        51

<210> SEQ ID NO 335
<211> LENGTH: 51
<212> TYPE: DNA
<213> ORGANISM: Artificial Sequence
<220> FEATURE:
<223> OTHER INFORMATION: Synthetic sequence

<400> SEQUENCE: 335
tattctattt ccgatctgga tgtgtcccag atggcatttg gtaagaatat c        51

<210> SEQ ID NO 336
<211> LENGTH: 51
<212> TYPE: DNA
<213> ORGANISM: Artificial Sequence
<220> FEATURE:
<223> OTHER INFORMATION: Synthetic sequence

<400> SEQUENCE: 336
gatattctta ccaaatgcca tctgggacac atccagatcg gaaatagaat a        51

```
<210> SEQ ID NO 337
<211> LENGTH: 51
<212> TYPE: DNA
<213> ORGANISM: Artificial Sequence
<220> FEATURE:
<223> OTHER INFORMATION: Synthetic sequence

<400> SEQUENCE: 337
tattctattt ccgatctgga tgtgtaccag atggcatttg gtaagaatat c          51

<210> SEQ ID NO 338
<211> LENGTH: 51
<212> TYPE: DNA
<213> ORGANISM: Artificial Sequence
<220> FEATURE:
<223> OTHER INFORMATION: Synthetic sequence

<400> SEQUENCE: 338
gatattctta ccaaatgcca tctggtacac atccagatcg gaaatagaat a          51

<210> SEQ ID NO 339
<211> LENGTH: 51
<212> TYPE: DNA
<213> ORGANISM: Artificial Sequence
<220> FEATURE:
<223> OTHER INFORMATION: Synthetic sequence

<400> SEQUENCE: 339
gaataaatta ttctaaagga tggaaaaact ttttggatat tggagaaat t            51

<210> SEQ ID NO 340
<211> LENGTH: 51
<212> TYPE: DNA
<213> ORGANISM: Artificial Sequence
<220> FEATURE:
<223> OTHER INFORMATION: Synthetic sequence

<400> SEQUENCE: 340
aatttctcca aatatccaaa aagttttttcc atcctttaga ataatttatt c          51

<210> SEQ ID NO 341
<211> LENGTH: 51
<212> TYPE: DNA
<213> ORGANISM: Artificial Sequence
<220> FEATURE:
<223> OTHER INFORMATION: Synthetic sequence

<400> SEQUENCE: 341
gaataaatta ttctaaagga tggaagaact ttttggatat tggagaaat t            51

<210> SEQ ID NO 342
<211> LENGTH: 51
<212> TYPE: DNA
<213> ORGANISM: Artificial Sequence
<220> FEATURE:
<223> OTHER INFORMATION: Synthetic sequence

<400> SEQUENCE: 342
aatttctcca aatatccaaa aagttcttcc atcctttaga ataatttatt c           51

<210> SEQ ID NO 343
<211> LENGTH: 51
<212> TYPE: DNA
<213> ORGANISM: Artificial Sequence
<220> FEATURE:
<223> OTHER INFORMATION: Synthetic sequence
```

<400> SEQUENCE: 343
ttgtatcatg tcaatgtatt acttatgcaa aaataataca ttaaaaaaaa t    51

<210> SEQ ID NO 344
<211> LENGTH: 51
<212> TYPE: DNA
<213> ORGANISM: Artificial Sequence
<220> FEATURE:
<223> OTHER INFORMATION: Synthetic sequence

<400> SEQUENCE: 344
atttttttta atgtattatt tttgcataag taatacattg acatgataca a    51

<210> SEQ ID NO 345
<211> LENGTH: 51
<212> TYPE: DNA
<213> ORGANISM: Artificial Sequence
<220> FEATURE:
<223> OTHER INFORMATION: Synthetic sequence

<400> SEQUENCE: 345
ttgtatcatg tcaatgtatt acttacgcaa aaataataca ttaaaaaaaa t    51

<210> SEQ ID NO 346
<211> LENGTH: 51
<212> TYPE: DNA
<213> ORGANISM: Artificial Sequence
<220> FEATURE:
<223> OTHER INFORMATION: Synthetic sequence

<400> SEQUENCE: 346
atttttttta atgtattatt tttgcgtaag taatacattg acatgataca a    51

<210> SEQ ID NO 347
<211> LENGTH: 54
<212> TYPE: DNA
<213> ORGANISM: Artificial Sequence
<220> FEATURE:
<223> OTHER INFORMATION: Synthetic sequence

<400> SEQUENCE: 347
aggtattcac taattttgag taacaaacac tgctcacaaa gtttggattt tggc    54

<210> SEQ ID NO 348
<211> LENGTH: 54
<212> TYPE: DNA
<213> ORGANISM: Artificial Sequence
<220> FEATURE:
<223> OTHER INFORMATION: Synthetic sequence

<400> SEQUENCE: 348
gccaaaatcc aaactttgtg agcagtgttt gttactcaaa attagtgaat acct    54

<210> SEQ ID NO 349
<211> LENGTH: 50
<212> TYPE: DNA
<213> ORGANISM: Artificial Sequence
<220> FEATURE:
<223> OTHER INFORMATION: Synthetic sequence

<400> SEQUENCE: 349
aggtattcac taattttgag taacactgct cacaaagttt ggattttggc    50

<210> SEQ ID NO 350
<211> LENGTH: 50

```
<212> TYPE: DNA
<213> ORGANISM: Artificial Sequence
<220> FEATURE:
<223> OTHER INFORMATION: Synthetic sequence

<400> SEQUENCE: 350
gccaaaatcc aaactttgtg agcagtgtta ctcaaaatta gtgaatacct            50

<210> SEQ ID NO 351
<211> LENGTH: 51
<212> TYPE: DNA
<213> ORGANISM: Artificial Sequence
<220> FEATURE:
<223> OTHER INFORMATION: Synthetic sequence

<400> SEQUENCE: 351
aggcaattaa tacttgcttc tggcagtttc ttattctcct tcagattcct a          51

<210> SEQ ID NO 352
<211> LENGTH: 51
<212> TYPE: DNA
<213> ORGANISM: Artificial Sequence
<220> FEATURE:
<223> OTHER INFORMATION: Synthetic sequence

<400> SEQUENCE: 352
taggaatctg aaggagaata agaaactgcc agaagcaagt attaattgcc t          51

<210> SEQ ID NO 353
<211> LENGTH: 51
<212> TYPE: DNA
<213> ORGANISM: Artificial Sequence
<220> FEATURE:
<223> OTHER INFORMATION: Synthetic sequence

<400> SEQUENCE: 353
aggcaattaa tacttgcttc tggcactttc ttattctcct tcagattcct a          51

<210> SEQ ID NO 354
<211> LENGTH: 51
<212> TYPE: DNA
<213> ORGANISM: Artificial Sequence
<220> FEATURE:
<223> OTHER INFORMATION: Synthetic sequence

<400> SEQUENCE: 354
taggaatctg aaggagaata agaaagtgcc agaagcaagt attaattgcc t          51

<210> SEQ ID NO 355
<211> LENGTH: 51
<212> TYPE: DNA
<213> ORGANISM: Artificial Sequence
<220> FEATURE:
<223> OTHER INFORMATION: Synthetic sequence

<400> SEQUENCE: 355
ttaaaaataa aaataagtta acactcgatt aaccctgaca tttccctatc c          51

<210> SEQ ID NO 356
<211> LENGTH: 51
<212> TYPE: DNA
<213> ORGANISM: Artificial Sequence
<220> FEATURE:
<223> OTHER INFORMATION: Synthetic sequence

<400> SEQUENCE: 356
``` ggataggga atgtcagggt taatcgagtg ttaacttatt tttatttta a      51

<210> SEQ ID NO 357
<211> LENGTH: 51
<212> TYPE: DNA
<213> ORGANISM: Artificial Sequence
<220> FEATURE:
<223> OTHER INFORMATION: Synthetic sequence

<400> SEQUENCE: 357
ttaaaaataa aataagtta acacttgatt aaccctgaca tttccctatc c      51

<210> SEQ ID NO 358
<211> LENGTH: 51
<212> TYPE: DNA
<213> ORGANISM: Artificial Sequence
<220> FEATURE:
<223> OTHER INFORMATION: Synthetic sequence

<400> SEQUENCE: 358
ggatagggaa atgtcagggt taatcaagtg ttaacttatt tttatttta a      51

<210> SEQ ID NO 359
<211> LENGTH: 51
<212> TYPE: DNA
<213> ORGANISM: Artificial Sequence
<220> FEATURE:
<223> OTHER INFORMATION: Synthetic sequence

<400> SEQUENCE: 359
agtgttaact tatttttatt tttaaaaaaa ttgttaaggg ctttccagca a      51

<210> SEQ ID NO 360
<211> LENGTH: 51
<212> TYPE: DNA
<213> ORGANISM: Artificial Sequence
<220> FEATURE:
<223> OTHER INFORMATION: Synthetic sequence

<400> SEQUENCE: 360
ttgctggaaa gcccttaaca atttttttaa aaataaaaat aagttaacac t      51

<210> SEQ ID NO 361
<211> LENGTH: 51
<212> TYPE: DNA
<213> ORGANISM: Artificial Sequence
<220> FEATURE:
<223> OTHER INFORMATION: Synthetic sequence

<400> SEQUENCE: 361
agtgttaact tatttttatt tttaagaaaa ttgttaaggg ctttccagca a      51

<210> SEQ ID NO 362
<211> LENGTH: 51
<212> TYPE: DNA
<213> ORGANISM: Artificial Sequence
<220> FEATURE:
<223> OTHER INFORMATION: Synthetic sequence

<400> SEQUENCE: 362
ttgctggaaa gcccttaaca attttcttaa aaataaaaat aagttaacac t      51

<210> SEQ ID NO 363
<211> LENGTH: 51
<212> TYPE: DNA
<213> ORGANISM: Artificial Sequence

```
<220> FEATURE:
<223> OTHER INFORMATION: Synthetic sequence

<400> SEQUENCE: 363
ctgcaagctc cgcttcccga gttcacgcca ttctcctgcc tcagtctccc a         51

<210> SEQ ID NO 364
<211> LENGTH: 51
<212> TYPE: DNA
<213> ORGANISM: Artificial Sequence
<220> FEATURE:
<223> OTHER INFORMATION: Synthetic sequence

<400> SEQUENCE: 364
tgggagactg aggcaggaga atggcgtgaa ctcgggaagc ggagcttgca g         51

<210> SEQ ID NO 365
<211> LENGTH: 51
<212> TYPE: DNA
<213> ORGANISM: Artificial Sequence
<220> FEATURE:
<223> OTHER INFORMATION: Synthetic sequence

<400> SEQUENCE: 365
ctgcaagctc cgcttcccga gttcatgcca ttctcctgcc tcagtctccc a         51

<210> SEQ ID NO 366
<211> LENGTH: 51
<212> TYPE: DNA
<213> ORGANISM: Artificial Sequence
<220> FEATURE:
<223> OTHER INFORMATION: Synthetic sequence

<400> SEQUENCE: 366
tgggagactg aggcaggaga atggcatgaa ctcgggaagc ggagcttgca g         51

<210> SEQ ID NO 367
<211> LENGTH: 51
<212> TYPE: DNA
<213> ORGANISM: Artificial Sequence
<220> FEATURE:
<223> OTHER INFORMATION: Synthetic sequence

<400> SEQUENCE: 367
tcttgatctc ctgacctcgt catccgccga ccttgtgatc cgcccacctc g         51

<210> SEQ ID NO 368
<211> LENGTH: 51
<212> TYPE: DNA
<213> ORGANISM: Artificial Sequence
<220> FEATURE:
<223> OTHER INFORMATION: Synthetic sequence

<400> SEQUENCE: 368
cgaggtgggc ggatcacaag gtcggcggat gacgaggtca ggagatcaag a         51

<210> SEQ ID NO 369
<211> LENGTH: 51
<212> TYPE: DNA
<213> ORGANISM: Artificial Sequence
<220> FEATURE:
<223> OTHER INFORMATION: Synthetic sequence

<400> SEQUENCE: 369
tcttgatctc ctgacctcgt catccccga ccttgtgatc cgcccacctc g          51
```

```
<210> SEQ ID NO 370
<211> LENGTH: 51
<212> TYPE: DNA
<213> ORGANISM: Artificial Sequence
<220> FEATURE:
<223> OTHER INFORMATION: Synthetic sequence

<400> SEQUENCE: 370
cgaggtgggc ggatcacaag gtcgggggat gacgaggtca ggagatcaag a        51

<210> SEQ ID NO 371
<211> LENGTH: 51
<212> TYPE: DNA
<213> ORGANISM: Artificial Sequence
<220> FEATURE:
<223> OTHER INFORMATION: Synthetic sequence

<400> SEQUENCE: 371 ggtaatttt tgtattttag tagagatggg gttttgccat gatgagcagg c          51

<210> SEQ ID NO 372
<211> LENGTH: 51
<212> TYPE: DNA
<213> ORGANISM: Artificial Sequence
<220> FEATURE:
<223> OTHER INFORMATION: Synthetic sequence

<400> SEQUENCE: 372
gcctgctcat catggcaaaa ccccatctct actaaaaata caaaaattac c         51

<210> SEQ ID NO 373
<211> LENGTH: 51
<212> TYPE: DNA
<213> ORGANISM: Artificial Sequence
<220> FEATURE:
<223> OTHER INFORMATION: Synthetic sequence

<400> SEQUENCE: 373 ggtaatttt tgtattttag tagaggtggg gttttgccat gatgagcagg c          51

<210> SEQ ID NO 374
<211> LENGTH: 51
<212> TYPE: DNA
<213> ORGANISM: Artificial Sequence
<220> FEATURE:
<223> OTHER INFORMATION: Synthetic sequence

<400> SEQUENCE: 374
gcctgctcat catggcaaaa ccccacctct actaaaaata caaaaattac c         51

<210> SEQ ID NO 375
<211> LENGTH: 51
<212> TYPE: DNA
<213> ORGANISM: Artificial Sequence
<220> FEATURE:
<223> OTHER INFORMATION: Synthetic sequence

<400> SEQUENCE: 375
ggattttgaa tgcggaacca actgcacttg ttgaactctg ctaagtataa c         51

<210> SEQ ID NO 376
<211> LENGTH: 51
<212> TYPE: DNA
<213> ORGANISM: Artificial Sequence
<220> FEATURE:
<223> OTHER INFORMATION: Synthetic sequence
```

<400> SEQUENCE: 376
gttatactta gcagagttca acaagtgcag ttggttccgc attcaaaatc c          51

<210> SEQ ID NO 377
<211> LENGTH: 51
<212> TYPE: DNA
<213> ORGANISM: Artificial Sequence
<220> FEATURE:
<223> OTHER INFORMATION: Synthetic sequence

<400> SEQUENCE: 377
ggattttgaa tgcggaacca actgcgcttg ttgaactctg ctaagtataa c          51

<210> SEQ ID NO 378
<211> LENGTH: 51
<212> TYPE: DNA
<213> ORGANISM: Artificial Sequence
<220> FEATURE:
<223> OTHER INFORMATION: Synthetic sequence

<400> SEQUENCE: 378
gttatactta gcagagttca acaagcgcag ttggttccgc attcaaaatc c          51

<210> SEQ ID NO 379
<211> LENGTH: 17
<212> TYPE: DNA
<213> ORGANISM: Artificial Sequence
<220> FEATURE:
<223> OTHER INFORMATION: Synthetic sequence

<400> SEQUENCE: 379
gctccaggcg tcggcgg                                                17

<210> SEQ ID NO 380
<211> LENGTH: 19
<212> TYPE: DNA
<213> ORGANISM: Artificial Sequence
<220> FEATURE:
<223> OTHER INFORMATION: Synthetic sequence

<400> SEQUENCE: 380
ggcgcggggc tcaacggag                                              19

<210> SEQ ID NO 381
<211> LENGTH: 20
<212> TYPE: DNA
<213> ORGANISM: Artificial Sequence
<220> FEATURE:
<223> OTHER INFORMATION: Synthetic sequence

<400> SEQUENCE: 381
gtctgggacg caaggcgccg                                             20

<210> SEQ ID NO 382
<211> LENGTH: 19
<212> TYPE: DNA
<213> ORGANISM: Artificial Sequence
<220> FEATURE:
<223> OTHER INFORMATION: Synthetic sequence

<400> SEQUENCE: 382
gatgcacgcg gggtggggc                                              19

<210> SEQ ID NO 383

```
<211> LENGTH: 17
<212> TYPE: DNA
<213> ORGANISM: Artificial Sequence
<220> FEATURE:
<223> OTHER INFORMATION: Synthetic sequence

<400> SEQUENCE: 383
attcaggttg atgtcct                                                    17

<210> SEQ ID NO 384
<211> LENGTH: 20
<212> TYPE: DNA
<213> ORGANISM: Artificial Sequence
<220> FEATURE:
<223> OTHER INFORMATION: Synthetic sequence

<400> SEQUENCE: 384
atcccattct gaggttctgg                                                 20

<210> SEQ ID NO 385
<211> LENGTH: 17
<212> TYPE: DNA
<213> ORGANISM: Artificial Sequence
<220> FEATURE:
<223> OTHER INFORMATION: Synthetic sequence

<400> SEQUENCE: 385
gcaggcagag aggagcc                                                    17

<210> SEQ ID NO 386
<211> LENGTH: 19
<212> TYPE: DNA
<213> ORGANISM: Artificial Sequence
<220> FEATURE:
<223> OTHER INFORMATION: Synthetic sequence

<400> SEQUENCE: 386
gcctggctaa agtaggctt                                                  19

<210> SEQ ID NO 387
<211> LENGTH: 18
<212> TYPE: DNA
<213> ORGANISM: Artificial Sequence
<220> FEATURE:
<223> OTHER INFORMATION: Synthetic sequence

<400> SEQUENCE: 387
gcttttagga cgcctcgg                                                   18

<210> SEQ ID NO 388
<211> LENGTH: 18
<212> TYPE: DNA
<213> ORGANISM: Artificial Sequence
<220> FEATURE:
<223> OTHER INFORMATION: Synthetic sequence

<400> SEQUENCE: 388
gcgggacact tcgagagg                                                   18

<210> SEQ ID NO 389
<211> LENGTH: 52
<212> TYPE: DNA
<213> ORGANISM: Artificial Sequence
<220> FEATURE:
<223> OTHER INFORMATION: Synthetic sequence

<400> SEQUENCE: 389
```

```
gtcgccccgc tccaggcgtc ggcgggggat cctttccgca tgggcctgcg cc        52
```

<210> SEQ ID NO 390
<211> LENGTH: 52
<212> TYPE: DNA
<213> ORGANISM: Artificial Sequence
<220> FEATURE:
<223> OTHER INFORMATION: Synthetic sequence

<400> SEQUENCE: 390

```
ggcgcaggcc catgcggaaa ggatccccg ccgacgcctg agcggggcg ac          52
```

<210> SEQ ID NO 391
<211> LENGTH: 52
<212> TYPE: DNA
<213> ORGANISM: Artificial Sequence
<220> FEATURE:
<223> OTHER INFORMATION: Synthetic sequence

<400> SEQUENCE: 391

```
gtcgccccgc tccaggcgtc ggcggggcat cctttccgca tgggcctgcg cc        52
```

<210> SEQ ID NO 392
<211> LENGTH: 52
<212> TYPE: DNA
<213> ORGANISM: Artificial Sequence
<220> FEATURE:
<223> OTHER INFORMATION: Synthetic sequence

<400> SEQUENCE: 392

```
ggcgcaggcc catgcggaaa ggatgccccg ccgacgcctg agcggggcg ac         52
```

<210> SEQ ID NO 393
<211> LENGTH: 49
<212> TYPE: DNA
<213> ORGANISM: Artificial Sequence
<220> FEATURE:
<223> OTHER INFORMATION: Synthetic sequence

<400> SEQUENCE: 393

```
ttacagtctc accacgcccc gtccctctc cgttgagccc cgcgccttc             49
```

<210> SEQ ID NO 394
<211> LENGTH: 49
<212> TYPE: DNA
<213> ORGANISM: Artificial Sequence
<220> FEATURE:
<223> OTHER INFORMATION: Synthetic sequence

<400> SEQUENCE: 394

```
gaaggcgcgg ggctcaacgg agagggacg gggcgtggtg agactgtaa             49
```

<210> SEQ ID NO 395
<211> LENGTH: 49
<212> TYPE: DNA
<213> ORGANISM: Artificial Sequence
<220> FEATURE:
<223> OTHER INFORMATION: Synthetic sequence

<400> SEQUENCE: 395

```
ttacagtctc accacgcccc gtccgctctc cgttgagccc cgcgccttc            49
```

<210> SEQ ID NO 396
<211> LENGTH: 49
<212> TYPE: DNA

<213> ORGANISM: Artificial Sequence
<220> FEATURE:
<223> OTHER INFORMATION: Synthetic sequence

<400> SEQUENCE: 396
gaaggcgcgg ggctcaacgg agagcggacg gggcgtggtg agactgtaa          49

<210> SEQ ID NO 397
<211> LENGTH: 49
<212> TYPE: DNA
<213> ORGANISM: Artificial Sequence
<220> FEATURE:
<223> OTHER INFORMATION: Synthetic sequence

<400> SEQUENCE: 397
gcgtctggga cgcaaggcgc cgtgggggct gccgggacgg gtccaagat          49

<210> SEQ ID NO 398
<211> LENGTH: 49
<212> TYPE: DNA
<213> ORGANISM: Artificial Sequence
<220> FEATURE:
<223> OTHER INFORMATION: Synthetic sequence

<400> SEQUENCE: 398
atcttggacc cgtcccggca gcccccacgg cgccttgcgt cccagacgc          49

<210> SEQ ID NO 399
<211> LENGTH: 49
<212> TYPE: DNA
<213> ORGANISM: Artificial Sequence
<220> FEATURE:
<223> OTHER INFORMATION: Synthetic sequence

<400> SEQUENCE: 399
gcgtctggga cgcaaggcgc cgtgagggct gccgggacgg gtccaagat          49

<210> SEQ ID NO 400
<211> LENGTH: 49
<212> TYPE: DNA
<213> ORGANISM: Artificial Sequence
<220> FEATURE:
<223> OTHER INFORMATION: Synthetic sequence

<400> SEQUENCE: 400
atcttggacc cgtcccggca gccctcacgg cgccttgcgt cccagacgc          49

<210> SEQ ID NO 401
<211> LENGTH: 49
<212> TYPE: DNA
<213> ORGANISM: Artificial Sequence
<220> FEATURE:
<223> OTHER INFORMATION: Synthetic sequence

<400> SEQUENCE: 401
tctgcgtcag ggtttccttc ttttccagcc ccaccccgcg tgcatccca          49

<210> SEQ ID NO 402
<211> LENGTH: 49
<212> TYPE: DNA
<213> ORGANISM: Artificial Sequence
<220> FEATURE:
<223> OTHER INFORMATION: Synthetic sequence

<400> SEQUENCE: 402
tgggatgcac gcggggtggg gctggaaaag aaggaaaccc tgacgcaga          49

<210> SEQ ID NO 403
<211> LENGTH: 49
<212> TYPE: DNA
<213> ORGANISM: Artificial Sequence
<220> FEATURE:
<223> OTHER INFORMATION: Synthetic sequence

<400> SEQUENCE: 403
tctgcgtcag ggtttccttc ttttgcagcc ccaccccgcg tgcatccca         49

<210> SEQ ID NO 404
<211> LENGTH: 49
<212> TYPE: DNA
<213> ORGANISM: Artificial Sequence
<220> FEATURE:
<223> OTHER INFORMATION: Synthetic sequence

<400> SEQUENCE: 404
tgggatgcac gcggggtggg gctgcaaaag aaggaaaccc tgacgcaga         49

<210> SEQ ID NO 405
<211> LENGTH: 49
<212> TYPE: DNA
<213> ORGANISM: Artificial Sequence
<220> FEATURE:
<223> OTHER INFORMATION: Synthetic sequence

<400> SEQUENCE: 405
ccctcattca ggttgatgtc ctaagcccca gaacctcaga atgggattg         49

<210> SEQ ID NO 406
<211> LENGTH: 49
<212> TYPE: DNA
<213> ORGANISM: Artificial Sequence
<220> FEATURE:
<223> OTHER INFORMATION: Synthetic sequence

<400> SEQUENCE: 406
caatcccatt ctgaggttct ggggcttagg acatcaacct gaatgaggg         49

<210> SEQ ID NO 407
<211> LENGTH: 49
<212> TYPE: DNA
<213> ORGANISM: Artificial Sequence
<220> FEATURE:
<223> OTHER INFORMATION: Synthetic sequence

<400> SEQUENCE: 407
ccctcattca ggttgatgtc ctaaccccca gaacctcaga atgggattg         49

<210> SEQ ID NO 408
<211> LENGTH: 49
<212> TYPE: DNA
<213> ORGANISM: Artificial Sequence
<220> FEATURE:
<223> OTHER INFORMATION: Synthetic sequence

<400> SEQUENCE: 408
caatcccatt ctgaggttct gggggttagg acatcaacct gaatgaggg         49

<210> SEQ ID NO 409
<211> LENGTH: 49
<212> TYPE: DNA
<213> ORGANISM: Artificial Sequence
<220> FEATURE:

<223> OTHER INFORMATION: Synthetic sequence

<400> SEQUENCE: 409
gtggcctggc taaagtaggc tttactgggc tcctctctgc ctgcatcac         49

<210> SEQ ID NO 410
<211> LENGTH: 49
<212> TYPE: DNA
<213> ORGANISM: Artificial Sequence
<220> FEATURE:
<223> OTHER INFORMATION: Synthetic sequence

<400> SEQUENCE: 410
gtgatgcagg cagagaggag cccagtaaag cctactttag ccaggccac         49

<210> SEQ ID NO 411
<211> LENGTH: 49
<212> TYPE: DNA
<213> ORGANISM: Artificial Sequence
<220> FEATURE:
<223> OTHER INFORMATION: Synthetic sequence

<400> SEQUENCE: 411
gtggcctggc taaagtaggc tttagtgggc tcctctctgc ctgcatcac         49

<210> SEQ ID NO 412
<211> LENGTH: 49
<212> TYPE: DNA
<213> ORGANISM: Artificial Sequence
<220> FEATURE:
<223> OTHER INFORMATION: Synthetic sequence

<400> SEQUENCE: 412
gtgatgcagg cagagaggag cccactaaag cctactttag ccaggccac         49

<210> SEQ ID NO 413
<211> LENGTH: 48
<212> TYPE: DNA
<213> ORGANISM: Artificial Sequence
<220> FEATURE:
<223> OTHER INFORMATION: Synthetic sequence

<400> SEQUENCE: 413
aatgctttta ggacgcctcg gcgggagtgg cggggcaggg gggggcg         48

<210> SEQ ID NO 414
<211> LENGTH: 48
<212> TYPE: DNA
<213> ORGANISM: Artificial Sequence
<220> FEATURE:
<223> OTHER INFORMATION: Synthetic sequence

<400> SEQUENCE: 414
cgcccccccc ctgccccgcc actcccgccg aggcgtccta aaagcatt         48

<210> SEQ ID NO 415
<211> LENGTH: 48
<212> TYPE: DNA
<213> ORGANISM: Artificial Sequence
<220> FEATURE:
<223> OTHER INFORMATION: Synthetic sequence

<400> SEQUENCE: 415
ggcgcgggac acttcgagag gaggcggggt ttggagctgg agagatgt         48

```
<210> SEQ ID NO 416
<211> LENGTH: 48
<212> TYPE: DNA
<213> ORGANISM: Artificial Sequence
<220> FEATURE:
<223> OTHER INFORMATION: Synthetic sequence

<400> SEQUENCE: 416
acatctctcc agctccaaac cccgcctcct ctcgaagtgt cccgcgcc            48

<210> SEQ ID NO 417
<211> LENGTH: 34
<212> TYPE: DNA
<213> ORGANISM: Artificial Sequence
<220> FEATURE:
<223> OTHER INFORMATION: Synthetic sequence

<400> SEQUENCE: 417
gtttaattga gttgtcatat gttaataacg gtat                          34

<210> SEQ ID NO 418
<211> LENGTH: 34
<212> TYPE: DNA
<213> ORGANISM: Artificial Sequence
<220> FEATURE:
<223> OTHER INFORMATION: Synthetic sequence

<400> SEQUENCE: 418
ataccgttat taacatatga caactcaatt aaac                          34

<210> SEQ ID NO 419
<211> LENGTH: 50
<212> TYPE: DNA
<213> ORGANISM: Artificial Sequence
<220> FEATURE:
<223> OTHER INFORMATION: Synthetic sequence

<400> SEQUENCE: 419
tgtcgccccg ctccaggcgt cggtcggcgg gagtggcggg gcagggggggg         50

<210> SEQ ID NO 420
<211> LENGTH: 83
<212> TYPE: DNA
<213> ORGANISM: Artificial Sequence
<220> FEATURE:
<223> OTHER INFORMATION: Synthetic sequence

<400> SEQUENCE: 420
tgtcgccccg ctccaggcgt cggataccgt tattaacata tgacaactca attaaaccgg    60
cgggagtggc ggggcagggg ggg                                           83

<210> SEQ ID NO 421
<211> LENGTH: 77
<212> TYPE: DNA
<213> ORGANISM: Artificial Sequence
<220> FEATURE:
<223> OTHER INFORMATION: Synthetic sequence

<400> SEQUENCE: 421
tgtcgccccg ctccaggcgt cggttattaa catatgacaa ctcaattaaa ccggcgggag    60
tggcggggca gggggggg                                                 77

<210> SEQ ID NO 422
<211> LENGTH: 85
<212> TYPE: DNA
```

```
<213> ORGANISM: Artificial Sequence
<220> FEATURE:
<223> OTHER INFORMATION: Synthetic sequence

<400> SEQUENCE: 422
tgtcgccccg ctccaggcgt cgggtttaat tgagttgtca tatgttaata acggtatctc    60
ggcgggagtg gcggggcagg ggggg                                          85

<210> SEQ ID NO 423
<211> LENGTH: 74
<212> TYPE: DNA
<213> ORGANISM: Artificial Sequence
<220> FEATURE:
<223> OTHER INFORMATION: Synthetic sequence

<400> SEQUENCE: 423
tcgccccgct ccaggcgtcg gtattaacat atgacaactc aattaaaccg gcgggagtgg    60
cggggcaggg gggg                                                      74

<210> SEQ ID NO 424
<211> LENGTH: 72
<212> TYPE: DNA
<213> ORGANISM: Artificial Sequence
<220> FEATURE:
<223> OTHER INFORMATION: Synthetic sequence

<400> SEQUENCE: 424
tgtcgccccg ctccaggcgt cggattaaca tatgacaact caattaaacc gggagtggcg    60
gggcaggggg gg                                                        72

<210> SEQ ID NO 425
<211> LENGTH: 17
<212> TYPE: DNA
<213> ORGANISM: Artificial Sequence
<220> FEATURE:
<223> OTHER INFORMATION: Synthetic sequence

<400> SEQUENCE: 425
gctccatgcg gcggcgg                                                   17

<210> SEQ ID NO 426
<211> LENGTH: 17
<212> TYPE: DNA
<213> ORGANISM: Artificial Sequence
<220> FEATURE:
<223> OTHER INFORMATION: Synthetic sequence

<400> SEQUENCE: 426
gcttcaggcg taggggg                                                   17

<210> SEQ ID NO 427
<211> LENGTH: 17
<212> TYPE: DNA
<213> ORGANISM: Artificial Sequence
<220> FEATURE:
<223> OTHER INFORMATION: Synthetic sequence

<400> SEQUENCE: 427
gctccggggg ccggcgg                                                   17

<210> SEQ ID NO 428
<211> LENGTH: 17
<212> TYPE: DNA
<213> ORGANISM: Artificial Sequence
```

```
<220> FEATURE:
<223> OTHER INFORMATION: Synthetic sequence

<400> SEQUENCE: 428
gctccaagcg gcggcgc                                                    17

<210> SEQ ID NO 429
<211> LENGTH: 18
<212> TYPE: DNA
<213> ORGANISM: Artificial Sequence
<220> FEATURE:
<223> OTHER INFORMATION: Synthetic sequence

<400> SEQUENCE: 429
gctcttaggc cgccgcgg                                                   18

<210> SEQ ID NO 430
<211> LENGTH: 17
<212> TYPE: DNA
<213> ORGANISM: Artificial Sequence
<220> FEATURE:
<223> OTHER INFORMATION: Synthetic sequence

<400> SEQUENCE: 430
gcaccaggcg gcggcgg                                                    17

<210> SEQ ID NO 431
<211> LENGTH: 18
<212> TYPE: DNA
<213> ORGANISM: Artificial Sequence
<220> FEATURE:
<223> OTHER INFORMATION: Synthetic sequence

<400> SEQUENCE: 431
gctttaagga tgccttgg                                                   18

<210> SEQ ID NO 432
<211> LENGTH: 18
<212> TYPE: DNA
<213> ORGANISM: Artificial Sequence
<220> FEATURE:
<223> OTHER INFORMATION: Synthetic sequence

<400> SEQUENCE: 432
acttttagga ggcctagg                                                   18

<210> SEQ ID NO 433
<211> LENGTH: 18
<212> TYPE: DNA
<213> ORGANISM: Artificial Sequence
<220> FEATURE:
<223> OTHER INFORMATION: Synthetic sequence

<400> SEQUENCE: 433
gcatttagga ggcctagg                                                   18

<210> SEQ ID NO 434
<211> LENGTH: 17
<212> TYPE: DNA
<213> ORGANISM: Artificial Sequence
<220> FEATURE:
<223> OTHER INFORMATION: Synthetic sequence

<400> SEQUENCE: 434
gctccaggcg tgggcgg                                                    17
```

<210> SEQ ID NO 435
<211> LENGTH: 18
<212> TYPE: DNA
<213> ORGANISM: Artificial Sequence
<220> FEATURE:
<223> OTHER INFORMATION: Synthetic sequence

<400> SEQUENCE: 435
gcttttggga cgcctcag                                                 18

<210> SEQ ID NO 436
<211> LENGTH: 21
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 19
<223> OTHER INFORMATION: n = a, c, t, or g
<220> FEATURE:
<221> NAME/KEY: misc_feature
<222> LOCATION: 20
<223> OTHER INFORMATION: r = a or g

<400> SEQUENCE: 436
gcttttagga cgcctcggnr g                                             21

<210> SEQ ID NO 437
<211> LENGTH: 21
<212> TYPE: DNA
<213> ORGANISM: Artificial Sequence
<220> FEATURE:
<223> OTHER INFORMATION: Synthetic sequence

<400> SEQUENCE: 437
gcttttagga ggtctcggcg g                                             21

<210> SEQ ID NO 438
<211> LENGTH: 20
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: 19
<223> OTHER INFORMATION: n = a, t, c, or g
<220> FEATURE:
<221> NAME/KEY: misc_feature
<222> LOCATION: 20
<223> OTHER INFORMATION: r = a or g

<400> SEQUENCE: 438
gctccaggcg tcggcggnrg                                               20

<210> SEQ ID NO 439
<211> LENGTH: 20
<212> TYPE: DNA
<213> ORGANISM: Artificial Sequence
<220> FEATURE:
<223> OTHER INFORMATION: Synthetic sequence

<400> SEQUENCE: 439
ggcggaggcg gcggcggcgg                                               20

<210> SEQ ID NO 440
<211> LENGTH: 20

```
<212> TYPE: DNA
<213> ORGANISM: Artificial Sequence
<220> FEATURE:
<223> OTHER INFORMATION: Synthetic sequence

<400> SEQUENCE: 440
ggttgaggcg gaggcggcgg                                                  20

<210> SEQ ID NO 441
<211> LENGTH: 20
<212> TYPE: DNA
<213> ORGANISM: Artificial Sequence
<220> FEATURE:
<223> OTHER INFORMATION: Synthetic sequence

<400> SEQUENCE: 441
ggacctggca gcggcggtgg                                                  20

<210> SEQ ID NO 442
<211> LENGTH: 80
<212> TYPE: RNA
<213> ORGANISM: Artificial Sequence
<220> FEATURE:
<223> OTHER INFORMATION: Synthetic sequence

<400> SEQUENCE: 442
guuuuagagc uagaaauagc aaguuaaaau aaggcuaguc cguuaucaac uugaaaaagu      60
ggcaccgagu cggugcuuuu                                                  80
```

US 11,473,084 B2

COMPOSITIONS AND METHODS FOR TREATING HUNTINGTON'S DISEASE AND RELATED DISORDERS

This application is a § 371 application of PCT/US2016/054617, filed Oct. 11, 2016, which claims priority under 35 U.S.C. § 119(e) to U.S. Provisional Patent Application No. 62/352,788, filed Jun. 21, 2016 and U.S. Provisional Patent Application No. 62/239,714, filed Oct. 9, 2015. The foregoing applications are incorporated by reference herein.

This invention was made with government support under grant number NS084475 awarded by the National Institutes of Health. The government has certain rights in the invention.

FIELD OF THE INVENTION

The present invention relates to polyglutamine (polyQ) disorders, particularly Huntington's disease. Specifically, the instant invention provides compositions and methods for the treatment and/or prevention of Huntington's disease and related disorders.

BACKGROUND OF THE INVENTION

Huntington disease (HD) is an autosomal dominant neurodegenerative disease that manifest in adults (adult-onset HD) or children (Juvenile HD). HD is part of the family of polyglutamine (polyQ) disorders comprising at least nine different neurodegenerative diseases that result from the expansion of a triplet CAG repeat in specific genes (Walker, F. O. (2007) Lancet, 369:218-228). In HD, the disease causing mutation is found in the first exon of the huntingtin gene, and although mutant huntingtin is ubiquitously expressed, the brain, and particularly the striatum and motor cortex are the earliest and most affected (Walker, F. O. (2007) Lancet, 369:218-228; The Huntington's Disease Collaborative Research Group (1993) Cell, 72, 971-983). Patients with HD develop progressive neurodegeneration leading to death, generally within 20 years of onset.

There is no cure for HD, and treatments are focused on managing its symptoms (Johnson et al. (2010) Hum. Mol. Genet., 19:R98-R102). Earlier studies using genetically modified mouse models showed that HD-like disease phenotypes can be resolved if mutant huntingtin expression is eliminated, even at advanced disease stages (Yamamoto et al. (2000) Cell, 101:57-66; Diaz-Hernandez et al. (2005) J. Neurosci., 25:9773-9781). RNA interference (RNAi), a method of reducing gene expression, has emerged as a leading therapeutic option. RNAi does not eliminate all mutant huntingtin, however, and therefore it remains expressed at low levels. For this reason, there is a need for effective therapeutics for HD.

SUMMARY OF THE INVENTION

In accordance with one aspect of the instant invention, methods and compositions for inhibiting, treating, and/or preventing a polyglutamine disorder (e.g., Huntington's disease) in a subject are provided. In accordance with another aspect of the instant invention, methods for reducing the expression of a mutant protein (e.g., mutant huntingtin) encoded by an allele of a gene associated with a polyglutamine disorder (e.g., Huntington's disease) in a cell are provided. In a particular embodiment, the methods of the instant invention comprise administering to the subject or cell a nucleic acid molecule encoding Cas9 and at least one guide RNA (e.g., sgRNA). In a particular embodiment, the guide RNA are administered to the subject or cell as a nucleic acid molecule (e.g., an expression vector or viral vector) encoding the guide RNA. In a particular embodiment, the methods of the instant invention comprise administering two guide RNAs to the subject or cell. In a particular embodiment, one guide RNA targets a sequence 5' of exon 1 (e.g., within the 5' untranslated region, within the promoter, or within the first 2 kb 5' of the transcription start site) and one guide RNA targets a sequence within intron 1. In a particular embodiment, at least one guide RNA administered to the subject or cell targets a sequence adjacent to a PAM present on only one allele of the gene (e.g., the mutant allele). In a particular embodiment, at least one of the guide RNAs targets a sequence specifically set forth herein.

The instant invention also encompasses guide RNAs, nucleic acid molecules (e.g., an expression vector or viral vector) encoding the guide RNAs, and compositions comprising the guide RNAs and/or nucleic acid molecules (e.g., an expression vector or viral vector) encoding the guide RNAs. In a particular embodiment, the composition and nucleic acid molecules (e.g., an expression vector or viral vector) encoding the guide RNAs contain or encode more than one guide RNA.

BRIEF DESCRIPTIONS OF THE DRAWING

Figure 1A:
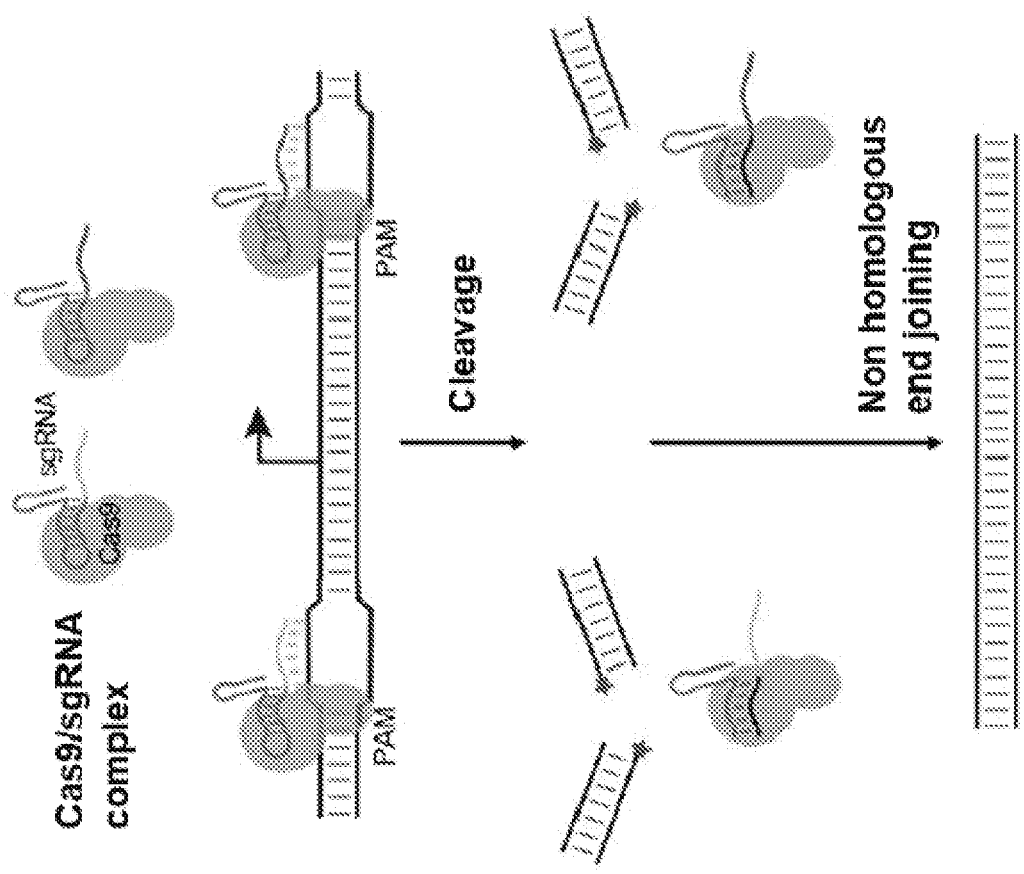
Figure 1C:
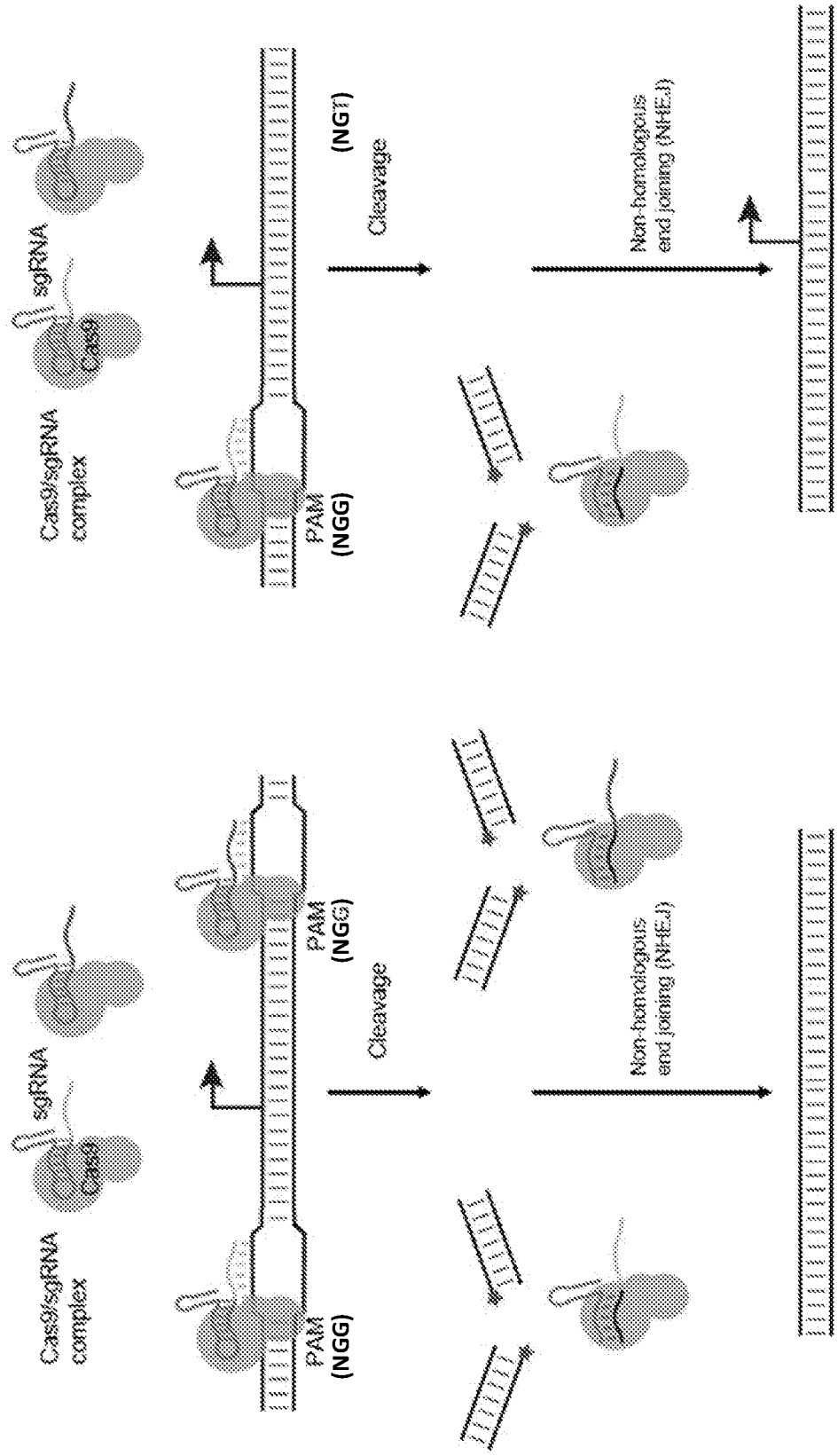

FIG. 1A provides a schematic depicting the genomic deletion mechanism by the sgRNA/Cas9 complex. FIG. 1B shows the targeting sequences of the HTT promoter (top) and PCR results demonstrating genomic deletion in transfected cells (bottom). FIG. 1C provides a schematic depicting genomic deletion mechanism by sgRNA/Cas9 complex (left) and strategy adopted to achieve allele specific gene editing based on location of single nucleotide polymorphisms at the third nucleotide sequence of the PAM motif (right).

Figure 2A:
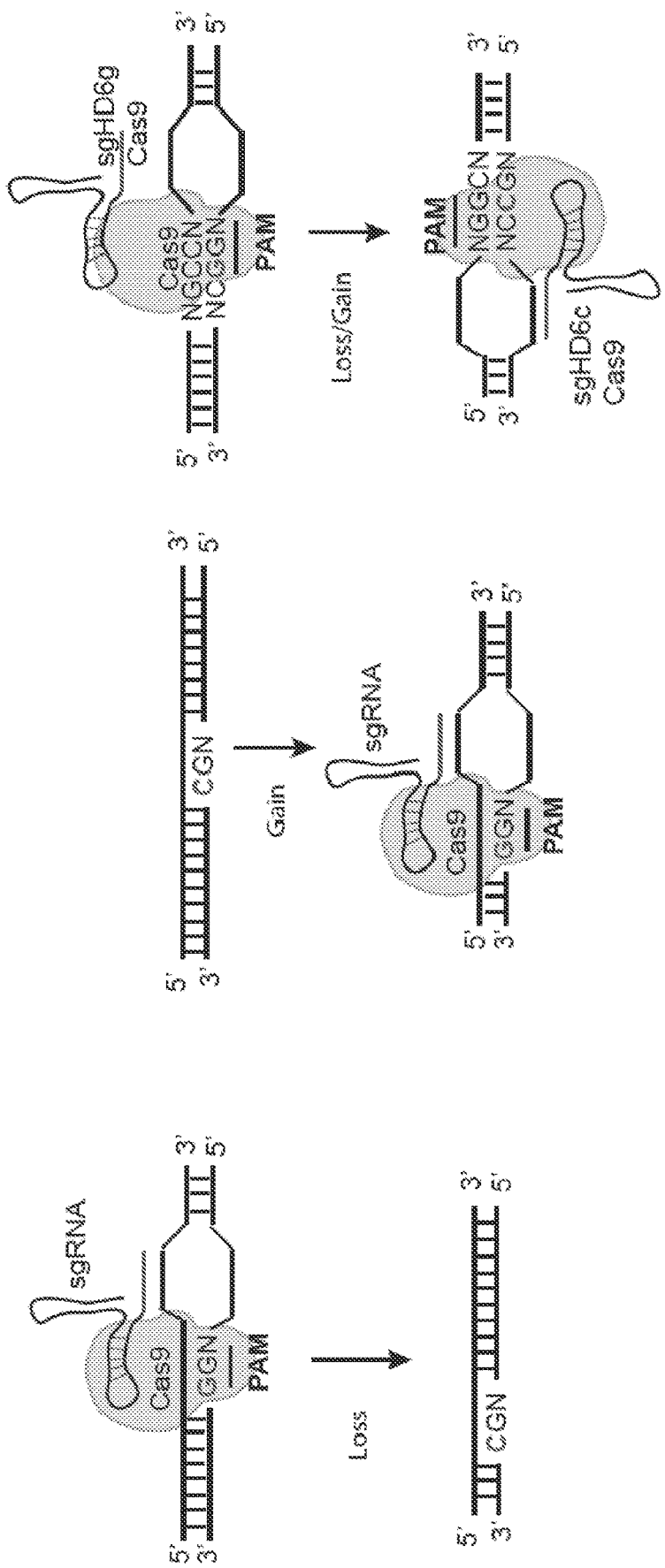

FIG. 2A provides a schematic of the targeting of Cas9 to allele specific PAM motifs by sgRNA. The loss of a PAM (left), gain of a PAM (center), and a loss/gain (right) are depicted. FIG. 2B provides examples of allele specific PAM motifs based on Streptococcus pyogenes (SpCas9; PAM—NRG) and Staphylococcus aureus Cas9 (SaCas9; PAM—NNGRR, NNGRRT). The nucleotide variation of a SNP within a PAM alters Cas9 recognition resulting in the loss (Left), the gain (Middle), or the simultaneous loss of a PAM in one DNA strand and the gain of a PAM on the opposite strand (Right). FIG. 2C shows the locations of examples (Table 1) of the SNP ID's and genomic localization of the nucleotide variants targeted by SpCas9/sgRNA complex in the promoter and first intron sequence of the human huntingtin genomic locus.

Figure 3A:
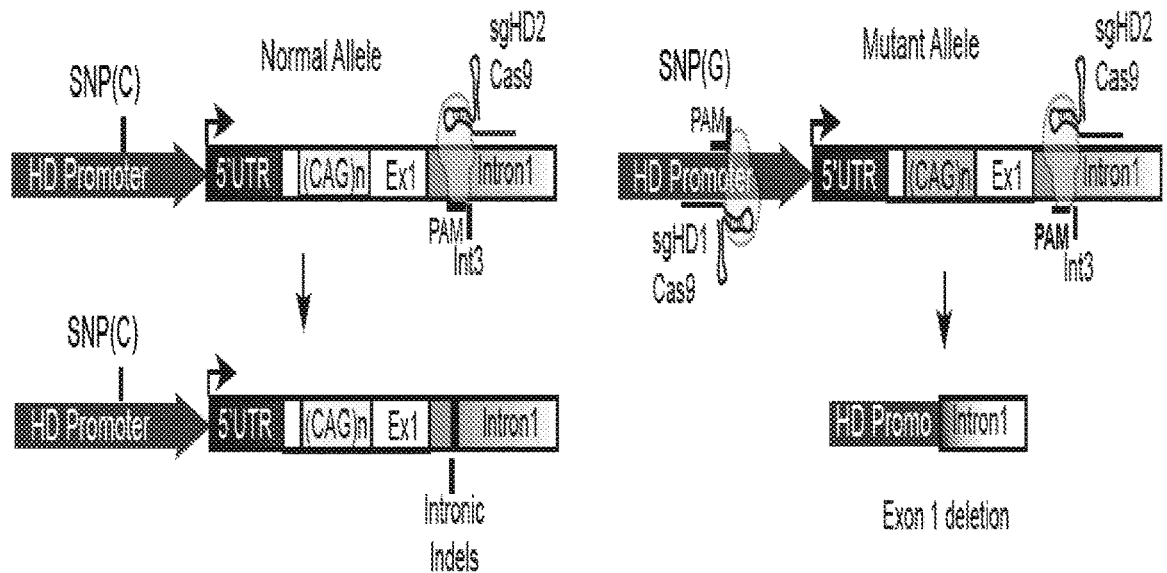
Figure 3B:
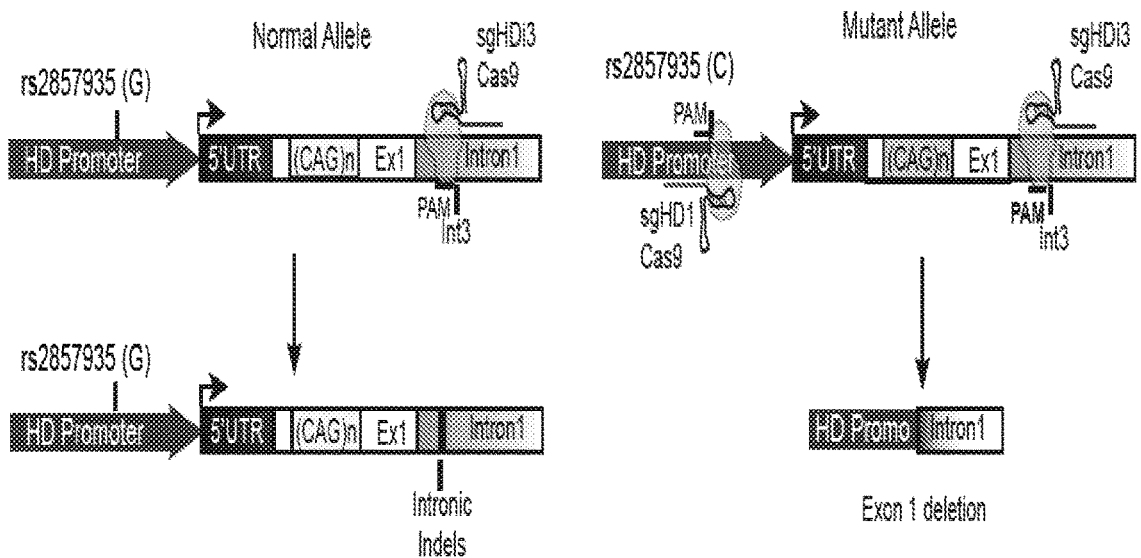
Figure 3C:
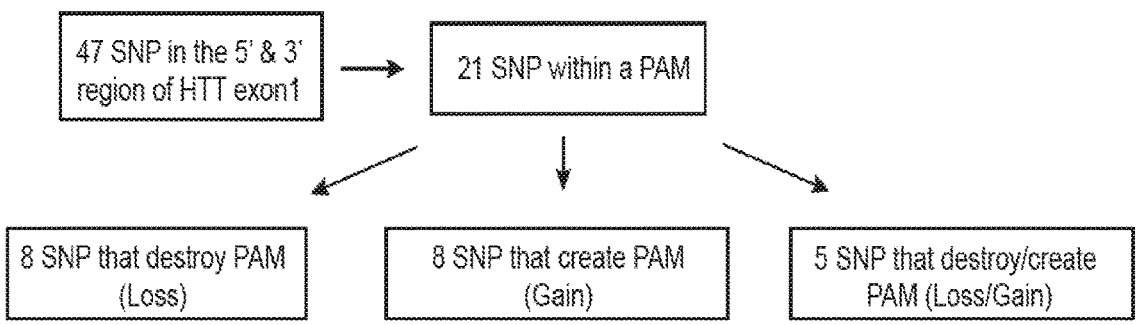

FIGS. 3A-3C: SNP dependent editing for Huntington disease therapy. FIG. 3A: Cartoon depicting the allele specific editing strategy to abrogate mutant HTT expression. SNPs within PAM sequences upstream of HTT exon1 permit specific targeted deletions of the mutant allele when present in heterozygosity. After DNA repair mutant HTT exon1 is deleted by a pair of sgRNA/Cas9 complexes binding upstream and downstream of exon1 (Right), whereas intronic indels could be generated by a single dsDNA break in the normal allele (Left). FIG. 3B provides a schematic of a normal allele and a mutant allele in the presence of sgHD1 and sgHDi3. The presence of both sgRNAs causes the cleavage of only the mutant allele. FIG. 3C: 21 out of 47 prevalent SNPs flanking HTT exon1 are located within predicted critical positions of a PAM sequence for the CRISPR/SpCas9 system analyzed. The minor frequency allele either mediates the loss (8 SNPs), again (8 SNPs) or a loss/gain (5 SNPs) of a PAM motif. FIGS. 3D-3J: List of the 36 prevalent SNPs upstream/downstream of HTT exon1 that fall within the nucleotide positions of the different CRISPR/Cas9 and CRISPR/Cpf1 systems analyzed. Sequences in FIG. 3D are SEQ ID NOs: 74-120, from top to bottom. FIG. 3K shows the flanking sequence of the indicated SNPs, the location of the PAMs, and an example of complementary sequence to target the site for cleavage. Nucleotide variations at specific genomic DNA sequences results in the loss or the loss/gain of SNP-dependent PAM motifs which generate or eliminate the recruitment of SpCas9/sgRNA to the huntingtin genomic locus. SEQ ID NOs are provided in parentheses.

Figure 4D:
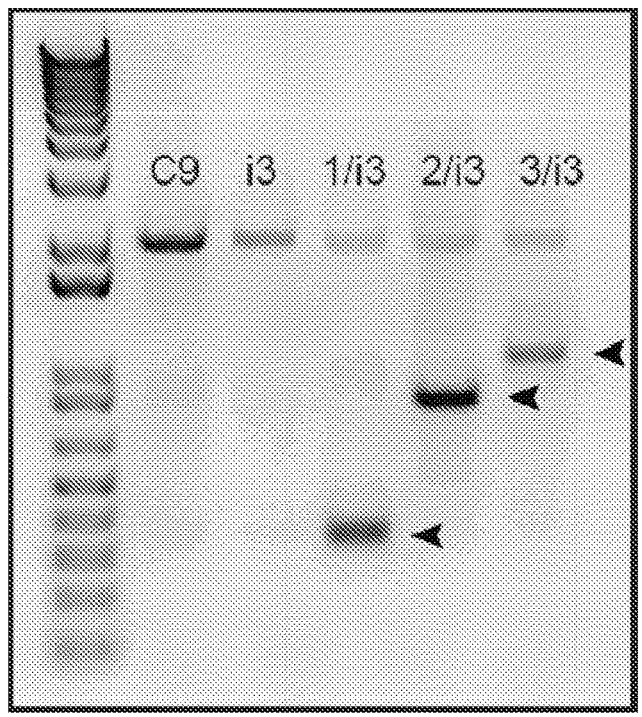
Figure 4E:
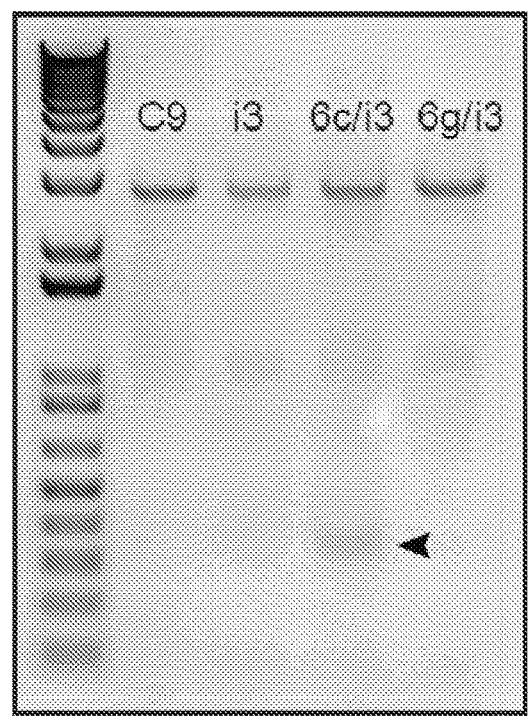
Figure 4F:
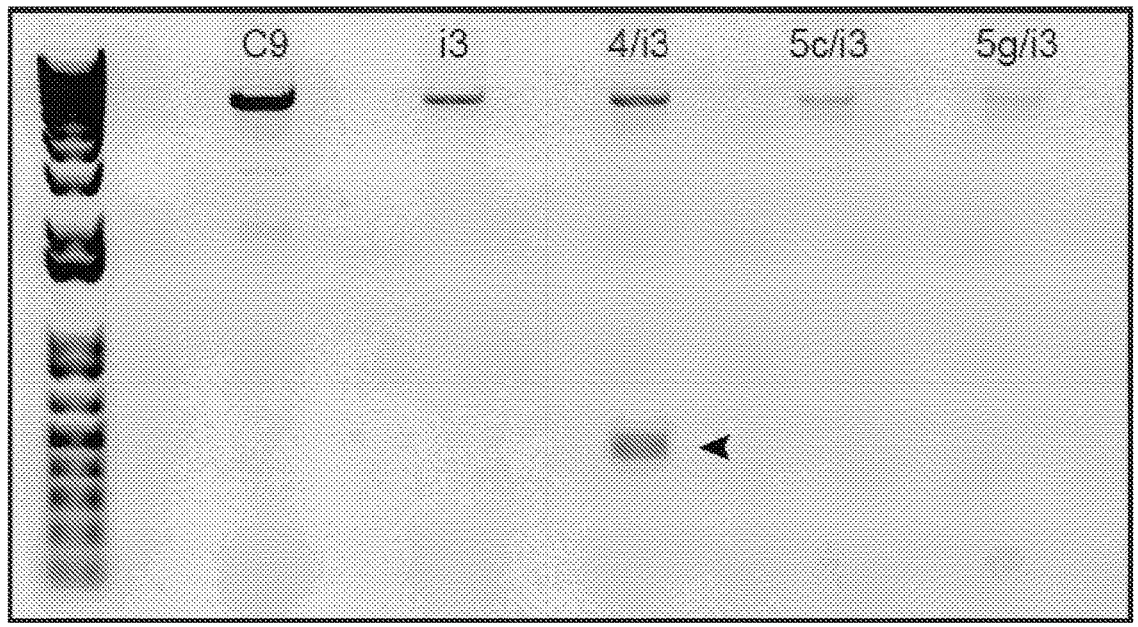
Figure 4G:
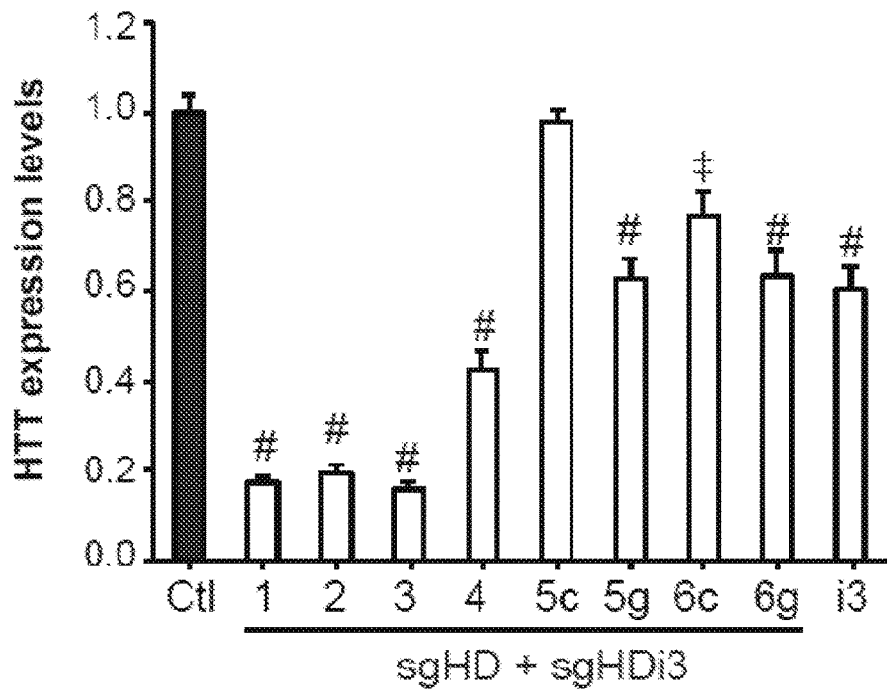
Figure 4H:
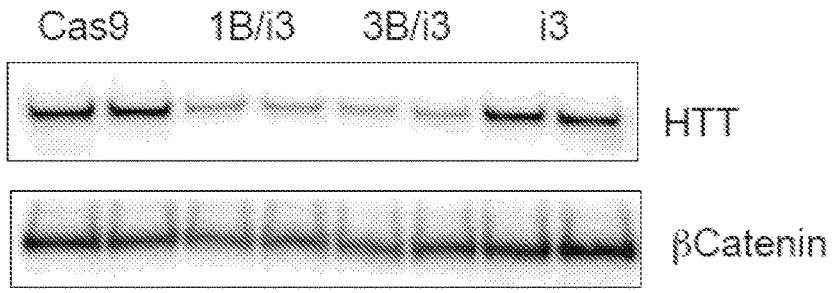
Figure 4I:
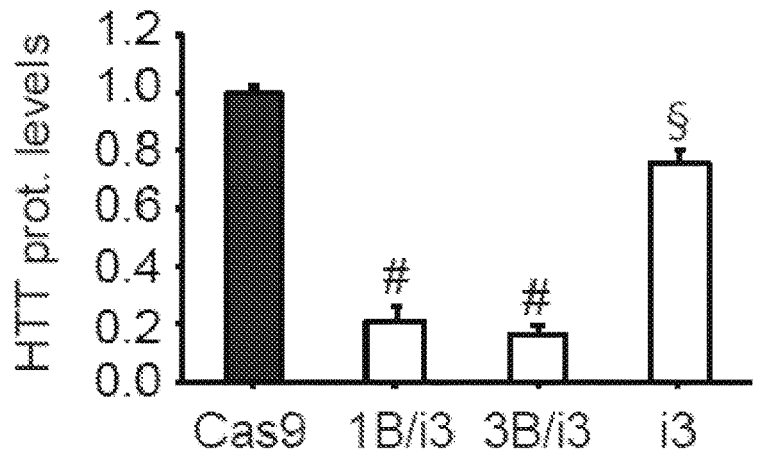
Figure 4K:
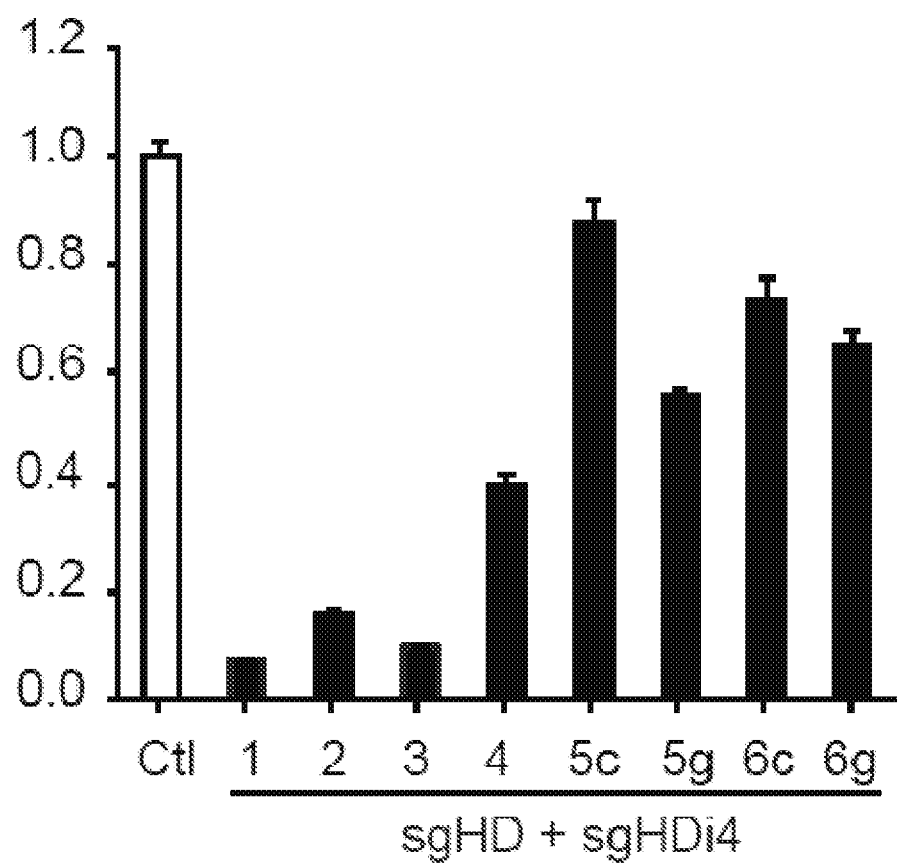
Figure 4L:
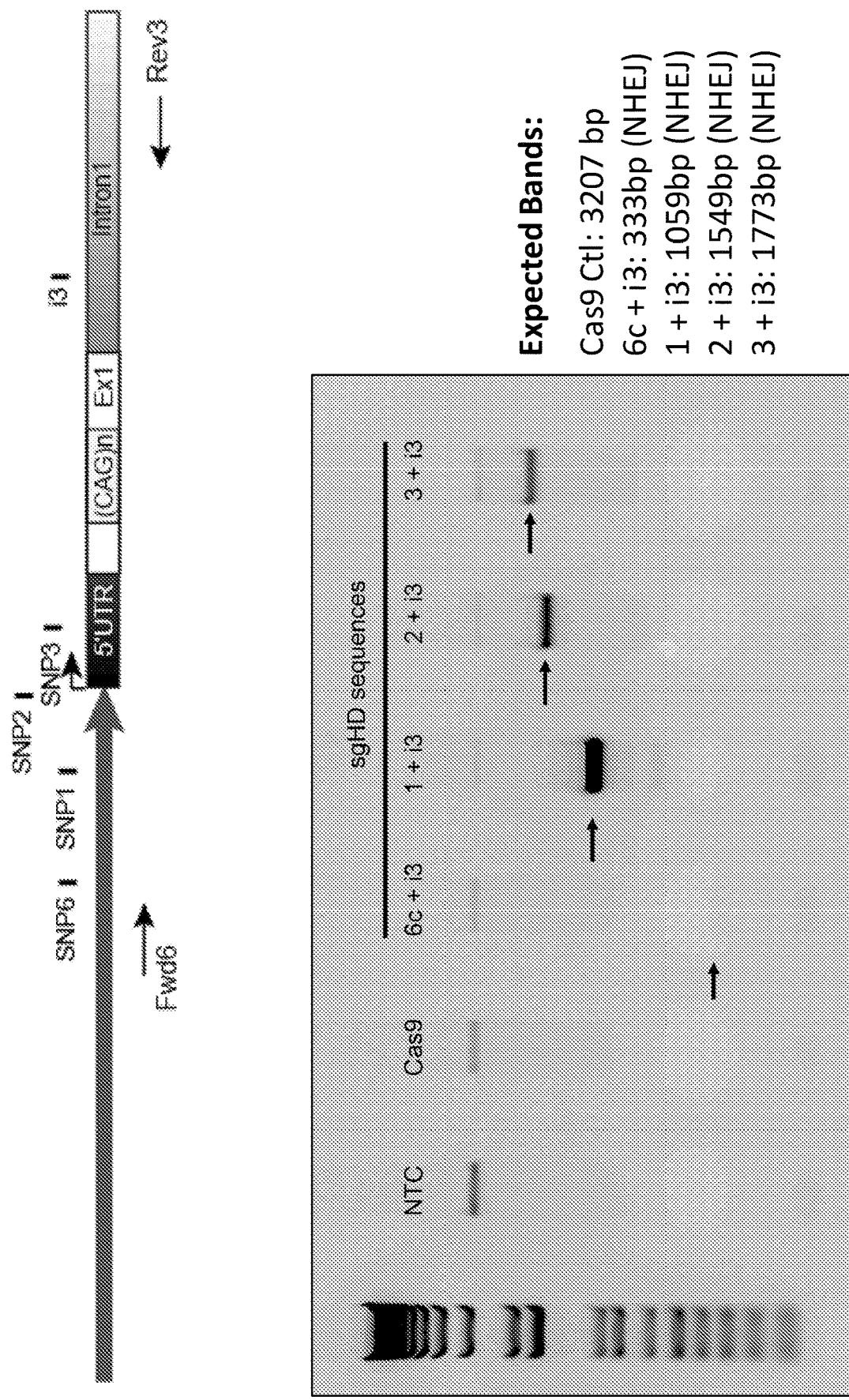
Figure 4M:
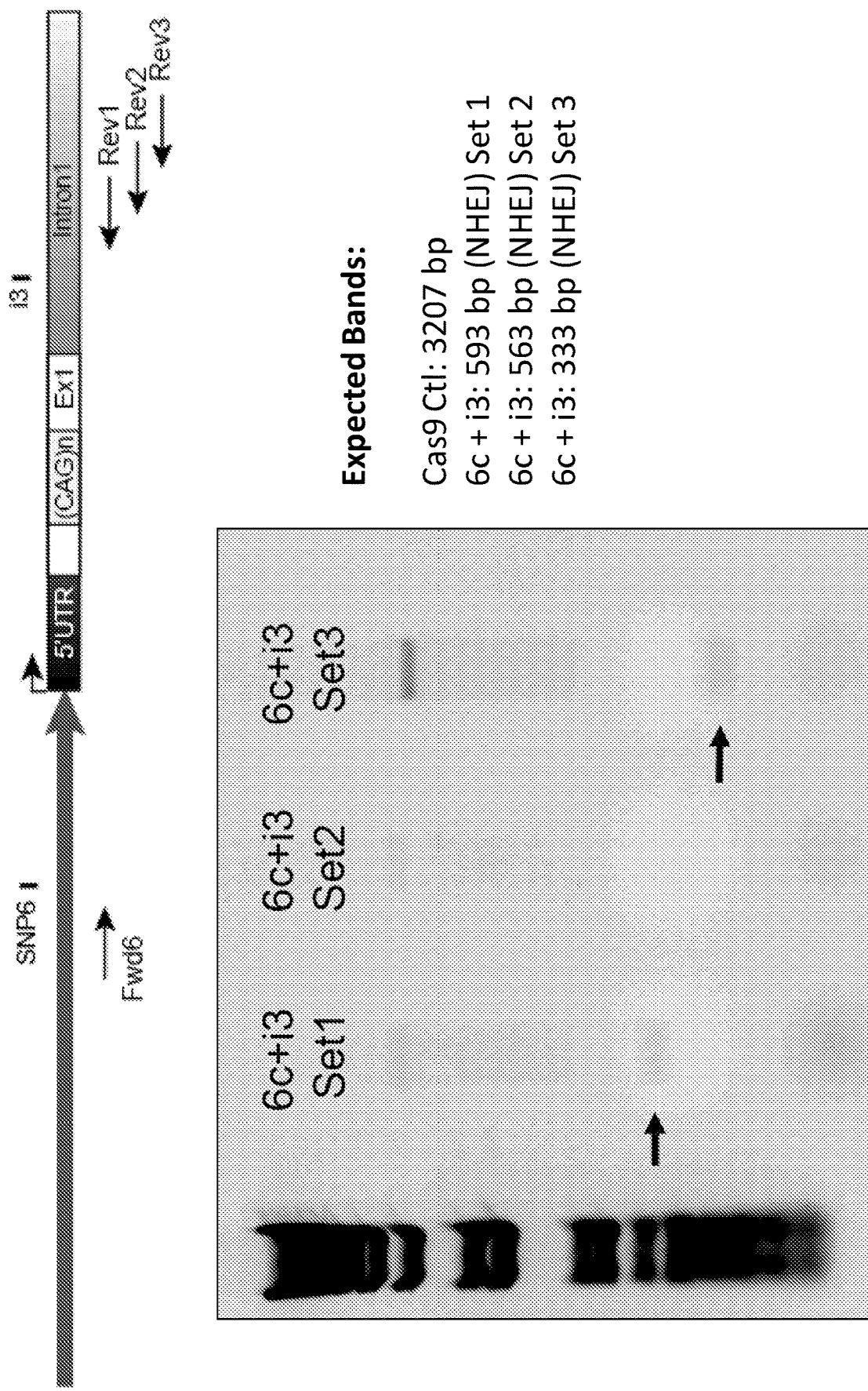
Figure 4N:
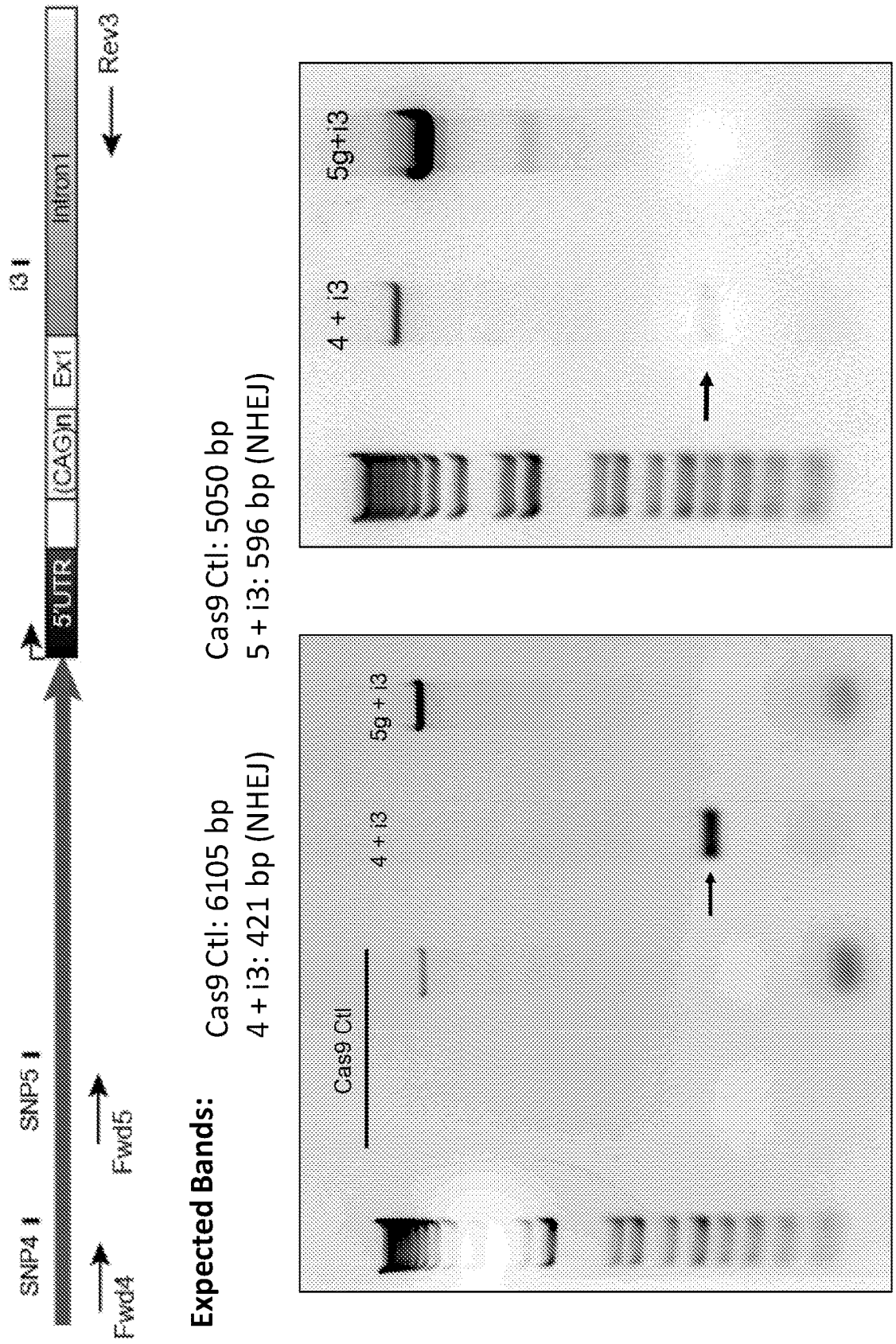

FIGS. 4A-4I: Cleavage of SNP-dependent sgHD/SpCas9 complexes in HEK293 cells. FIG. 4A: Cartoon depicting the relative position of the 6 prevalent SNP-dependent PAMs upstream of HTT exon1, and 2 common PAMs within HTT intron 1. The estimated size of the targeted deleted sequence is indicated. FIG. 4B: Genotype of the prevalent SNPs within the HTT promoter in HEK293 cells. All SNPs were homozygous for the nucleotide variation and the PAM motif was present for the sgRNA indicated. FIG. 4C: Diagram of the CRISPR expression systems transfected into HEK293 cells. FIGS. 4D-4F: Genomic PCR showing HTT exon1-targeted deletion by sgRNA/SpCas9 pair complexes binding upstream and downstream of the target sequence. FIG. 4G: RT-qPCR analysis of HTT mRNA levels in HEK293 cells transfected with sgHD/SpCas9 expression cassettes targeting upstream promoter SNPs and the common intronic sgHDi3 sequence. All samples are normalized to human GAPDH and results are the mean±SEM relative to cells transfected with plasmids containing the SpCas9 only control. (n=6; ‡P<0.001, #P<0.0001, One way ANOVA followed by a Bonferroni's post-hoc). FIG. 4H: sgHD1/i3/SpCas9 and sgHD3/i3/SpCas9 and sgHDi3/SpCas9 expression cassettes were transfected into HEK293 cells, and endogenous HTT protein levels were determined after puromycin selection and expansion. Cells transfected with Cas9 only was used as a control and betacatenin served as a loading control. FIG. 4I: Quantification of HTT protein levels after treatment with sgHD/SpCas9 complexes. Data are the mean±SEM relative to cells transfected with plasmids containing SpCas9 only control. (n=6; #P<0.0001, § P<0.001, one way ANOVA followed by Bonferroni's post-hoc). FIG. 4J: Sanger sequencing of PCR amplified products after of HTT exon1 editing with sgHD/Cas9 expression vectors targeting upstream promoter SNPs and the intronic i3 PAM. SEQ ID NOs are provided in parentheses. FIG. 4K: RT-qPCR analysis of HTT mRNA levels in HEK293 cells transfected with sgHD/SpCas9 expression cassettes targeting upstream promoter SNPs and common intronic sgHDi4 sequences. All samples are normalized to human GAPDH and results are mean±SEM relative to cells transfected with plasmids containing SpCas9 only control. (n=4). FIG. 4L provides a schematic depicting the strategy to delete 1st exon sequence of mutant huntingtin gene using the CRISPR/Cas9 system targeting the SNP-derived PAM motifs at positions SNP1, SNP2, SNP3 and SNP6 in combination with the intronic i3 PAM motif (top). A representative experiment is also provided (bottom) showing deletion of HTT genomic fragment after coexpression of SNP and i3 targeting CRISPR/Cas9 expression systems. Arrow indicates expected DNA bands derived from cleavage and NHEJ recombination. FIG. 4M provides a schematic depicting the strategy to delete 1st exon sequence of mutant huntingtin gene using the CRISPR/Cas9 system targeting the SNP6 in combination with i3 PAM motif (top). A representative experiment is also provided (bottom) showing deletion of HTT genomic fragment after coexpression of SNP6 and i3 targeting CRISPR/Cas9 expression systems. Arrow indicates expected DNA bands derived from cleavage and NHEJ recombination using 3 different primer sets. FIG. 4N provides a schematic depicting the strategy to delete 1st exon sequence of mutant huntingtin gene using the CRISPR/Cas9 system targeting the SNP4, SNP5 derived PAM motifs in combination with i3 PAM motif (top). Representative experiments are provided (bottom) showing deletion of HTT genomic fragment after coexpression of SNP targeting CRISPR/Cas9 systems. Arrow indicates expected DNA bands derived from cleavage and NHEJ recombination.

FIGS. 5A-5O: List of SNP-dependent PAMs targeted by different CRISPR systems. SEQ ID NOs are provided in parentheses.

FIGS. 6A-6B: List of sgRNA sequence designed for targeting prevalent SNP-dependent PAM motifs present upstream 5' of HTT exon1, and common sgHD sequences within HTT intron 1. SEQ ID NOs are provided in parentheses.

Figure 7A:
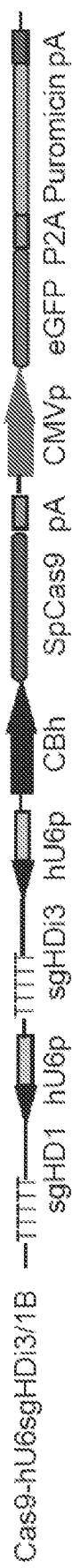
Figure 7B:
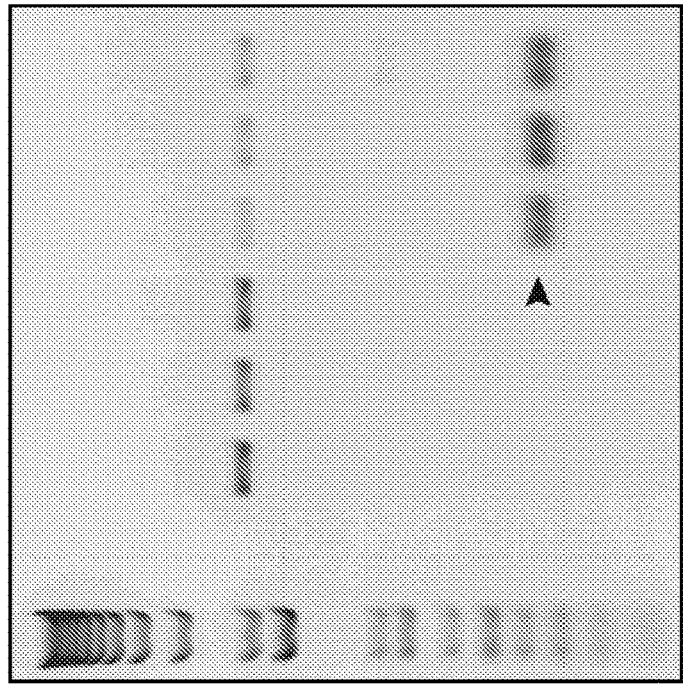
Figure 7C:
Figure 7D:
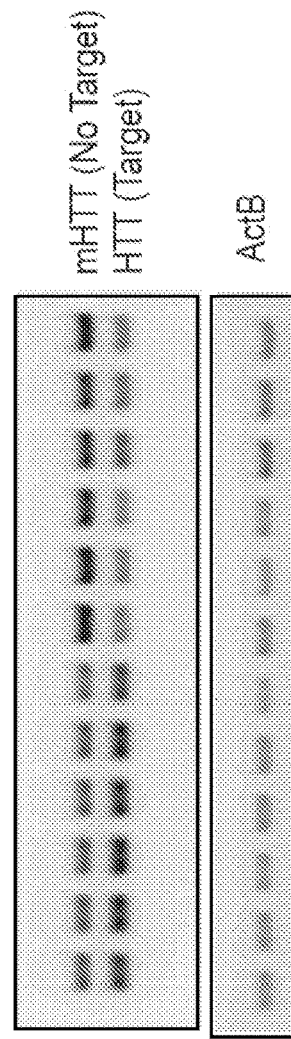
Figure 7E:
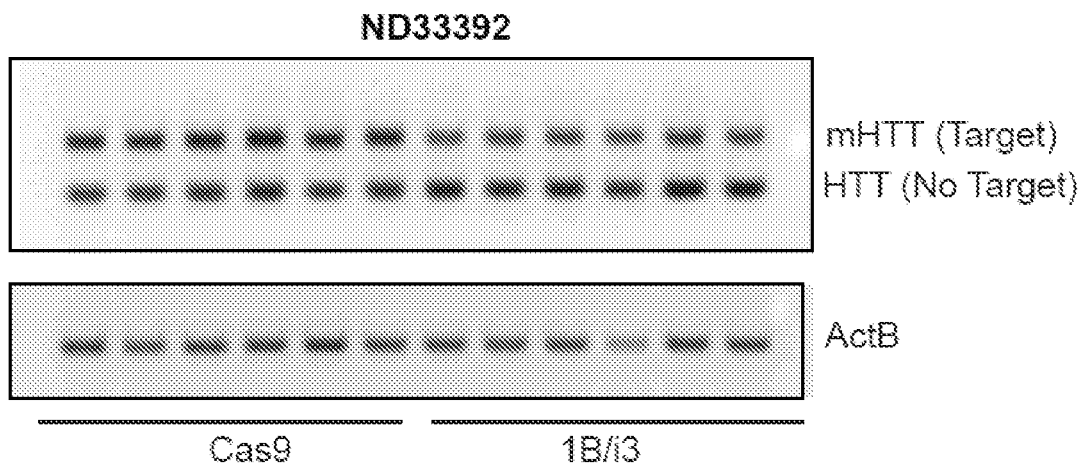
Figure 7F:
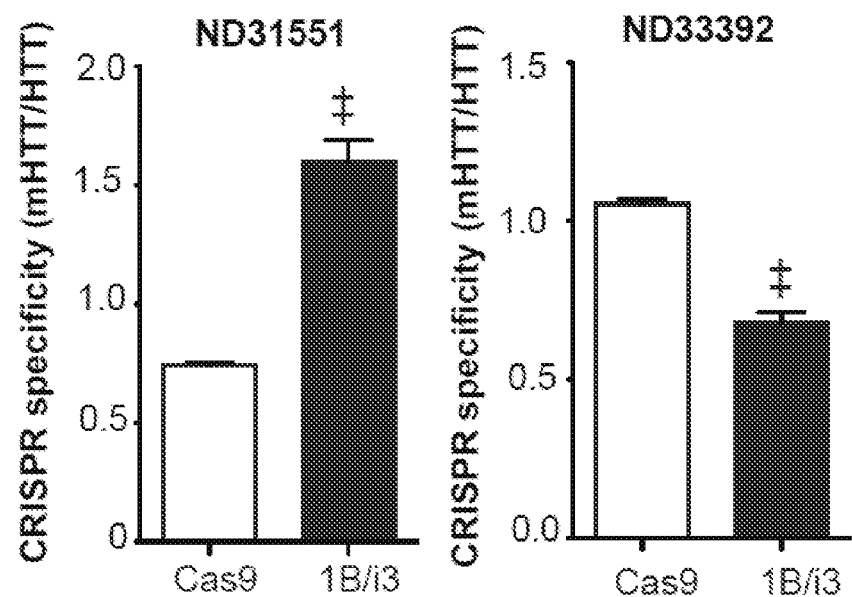
Figure 7G:
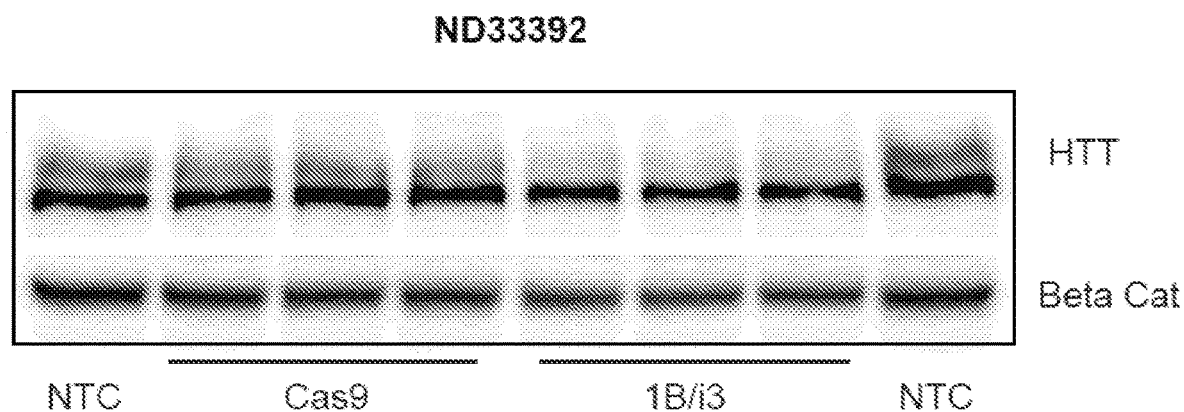
Figure 7H:
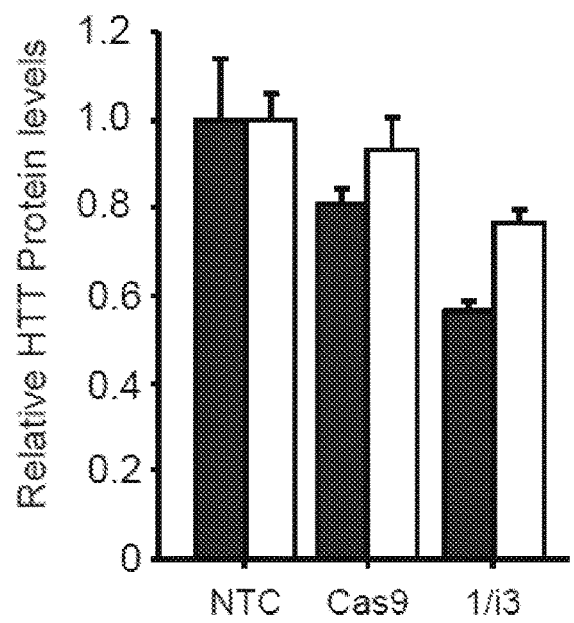

FIGS. 7A-7H: Assessment of allele specific cleavage in human HD fibroblasts. FIG. 7A: Cartoon depicting the CRISPR expression plasmid use to co-express sgHD1 and sgHDi3 expression cassettes. SpCas9 and the selective reporter eGFP/puromycin expression cassettes present in the same plasmid are also shown. FIG. 7B: ND31551 and ND33392 HD fibroblasts lines were selected to determine allele specific target deletions of HTT. CAG repeat length, nucleotide variation and the allele location of the PAM motif are indicated. FIG. 7C: Representative genomic PCR showing HTT exon1 deletion of DNA harvested from the electroporated ND31551 HD fibroblast cell line. Arrow indicates the expected PCR amplification product resulting from allele specific deletion. FIGS. 7D and 7E: Semi-quantitative PCR reaction showing reduction of the targeted allele containing the conserved PAM sequence. For ND31551 fibroblasts the PAM sequence is conserved in the normal allele, while for ND33392 fibroblasts the PAM sequence is in the mutant allele. Expression levels are reduced only on the PAM-containing allele. FIG. 7F: Quantification of mRNA reduction in treated HD fibroblasts. Data show the ratio between mRNA levels of the mutant with respect to the normal allele, relative to cells electroporated with vectors expressing only the Cas9 control. The results are mean±SEM relative to cells transfected with plasmids containing SpCas9 only control. (n=6; ‡ P<0.01, Mann Whitney T-test). FIG. 7G: Representative western blot showing allele specific depletion (upper band of HTT doublet consisting of normal (lower) and expanded polyQ-containing proteins) after electroporation of HD fibroblasts with sgHD/SpCas9 expression vectors. FIG. 7H: Western blot quantification of HD fibroblasts electroporated with Cas9-hU6sgHD1/i3 expression vector.

FIGS. 8A-8D: Assessing off target activity of sgHD1 and sgHDi3/Cas9. FIG. 8A: Table depicting the number of off-target sites for the most active sequences predicted to bind with 1, 2 or 3 mismatches. The nucleotide length of the complementary guide sequence is also indicated. FIG. 8B: Table highlighting the number of off-target sites binding at different genomic regions using the UCSC genome browser. FIG. 8C: HD fibroblasts were electroporated with plasmids expressing sgHD1/i3 and SpCas9 along with an ODN sequence (SEQ ID NO: 417 and SEQ ID NO: 418 (reverse complement)). Sanger sequencing results showed the incorporation of the ODN sequence at the DNA cleavage site.

HTT promoter sequence and HTT intron sequence outside the ODN sequence are also depicted (SEQ ID NOs: 419-424, from top to bottom). FIG. 8D: Sanger sequencing results from 11 predicted off target sites. Gene name, chromosome position, DNA strand, number of mismatches and position within the guide, gene location, sgRNA sequence and indel presence or absence are indicated. Sequences are SEQ ID NOs: 425-435, from top to bottom.

Figure 9A:
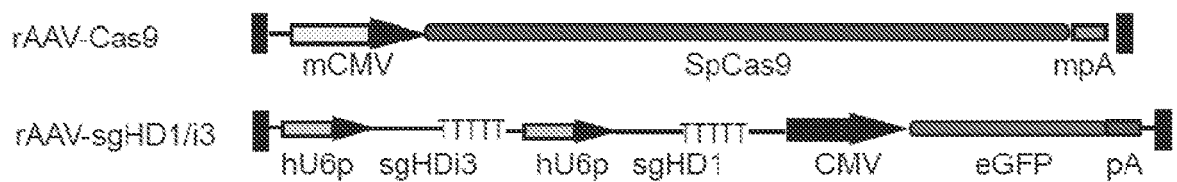
Figure 9B:
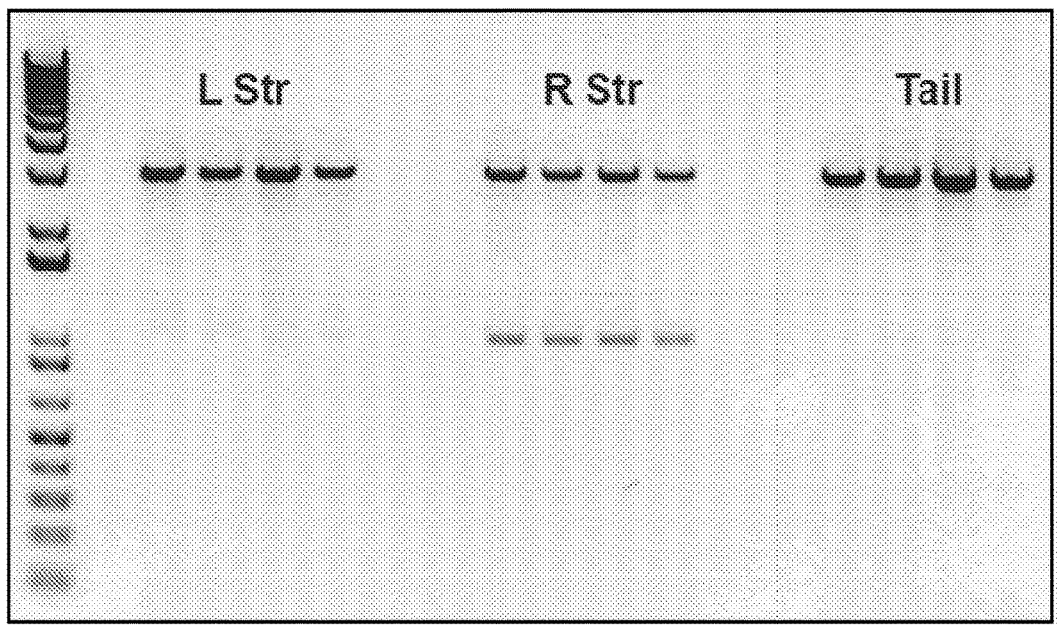
Figure 9C:
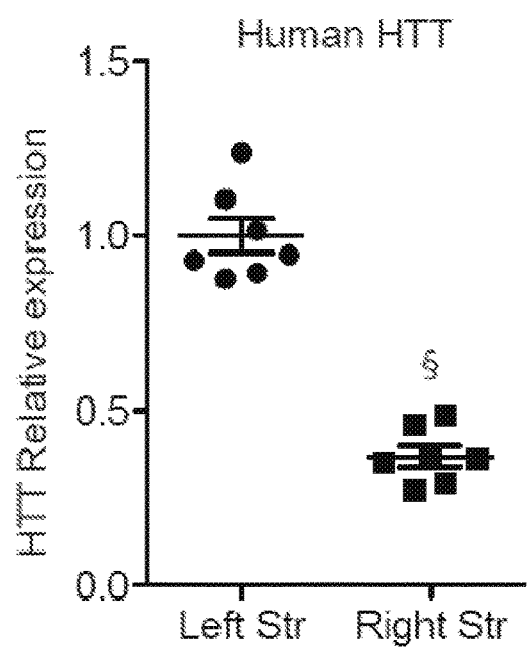

FIGS. 9A-9C: In vivo gene editing of the mutant HTT allele. FIG. 9A: Cartoon depicting rAAV shuttle vectors containing the SpCas9 and sgHD1/i3 expression cassettes. mCMV, minimal CMV promoter; mpA, minimal polyA. hU6p, human U6 promoter; pA, SV40 polyA. FIG. 9B: PCR of isolated genomic DNA showing human HTT exon1 targeted deletion after injection of vectors expressing SpCas9 and sgRNA sequences. LStr, left Striatum; RStr, Right Striatum. FIG. 9C: RT-QPCR analysis of HTT mRNA levels in striatum samples harvested 3 weeks after SpCas9 and sgHD1/i3delivery. All samples were normalized to beta actin and results are mean±SEM relative to uninjected striatal samples (n=7 animals per group, § P<0.001, Mann Whitney test). FIG. 9D: Genomic PCR products of DNA harvested after HTT exon1 editing in HEK 293 cells with rAAV2/1 SpCas9 and rAAV2/1 vectors (Left) and representative western blot showing reduced human HTT protein levels in HEK293 cells after editing with rAAV2/1 SpCas9 and rAAV2/1 vectors (Right). FIG. 9E: RT-QPCR analysis of mouse Htt mRNA levels in striatum samples harvested 3 weeks after rAAV.SpCas9 and rAAV.sgHDi3/1 injection. All samples were normalized to beta actin and results are mean±SEM relative to uninjected striatal samples (n=7 animals per group, § P<0.001, Mann Whitney test). Pairing between sgHD1 and sgHDi3 to mouse HTT exon1 sequences is also shown. One off-target site was identified for sgHDi3 in mouse Htt that contained 2 mismatches. Three off-targets were identified in the case of sgHD1, all with 5 mismatches between the mouse genomic sequence and the small guide RNA sequence. Sequences are SEQ ID NOs: 436-441, from top to bottom.

DETAILED DESCRIPTION OF THE INVENTION

Herein, therapeutics tools to inhibit mutant protein expression using genome-editing strategies based on the CRISPR/Cas9 technology are provided. Targeted gene deletions can be introduced when guide RNAs (e.g., two guide RNAs) complex with Cas9 and mediate dsDNA breaks followed by DNA repair. Given the potency of the CRISPR/Cas9 technology for targeting both alleles, and the fact that huntingtin is an important protein for cell viability, a concern of this method is that one will eliminate all huntingtin in the cell—good and bad. Thus, approaches that selectively target the expression of the mutant huntingtin allele are desirable. Here, a gene editing approach for specific targeting of the mutant huntingtin allele is provided. The strategy takes advantage of single nucleotide polymorphisms prevalent in the population for which a targeting sequence (PAM motif) is generated depending on the nucleotide variation. gRNA sequences have been developed that recruit CRISPR/Cas9 complex to this allele-specific PAM motif. The safety and allele specificity may be examined in vitro using human cell lines (e.g., HEK293, NT2, HELA, neuronal precursor cell lines, HD fibroblasts (e.g., derived from human patients) and in vivo with a new transgenic mouse expressing the nucleotide variants within the HTT locus.

As explained above, the therapeutic benefit of RNA interference (RNAi) to reduce mutant huntingtin expression in different mouse models has been shown (Harper et al. (2005) Proc. Natl. Acad. Sci., 102:5820-5825; Boudreau et al. (2009) Mol. Ther., 17:1053-1063; Drouet et al. (2009) Annals of Neurol., 65:276-285). However, RNAi treatment does not completely eliminate mutant huntingtin expression, and the mutant protein remains present at low levels. This remaining protein may mitigate positive effects of RNAi therapy in HD patients. Thus, efforts to eliminate expression of all mutant HTT protein have been sought. Genome editing nucleases present such an opportunity.

Gene editing based on bacterial endonucleases such as CRISPR-associated protein-9 (Cas9) from *Streptococcus pyogenes* has revolutionized the field (Cong et al. (2013) Science 339:819-823; Ran et al. (2013) Nature Protocols 8:2281-2308; Mali et al. (2013) Science 339:823-826; Jinek et al. (2012) Science 337:816-821). The RNA-guided CRISPR/Cas9 system involves expressing Cas9 along with a guide RNA molecule (gRNA). When coexpressed, gRNAs bind and recruit Cas9 to a specific genomic target sequence where it mediates a double strand DNA (dsDNA) break and activates the dsDNA break repair machinery. Specific DNA fragments can be deleted when two gRNA/Cas9 complexes generate dsDNA breaks at relative proximity, and the genomic DNA (genDNA) is repaired by nonhomologous end joining (FIG. 1A). gRNAs were originally designed for recruiting the CRISPR/Cas9 complex to the HTT promoter to delete regulatory sequences and inhibit HTT expression (FIG. 1B). However, the complete elimination of the expression of both the normal and mutant alleles is likely not tolerable in human adults with HD. As such, an allele specific genome editing approach is provided herein where the CRISPR/Cas9 complex is targeted to the mutant HTT allele.

The binding specificity of the CRISPR/Cas9 complex depends on two different elements. First, the binding complementarity between the targeted genDNA sequence and the complementary recognition sequence of the gRNA. Second, the presence of a protospacer-adjacent motif (PAM) juxtaposed to the genDNA/gRNA complementary region. Whereas single point mutations in the complementary recognition sequence permit Cas9-mediated DNA cleavage, the preservation of an intact PAM motif is critical (Jinek et al. (2012) Science 337:816-821; Hsu et al. (2013) Nat. Biotech., 31:827-832; Sternberg et al. (2014) Nature 507:62-67). The PAM motif for S. *Pyogenes* Cas9 has been fully characterized, and is NGG or NAG (Jinek et al. (2012) Science 337:816-821; Hsu et al. (2013) Nat. Biotech., 31:827-832). While any nucleotide type can be found at the first position of the PAM motif, a C/T nucleotide at position 2 and/or a C/T/A nucleotide at position 3 can disrupt the PAM motif and subsequently inhibit Cas9-mediated dsDNA cleavage. Thus, PAM motifs containing single nucleotide polymorphisms (SNP) at positions two or three will confer allele cleavage selectivity when targeted with CRISPR/Cas9 complexes.

The CAG (encoding glutamine) disease expansion in HTT is located within the $1^{st}$ exon of the HTT gene (The Huntington's Disease Collaborative Research Group (1993) Cell 72:971-983). A short exon 1 HTT polyadenylated mRNA resulting from aberrant splicing of the mutant allele is reported to be translated into a pathogenic exon 1 HTT protein and contribute to disease progression (Sathasivam et al. (2013) Proc. Natl. Acad. Sci., 110:2366-2370; Gipson et al. (2013) RNA Biol., 10:1647-1652). The main regulatory regions of the HTT promoter are located within the first 2 Kb upstream of the transcription start site (Holzmann et al. (2001) Brain Res., 92:85-97). The 1000 Genome database has reported the location and allele frequency of prevalent SNPs located in the promoter and within the first intronic sequence of the HTT gene (Abecasis et al. (2010) Nature 467:1061-1073). Table 1 provides selected SNPs for allele-specific gene editing on the promoter of the HTT gene. Two examples of SNPs in the first intron of the HTT gene are rs28377140 (3,079,906; G/C; + strand; gain/loss) and rs4498089 (3,080,199; A/G; + strand; gain.

TABLE 1

Prevalence of the targeted SNPs in the human huntingtin locus. From left to right the table information is: genomic location of the SNP (promoter, 5'UTR), variant ID (SNP identification), location (genomic position), SNP (nucleotide variation), allele frequency based on information obtained from 1000 Genomes data base (Reference nucleotide vs variant nucleotide polymorphism), strand (positive or negative genomic DNA strand), PAM (single nucleotide variation produces either the loss or the loss/gain of a PAM motif at the opposite genomic DNA strand).

| Location | Variant ID | Location | SNP | Allele frequency Reference | 1000 G MAF | Strand | PAM |
|---|---|---|---|---|---|---|---|
| Promoter | rs35631490 | 3,071,679 | C/G | C = 0.8926 | G = 0.1074 | + | Loss |
| Promoter | rs61792464 | 3,073,385 | G/C | G = 0.8628 | C = 0.1372 | + | Gain/Loss |
| Promoter | rs9996199 | 3,074,965 | C/G | C = 0.8425 | G = 0.1575 | + | Gain/Loss |
| Promoter | rs2857935 | 3,075,691 | C/G/T | C = 0.7710 | G = 0.2260 | − | Loss |
| Promoter | rs13122415 | 3,076,181 | C/G | C = 0.8918 | G = 0.1082 | + | Loss |
| 5'UTR | rs13102260 | 3,076,405 | G/A | G = 0.8419 | A = 0.1581 | + | Loss |

FIG. 2A provides a schematic of the targeting of Cas9 to allele specific PAM motifs by gRNA. The loss of a PAM (left), gain of a PAM (center), and a loss/gain (right) are depicted. FIG. 2B provides examples of allele specific PAM motifs based on *Streptococcus pyogenes* (SpCas9; PAM—NRG) and *Staphylococcus aureus* Cas9 (SaCas9; PAM—NNGRR, NNGRRT; Ann Ran et al. (2015) Nature 520:186-191). FIG. 2C shows the locations of the alleles listed in Table 1.

Clustered, regularly interspaced, short palindromic repeat (CRISPR)/Cas9 technology is well known in the art (see, e.g., Sander et al. (2014) Nature Biotech., 32:347-355; Jinek et al. (2012) Science, 337:816-821). Cas9 possesses two nuclease domains, a RuvC-like nuclease domain and a HNH-like nuclease domain, and is responsible for the destruction of the target DNA (Jinek et al. (2012) Science, 337:816-821; Sapranauskas et al. (2011) Nucleic Acids Res. 39:9275-9282). The two nucleases generate double-stranded breaks. The double-stranded endonuclease activity of Cas9 requires a target sequence (e.g., ~20 nucleotides) and a short conserved sequence (~2-5 nucleotides; e.g., 3 nucleotides) known as protospacer-associated motif (PAM), which follows immediately 3'—of the CRISPR RNA (crRNA) complementary sequence (Jinek et al. (2012) Science, 337: 816-821; Nishimasu et al. (2014) Cell 156(5):935-49; Swarts et al. (2012) PLoS One, 7:e35888; Sternberg et al. (2014) Nature 507(7490):62-7). Guidelines and computer-assisted methods for generating gRNAs are available (see, e.g, CRISPR Design Tool (crispr.mit.edu/); Hsu et al. (2013) Nat. Biotechnol. 31:827-832; www.addgene.org/CRISPR; and CRISPR gRNA Design tool—DNA2.0 (www.dna20.com/eCommerce/startCas9)). Typically, the PAM sequence is present in the DNA target sequence but not in the gRNA sequence.

As stated above, wild-type Cas9 creates a site-specific double-stranded DNA break. The double strand break can be repaired by non-homologous end joining (NHEJ) pathway yielding an insertion and/or deletion or, in the presence of a donor template, by homology-directed repair (HDR) pathway for replacement mutations (Overballe-Petersen et al. (2013) Proc. Natl. Acad. Sci. U.S.A. 110:19860-19865; Gong et al. (2005) Nat. Struct. Mol. Biol. 12:304-312). A Cas9 mutant may also be used in the instant invention (e.g., a mutant with an inactivated HNH and/or RuvC nuclease). In a particular embodiment, the mutant is Cas9 D10A. Cas9 D10A nicks single-strand DNA rather than generate a double strand break (Cong et al. (2013) Science, 339:819-823; Davis et al. (2014) Proc. Natl. Acad. Sci., 111:E924-932). The nicks are repaired by HDR pathway. Two gRNAs can be used to generate a staggered double strand break with Cas9 D10A.

In accordance with the instant invention, methods of treating, inhibiting, and/or preventing a polyglutamine disorder (e.g., Huntington's disease) are provided. In accordance with another aspect of the instant invention, methods for reducing the expression of a mutant protein (e.g., mutant huntingtin) encoded by an allele of a gene associated with a polyglutamine disorder (e.g., Huntington's disease) in a cell are provided. Polyglutamine (polyQ) disorder are generally neurodegenerative disorders which are caused by expanded cytosine-adenine-guanine (CAG) repeats (e.g., greater than about 36 repeats) encoding a long polyQ tract in the respective proteins. Polyglutamine (polyQ) disorders include, without limitation, spinocerebellar ataxia (SCA; types 1, 2, 3, 6, 7, 17), Machado-Joseph disease (MJD/SCA3), Huntington's disease (HD), dentatorubral pallidoluysian atrophy (DRPLA), and spinal and bulbar muscular atrophy, X-linked 1 (SMAX1/SBMA). In a particular embodiment, the methods of the instant invention comprise inhibiting, reducing, or eliminating mutant protein (e.g., HTT) expression. In a particular embodiment, the method comprises inactivating (e.g., cleaving and/or deleting (at least partially (e.g., deleting the first exon))) mutant alleles (e.g., HTT alleles) using CRISPR/Cas9 technology. In a particular embodiment, the method comprises administering at least one Cas9 (e.g., a nucleic acid molecule encoding Cas9) and at least one gRNA (e.g., a nucleic acid molecule encoding said gRNA) to said subject. Examples of Cas9 include, without limitation, *Streptococcus pyogenes* Cas9, Cas9 D10A, high fidelity Cas9 (Kleinstiver et al. (2016) Nature, 529:490-495; Slaymaker et al. (2016) Science, 351:84-88), Cas9 nickase (Ran et al. (2013) Cell, 154:1380-1389), *Streptococcus pyogenes* Cas9 with altered PAM specificities (e.g., SpCas9_VQR, SpCas9_EQR, and SpCas9_VRER; Kleinstiver et al. (2015) Nature, 523:481-485), *Staphylococcus aureus* Cas9, the CRISPR/Cpf1 system of *Acidaminococcus*, and the CRISPR/Cpf1 system of Lachnospiraceae. In a particular embodiment, the Cas9 is *S. pyogenes* Cas9. In a particular embodiment, the Cas9 has an inactivated HNH and/or RuvC nuclease, particularly Cas9 D10A. In a particular embodiment, at least two gRNAs are delivered. In a particular embodiment, at least one gRNA targets a region adjacent to a PAM present in only one allele (e.g., in the mutant allele). In a particular embodiment, the targeted PAM is in the 5'UTR, promoter, or first intron. In a particular embodiment, a second gRNA which is not targeted to the allele specific PAM is provided. In a particular embodiment, the second gRNA targets anywhere from the 5'UTR to the 3'UTR of the gene (e.g., HTT gene), particularly within the first intron. In a particular embodiment, the method further comprises the administration of a donor nucleic acid molecule (e.g., DNA; e.g., a nucleic acid molecule encoding the desired sequence). The donor DNA may be a replacement sequence (e.g., wild-type) for the sequence excised from the mutant. The nucleic acids of the instant invention may be administered consecutively (before or after) and/or at the same time (concurrently). The nucleic acid molecules may be administered in the same composition or in separate compositions. In a particular embodiment, the nucleic acid molecules are delivered in a single vector (e.g., a viral vector).

The methods of the instant invention may also comprise the administration of an additional therapeutic for Huntington's disease or the related disorder. Other therapeutics include, without limitation: haloperidol, tetrabenazine, amantadine, huintingtin antisense, huntingtin siRNA, antidepressants, and antianxiety medications. The nucleic acids of the instant invention and the other therapeutics may be administered consecutively (before and/or after) and/or at the same time (concurrently). The other therapeutics may be administered in the same composition or in separate compositions as the nucleic acid molecules of the instant invention.

In a particular embodiment, the nucleic acid molecules of the instant invention are delivered (e.g., via infection, transfection, electroporation, etc.) and expressed in cells via a vector (e.g., a plasmid), particularly a viral vector. The expression vectors of the instant invention may employ a strong promoter, a constitutive promoter, and/or a regulated promoter. In a particular embodiment, the nucleic acid molecules are expressed transiently. Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). Examples of expression vectors for expressing the molecules of the invention include, without limitation, plasmids and viral vectors (e.g., adeno-associated viruses (AAVs), adenoviruses, retroviruses, and lentiviruses).

In a particular embodiment, the guide RNA of the instant invention may comprise separate nucleic acid molecules. For example, one RNA specifically hybridizes to a target sequence (crRNA) and another RNA (trans-activating crRNA (tracrRNA)) which specifically hybridizes with the crRNA. In a particular embodiment, the guide RNA is a single molecule (sgRNA) which comprises a sequence which specifically hybridizes with a target sequence (crRNA; complementary sequence) and a sequence recognized by Cas9 (e.g., a tracrRNA sequence; scaffold sequence). Examples of gRNA scaffold sequences are well known in the art (e.g., 5'-GUUUUAGAGC UAGAAAUAGC AAGUUAAAAU AAGGCUAGUC CGUUAUCAAC UUGAAAAAGU GGCACCGAGU CGGUGCUUUU; SEQ ID NO: 442). As used herein, the term "specifically hybridizes" does not mean that the nucleic acid molecule needs to be 100% complementary to the target sequence. Rather, the sequence may be at least 80%, 85%, 90%, 95%, 97%, 99%, or 100% complementary to the target sequences. The greater the complementarity reduces the likelihood of undesired cleavage events at other sites of the genome. In a particular embodiment, the region of complementarity (e.g., between a guide RNA and a target sequence) is at least about 10, at least about 12, at least about 15, at least about 17, at least about 20, at least about 25, at least about 30, at least about 35, or more nucleotides. In a particular embodiment, the region of complementarity (e.g., between a guide RNA and a target sequence) is about 15 to about 25 nucleotides, about 15 to about 23 nucleotides, about 16 to about 23 nucleotides, about 17 to about 21 nucleotide, or about 20 nucleotides. In a particular embodiment, the guide RNA targets a sequence or comprises a sequence (inclusive of RNA version of DNA molecules) as set forth in the Example or Figures provided herein (see, e.g., the guide or target sequences provided in FIGS. 5 and 6). In a particular embodiment, the guide RNA targets a sequence or comprises a sequence which has at least 80%, 85%, 90%, 95%, 97%, 99%, or 100% homology or identity to a sequence set forth in the Examples and/or Figures (e.g., FIGS. 5 and 6) provided herein. In a particular embodiment, the guide RNA targets a sequence selected from the group consisting of SEQ ID NOs: 156-228 and 379-388. In a particular embodiment, the guide RNA comprises a sequence selected from the group consisting of SEQ ID NOs: 156-228 and 379-388 (e.g., in RNA form). The sequences may be extended or shortened by 1, 2, 3, 4, or 5 nucleotides at the end of the sequence opposite from the PAM (i.e., the 5' end). When the sequence is extended the added nucleotides should correspond to the HTT sequence. In a particular embodiment, one gRNA comprises sgHD1, sgHD2, sgHD3, sgHD4, sgHD5c, sgHD6c, or sgHD6g. In a particular embodiment, the second gRNA comprises sgHDi3 or sgHDi4. In a particular embodiment, one gRNA comprises sgHD1 and one gRNA comprises sgHDi3.

As stated hereinabove, the instant invention provides nucleic acid molecules, vectors, and compositions and methods for the inhibition, treatment, and/or prevention of Huntington's disease and related disorders. Compositions comprising at least one nucleic acid described herein are also encompassed by the instant invention. In a particular embodiment, the composition comprises at least one, particularly at least two, guide RNA (e.g., a nucleic acid molecule encoding the guide RNA (e.g., an expression vector)) and at least one pharmaceutically acceptable carrier. The composition may further comprise at least one Cas9 (e.g., a nucleic acid molecule encoding Cas9) and/or at least one donor nucleic acid molecule. The composition may further comprise at least one additional therapeutic (as described above). In a particular embodiment, all of the nucleic acid molecules are encoded within a single expression vector (e.g., viral vector (e.g., AAV)). Alternatively, the other nucleic acid molecules may be contained within a separate composition(s) with at least one pharmaceutically acceptable carrier. The present invention also encompasses kits comprising a first composition comprising at least one guide RNA (e.g., a nucleic acid molecule encoding the guide RNA (e.g., an expression vector)) and a second composition comprising at least one Cas9 (e.g., a nucleic acid molecule encoding Cas9) and/or at least one donor nucleic acid molecule. The first and second compositions may further comprise at least one pharmaceutically acceptable carrier. In a particular embodiment, the kits of the instant invention comprise a first composition comprising at least one guide RNA (e.g., a nucleic acid molecule encoding the guide RNA (e.g., an expression vector)), at least one Cas9 (e.g., a nucleic acid molecule encoding Cas9), and/or at least one donor nucleic acid molecule (optionally all within a single vector) and a second composition comprising at least one additional therapeutic. The first and second compositions may further comprise at least one pharmaceutically acceptable carrier.

As explained hereinabove, the compositions of the instant invention are useful for treating Huntington's disease and related disorders. A therapeutically effective amount of the composition may be administered to a subject in need thereof. The dosages, methods, and times of administration are readily determinable by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

Selection of a suitable pharmaceutical preparation depends upon the method of administration chosen. For example, the components of the invention may be administered by direct injection into any desired tissue (e.g., brain) or into the surrounding area. In this instance, a pharmaceutical preparation comprises the components dispersed in a medium that is compatible with blood or the target tissue.

The therapy may be, for example, administered parenterally, by injection into the blood stream (e.g., intravenous), or by subcutaneous, intramuscular or intraperitoneal injection. Pharmaceutical preparations for injection are known in the art. If injection is selected as a method for administering the therapy, steps must be taken to ensure that sufficient amounts of the molecules reach their target cells to exert a biological effect.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Injectable suspensions may be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient.

Appropriate concentrations for alleviation of a particular pathological condition may be determined by dosage concentration curve calculations, as known in the art.

The methods of the instant invention may further comprise monitoring the disease or disorder in the subject after administration of the composition(s) of the instant invention to monitor the efficacy of the method. For example, the subject may be monitored for characteristics of Huntington's disease and related disorders.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, preservative, antioxidant, solubilizer, emulsifier, adjuvant, excipient, bulking substances, auxiliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described, for example, in "Remington's Pharmaceutical Sciences" by E. W. Martin.

The term "treat" as used herein refers to any type of treatment that imparts a benefit to a patient suffering from an injury, including improvement in the condition of the patient (e.g., in one or more symptoms), delay in the progression of the condition, etc.

As used herein, the term "prevent" refers to the prophylactic treatment of a subject who is at risk of developing a condition and/or sustaining an injury, resulting in a decrease in the probability that the subject will develop conditions associated with the injury.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated traumatic brain injury in a patient.

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. A vector may comprise expression operons or elements such as, without limitation, transcriptional and translational control sequences, such as promoters, enhancers, translational start signals, polyadenylation signals, terminators, and the like, and which facilitate the expression of a polynucleotide or a polypeptide coding sequence in a host cell or organism.

The following example describes illustrative methods of practicing the instant invention and is not intended to limit the scope of the invention in any way.

Example

Huntington disease (HD) is a fatal dominantly inherited neurodegenerative disorder caused by CAG repeat expansion (~<36 repeats) within the first exon of the huntingtin gene. Although mutant huntingtin (mHTT) is ubiquitously expressed, the brain shows robust and early degeneration. Current RNA interference-based approaches for lowering mHTT expression have been efficacious in mouse models, but basal mutant protein levels are still detected. To fully mitigate expression from the mutant allele, allele specific genome editing can occur via prevalent promoter-resident single nucleotide polymorphisms (SNP) in heterozygosity with the mutant allele. Here, SNPs are identified that either cause or destroy PAM motifs critical for CRISPR selective editing of one allele vs. the other in cell from HD patients, and in a transgenic HD model harboring the human allele.

Briefly, SNPs within the promoter or intron 1 with an allele frequency >10% in the population were identified using the NCBI website and the 1000 Genome database. 8 SNPs in which the nucleotide change either disrupt and/or generate a PAM motif to allow target specifically of the mutant HTT allele were identified (Table 1 provides certain examples). gRNA sequences targeting selected allele specific PAM motifs were designed and cloned into a CRISPR/Cas9 expression cassette containing a puromycin selection marker.

Standard human laboratory cell lines (e.g., HEK293, HELA, and NT2), patient fibroblasts, and iPS cells may be genotyped for the selected SNPs. Different cell lines containing the selected nucleotide variants can be used to determine allele selectivity and safety of the approach. For HD fibroblasts containing heterozygous SNPs, direct sequencing of PCR amplified genome sequences containing CAG repeat or SNP linkage by circularization (SLiC) can be used to identify the linkage between CAG repeat length and the nucleotide identity (Liu et al. (2008) Nature Methods 5:951-953). After transfection, genomic DNA can be isolated and CRISPR/Cas9 mediated deletions determined by PCR. The effects on huntingtin expression can be determined by measuring RNA and protein levels by Q-PCR and Western blot, respectively. Unintended cleavage of selected sequences can be determined by using GUIDE-seq method (Tsai et al. (2015) Nature Biotechnol., 33:187-197). Knock in transgenic mice can also be generated where the promoter, the first exon and/or the first intronic sequence of the mouse Htt gene are replaced by the orthologous human HTT sequence containing the different SNP-nucleotide variants on each allele. The therapeutic efficacy of the selected sgRNA sequences (e.g., delivered by an AAV viral vector) can be studied in vivo using current mouse models which exhibit disease phenotypes or the knock in mice.

As explained above, Huntington Disease (HD) is a fatal neurodegenerative disorder due to polyglutamine (polyQ) disorder caused by triplet CAG repeat expansion in the huntingtin (HTT) gene. Although huntingtin is ubiquitously expressed, the neuropathology of HD is characterized by early striatal atrophy followed by volume loss in other brain areas (Walker, F. O. (2007) Seminars Neurol., 27:143-150; The Huntington's Disease Collaborative Research Group (1993) Cell, 72:971-983). There is no cure for HD and treatments are focused on symptom management (Johnson et al. (2010) Hum. Mol. Genet., 19:R98-R102). Earlier studies using genetically modified mouse models showed that HD-like phenotypes can be resolved if mutant huntingtin expression is eliminated, even at advanced disease stages (Yamamoto et al. (2000) Cell, 101:57-66; Diaz-Hernandez et al. (2005) J. Neurosci., 25:9773-9781), suggesting that therapeutic strategies focused on eliminating mutant huntingtin expression will be highly beneficial. As examples, knock down strategies using RNA interference (RNAi) or antisense oligonucleotides, which reduce mutant huntingtin expression either alone or together with the normal huntingtin, are beneficial in various mouse models (Harper et al. (2005) Proc. Natl. Acad. Sci., 102:5820-5825; Boudreau et al. (2009) Mol. Ther., 17:1053-1063; Drouet et al. (2009) Ann. Neurol., 65:276-285; Kordasiewicz et al. (2012) Neuron, 74:1031-1044). Other strategies, such as genome editing with zinc finger nucleases targeted to the CAG-repeat expansion region, have also been tried (Garriga-Canut et al. (2012) Proc. Natl. Acad. Sci., 109:E3136-3145).

Genome editing with the recently discovered CRISPR/Cas9 system represents an exciting alternative for tackling dominantly inherited genetic disorders such as HD (Jinek et al. (2012) Science, 337:816-821; Mali et al. (2013) Science, 339:823-826; Cong et al. (2013) Science, 339:819-823). The most recent system advancements involves expressing Cas9 along with a guide RNA such as a single guide RNA molecule. When co-expressed, gRNAs bind and recruit Cas9 to a specific genomic target sequence where it mediates a double strand DNA (dsDNA) break, activating the dsDNA break repair machinery. Targeted gene deletions by non-homologous end joining (NHEJ) can be made when a pair of gRNA/Cas9 complexes bind in proximity and produce dsDNA breaks (Cong et al. (2013) Science, 339:819-823; Ran et al. (2013) Nat. Protoc., 8:2281-2308; Jinek et al. (2013) eLife, 2:e00471).

Given the potency and sequence specificity of the CRISPR/Cas9 targeting, and the fact that huntingtin is an important protein for cell viability (Dragatsis et al. (2000) Nat. Genet., 26:300-306), the use of CRISPR/Cas9 to direct allele specific genome editing is an attractive alternative to the partial reduction approach using ASOs or RNAi methods. Targeting specificity of the CRISPR/Cas9 complex is regulated by two different elements, first, the binding complementarity between the targeted genomic DNA sequence (genDNA) and the ~20 nt-guiding sequence of the gRNA, and secondly, the presence of a protospacer-adjacent motif (PAM) juxtaposed to the genDNA/gRNA complementary region (Jinek et al. (2012) Science, 337:816-821; Cong et al. (2013) Science, 339:819-823; Sternberg et al. (2014) Nature, 507:62-67). While previous studies have shown that nucleotide mismatches at positions 1-10 on the sgRNA-target site interface are not well tolerated for cleavage, sequence context at this region is crucial to determine which nucleotide positions are more effective to influence cleavage (Jinek et al. (2012) Science, 337:816-821; Ran et al. (2013) Nat. Protoc., 8:2281-2308; Sternberg et al. (2014) Nature, 507:62-67; Fu et al. (2013) Nat. Biotech., 31:822-826; Kuscu et al. (2014) Nat. Biotech., 32:677-683). However, the preservation of an intact PAM motif appears to be critical and genome wide studies searching for Cas9 off-target cleavage events demonstrate that mutations on the PAM motif result on an important reduction of cleavage efficacy (Anders et al. (2014) Nature, 513:569-573; Kleinstiver et al. (2015) Nature, 523:481-485; Tsai et al. et al. (2015) Nat. Biotech., 33:187-197; Zetsche et al. (2015) Cell, 163:759-771; Ran et al. (2015) Nature, 520:186-191). Therefore, allele specific gene editing can be achieved by taking advantage of prevalent single nucleotide polymorphisms (SNPs) that either eliminate or create a PAM sequence. In HD, polyglutamine repeat expansion occurs within exon 1 (Walker, F. O. (2007) Seminars Neurol., 27:143-150). Because the main regulatory elements for HTT expression reside within the first 2 Kb 5' of the transcription start site (Coles et al. (1998) Hum. Mol. Genet., 7:791-800), SNP-dependent PAMs in heterozygosity with the mutation are natural CRISPR/Cas9 targets for allele specific editing. Genomic regions adjacent to HTT exon-1 were screened to identify SNPs that were prevalent, and were within the critical position for CRISPR/Cas9- or CRISPR/Cpf1-directed editing. Their utility was tested for allele-specific editing in HD patient cell lines and a mouse model expressing full length mutant human HTT.

Methods

Prediction of SNP-Dependent PAM Motifs:

SNPs with a prevalence of ≥5% located upstream (6.5 Kb) and downstream (Intron 1) HTT exon1 were obtained from the 1000 Genomes database using the NCBI variation viewer website (www.ncbi.nlm.nih.gov/variation/view/?q=HTT&filters=source:dbsnp&assm=GCF_000001405.25). To predict SNP-dependent PAM motifs, SNPs were screened against the consensus PAM sequences of *Streptococcus Pyogenes* (SpCas9, NGG or NAG) and *Staphylococcus aureus* (SaCas9 NNGRRT), or the CRISPR/Cpf1 systems of *Acidaminococcus* (AsCpf1, NTTT) and *Lachnospiraceae* (LbCpf1, heterogenous PAMs). Only those SNPs positioned in a conserved nucleotide PAM position in which the nucleotide variation disrupted the consensus PAM were predicted as SNP-dependent PAM motifs.

Cell Culture and Transfection:

Human embryonic kidney (HEK293) cells were maintained in DMEM media containing 10% Fetal Bovine Serum (FBS), 1% L-Glutamine and 1% penicillin/streptomycin at 37° C. with 5% $CO_2$. Cells were cultured in 24 well plates and transfected at 80-90% confluence using Lipofectamine® 2000 transfection reagent, according to the manufacturer's protocol. Human HD patient fibroblasts were maintained on MEM media supplemented with 15% Fetal Bovine Serum (FBS), 1% MEM non-essential amino acids, 1% penicillin/streptomycin and 1% L-Glutamine at 37° C. with 5% $CO_2$. DNA transfection was done by electroporation using Invitrogen Neon® transfection reagent using the electroporation conditions (ND31551: 1650V, 10 ms, 3 pulses; ND33392: 1450V, 20 ms, 2 pulses), and following the guidelines provided by manufacturer.

sgRNA and Cas9 Plasmid Construction:

The plasmid pX330 containing the SpCas9 and sgRNA expression cassettes was used as a template for further modifications. To determine transfection efficacy and for selecting positive transfected cells a CMV reporter cassette expressing eGFP/P2A/puromycin fusion protein was cloned downstream of the SpCas9expression cassette. For all sgRNAs the guide complementary sequences were cloned using a single cloning step with a pair of partially complementary oligonucleotides. The oligo pairs encoding the genomic complementary guide sequences were annealed and ligated into the BbsI cloning site upstream and in frame with the invariant scaffold of the sgRNA sequence.

Genomic DNA Extraction, SNP Genotyping and Genome Editing Analysis:

Genomic DNA from HD fibroblast and HEK293 cell lines was extracted using DNeasy® Blood & Tissue kit (Qiagen) according to manufacturer's instructions. SNPs were genotyped by direct Sanger sequencing of PCR amplified products containing the SNPs and using the primers listed on Table 2. To determine which nucleotide variation of SNP1 (rs2857935) was linked to the normal or the mutant allele the genomic sequence containing SNP1 and the CAG repeat was amplified by PCR and cloned into TOPO® plasmids using the TOPO TA cloning kit, and subsequently transformed into DH5alpha competent cells. Individual colonies were analyzed using Sanger sequencing to determine which nucleotide variant is associated with the normal or mutant allele. Deletions of HTT exon 1 were confirmed on genomic DNA samples by PCR, using primers binding outside the intervening segment cleaved by the sgRNA/SpCas9 complex pair (Table 2).

TABLE 2

List of primers and oligonucleotides.

| Oligos to generate guide sequences: | |
|---|---|
| Name: | Sequence (SEQ ID NOs: 1-20) |
| PosCRPAS1 | caccGCTCCAGGCGTCGGCGG |
| NegCRPAS1 | aaaaCCGCCGACGCCTGGAGC |
| PosCRPAS2 | caccGGCGCGGGGCTCAACGGAG |
| NegCRPAS2 | aaaaCTCCGTTGAGCCCCGCGCC |
| PosCRPAS3 | caccGTCTGGGACGCAAGGCGCCG |
| NegCRPAS3 | aaaaCGGCGCCTTGCGTCCCAGAC |
| PosCRPAS4 | caccGATGCACGCGGGGTGGGGC |
| NegCRPAS4 | aaaaGCCCCACCCCGCGTGCATC |
| PosCRPAS5G | tcccATTCAGGTTGATGTCCT |
| NegCRPAS5G | aaaaAGGACATCAACCTGAAT |
| PosCRPAS5C | tcccATCCCATTCTGAGGTTCTGG |
| NegCRPAS5C | aaaaCCAGAACCTCAGAATGGGAT |
| PosCRPAS6C | caccGCAGGCAGAGAGGAGCC |
| NegCRPAS6C | aaaaGGCTCCTCTCTGCCTGC |
| PosCRPAS6G | caccGCCTGGCTAAAGTAGGCTT |
| NegCRPAS6G | aaaaAAGCCTACTTTAGCCAGGC |
| PosCRi3 | caccGCTTTTAGGACGCCTCGG |
| NegCRi3 | aaaaCCGAGGCGTCCTAAAAGC |
| PosCRi4 | caccGCGGGACACTTCGAGAGG |
| NegCRi4 | aaaaCCTCTCGAAGTGTCCCGC |

| Primers to assess cleavage | |
|---|---|
| Name: | Sequence (SEQ ID NOs: 21-25) |
| Fwd1SNP | 5'-GAC CAC GCG CAT TCT CT-3' |
| Fwd4SNP | 5'-GGA AAC AGG ACA GAT GAA GGAG-3' |
| Fwd5SNP | 5'-CAG CTC AGA CGG AAG TGT ATT T-3' |
| Fwd6SNP | 5'-CTC CCA AGA ACT GGG AAC TAA C 3' |
| Rev3Cleavage | 5'-ACC ACC GTG ATC ATG AAC TAA A-3' |

| Primers for genotyping | |
|---|---|
| Name: | Sequence (SEQ ID NOs in parentheses) |
| Fwd1SNP | 5'-GAC CAC GCG CAT TCT CT-3' (21) |
| Rev1SNP | 5'-CGG GAC TGC ATG GTA AGG-3' (26) |
| Seq1SNP | 5'-GCT GTC CGG GTG AGT ATG-3' (27) |

TABLE 2-continued

List of primers and oligonucleotides.

| Name | Sequence |
|---|---|
| FwdSNP2 | 5'-CCC ACC TCT CAC CTT CCT-3' (28) |
| RevSNP2 | 5'-CAG CAT GAT TGA CAG CCC TA-3' (29) |
| Seq2SNP | 5'-CCG CGA CAC TTC ACA CA-3' (30) |
| FwdSNP3 | 5'-CCG CGA CAC TTC ACA CA-3' (31) |
| RevSNP3 | 5'-TGC TGC TGG AAG GAC TTG 3' (32) |
| Seq3SNP | 5'-TAG GGC TGT CAA TCA TGC TG 3' (33) |
| Fwd4SNP | 5'-GGA AAC AGG ACA GAT GAA GGA G-3' (22) |
| Rev4SNP | 5'-GGG AAT TGA GGG CGG TTT AT-3' (34) |
| Seq4SNP | 5'-TTT ACC AGC TCC TGG CTT TC-3' (35) |
| Fwd5SNP | 5'-CAG CTC AGA CGG AAG TGT ATT T-3' (23) |
| Rev5SNP | 5' GAG CAT GTC CGT GTC CTA ATC-3' (36) |
| Seq5SNP | 5'-TCC CTG GCT AGC ACT TAC TT-3' (37) |
| Fwd6SNP | 5'-CTC CCA AGA ACT GGG AAC TAA C 3' (24) |
| Rev6SNP | 5'-TGT GAT TAG TGC AGC GAG AAG-3' (38) |
| Seq6SNP | 5'-CTG TTT CTC TGC TGT CCT TCT C-3' (39) |

Primers for SQ-PCR reaction

| Name: | Sequence (SEQ ID NOs: 40-43) |
|---|---|
| FwdHTT | TCGGTGCAGCGGCTCCTC |
| Rev HTT | ATGGCGACCCTGGAAAAGCTG |
| FwdActB | TTCGCGGGCGACGATGC |
| RevActB | CGTACATGGCTGGGGTGTTG |

Primers to determine off target indels

| Name: | Sequence (SEQ ID NOs: 44-65) |
|---|---|
| CBFA2T3_Fwd | TCTGTGGTTCAGCCGACTTC |
| CBFA2T3_Rev | ACACAATACCGTGGCAGAGG |
| SLC45A_Fwd | GACCCAAGCTTGCCGTAGTA |
| SLC45A_Rev | ACCTGTTCAGCATCGACGAG |
| STT3B_Fwd | CCTAACGGACCTGTCGCTTT |
| STT3B_Rev | TGAGGGACGACTTGTGCTTG |
| NAV2_Fwd | CCACGAGTGCACACAGTTTG |
| NAV2_Rev | CTCAAGGACTGCTGGCTCAA |
| NUP210_Fwd | AGCTGCGTGATCTTGACCAA |
| NUP210_Rev | GGTGGTTCAGGCTCTTTCCA |
| DNAJC16_Fwd | TCTCATGCACCTCCTCCCAT |
| DNAJC16_Rev | TGAGTGCAGCGACATGATCA |
| LEPR_Fwd | TGAGATGTGCCTCCCTCAGA |
| LEPR_Rev | AACTAGTGGCATGCGTTTGC |
| CHRNA2_Fwd | CCTTCTGCATGTGGGGTGAT |
| CHRNA2_Rev | TGAGATCATCCCGTCCACCT |
| TRIB1_Fwd | TCCCGGGACTTAAAAAGCCG |
| TRIB1_Rev | ACCTGGTCAAATGGCGTCTT |
| SMARCD1_Fwd | TATGGTTTTCCCTCCCGGAC |
| SMARCD1_Rev | AGCAGGTGTGTAACTGCCTC |
| COX11_Fwd | GTTAGAGGCTGCGGACCTTT |
| COX11_Rev | GCCGTTTCTTAGGCCAGAGT |

RNA Extraction, RT-QPCR and SQ-PCR of HTT Expression Levels:

Total RNA was extracted using TRIzol® (Life Technologies, Grand Island, N.Y., USA) according to the manufacturer's protocol, with the exception of 1 μl Glycoblue™ (Life Technologies, Grand Island, N.Y.) in addition to the aqueous phase on the isopropanol precipitation step and a single wash with cold 70% ethanol. RNA samples were quantified by spectrophotometry and subsequently cDNAs were generated from 1 μg of total RNA with random hexamers (TaqMan® RT reagents, Applied Biosystems). To determine human HTT expression levels in HD fibroblasts and HEK293 cells, TaqMan® probes for human HTT and glyceraldehyde 3-phosphate dehydrogenase (GAPDH) mRNAs obtained from Applied Biosystems were used. For determining human and mouse HTT expression levels in BACHD mice samples TaqMan® Probes for human HTT mRNA, mouse Htt mRNA and mouse beta actin mRNA obtained from Applied Biosystems were used. Relative HTT gene expression was determined using the ddCt method. Allele specific editing was determined by a Semi Quantitative PCR amplification of the CAG repeat within HTT exon 1. RT-PCR experiments were carried out with cDNAs generated from 1 μg of total RNA and using 80 ng for PCR amplification. The RT-exponential phase was determined on 25-30 cycles to allow semi-quantitative (SQ) comparison of cDNAs developed from identical reactions with Biolase™ Taq Polymerase (Bioline Inc, MA). A SQ-PCR reaction for Actin B (20 cycles) was used as a reference gene to determine loading differences between samples. The primers are shown in Table 2. Briefly, the high capacity cDNA kit from Applied Biosystems was used for the Rt-reaction with random hexamers.

Huntingtin Western Blots:

HEK293 cells were transfected with sgRNA/SpCas9 expression cassettes, selected for 2 days with puromycin (3 μM) and expanded until cells reached confluence. Then, cells were rinsed once with PBS and lysed with passive lysis buffer (PBL, Promega). Protein concentrations were determined using the DC protein assay (BioRad) and 15 μg of protein loaded on a 3-8% NuPAGE® Tris-Acetate gel (Novex Life Technologies). HD fibroblast cells were electroporated with sgRNA/SpCas9 expression cassettes, selected for 2 days with puromycin (2 μM) and expanded until cells reached confluence. Cells were then rinsed with iced-cold PBS, de-attached, pelleted, snap froze, and lysed with SDP lysis buffer (50 mM Tris pH8.0, 150 mM NaCl, 1% NP40, 1× complete protease inhibitors, 1× phosphatase inhibitors, 100 mM PMSF) followed by incubation on ice for 20 minutes with occasional vortexing. Debris was removed by centrifugation (15 min, 20,000 g 4° C.) and the supernatant retained. Protein concentrations were determined using the DC protein assay (BioRad). Samples (25 μg) were prepared for immunoblotting by denaturing the lysates in LDS sample buffer (Invitrogen) with 2× reducing agent (100 mM DTT, Invitrogen) and heating to 70° C. for 10 minutes. Samples were resolved on a 10% low-bis acrylamide gels (200:1 acrilamide:Bis) with Tris-glycine running buffer (25 mM Tris, 190 mM Glycine, 0.1% SDS) containing 10.7 mM Beta mercaptoethanol. Gels were run on ice for 40 minutes at 90V through the stack, then at 190 V. Proteins were transferred overnight at 30V and 4° C. onto polyvinylidene fluoride (PVDF) membranes with NuPage® transfer buffer (Invitrogen: 25 mM Bicine, 25 mM Bis-Tris, 1.025 mM EDTA, 5% MeOH, pH7.2). Membranes were blocked with 5% milk in PBS-T and then blotted with a Human anti-HTT (1:5000, Millipore, CA, USA), or rabbit anti beta-actin (1:40000, Sigma) antibodies followed by horseradish peroxidase-coupled antibodies (1:10,000, mouse; or 1:50,000, Rabbit; Jackson ImmunoResearch, West Grove, Pa.). Blots were developed with ECL Plus reagents (Amersham Pharmacia). HTT reduction was determined by densitometry (n=3 independent experiments) of protein levels relative to beta catenin with the VersaDoc™ Imaging System (Biorad) and Quantity One analysis software.

rAAV Vector Design and Production:

For in vivo studies, two different rAAV vectors were generated. One expressed SpCas9 and one the sgRNAs expression cassettes. SpCas9 was expressed under the control of a minimal cytomegalovirus immediate-early gene enhancer/promoter region (CMV promoter) and cloned upstream of a minimal poly A sequence (FBAAV-Cas9). The sgRNA expression cassettes were moved into an AAV shuttle plasmid containing an eGFP gene under the control of the CMV promoter and upstream of a SV40 pA signal. All rAAV plasmid shuttles have AAV2 inverted terminal repeat sequences. RAAV vectors were produced by standard calcium phosphate transfection method in HEK293 cells by using the Ad Helper, AAV1 transpackaging and AAV shuttle plasmids. Vector titers were determined by RT PCR and were $1 \times 10^{13}$ vg/ml. Vector purity was also tested by silver stain.

Off-Target Analysis:

Potential off target loci for sgHD guide sequences in the human genome were determined using the Cas9-Off finder algorithm (Bae et al. (2014) Bioinform., 30:1473-1475). Genomic DNA was extracted from HD human fibroblasts electroporated with sgHD1 and sgHDi3 and amplicons generated with Phusion® polymerase using PCR primers flanking the potential site. Amplicons were subjected to Sanger sequencing to determine mutations in the cleavage site using specific primers, as well as cloned into TOPO-cloning system for sequence confirmation using 3-4 colonies/site.

Mouse Studies:

BACHD mice were obtained from Jackson Laboratories (Bar Harbor, Me.). Mice were housed in a temperature-controlled environment on a 12-hour light/dark cycle. Food and water were provided ad libitum. Mice were injected with a combination 1:1 of rAAV2/1-SpCas9 virus and rAAV-hU6sgRNA/eGFP virus. For rAAV injections, mice were anesthetized with isofluorane, and 5 μl of rAAV mixture injected unilaterally into the right striata at 0.2 μl/min (coordinates: +0.86 mm rostral to Bregma, +/−1.8 mm lateral to medial, −2.5 mm ventral from brain surface). After 3 weeks, mice were anesthetized with a Ketamine and Xylacine mix and perfused with 18 ml of 0.9% cold saline mixed with 2-ml RNAlater® (Ambion) solution. Brains were removed, blocked and cut into 1-mm-thick coronal slices. Tissue punches from striata were taken using a tissue corer (1.4-mm in diameter; Zivic Instruments, Pittsburgh, Pa.). All tissue punches were flash frozen in liquid nitrogen and stored at −80° C. until use.

Statistical Analysis

All statistical analyses were performed using Graph-Pad Prism v5.0 software. All data was analyzed using one-way ANOVA followed by a Bonferroni's post-hoc, or a Mann Whitney test as indicated. Statistical significance was considered * $P<0.05$, ‡ $P<0.01$, § $P<0.001$, # $P<0.0001$.

Results

Screening SNP-Derived PAM Motifs in the HTT Genomic Locus

A goal was to delete the mutant HTT allele using SNP-dependent PAMs flanking HTT exon 1 that when present in heterozygosity would tether the Cas9 protein to the mutant, but not the normal allele (FIG. 3A). The CRISPR/SpCas9 system from *Streptococcus pyogenes* is the most widely used, and its PAM sequence (NRG, where N represents any nucleotide, R a purine and the conservation of a guanine) have been characterized (Jinek et al. (2012) Science, 337: 816-821; Cong et al. (2013) Science, 339:819-823). SNPs present at specific PAM positions could generate, remove, or simultaneously do both in a strand specific way (FIG. 3B). Using the NCBI website and the 1000 Genomes database, the upstream (3 Kb, Promoter/5'UTR) and downstream (6.5 Kb, Intron 1) genomic sequences of HTT exon-1 were screened and 47 SNPs with a prevalence of more than 5% were identified. Of these, 21 were present within the conserved third nucleotide of the PAM sequence of SpCas9 (FIG. 3C, FIG. 5A-5O, FIGS. 3D-3J). Overall, the nucleotide variation caused the loss (8 SNPs), gain (8 SNPs), or simultaneously the loss in one DNA strand and the gain on the opposite strand (5 SNPs, Loss/Gain) (FIG. 1C, FIGS. 3D-3J). FIG. 3K shows the flanking sequence of the indicated SNPs, the location of the PAMs, and an example of complementary sequence to target the site for cleavage.

Experimental Validation of HTT Promoter SNP-Dependent PAM Motifs

Small guide RNAs (sgRNAs; single guide RNAs) were generated that bind adjacent to PAM sequences representing 5 of the identified SNPs in the upstream ~6 Kb (SNPs 1, 2, 4, 5, and 6) and to a SNP-dependent PAM near the transcription start site (SNP3) (FIGS. 4A, 4B, 6A, and 6B) to test as candidates for CRISPR/Cas9 cleavage in HEK 293 cells. These SNPs have an allele frequency of >10% in the general population, and the nucleotide variations cause the Loss or a Loss/Gain of the PAM motif (Table 3). Common sgRNAs were also designed for the first HTT intron (sgHDi3 and sgHDi4; FIG. 4A and FIGS. 6A and 6B). The sgRNAs were cloned downstream of the hU6 or hH1 promoter, along with other elements as depicted (FIG. 2C). HEK 293 cells, which are homozygous for the targeting SNPs (FIG. 4B) were transfected with SpCas9 and sgRNA expression plasmids and genomic deletion assessed. DNA products of the anticipated size were amplified in most of the sgRNA/SpCas9 pair complexes tested (FIG. 4D, 4E, 4F). As expected, HTT remained intact in cells expressing SpCas9 or sgHDi3 only, or co-expressing sgHDi3 with a sgRNA sequence for which a PAM sequence is absent in the HTT promoter (sgHD5c/i3 and sgHD6g/i3). HTT exon1 cleavage in cells was not detected transfected with sgHD5g/i3, in spite of the presence of the PAM. Both sgHD1 and sgHD5g have a 17 nt complementary sequence, yet sgHD1/i3 eliminated HTT exon 1 while sgHD5/i3 did not. Interestingly, sgHD1 has 8 guanines, 6 cytosines and 1 adenosine whereas sgHD5g has 4 guanines, 3 cytosines and 3 adenosines. This is consistent with work showing a direct correlation between the sequence composition of the sgRNA complementary region to sgRNA activity, with the most active sequences enriched for guanine and cytosine and depleted of adenosine (Moreno-Mateos et al. (2015) Nat. Meth., 12:982-988). Sanger sequencing of the small-amplified PCR products confirmed HTT exon1 deletion and dsDNA repair (FIG. 4J).

TABLE 3

List of prevalent SNPs located upstream of human HTT exon1. SNP ID, location, nucleotide variation, allele nucleotide frequency, strand and the effect of the nucleotide variation on the PAM sequence are indicated.

| SNP ID | Variant ID | Location | SNP | Allele frequency Reference | 1000 G MAF | Strand | PAM |
|---|---|---|---|---|---|---|---|
| SNP4 | rs35631490 | 3,071,679 | C/G | C = 0.8926 | G = 0.1074 | + | Loss |
| SNP5 | rs61792464 | 3,073,385 | G/C | G = 0.8628 | C = 0.1372 | + | Gain/Loss |
| SNP6 | rs9996199 | 3,074,965 | C/G | C = 0.8425 | G = 0.1575 | + | Gain/Loss |
| SNP1 | rs2857935 | 3,075,691 | C/G/T | C = 0.7710 | G = 0.2260 | − | Loss |
| SNP2 | rs13122415 | 3,076,181 | C/G | C = 0.8918 | G = 0.1082 | + | Loss |
| SNPS | rs13102260 | 3,076,405 | G/A | G = 0.8419 | A = 0.1581 | + | Loss |

HTT mRNA and protein levels were reduced in cells following editing, as determined by Q-PCR and western blot, respectively (FIGS. 4G, 4H, 4I, and 4K). Reduction of HTT mRNA levels was greater in cells expressing sgRNA/SpCas9 complex pairs that generated small targeted deletions, indicating that HTT exon 1 removal efficacy may be influenced by the distance between the two dsDNA breaks (compare sgHD1, 2 and 3 versus sgHD4 and 6) (FIG. 4G). Also, the results indicate a preference of SpCas9 for NGG over NAG PAM sequences (compare sgHD1, 2, 3, 4 (NGG) vs sgHD6c (NAG)) (FIG. 4G). Interestingly, cells expressing sgHDi3 alone, or in combination with sgHD6g or sgHD5g, also showed reduced HTT mRNA and protein levels albeit not to as great an extent as those where HTT exon 1 was removed. This indicates that elements within the first intron, disrupted after DNA repair, could affect expression of the normal HTT allele (FIGS. 4G, 4H, 4I).

FIG. 4L provides a schematic depicting the strategy to delete 1st exon sequence of mutant huntingtin gene using the CRISPR/Cas9 system targeting the SNP-derived PAM motifs at positions SNP1, SNP2, SNP3 and SNP6 in combination with the intronic i3 PAM motif. FIG. 4M provides a schematic depicting the strategy to delete 1st exon sequence of mutant huntingtin gene using the CRISPR/Cas9 system targeting the SNP6 in combination with i3 PAM motif. FIG. 4N provides a schematic depicting the strategy to delete 1st exon sequence of mutant huntingtin gene using the CRISPR/Cas9 system targeting the SNP4, SNP5 derived PAM motifs in combination with i3 PAM motif.

Assessment of Allele Specificity of Editing in HD Human Fibroblasts.

Expression vectors for sgHD1/i3 and SpCas9, or SpCas9 only, were generated (FIG. 7A) for screening in HD fibroblast cell lines. Twenty-three lines were screened for SNP heterozygosity using direct Sanger sequencing of PCR amplified products. Eleven lines were heterozygous for SNP1, 1 line was heterozygous for SNP2, SNP4 and SNP6, and 2 lines were heterozygous for SNP3 and SNP5 (Table 4). Two lines, ND31551 and ND33392, which are heterozygous for the SNP1 on opposite alleles, were chosen for specificity testing (FIG. 7B, Table 5). PCR of genomic DNA showed target cleavage in cells transfected with plasmids expressing sgHD1/i3 and SpCas9 relative to those lacking sgRNAs (FIG. 7C). Semi-quantitative PCR for the normal and mutant HTT mRNAs showed target mRNA knockdown (FIGS. 7D, 7E, 7F), which for ND31551 is the normal allele, and for ND33392 is the mutant allele. Western blot for protein confirmed allele specific reduction of the target allele (FIGS. 7G, 7H).

TABLE 4

List of Huntington's disease (HD) fibroblast genotypes for the various SNPs. HD fibroblast ID, CAG repeat length of the normal and mutant allele, and presence or absence of the SNP heterozygosity are indicated.

| HD Fibroblast | CAG repeat | SNP1 rs2857935 (C > G/T) 0.226 | SNP2 rs13122415 (C > G) 0.1082 | SNP3 rs13102260 (G > A) 0.1581 | SNP4 rs35631490 (C > G) 0.1074 | SNP5 rs61792464 (C > G) 0.1372 | SNP6 rs9996199 (C > G) 0.1575 |
|---|---|---|---|---|---|---|---|
| GM04723 | CAG: 72 | C/G | C | G | C | G | C |
| GM04869 | CAG: 50 | C | C | G | C | G | C |
| GM04767 | CAG: 47 | C/G | C | G | C | G | C |
| GM04887 | ND | C | C | G | C | G | C |
| GM04849 | ND | C | C | G | C | G | C |
| GM04689 | CAG: 46 | C | C | G | C | G | C |
| ND29801 | CAG: 40 | C | C | G | C | G | C |
| ND29970 | CAG: 40 | C | C | G/A | C | G/C | G/C |
| ND30013 | CAG: 43 | C | C | G | C | G | C |
| ND30015 | CAG: 41 | C/G | C | G | C | G | C |
| ND30016 | CAG: 41 | C/G | C | G | C | G | C |
| ND30047 | CAG: 41 | C/G | C | G | C | G | C |
| ND30259 | CAG: 38 | C | C | G | C | G | C |
| ND30422 | CAG: 40 | C/G | C | G | C | G | C |
| ND30626 | CAG: 41 | C/G | C | G | C | G | C |
| ND30967 | CAG: 43 | C | C | G | C | G | C |
| ND31038 | CAG: 44 | C/G | C | G | C | G | C |
| ND31551 | CAG: 39 | C/G | C/G | G/A | C/G | G | G/C |
| ND31846 | CAG: 40 | C | C | G | C | G | C |
| ND33392 | CAG: 57 | C/G | C | G | C | G | C |

TABLE 4-continued

List of Huntington's disease (HD) fibroblast genotypes for the various SNPs. HD fibroblast ID, CAG repeat length of the normal and mutant allele, and presence or absence of the SNP heterozygosity are indicated.

| HD Fibroblast | CAG repeat | SNP1 rs2857935 (C > G/T) 0.226 | SNP2 rs13122415 (C > G) 0.1082 | SNP3 rs13102260 (G > A) 0.1581 | SNP4 rs35631490 (C > G) 0.1074 | SNP5 rs61792464 (C > G) 0.1372 | SNP6 rs9996199 (C > G) 0.1575 |
|---|---|---|---|---|---|---|---|
| ND33947 | CAG: 40 | C/G | C | G | C | G | C |
| ND40536 | CAG: 66 | C | C | G | C | G | C |
| ND40534 | CAG: 46/26 | C | C | G | C | G | C |

TABLE 5

Genotypes of 11 HD fibroblast lines heterozygous for SNP1. Fibroblast ID, CAG repeat length, nucleotide variation for normal and mutant allele, allele that contains the PAM motif and family ID of the HD fibroblast line are indicated.

| HD Fibroblast | CAG repeat | SNP | Huntingtin Allele Normal | Huntingtin Allele Mutant | Targeted | Family |
|---|---|---|---|---|---|---|
| GM04723 | CAG: 72/17 | C/G | G | C | Mutant | 691 |
| GM04767 | CAG: 47/18 | C/G | G | C | Mutant | 691 |
| ND30015 | CAG: 41/20 | C/G | G | C | Mutant | NINDS3749 |
| ND30016 | CAG: 41/21 | C/G | G | C | Mutant | NINDS3749 |
| ND30047 | CAG: 41/18 | C/G | G | C | Mutant | NINDS3753 |
| ND30422 | CAG: 40/18 | C/G | G | C | Mutant | NINDS3751 |
| ND30626 | CAG: 41/21 | C/G | G | C | Mutant | NINDS3752 |
| ND31038 | CAG: 44/19 | C/G | C | G | Normal | NINDS3752 |
| ND31551 | CAG: 39/18 | C/G | C | G | Normal | Unknown |
| ND33392 | CAG: 57/17 | C/G | G | C | Mutant | NINDS4250 |
| ND33947 | CAG: 40/18 | C/G | G | C | Mutant | Unknown |

Assessment of Off-Target Cleavage Sites in HD Human Edited Fibroblasts.

Although truncated sgRNA sequences (~<20 nt) are reported to have higher selectivity for the on-target site, any sgRNA/Cas9 complex can also generate unwanted dsDNA breaks at off-target sites that resemble the on-target sequence (Fu et al. (2013) Nat. Biotech., 31:822-826; Kleinstiver et al. (2015) Nature, 523:481-485; Hsu et al. (2013) Nat. Biotech., 31:827-832; Cho et al. (2013) Nat. Biotech., 31:230-232). The Cas9-Off finder algorithm was used to predict the number of potential off-target sites for the most effective sgRNAs (sgHD1, sgHD2, sgHD3 and sgHDi3), and the UCSC genome browser for mapping their location in the human genome (Bae et al. (2014) Bioinform., 30:1473-1475). The screen identified 416 sites for sgHD1, whereas 40, 21 and 7 off-targets are predicted for sgHD2, sgHDi3 and sgHD3, respectively (FIG. 8A). Of note, sgHD1 has the shortest complementary sequence (17nt), which could explain its higher frequency for genomic off-targets. Importantly, all guides showed full complementary only to HTT, and more than 90% of the off-targets have 3 mismatches. As expected, they occur in the promoter, 5'UTR, exons, introns, 3' UTR, and intergenic regions. The highest number was predicted within introns (FIG. 8B). HD fibroblasts were electroporated with vectors expressing SpCas9 and sgHD1/i3, along with a short ODN sequence for mapping off-target dsDNA breaks (Tsai et al. (2015) Nat. Biotech., 33:187-197). As expected, the ODN was incorporated within the HTT gene locus (FIG. 8C) but it was not detected in any of the 11 top off-target sites tested (FIG. 8D).

Allele-Specific Editing In Vivo.

BacHD mice are transgenic for a modified human HD allele (Gray et al. (2008) J. Neurosci., 28:6182-6195), which fortuitously contains SNPs 1, 2 and 3. These mice were used to first evaluate the efficacy of mutant HTT editing in vivo at the genomic level. For this, recombinant AAVs (rAAVs) expressing either SpCas9 (rAAV.SpCas9) or the sgRNAs (rAAV.sgHD1/i3) were generated, which effectively delete human HTT exon 1 in vitro (FIG. 9A, 9D). Mice were injected on the right hemisphere with rAAV.SpCas9 plus rAAV.sgHD1B/i3. The left hemisphere was used as a control and left uninjected. Brains were harvested 3 weeks later and genomic DNA isolated. PCR amplification of genomic DNA demonstrates cleavage in the setting of Cas9 and sgRNA expressing AAVs only (FIG. 9B). Accordingly, HTT mRNA levels reduced on the right, but not the left hemisphere, in concordance with DNA cleavage (FIG. 9C). Interestingly, mouse Httm RNA levels were also reduced on the injected hemisphere, although to a lesser degree than the human HTT allele. Several binding sites for sgHD1 and sgHDi3 were identified within the mouse Htt locus. Three binding sites were identified for sgHD1, all within exon 1 and containing 5 mismatches. In contrast, a single binding site with 2 mismatches within the first intron was predicted for sgHDi3 (FIG. 9E). Indels within the intron caused by sgHDi3 may disrupt transcription factor binding sites, and similar to HEK293 cells expressing sgHDi3 alone (FIG. 4G), reduce mouse HTT expression.

Other Cas9 Systems for Silencing the HTT Allele.

It was then screened which of the 47 SNPs flanking HTT exon1 were contained within their conserved PAM nucleotide positions. Engineered SpCas9 variants from *Streptococcus Pyogenes* with altered PAM specificities have been generated (SpCas9_VQR, SpCas9_EQR, and SpCas9_VRER) (Kleinstiver et al. (2015) Nature, 523:481-485). The SpCas9_VQR variant strongly recognizes sequences bearing the NGAN PAM and with lower efficiency those sites with a NGNG motif. SpCas9_EQR is more specific for an NGAG PAM. In contrast, SpCas9_VRER has a strong selectivity for a NGCG PAM sequence with no cleavage activity when this is varied. For SpCas9_VQR, the SNP could be positioned at the 2nd or the 3rd nucleotide of the NGAN PAM, as well as at the 2nd and 4th nucleotide of the NGNG PAM sequence. In contrast, because of the selectivity of the SpCas9_EQR for NGAG and SpCas9_VRER for NGCG sequences, the SNP could be permitted at any position of their PAM (FIG. 5A-5O, FIGS. 3D-3J). The discovery of SaCas9 from *Staphylococcus aureus* has extended the number of CRISPR/Cas9 systems, with the advantage that a SaCas9-encoding transgene can be easily package into AAV viral vectors (Ran et al. (2015) Nature, 520:186-191). SaCas9 primarily recognizes a NNGRRT PAM, although dsDNA breaks are also observed at DNA targets adjacent to NNGRR motifs. For SaCas9 only those SNPs positioned at the 3rd nucleotide of the PAM would allow for allele specificity (FIG. 5A-5O, FIGS. 3D-3J). A new Class 2 CRISPR system was recently identified that contains Cpf1 as effector protein to mediate dsDNA breaks (Zetsche et al. (2015) Cell, 163:759-771). Unlike Cas9 that recognizes a G-rich PAM motif, the Cpf1 PAM motif is T-rich. Currently, 16 Cpf1-family proteins have been characterized, but only the Cpf1 proteins from *Acidaminococcus* (AsCpf1) and Lachnospiraceae (LbCpf1) have shown robust DNA interference activity when expressed in mammalian cells. AsCpf1 has strong selectivity for a TTTN PAM and does not recognize any sequence variants. Therefore, SNP presents at any position of the TTTN PAM could disrupt AsCpf1 recognition. In contrast, LbCpf1 recognizes multiple T-rich PAMs, albeit with different cleavage activity. Thus, for LbCpf1, only those SNPs where the variant nucleotide did not generate any other PAM that could be recognized above LbCpf1 cleavage threshold activity could be considered for allele discrimination (Zetsche et al. (2015) Cell, 163:759-771) (FIGS. 5A-5O, FIGS. 3D-3J).

Overall, 36 SNPs located within the specific PAM positions described above were identified. Again, instances where the nucleotide variation caused the loss (12 SNPs), gain (11 SNPs), or a simultaneous loss in one DNA strand and a gain on the opposite strand (13 SNPs) were identified (FIGS. 5A-5O, FIGS. 3D-3J). Of special interests are the SNPs that generate a Loss/Gain, since CRISPR complexes could be designed for any of the two possible nucleotides linked to the mutant allele. Of note, instances were found where the same Cas9 protein could target each nucleotide variation using a different sgRNA sequence, or alternatively, a different CRISPR effector protein could be used to target each nucleotide variant. Two interesting observations also arose from the screen. One, in the rs113331544 SNP, for which the minor allele contains a six-nucleotide insertion, the same PAM sequence is present on both alleles, but a different sgRNA sequence could be designed to tether SpCas9 to the mutant allele depending on the nucleotide variation. Two, for the rs28393280 and the rs28583447 SNPs, the nucleotide variation causes the gain of 2 PAM motifs on the same allele, one on the positive and the other on the negative DNA strand. Those SNPs could be appropriate for targeting with a nickase effector protein, which would efficiently generate on-target dsDNA breaks without detectable damage at potential off-target sites (Ran et al. (2013) Cell, 154:1380-1389).

Currently, reduction of HTT mRNA levels with RNAi and ASOs are the leading therapeutic options for HD (Kordasiewicz et al. (2012) Neuron, 74:1031-1044; McBride et al. (2011) Mol. Ther., 19:2152-2162). However, it is unknown whether these treatments will be beneficial in HD patients, since the mutant protein is not completely eliminated. Additionally, the normal allele is reduced relative to normal levels as a consequence of the non-allele specific gene silencing approach.

Targeted gene deletions can be generated when two sgRNA/Cas9 complexes cause dsDNA breaks followed by DNA repair (Cong et al. (2013) Science, 339:819-823; Jinek et al. (2013) eLife, 2:e00471). Given the potency of CRISPR/Cas9 and the high likelihood of cleaving both HTT alleles, the role of HTT protein on important cellular functions, and the fact that a complete loss of the huntingtin gene in adult mice causes progressive neurodegeneration (Dragatsis et al. (2000) Nat. Genet., 26:300-306), allele specificity for editing is imperative. Earlier work demonstrated that Cas9 causes dsDNA breaks when mismatches are present between the guide and the targeted sequence, but only if a PAM motif is near the target sequence (Fu et al. (2013) Nat. Biotech., 31:822-826; Hsu et al. (2013) Nat. Biotech., 31:827-832). Genome wide studies and in vitro library screens have provided information regarding the conservation for each nucleotide within a PAM sequence for several of the available Cas9 proteins (Kleinstiver et al. (2015) Nature, 523:481-485; Tsai et al. (2015) Nat. Biotech., 33:187-197; Zetsche et al. (2015) Cell, 163:759-771; Ran et al. (2015) Nature, 520:186-191). Cas9 PAM recognition could be disrupted on a single allele if a SNP located at these conserved nucleotides were present in heterozygosity. Thus, single allele targeted deletions could be generated to mitigate the expression of the mutant, but not the normal allele.

Guide RNAs were designed that bind and tether SpCas9 to six prevalent SNPs located 5' of HTT exon1, which in combination with a guide binding within the first HTT intron effectively eliminate expression of the HTT protein. The distance between upstream and downstream guides influenced editing efficacy, as well as confirmed the SpCas9 preference in HD cell lines. The studies also indicate that intronic transcription binding sites may effect HTT gene expression, since indels generated by SpCas9 within the HTT intron reduced gene expression. This is important when designing intronic guide sequences, since expression of the normal allele could also be affected. The allele specificity of the instant approach was demonstrated using human fibroblast cell lines for which these SNPs are present in heterozygosity. HTT exon 1 excision was observed only on the alleles where the nucleotide variation did not disrupt the PAM motif.

Interestingly, SNP1 (rs2857935) has a prevalence of 22% among the human population. In the HD fibroblast lines, 9 out of 11 were heterozygous for the SNP and the PAM was linked to the mutant allele. This raises the exciting possibility that this SNP is in linkage disequilibrium with the mutant allele in the general HD population.

The importance of on-target selectivity is crucial when using gene-editing approaches. In the instant strategy truncated sgRNA guides were used, which have been shown to minimize unintended dsDNA breaks (Fu et al. (2014) Nat. Biotech., 32:279-284). Potential off-targets from the guides were screened for using an in silico approach, and most of the off-target binding sites contained 3 mismatches within intronic regions. Notably, additional tools with significant on-target selectivity such as the High fidelity Cas9 proteins and the Cas9 nickases can be used in the instant methods (Ran et al. (2013) Cell, 154:1380-1389; Kleinstiver et al. (2016) Nature, 529:490-495; Slaymaker et al. (2016) Science, 351:84-88).

The approach was also demonstrated in vivo using an HD mouse model. rAAV delivery of the sgRNA/SpCas9 complexes reduced human mutant HTT expression to 40% in treated hemispheres, a level of reduction known to provide benefit by RNAi or ASOs (Harper et al. (2005) Proc. Natl. Acad. Sci., 102:5820-5825; Boudreau et al. (2009) Mol. Ther., 17:1053-1063; Kordasiewicz et al. (2012) Neuron, 74:1031-1044). Notably, Cas9 and/or the sgRNAs may be transiently expressed in the instant methods (Hendel et al. (2015) Nat. Biotech., 33:985-989; Randar et al. (2015) Proc. Natl. Acad. Sci., 112:E7110-7117).

Thus, a strategy for allele specific genome-editing of mutant HTT based on CRISPR/Cas9 technology has been developed that takes advantage of highly prevalent SNPs at the HTT locus for guiding mutant allele specific cleavage.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for inhibiting, treating, and/or preventing a polyglutamine disorder in a subject in need thereof, said method comprising reducing the expression of a mutant protein encoded by an allele of a gene associated with the polyglutamine disorder in said subject,
   wherein said polyglutamine disorder is characterized by an abnormally high number of cytosine-adenine-guanine (CAG) repeats resulting in an extended polyglutamine tract in the encoded for mutant protein, and
   wherein said method comprising administering to the subject a nucleic acid molecule encoding Cas9 and at least two guide RNA or a nucleic acid molecule encoding said at least two guide RNA,
   wherein at least one of the guide RNA comprises a complementary sequence which comprises a sequence immediately 5' to a protospacer-adjacent motif (PAM) present only on the mutant allele of the gene,
   wherein a first guide RNA comprises a sequence which is completely complementary to a sequence within the promoter or 5' untranslated region of the gene and a second guide RNA comprises a complementary sequence which is completely complementary to a sequence within the first intron of the gene,
   wherein the first guide RNA comprises SEQ ID NO: 379, SEQ ID NO: 380, SEQ ID NO: 382, SEQ ID NO: 383, SEQ ID NO: 384, SEQ ID NO: 385, or SEQ ID NO: 386, and
   wherein said polyglutamine disorder is Huntington's disorder, said gene is the huntingtin (HTT) gene, and said CAG repeats are contained with the first exon of the HTT gene.

2. The method of claim 1, wherein said method further comprises administering to the subject at least one donor DNA.

3. The method of claim 1, wherein said guide RNA are administered as a nucleic acid molecule encoding said guide RNA.

4. The method of claim 3, wherein said nucleic acid molecules are administered in an expression vector.

5. The method of claim 4, wherein said expression vector is a viral vector.

6. The method of claim 1 wherein the first guide RNA comprises SEQ ID NO: 379, SEQ ID NO: 380, or SEQ ID NO: 382.

7. The method of claim 1 wherein the first guide RNA comprises SEQ ID NO: 379 or SEQ ID No: 380.

8. A method for reducing the expression of a mutant protein encoded by an allele of a gene associated with a polyglutamine disorder in a cell, said method comprising delivering to the cell a nucleic acid molecule encoding Cas9 and at least two guide RNA or a nucleic acid molecule encoding said at least two guide RNA,
   wherein said polyglutamine disorder is characterized by an abnormally high number of cytosine-adenine-guanine (CAG) repeats resulting in an extended polyglutamine tract in the encoded for mutant protein,
   wherein at least one of the guide RNA comprises a complementary sequence which comprises a sequence immediately 5' to a protospacer-adjacent motif (PAM) present only on the mutant allele of the gene,
   wherein a first guide RNA comprises a complementary sequence which is completely complementary to a sequence within the promoter or 5' untranslated region of the gene and a second guide RNA comprises a complementary sequence which is completely complementary to a sequence within the first intron of the gene,
   wherein the first guide RNA comprises SEQ ID NO: 379, SEQ ID NO: 380, SEQ ID NO: 382, SEQ ID NO: 383, SEQ ID NO: 384, SEQ ID NO: 385, or SEQ ID NO: 386, and wherein said polyglutamine disorder is Huntington's disorder, said gene is the huntingtin (HTT) gene, and said CAG repeats are contained with the first exon of the HTT gene.

9. An isolated guide RNA which comprises SEQ ID NO: 379, SEQ ID NO: 380, SEQ ID NO: 382, SEQ ID NO: 383, SEQ ID NO: 384, SEQ ID NO: 385, or SEQ ID NO: 386.

10. An isolated nucleic acid molecule encoding at least one of the guide RNA of claim 9.

11. A vector comprising the nucleic acid molecule of claim 10.

12. The vector of claim 11, which is a viral vector.

13. The vector of claim 11, further comprising a nucleic acid molecule encoding Cas9.

14. A composition comprising at least one nucleic acid molecule of claim 10 and a carrier.

15. A composition comprising at least one guide RNA of claim 9 and a carrier.

16. A method for inhibiting, treating, and/or preventing a polyglutamine disorder in a subject in need thereof, said method comprising reducing the expression of a mutant protein encoded by an allele of a gene associated with the polyglutamine disorder in said subject,
wherein said polyglutamine disorder is characterized by an abnormally high number of cytosine-adenine-guanine (CAG) repeats resulting in an extended polyglutamine tract in the encoded for mutant protein,
wherein said method comprising administering to the subject a nucleic acid molecule encoding Cas9 and at least two guide RNA or a nucleic acid molecule encoding said at least two guide RNA,
wherein at least one of the guide RNA comprises a complementary sequence which comprises a sequence immediately 5' to a protospacer-adjacent motif (PAM) present only on the mutant allele of the gene,
wherein a first guide RNA comprises a complementary sequence which is completely complementary to a sequence within the promoter or 5' untranslated region of the gene and a second guide RNA comprises a complementary sequence which is completely complementary to a sequence within the first intron of the gene, and
wherein the second guide RNA comprises SEQ ID NO: 387 or SEQ ID NO: 388 or wherein the first guide RNA comprises SEQ ID NO: 379.

17. The method of claim 16, wherein the second guide RNA comprises SEQ ID NO: 387.

18. The method of claim 16, wherein the first guide RNA comprises SEQ ID NO: 379.

19. The method of claim 16, wherein the first guide RNA comprises SEQ ID NO: 379 and the second guide RNA comprises SEQ ID NO: 387.

20. A method for reducing the expression of a mutant protein encoded by an allele of a gene associated with a polyglutamine disorder in a cell, said method comprising delivering to the cell a nucleic acid molecule encoding Cas9 and at least two guide RNA or a nucleic acid molecule encoding said at least two guide RNA,
wherein said polyglutamine disorder is characterized by an abnormally high number of cytosine-adenine-guanine (CAG) repeats resulting in an extended polyglutamine tract in the encoded for mutant protein,
wherein at least one of the guide RNA comprises a complementary sequence which comprises a sequence immediately 5' to a protospacer-adjacent motif (PAM) present only on the mutant allele of the gene,
wherein a first guide RNA comprises a targeting sequence which is completely complementary to a sequence within the promoter or 5' untranslated region of the gene and a second guide RNA comprises a targeting sequence which is completely complementary to a sequence within the first intron of the gene, and
wherein the second guide RNA comprises SEQ ID NO: 387 or SEQ ID NO: 388 or wherein the first guide RNA comprises SEQ ID NO: 379.

* * * * *